(12) United States Patent
Cha et al.

(10) Patent No.: US 11,407,718 B2
(45) Date of Patent: Aug. 9, 2022

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Yong Bum Cha, Daejeon (KR); Yeon Ho Cho, Daejeon (KR); Yeon Hwan Kim, Daejeon (KR); Sang Young Jeon, Daejeon (KR); Sung Jae Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 415 days.

(21) Appl. No.: 16/484,777

(22) PCT Filed: Apr. 26, 2018

(86) PCT No.: PCT/KR2018/004871
§ 371 (c)(1),
(2) Date: Aug. 8, 2019

(87) PCT Pub. No.: WO2018/236040
PCT Pub. Date: Dec. 27, 2018

(65) Prior Publication Data
US 2019/0389810 A1      Dec. 26, 2019

(30) Foreign Application Priority Data

Jun. 21, 2017  (KR) ........................ 10-2017-0078693

(51) Int. Cl.
*C07D 239/26*   (2006.01)
*C07D 213/06*   (2006.01)
(Continued)

(52) U.S. Cl.
CPC ......... *C07D 239/26* (2013.01); *C07D 213/06* (2013.01); *C07D 251/24* (2013.01);
(Continued)

(58) Field of Classification Search
CPC .. C07D 213/06; C07D 239/26; C07D 251/24; H01L 51/0067
See application file for complete search history.

(56) References Cited

U.S. PATENT DOCUMENTS 10,522,762 B2 * 12/2019 Huh .................... H01L 51/0058
2014/0231713 A1   8/2014 Bascour et al.
(Continued)

FOREIGN PATENT DOCUMENTS

CN      105601558 A    5/2016
KR    2000-0051826 A   8/2000
(Continued)

OTHER PUBLICATIONS

Computer-generated English-language translation of KR 20160032414A.*

*Primary Examiner* — Vu A Nguyen
(74) *Attorney, Agent, or Firm* — Dentons US LLP

(57) ABSTRACT

The present disclosure relates to a cyclic compound represented by Chemical Formula 1 and an organic light emitting device including the same. The cyclic compound used as a material of an organic material layer of the organic light emitting device, provides improved efficiency, low driving voltage, and improved lifetime characteristics.

(Continued)

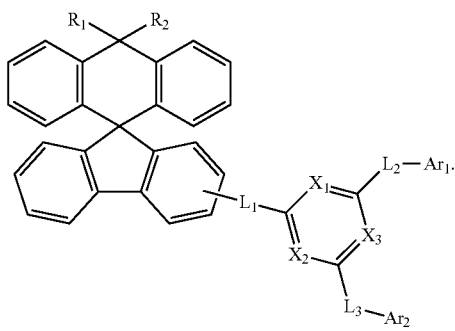

8 Claims, 1 Drawing Sheet

(51) Int. Cl.
*C07D 251/24* (2006.01)
*H01L 51/00* (2006.01)
*H01L 51/50* (2006.01)

(52) U.S. Cl.
CPC ........ *H01L 51/0067* (2013.01); *H01L 51/508* (2013.01); *H01L 51/5064* (2013.01)

(56) References Cited

U.S. PATENT DOCUMENTS

| | | |
|---|---|---|
| 2014/0231716 A1 | 8/2014 | Bascour et al. |
| 2014/0326979 A1 | 11/2014 | Bascour et al. |
| 2017/0012219 A1 | 1/2017 | Parham et al. |
| 2017/0222157 A1 | 8/2017 | Jatsch et al. |
| 2018/0002256 A1 | 1/2018 | Cha et al. |
| 2018/0006233 A1 | 1/2018 | Cha et al. |

FOREIGN PATENT DOCUMENTS

| | | |
|---|---|---|
| KR | 10-2011-0107680 A | 4/2011 |
| KR | 10-2014-0009019 A | 1/2014 |
| KR | 10-2014-0069236 A | 6/2014 |
| KR | 10-2014-0147802 A | 12/2014 |
| KR | 10-2016-0100698 A | 8/2016 |
| KR | 10-2016-0126076 A | 11/2016 |
| KR | 10-2017-0032414 A | 3/2017 |
| KR | 10-2017-0049391 A | 5/2017 |
| KR | 10-2018-0065246 A | 6/2018 |
| KR | 10-2018-0116635 A | 10/2018 |
| WO | 03/012890 A2 | 2/2003 |
| WO | 2016012075 A1 | 1/2016 |

\* cited by examiner

【FIG. 1】
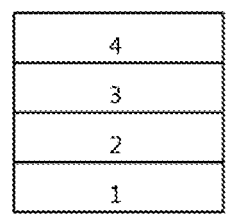
【FIG. 2】
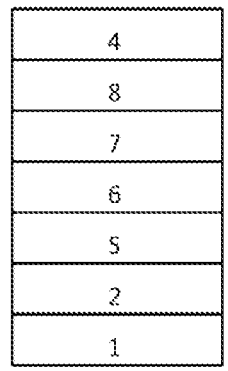

HETEROCYCLIC COMPOUND AND ORGANIC LIGHT EMITTING DEVICE COMPRISING THE SAME

CROSS-REFERENCE TO RELATED APPLICATION(S)

The present application is a National Phase entry pursuant to 35 U.S.C. § 371 of International Application No. PCT/KR2018/004871, filed on Apr. 26, 2018 and claims priority to and the benefit of Korean Patent Application No. 10-2017-0078693 filed on Jun. 21, 2017, the disclosures of which are incorporated herein by reference in their entirety.

TECHNICAL FIELD

The present disclosure relates to a novel heterocyclic compound, and to an organic light emitting device including the same.

BACKGROUND OF DISCLOSURE

In general, an organic light emitting phenomenon refers to one where electrical energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and the electrons meet, an exciton is formed, and light is emitted when the exciton falls to a ground state.

There is a continuing need for the development of new materials for the organic materials used in such organic light emitting devices.

RELATED ART

Korean Patent Laid-open Publication No. 10-2000-0051826

SUMMARY OF DISCLOSURE

Technical Problem

It is an object of the present disclosure to provide a novel heterocyclic compound and an organic light emitting device including the same.

Technical Solution

The present disclosure provides a compound represented by the following Chemical Formula 1:

[Chemical Formula 1]

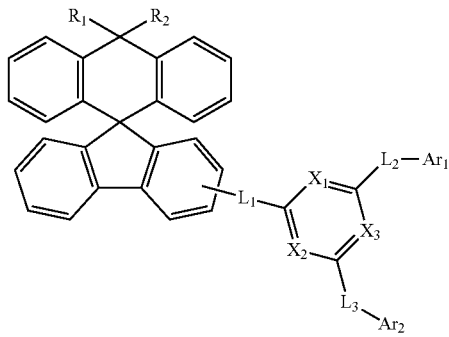

wherein, in Chemical Formula 1, $R_1$ and $R_2$ are each independently a substituted or unsubstituted $C_{1-60}$ alkyl, or a substituted or unsubstituted $C_{6-60}$ aryl;

$L_1$, $L_2$, and $L_3$ are each independently a direct bond, a substituted or unsubstituted $C_{6-60}$ arylene, or a $C_{2-60}$ heteroarylene containing at least one heteroatom selected from the group consisting of O, N, S and Si;

$X_1$ to $X_3$ are each independently N or CR', provided that at least one of them is N;

R' is hydrogen or a substituted or unsubstituted $C_{1-60}$ alkyl; and $Ar_1$ and $Ar_2$ are each independently a substituted or unsubstituted $C_{6-60}$ aryl.

The present disclosure also provides an organic light emitting device including: a first electrode; a second electrode provided opposite to the first electrode; and at least one layer of the organic material layers provided between the first electrode and the second electrode, wherein the at least one layer of the organic material layers includes the compound represented by Chemical Formula 1.

Advantageous Effects

The compound represented by Chemical Formula 1 can be used as a material of an organic material layer of an organic light emitting device, and may improve the efficiency, achieve a low driving voltage, and/or improve lifetime characteristics of the organic light emitting device. In particular, the compound represented by Chemical Formula 1 can be used as a material for hole injection, hole transport, hole injection and transport, light emitting, electron transport, or electron injection.

BRIEF DESCRIPTION OF DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present disclosure will be described in more detail to help understanding of the present disclosure.

The present disclosure provides a compound represented by Chemical Formula 1.

In the present disclosure, the notations ┆ and

mean bonds for connection to another compound.

In the present disclosure, the term "substituted or unsubstituted" means being unsubstituted or substituted with one or more substituents selected from the substituent group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group containing at least one of N, O, and S atoms, or being unsubstituted or substituted with a substituent from the above substituent group which is further substituted by one or more selected from the above substituent group.

In the present disclosure, the number of carbon atoms of a carbonyl group is not particularly limited, but is preferably 1 to 40. Specifically, the carbonyl group may be a compound having the following structures, but is not limited thereto.

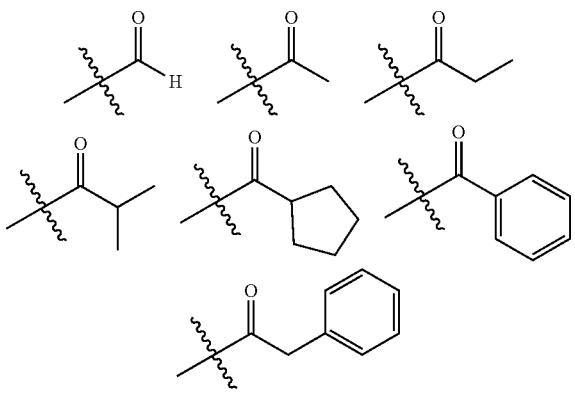

In the present disclosure, for an ester group, the oxygen of the ester group may be substituted with a straight-chained, branch-chained, or cyclic alkyl group having 1 to 25 carbon atoms, or an aryl group having 6 to 25 carbon atoms. Specifically, the ester group may be a compound having the following structural formulae, but is not limited thereto.

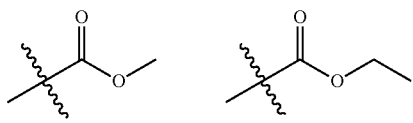

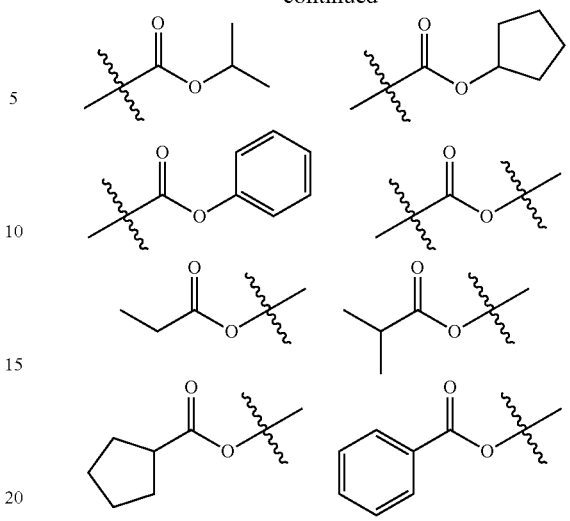

In the present disclosure, the number of carbon atoms of an imide group is not particularly limited, but is preferably 1 to 25. Specifically, the imide group may be a compound having the following structures, but is not limited thereto.

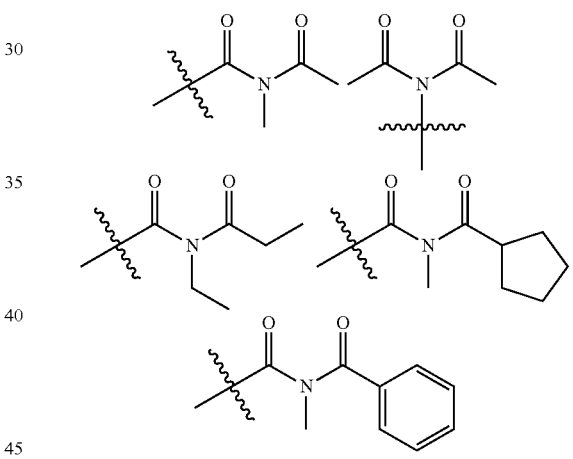

In the present disclosure, a silyl group may specifically include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present disclosure, a boron group may specifically include a trimethylboron group, a triethylboron group, a t-butyldimethylboron group, a triphenylboron group, a phenylboron group, and the like, but is not limited thereto.

In the present disclosure, examples of a halogen group include fluorine, chlorine, bromine, and iodine.

In the present disclosure, the alkyl group may be straight-chained or branch-chained, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methyl pentyl, 2-methylpentyl, 4-methyl-2-pentyl, 3,3-dimethylbutyl, 2-ethylbutyl, heptyl, n-heptyl, 1-methylhexyl, cyclopentylmethyl, cycloheptylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present disclosure, the alkenyl group may be straight-chained or branch-chained, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but preferably has 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to still another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, the aryl group is not particularly limited, but preferably has 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present disclosure, a fluorenyl group may be substituted, and two substituent groups may be linked with each other to form a spiro structure. In the case where the fluorenyl group is substituted,

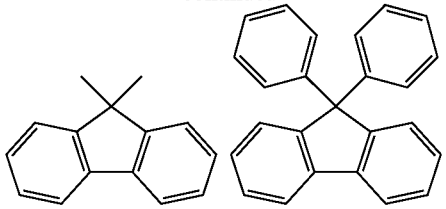

and the like can be formed. However, the structure is not limited thereto.

In the present disclosure, a heterocyclic group is a heterocyclic group including one or more of O, N, Si, and S as a hetero atom, and the number of carbon atoms thereof is not particularly limited, but is preferably 2 to 60. Examples of the heterocyclic group include a thiophene group, a furan group, a pyrrole group, an imidazole group, an oxazole group, an oxadiazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present disclosure, the aryl group in the aralkyl group, the aralkenyl group, the alkylaryl group, and the arylamine group is the same as the examples of the aryl group as defined above. In the present disclosure, the alkyl group in the aralkyl group, the alkylaryl group, and the alkylamine group is the same as the examples of the alkyl group as defined above. In the present disclosure, the heteroaryl in the heteroarylamines can be applied to the above-mentioned description of the heterocyclic group. In the present disclosure, the alkenyl group in the aralkenyl group is the same as the examples of the alkenyl group as defined above. In the present disclosure, the above-mentioned description of the aryl group may be applied except that the arylene is a divalent group. In the present disclosure, the above-mentioned description of the heterocyclic group can be applied except that the heteroarylene is a divalent group. In the present disclosure, the above-mentioned description of the aryl group or cycloalkyl group can be applied except that the hydrocarbon ring is not a monovalent group but is formed by combining two substituent groups. In the present disclosure, the above-mentioned description of the heterocyclic group can be applied, except that the heterocycle is not a monovalent group but is formed by combining two substituent groups.

Preferably, Chemical Formula 1 may be any one selected from compounds represented by the following Chemical Formulas 1-1 to 1-5.

[Chemical Formula 1-1]

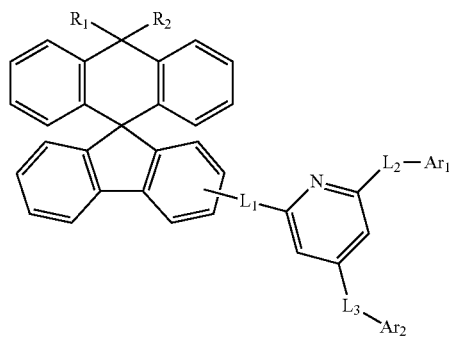

[Chemical Formula 1-2]

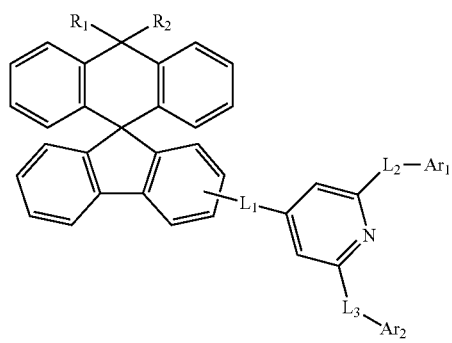

[Chemical Formula 1-3]

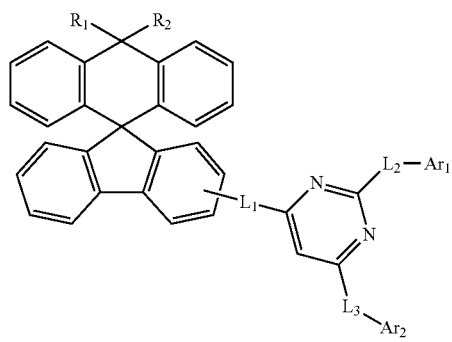

[Chemical Formula 1-4]

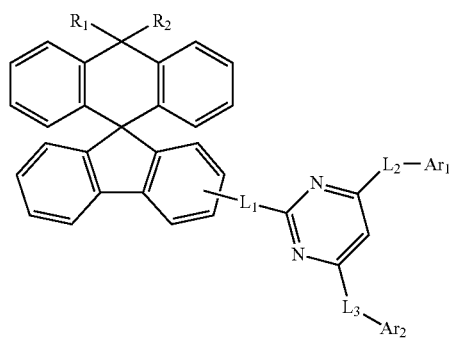

[Chemical Formula 1-5]

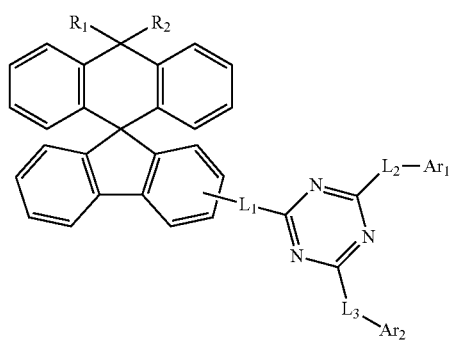

Preferably, $R_1$ and $R_2$ may each independently be methyl or benzyl.

Preferably, $L_1$, $L_2$, and $L_3$ may each independently be a direct bond or selected from the group consisting of the following.

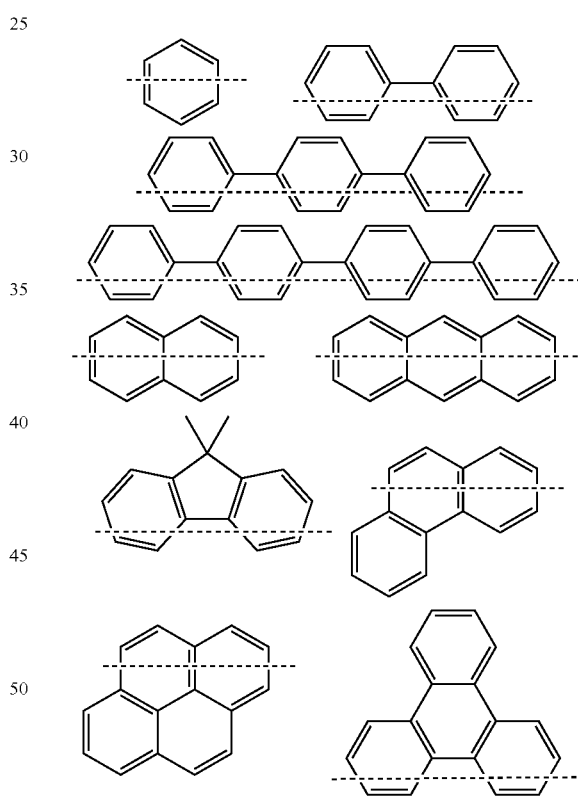

Further, preferably, $L_1$, $L_2$, and $L_3$ may each independently be a direct bond or

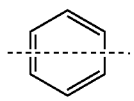

Preferably, $Ar_1$ and $Ar_2$ may each independently be selected from the group consisting of the following.

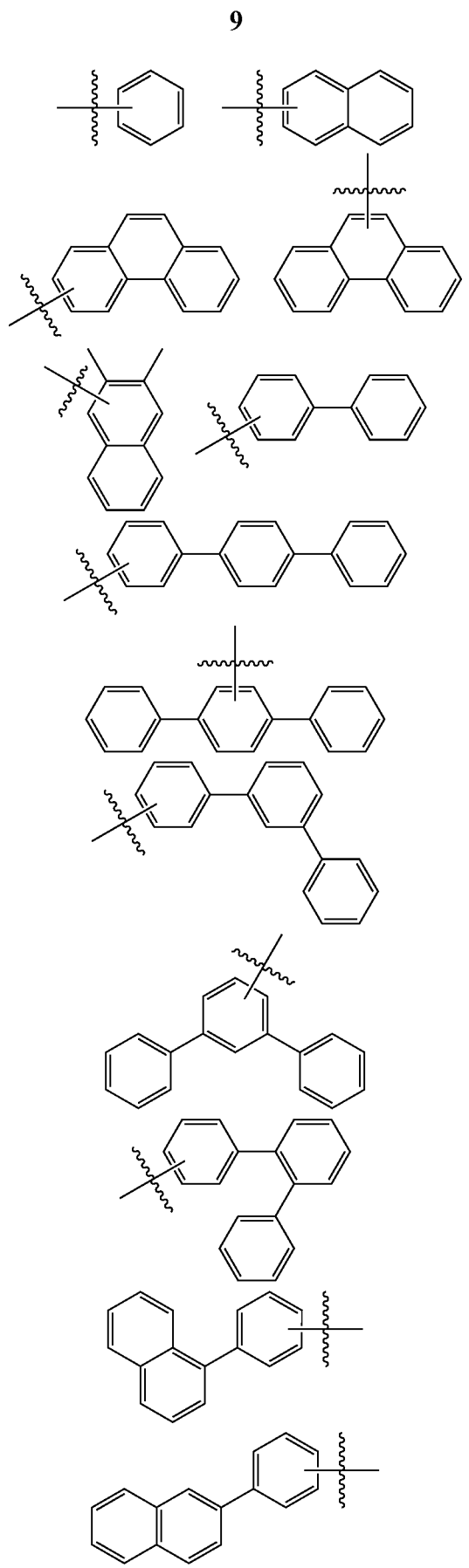
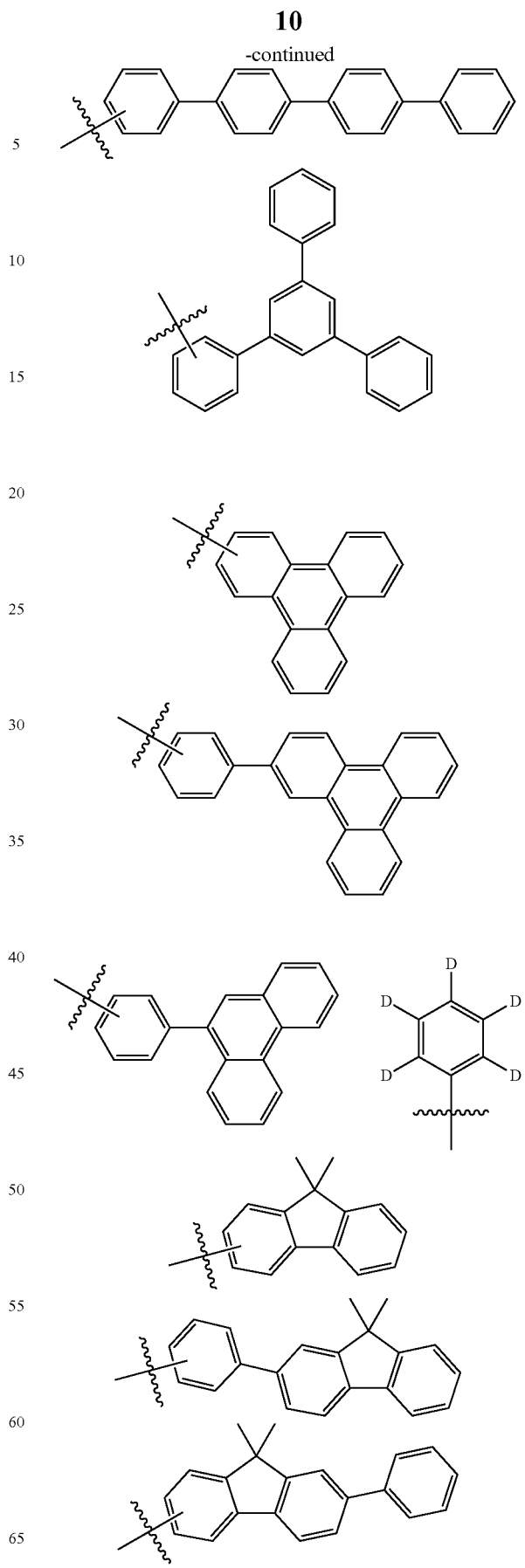

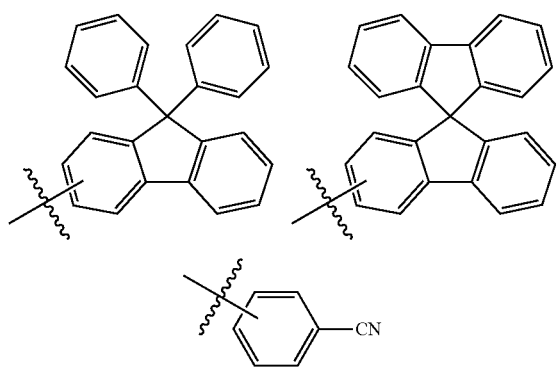
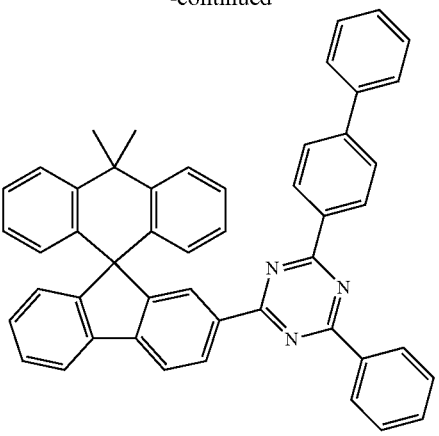
Preferably, the compound represented by Chemical Formula 1 may be any one selected from the group consisting of the following.
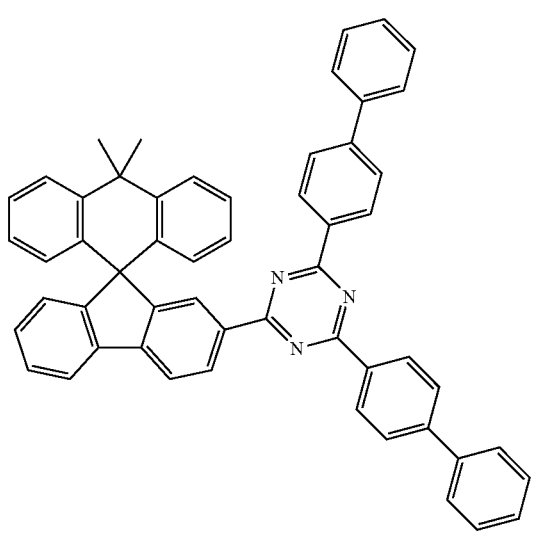
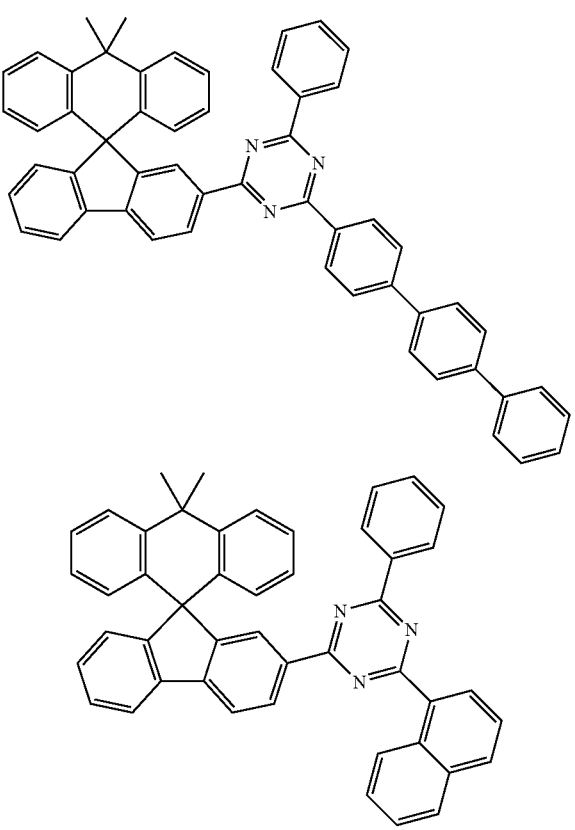
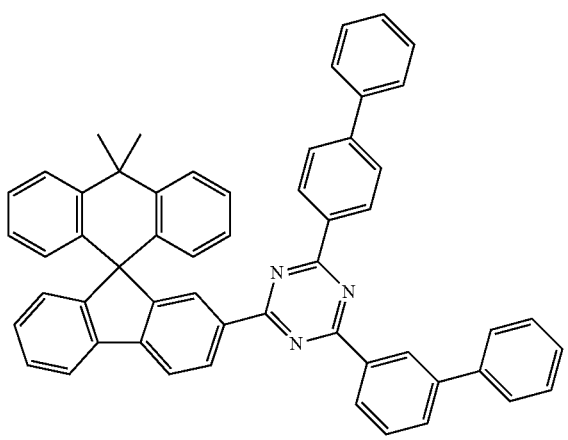
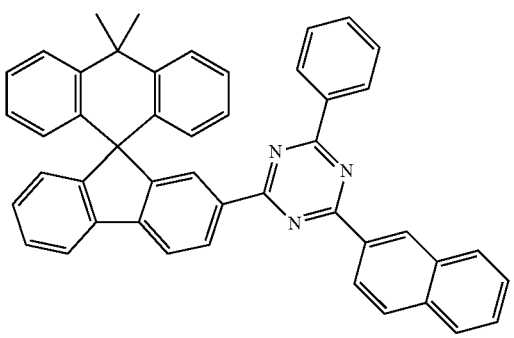

-continued
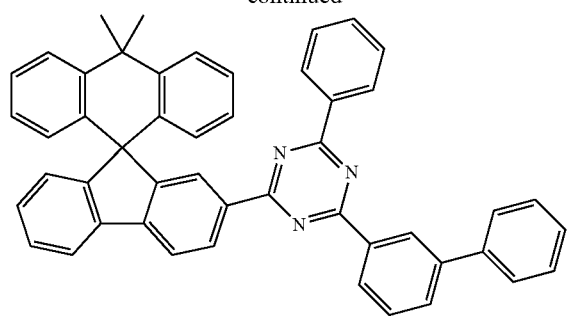
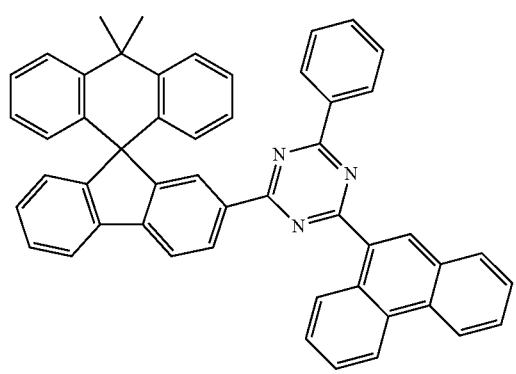
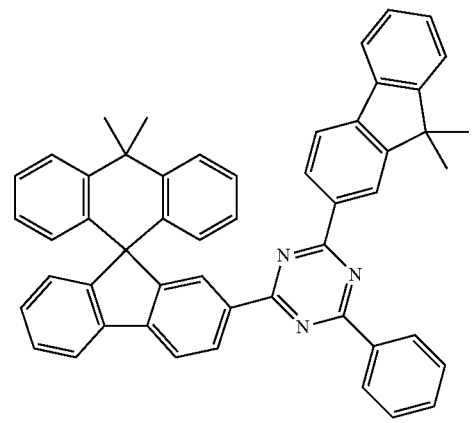
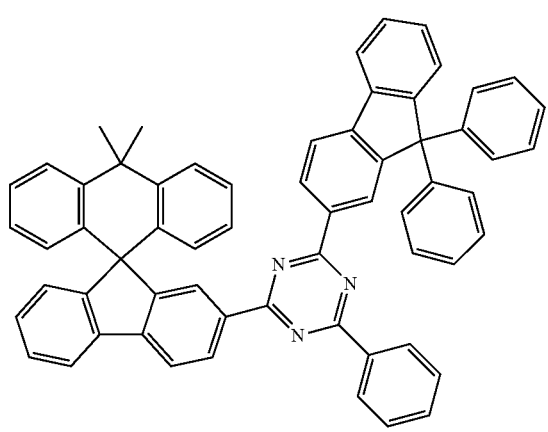
-continued
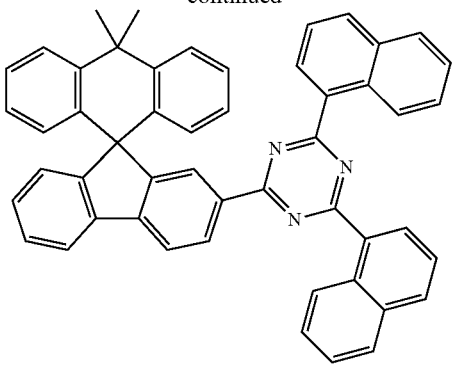
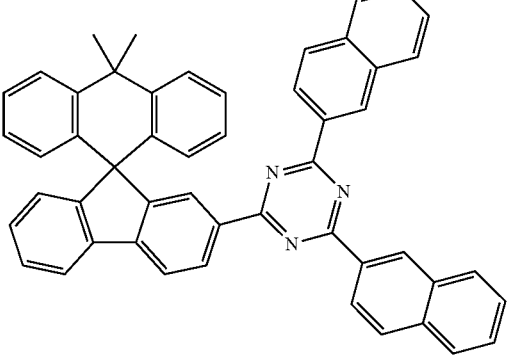
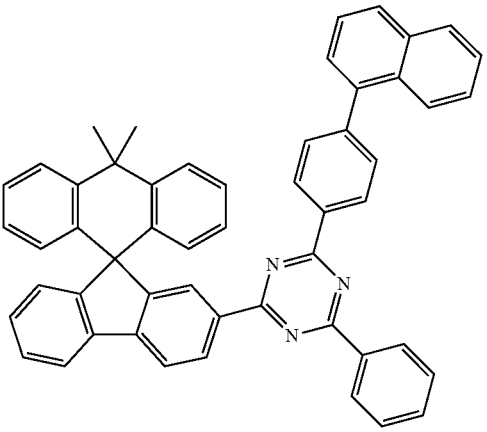
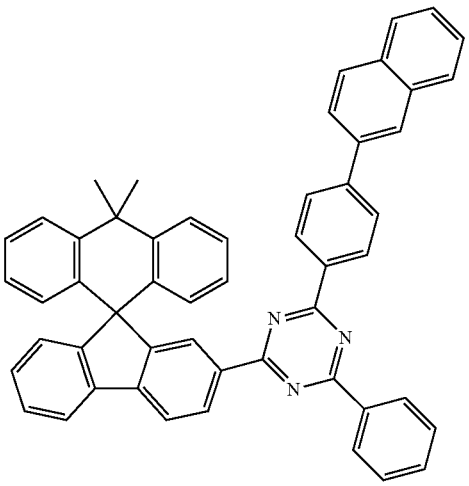

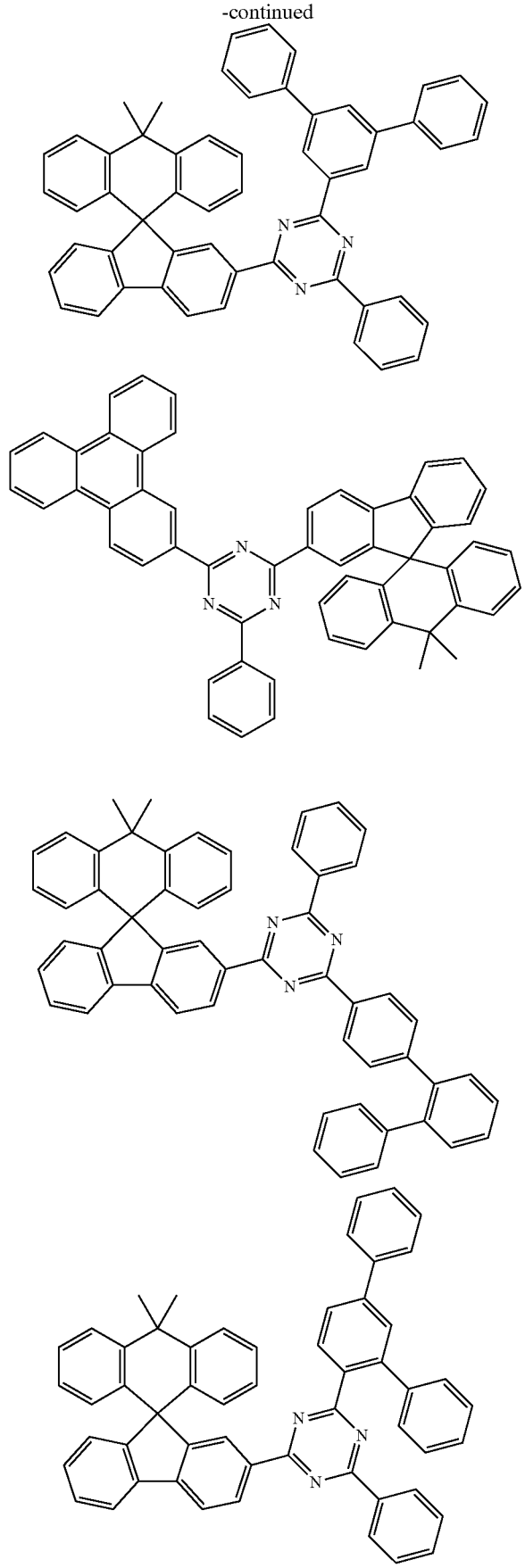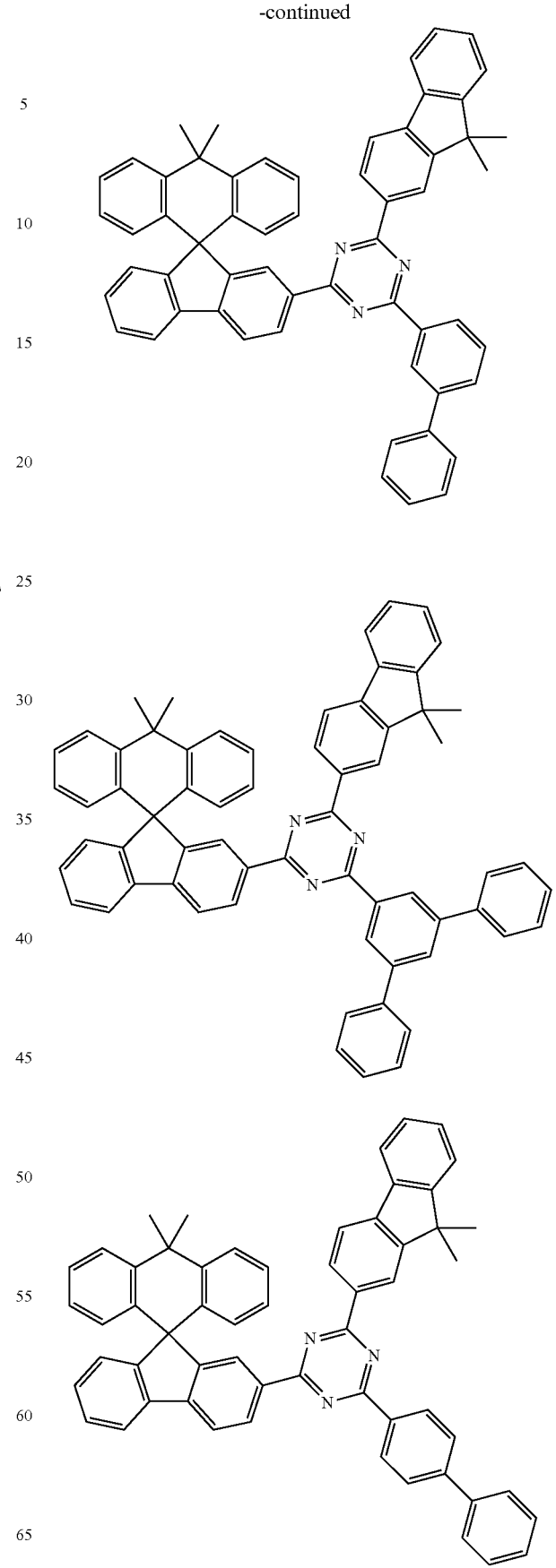

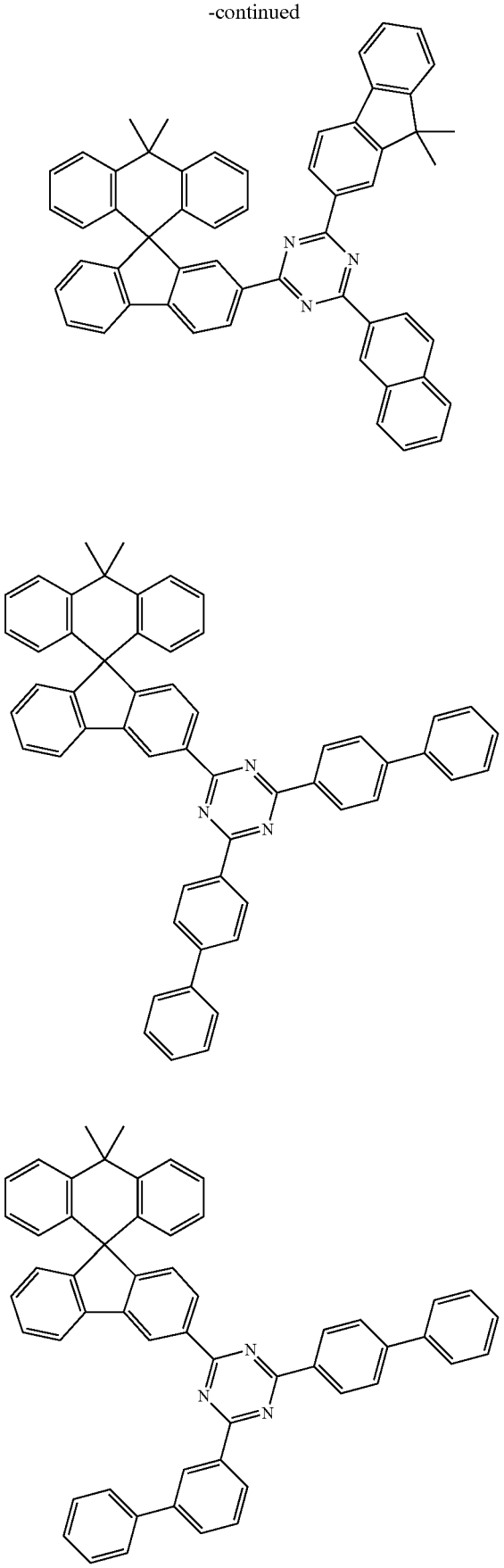
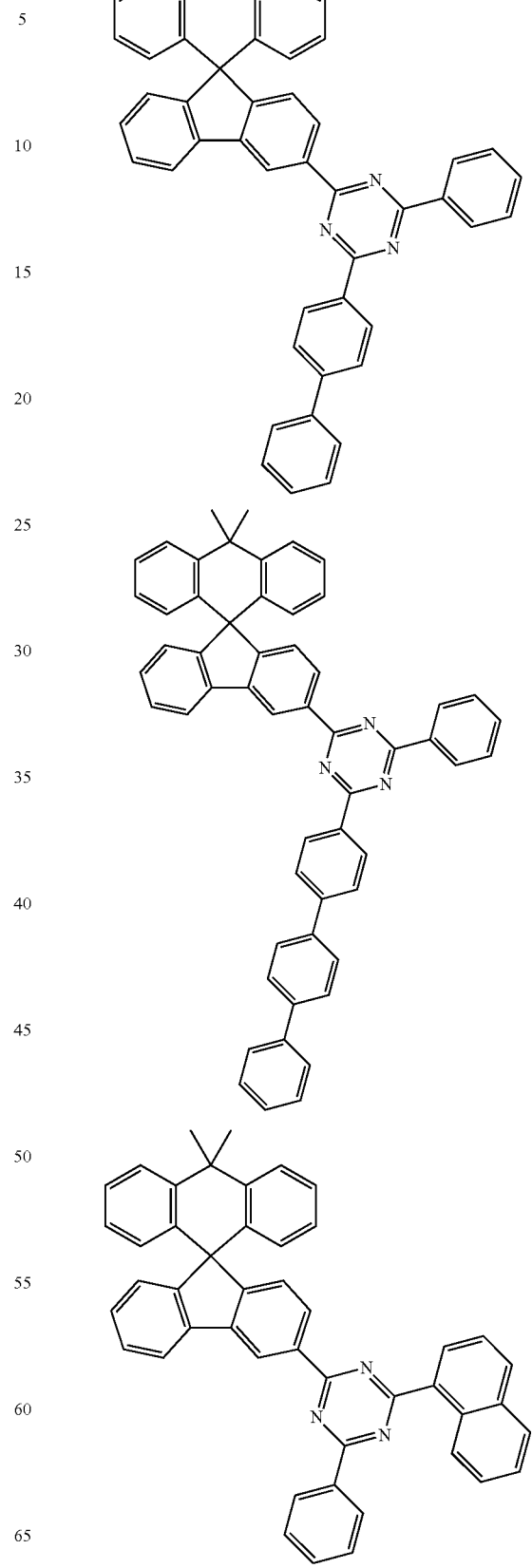

-continued
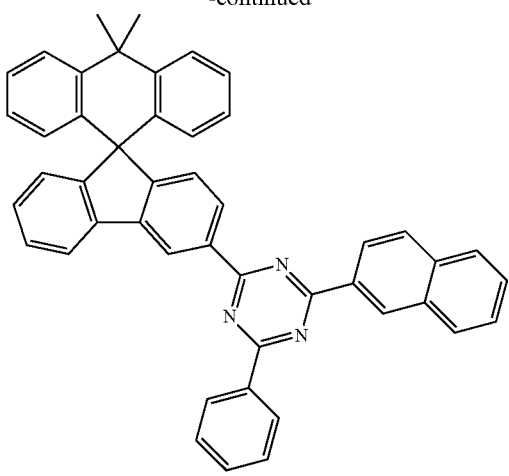
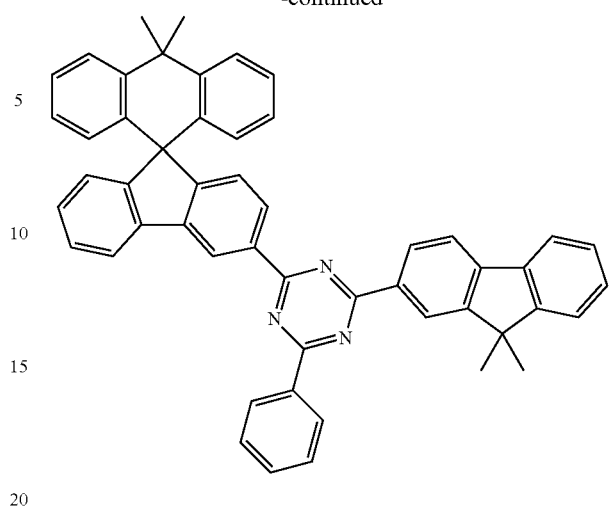
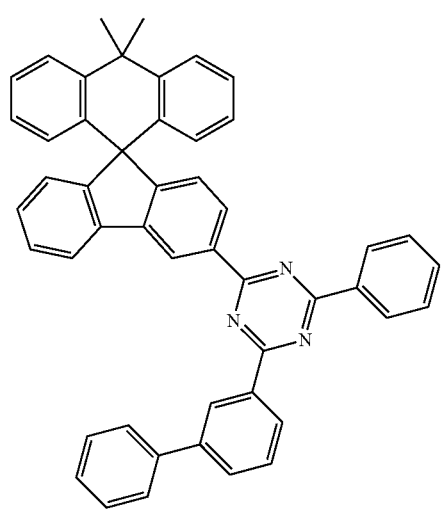
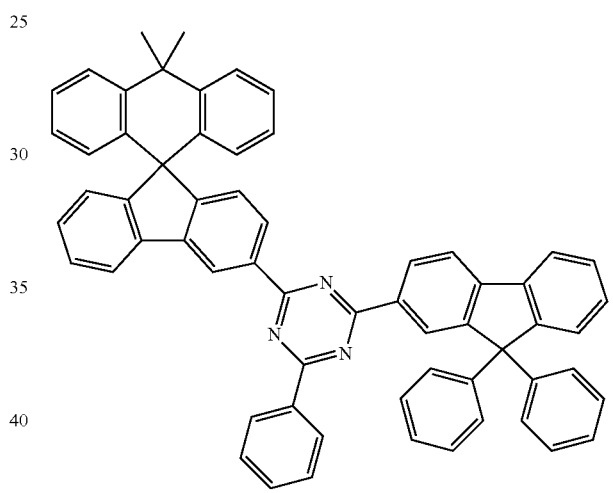
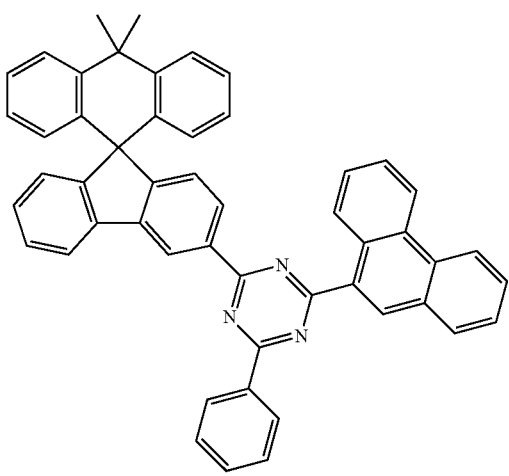
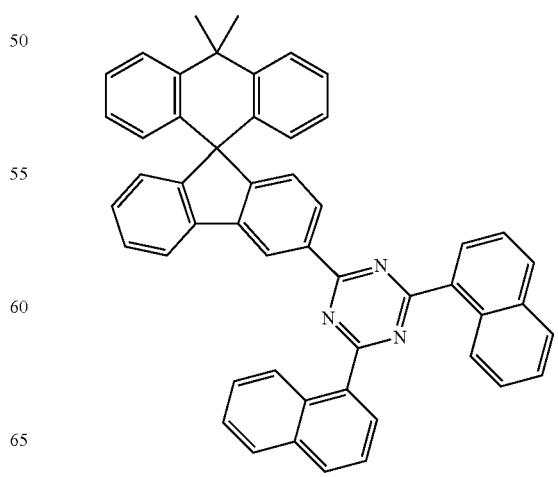

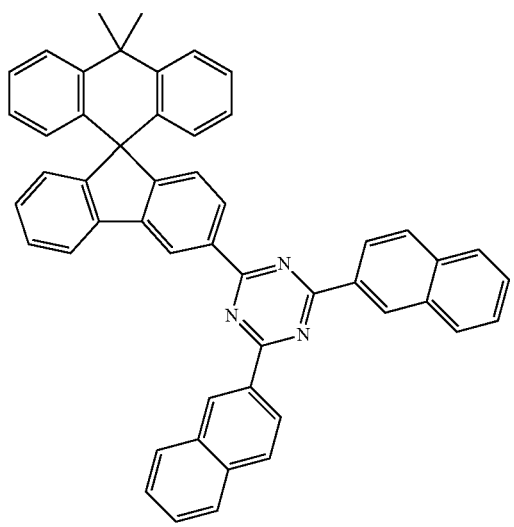
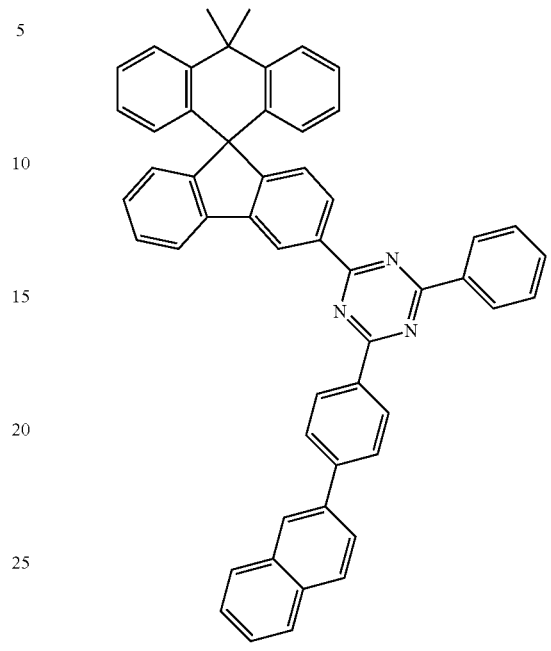
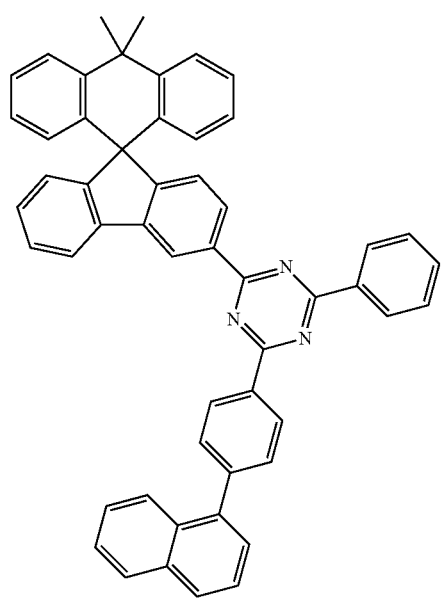
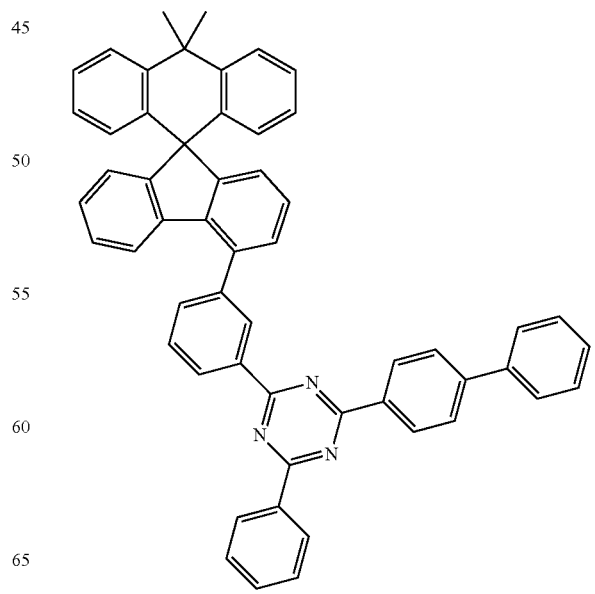

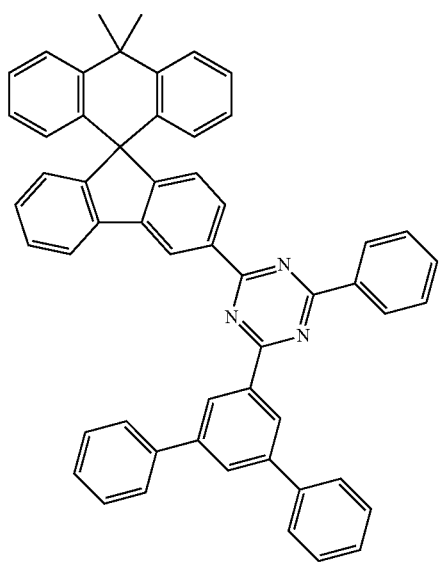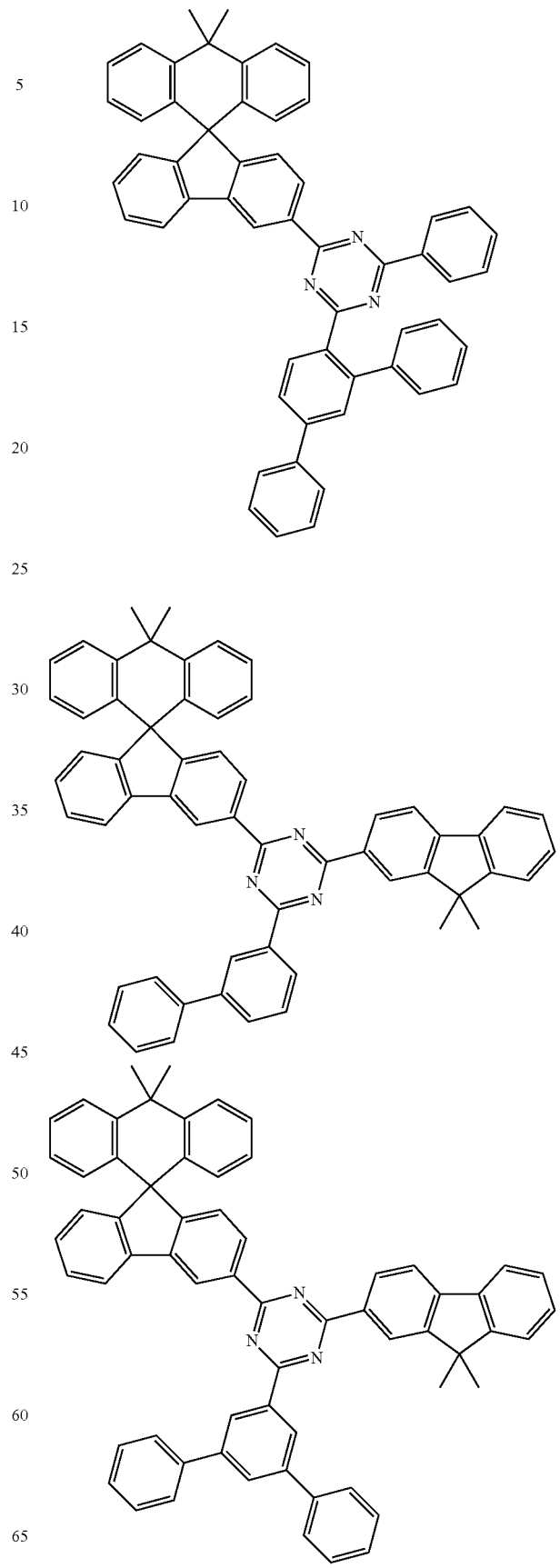

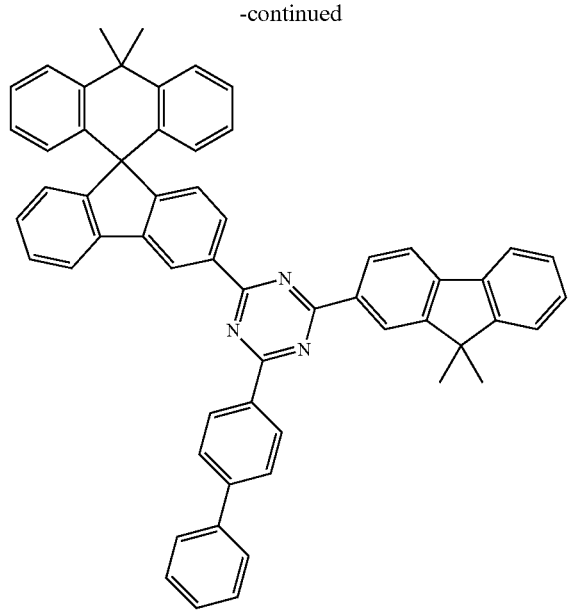
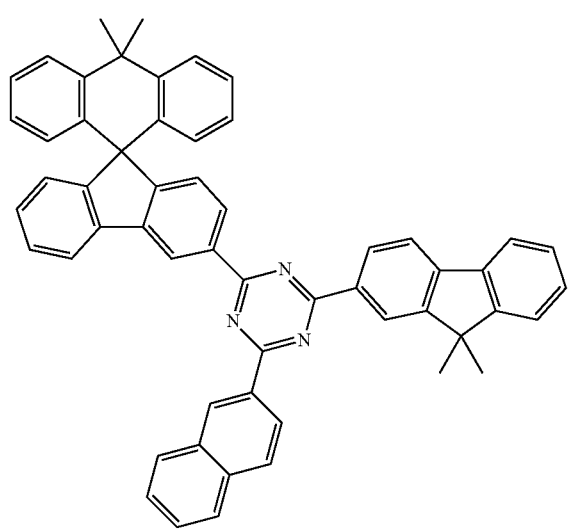
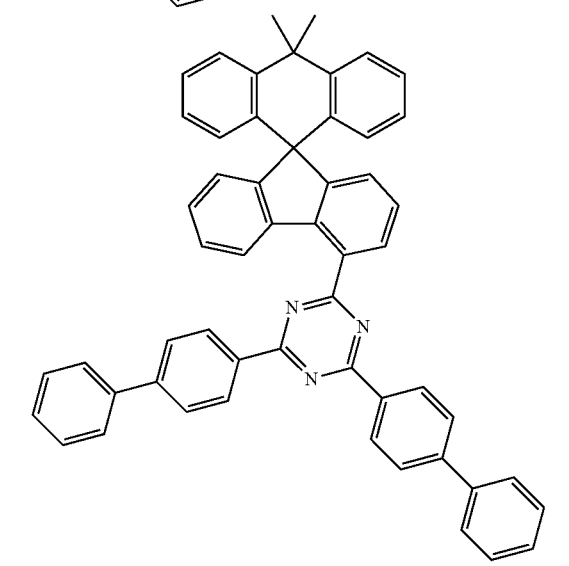
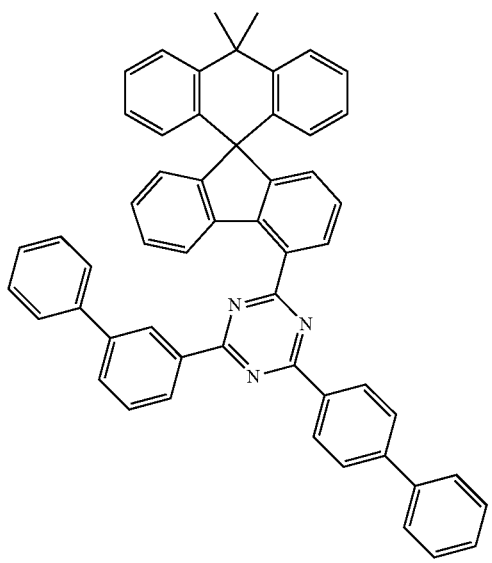
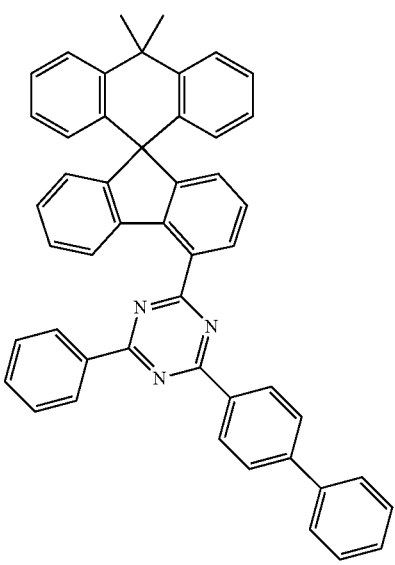

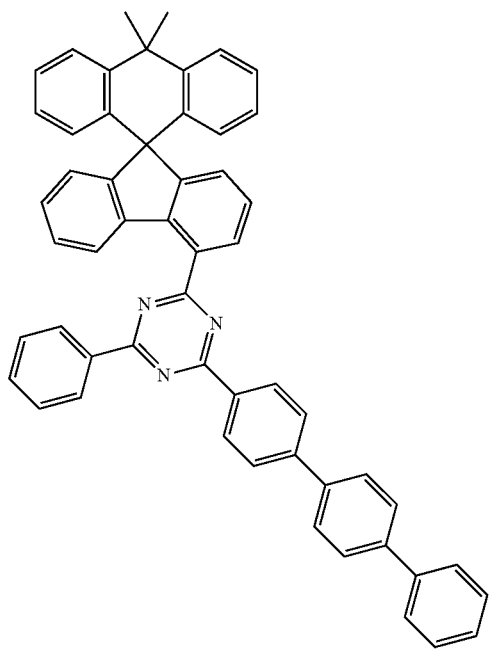
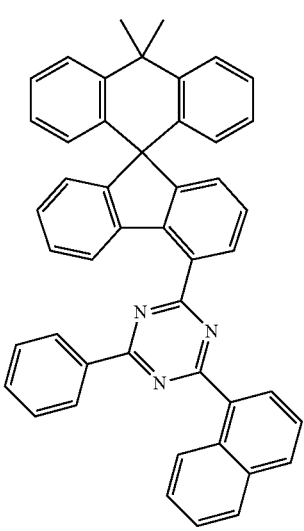
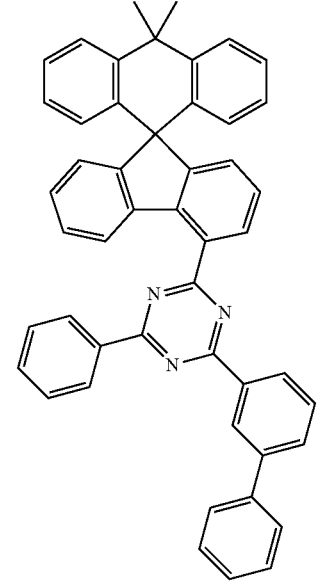
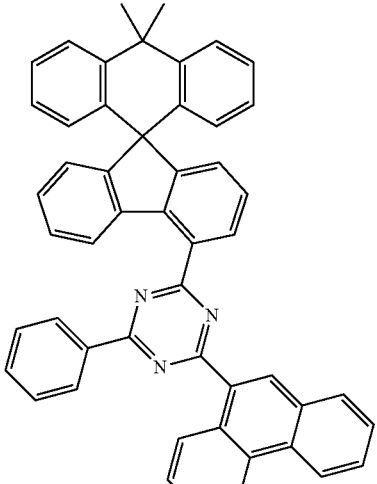
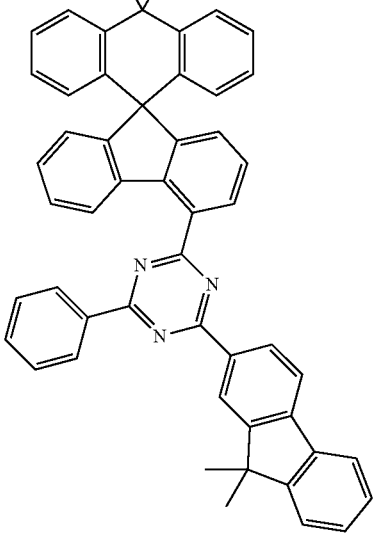

29
-continued
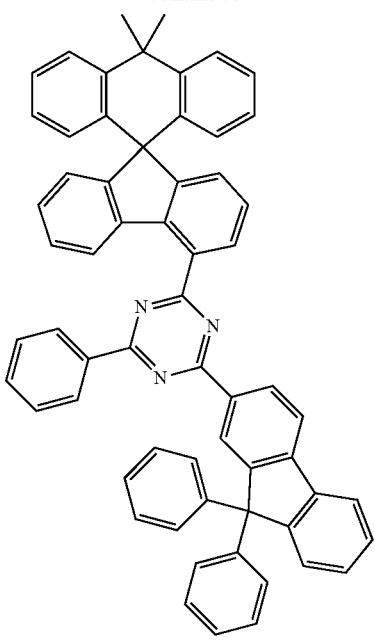
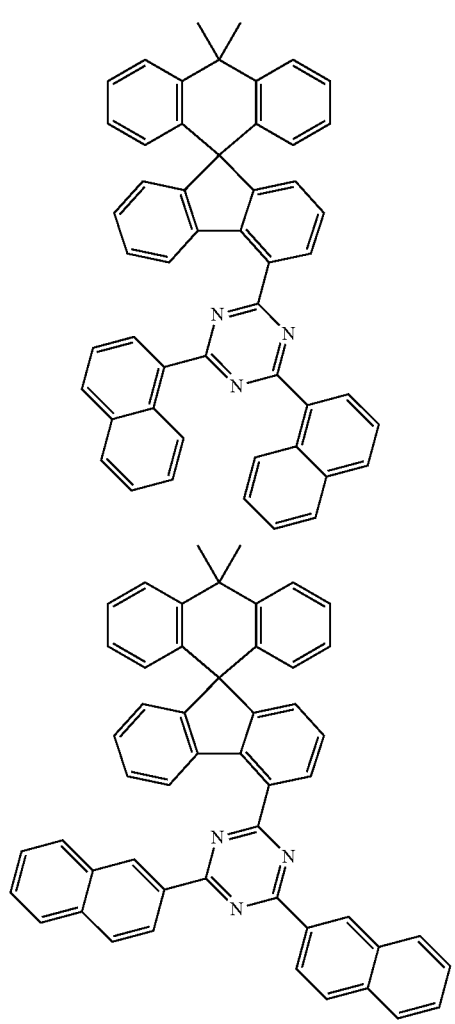
30
-continued
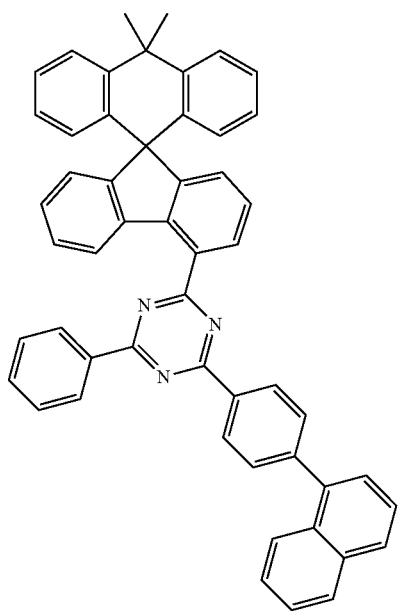
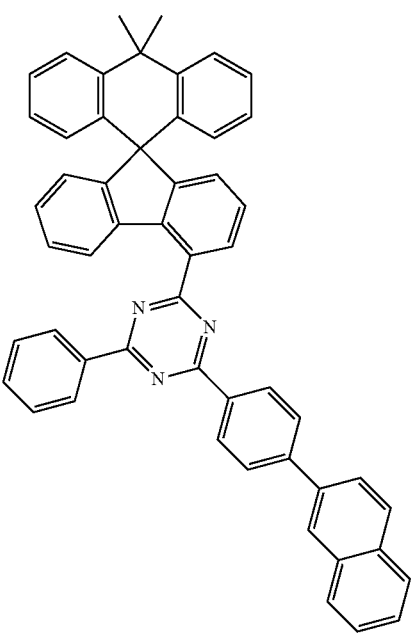

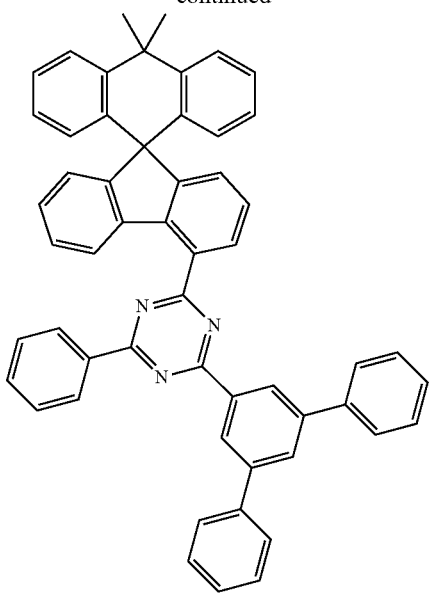
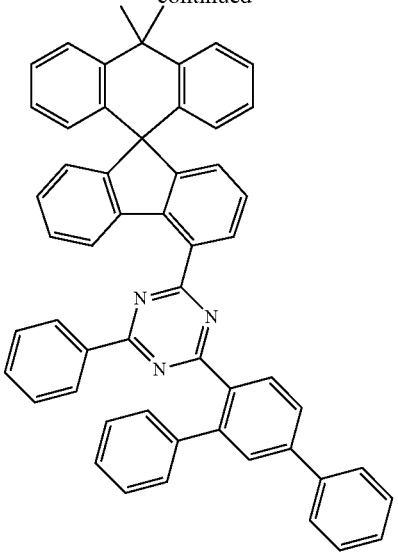
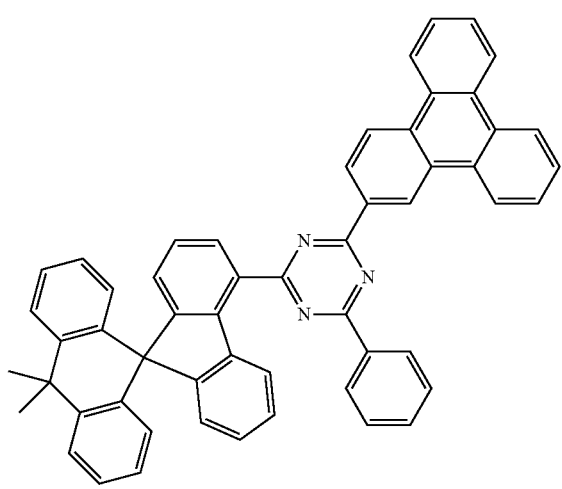
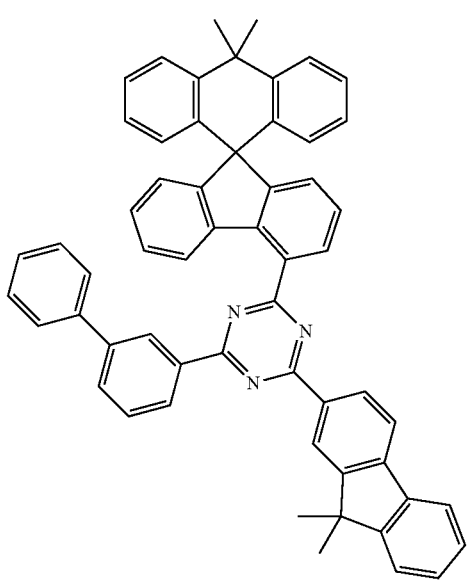
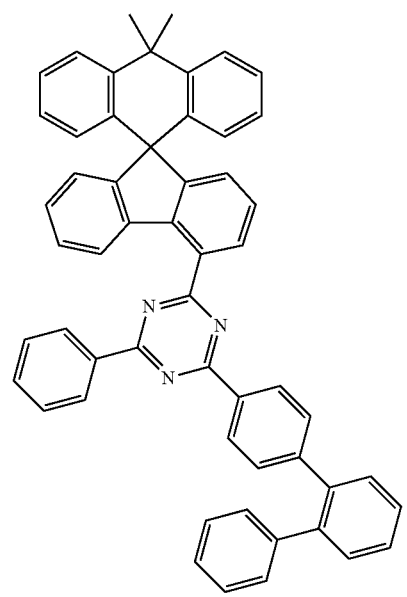
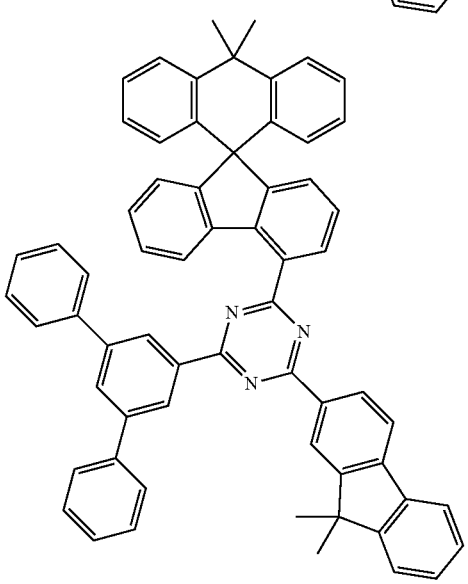

33
-continued
34
-continued
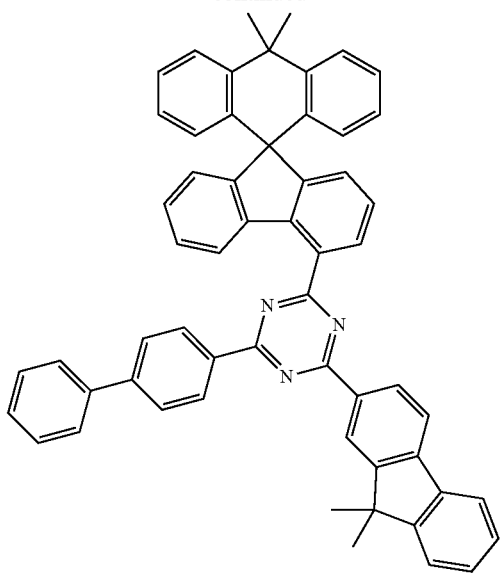
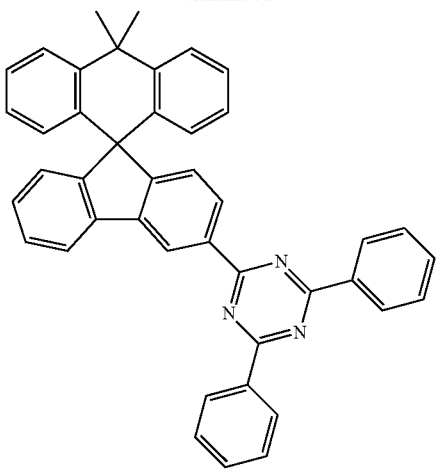
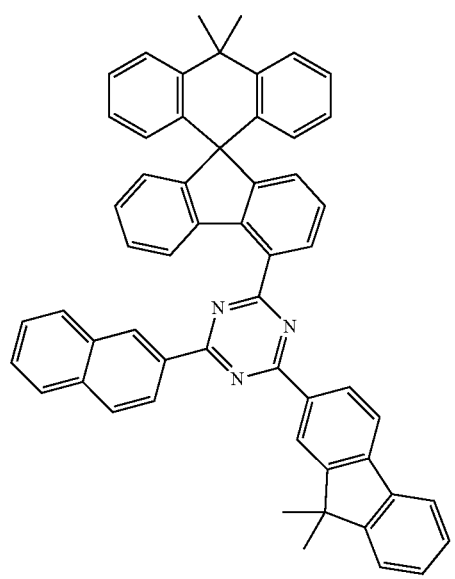
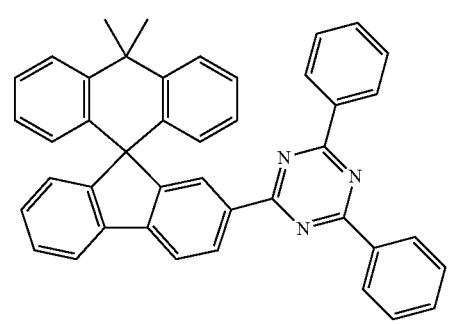
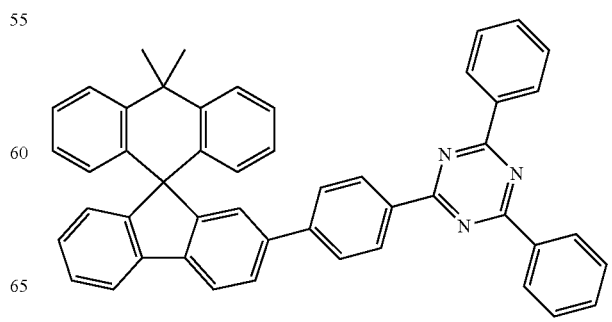

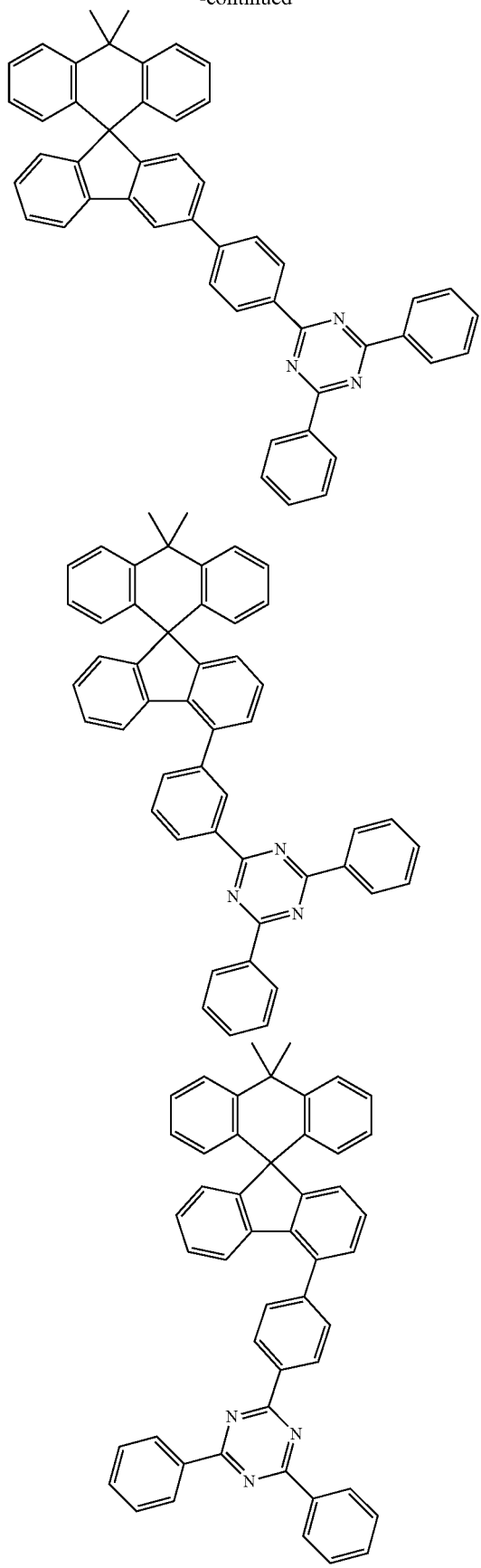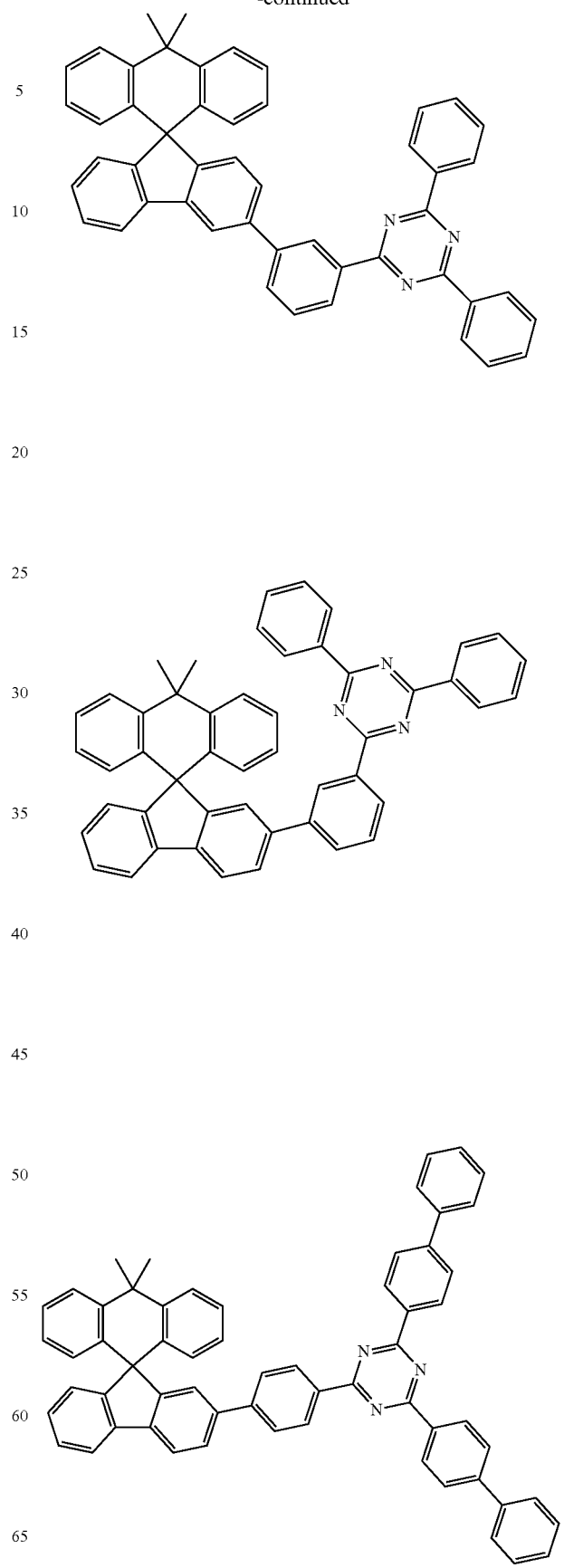

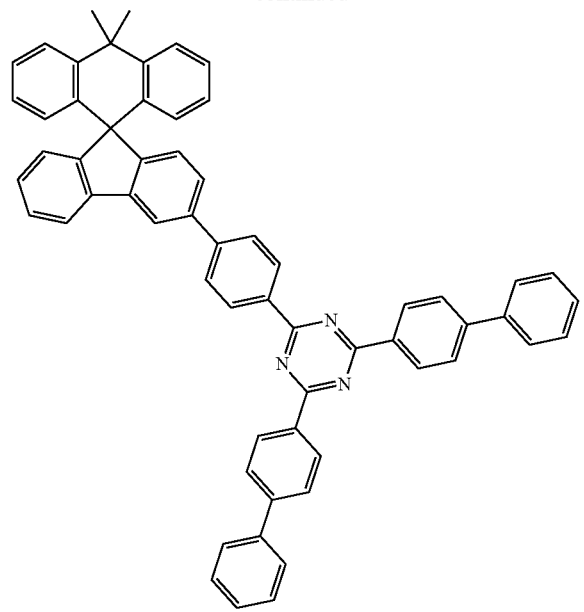
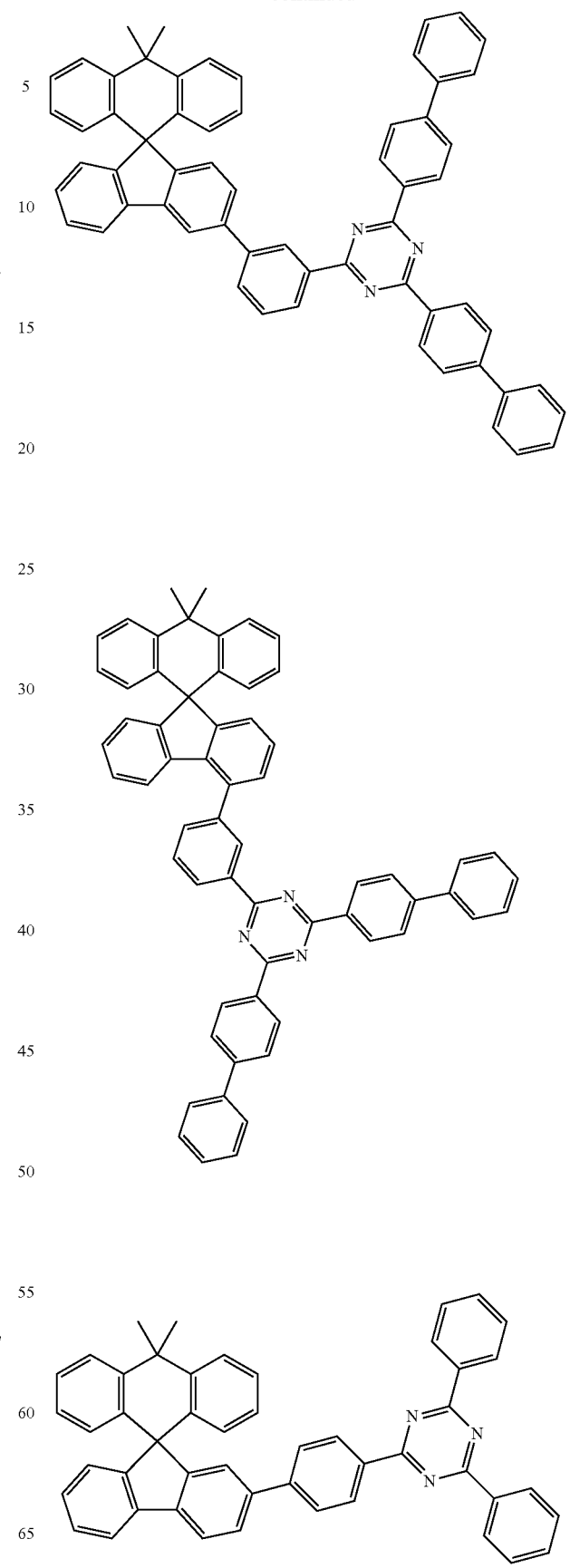

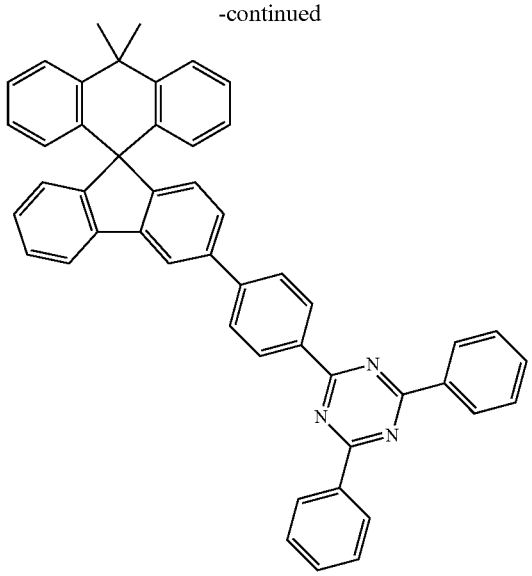
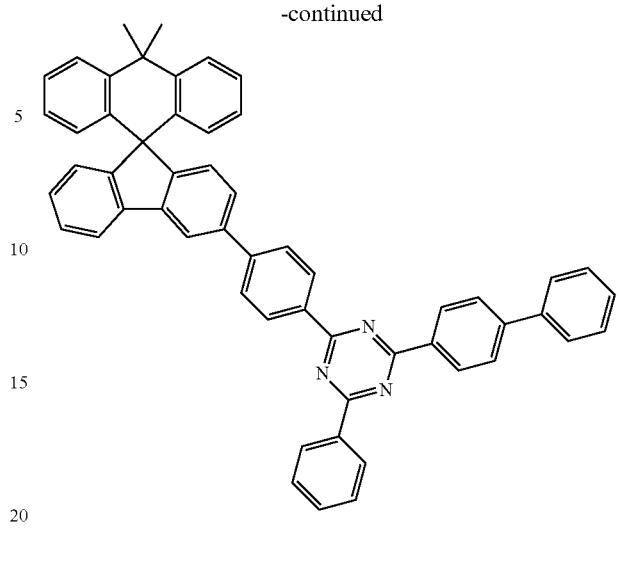
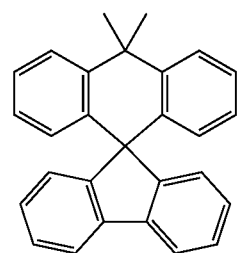
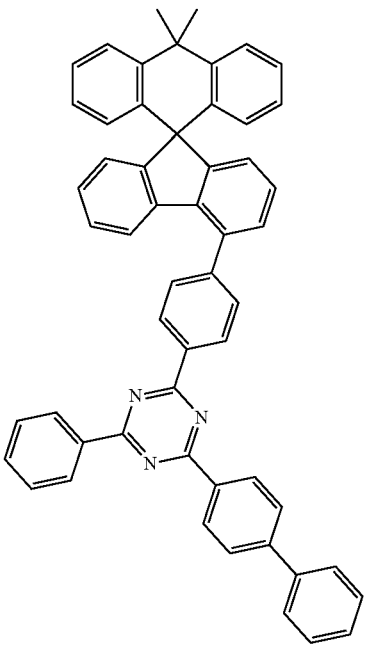
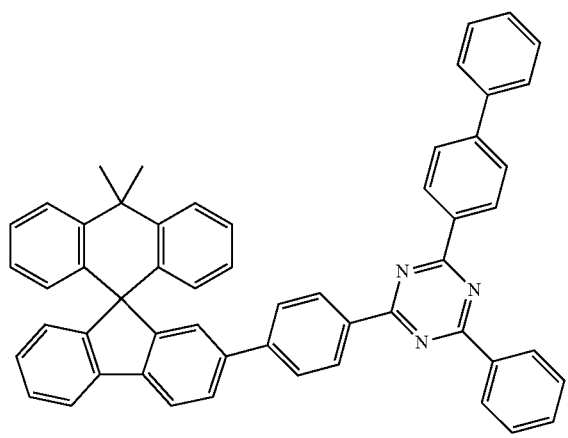
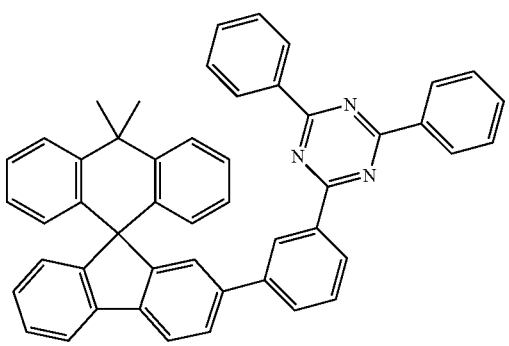

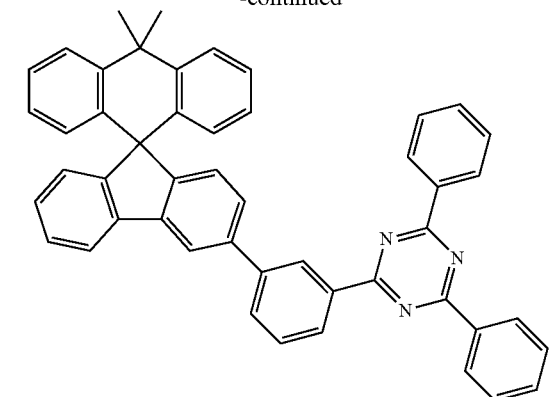
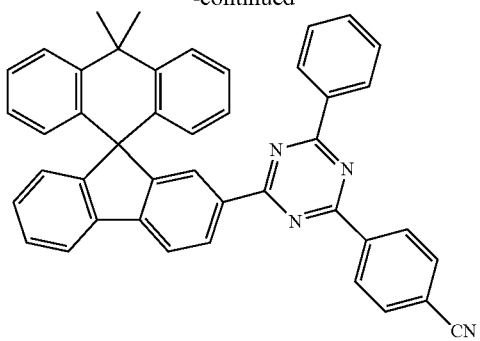
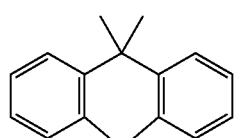
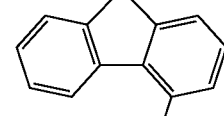
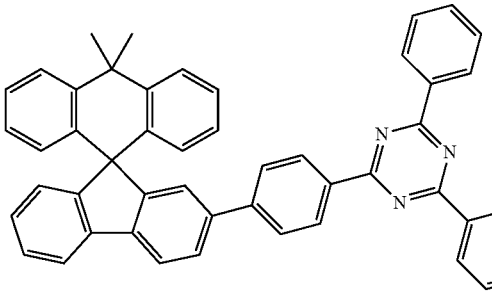
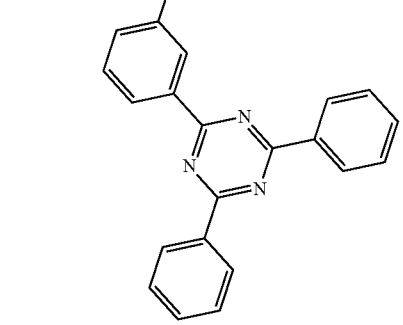
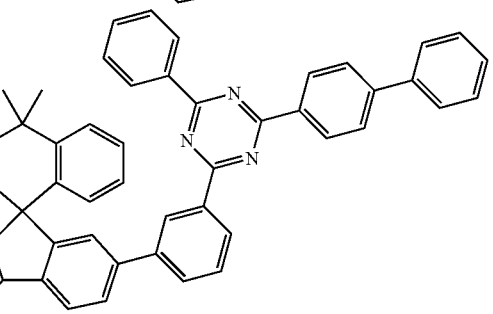
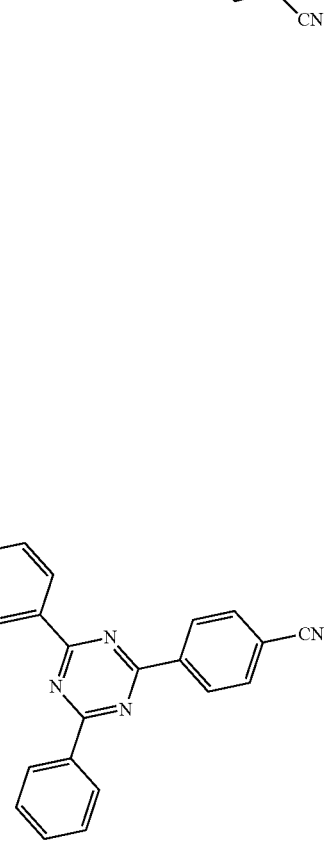
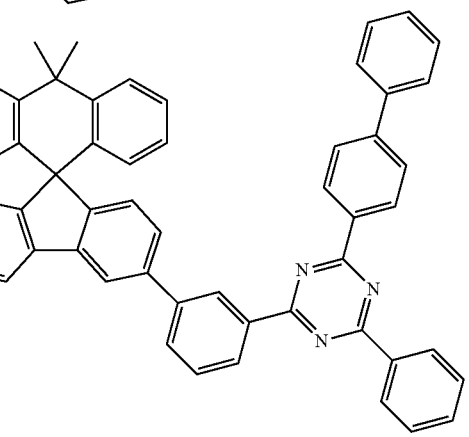

43
-continued
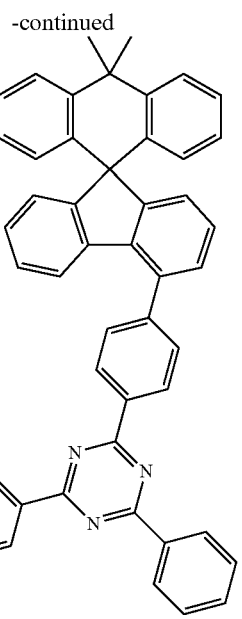
44
-continued
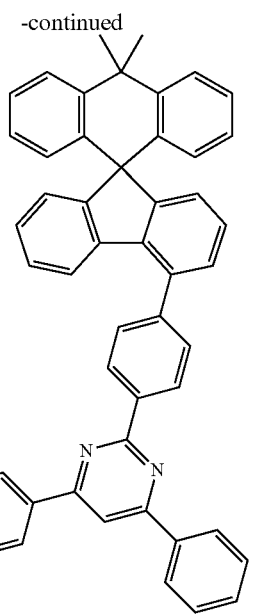
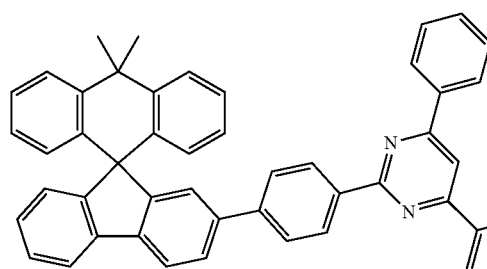
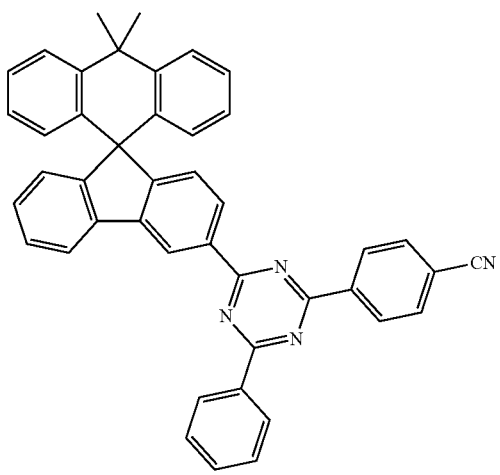
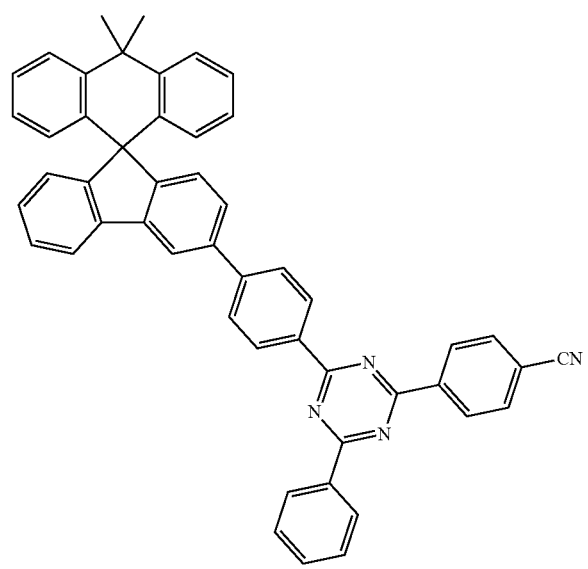
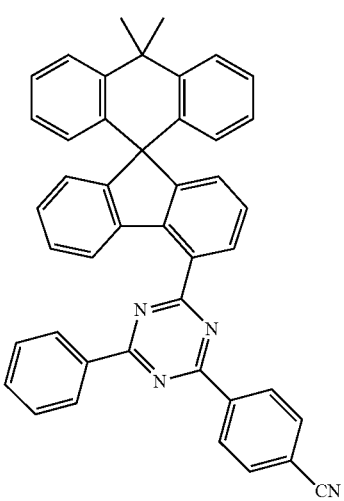

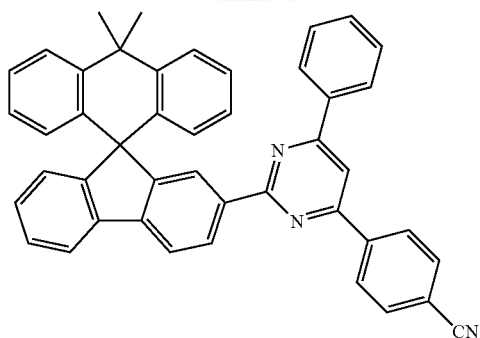
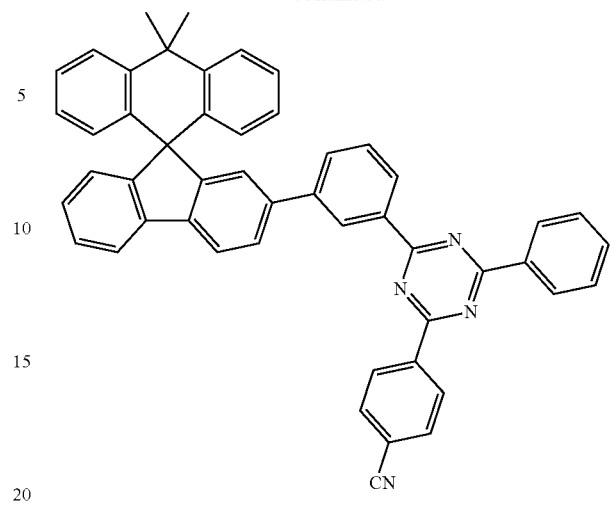
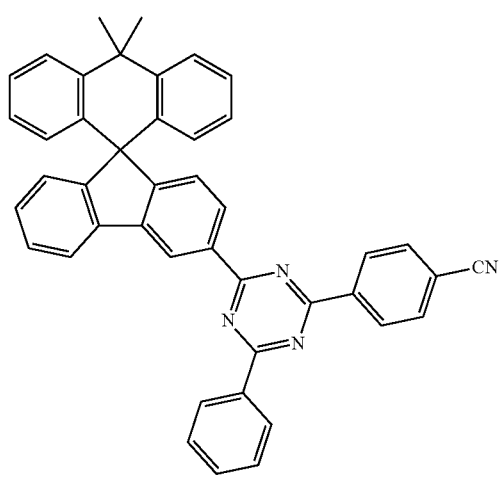
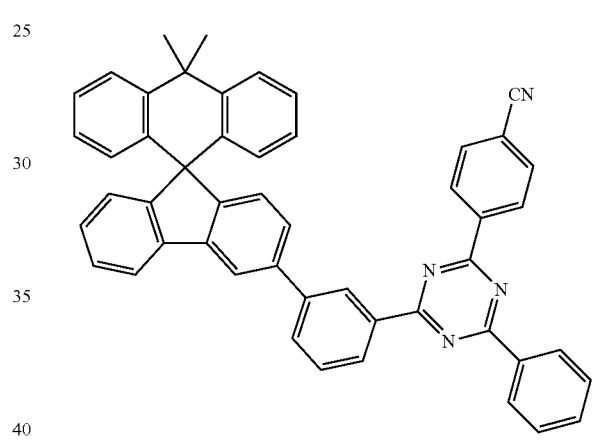
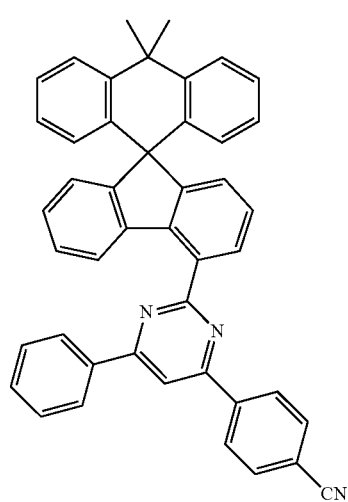
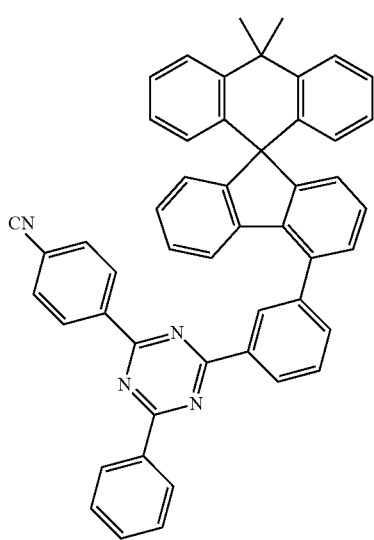

47
-continued
48
-continued
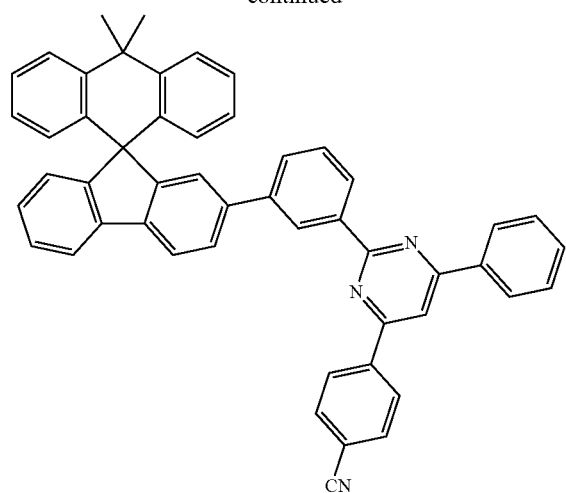
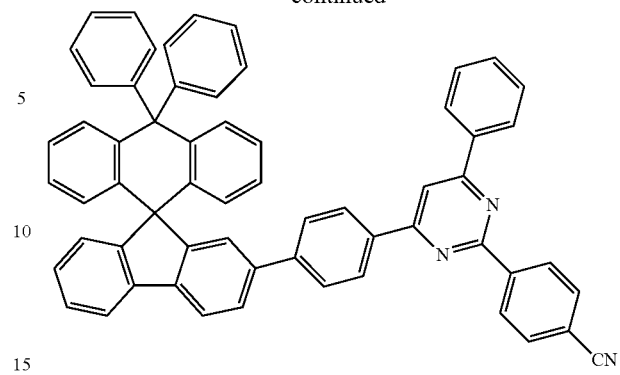
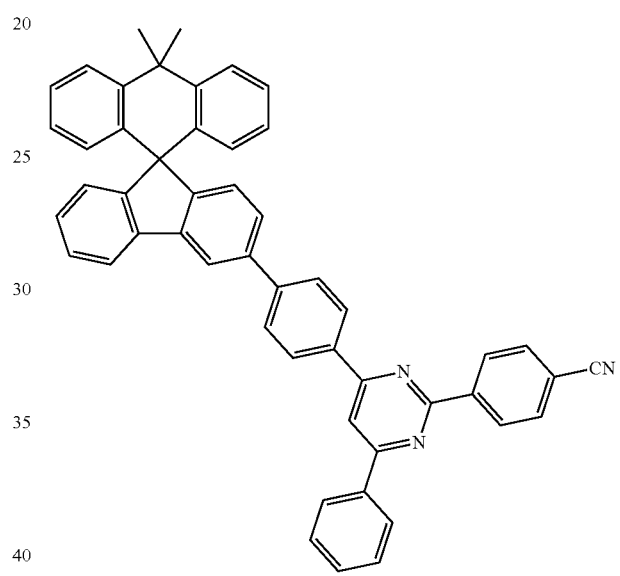
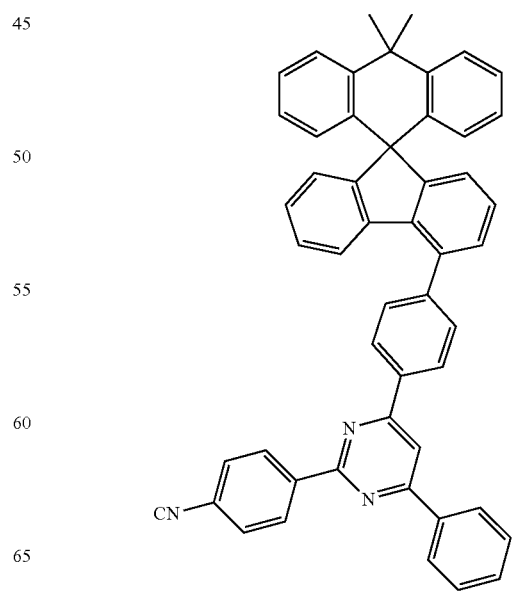

49
-continued
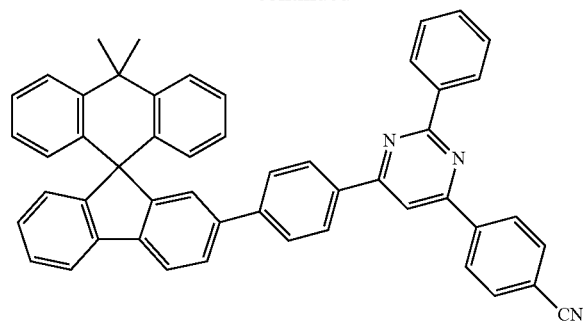
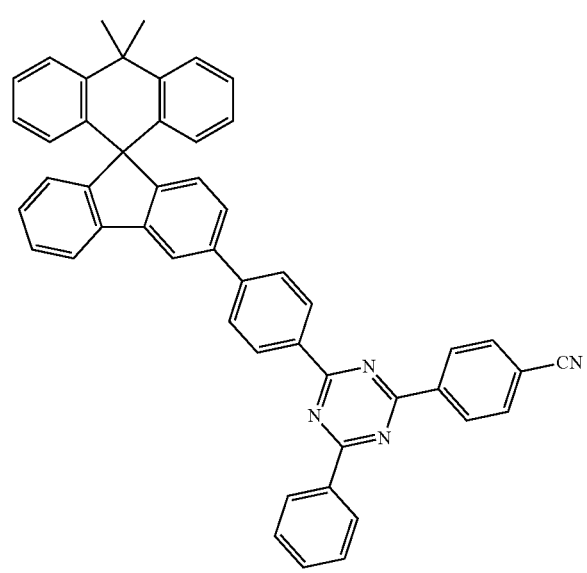
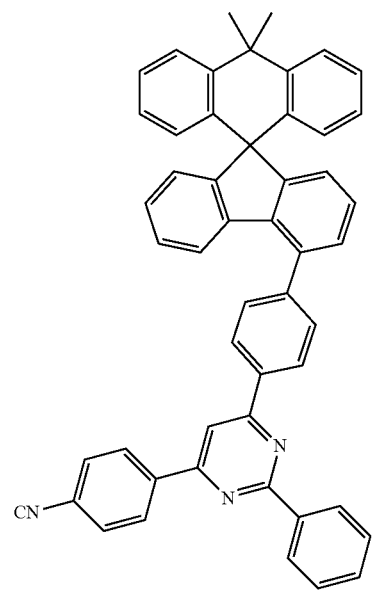
50
-continued
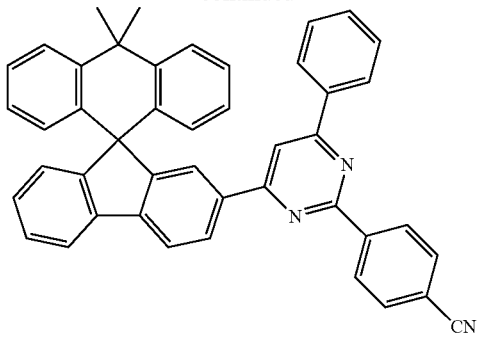
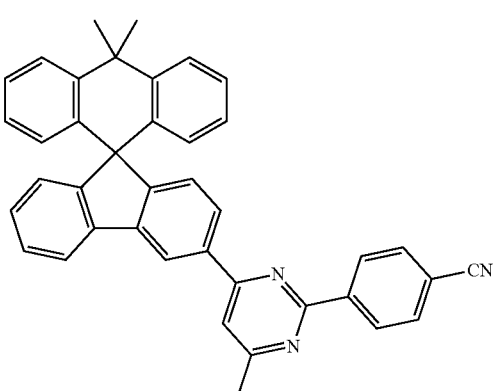

51
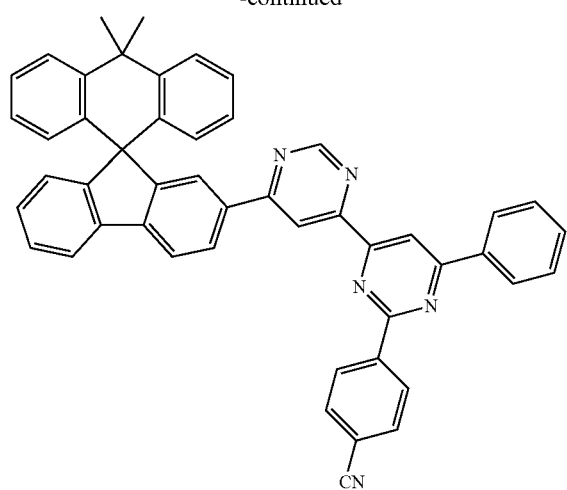
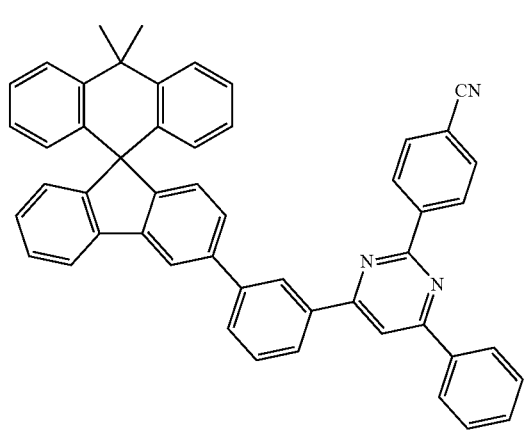
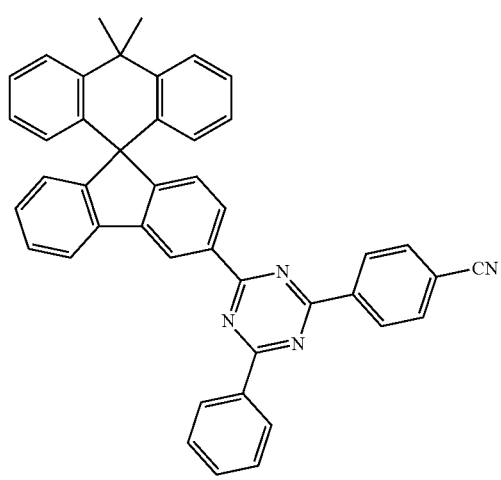
52
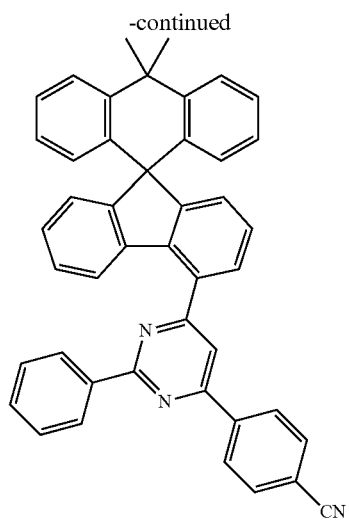
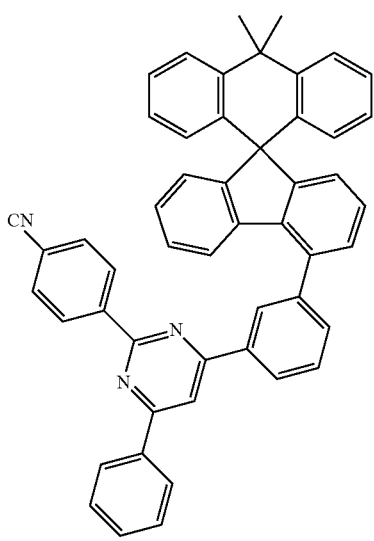
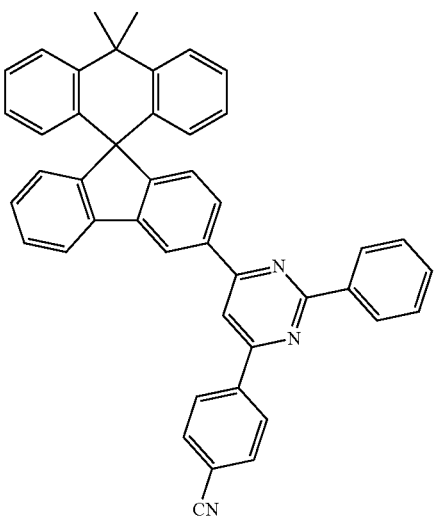

53
-continued
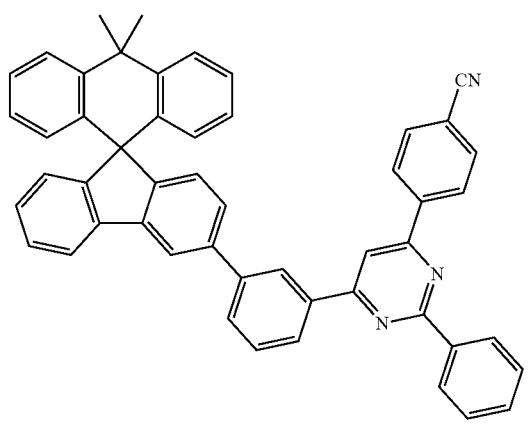
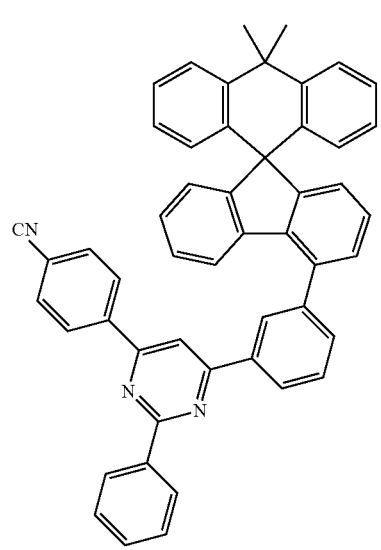
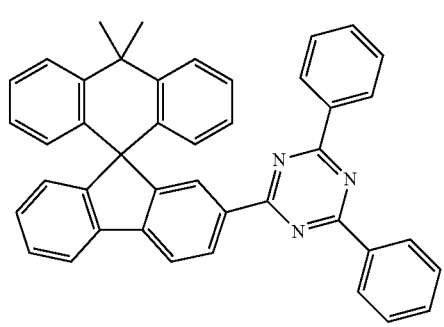
54
-continued
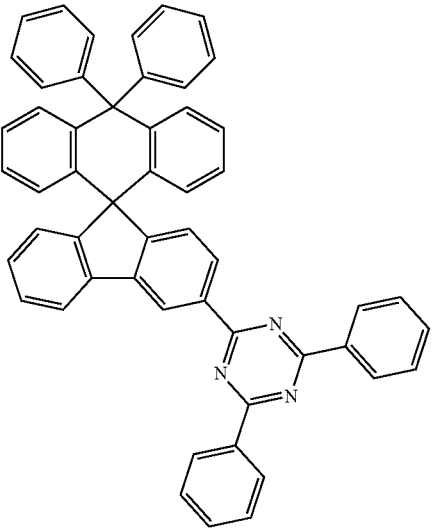
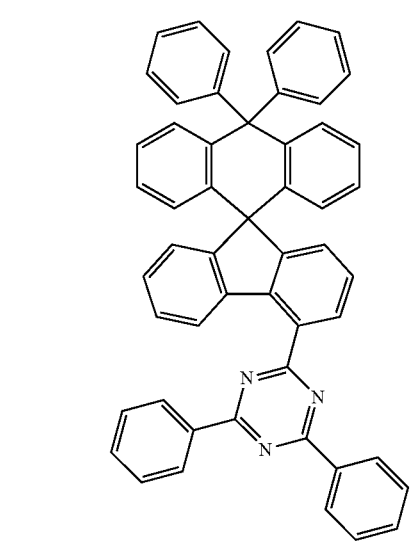

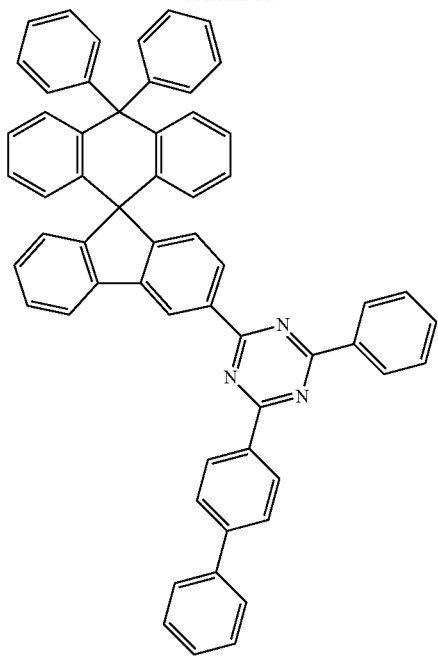
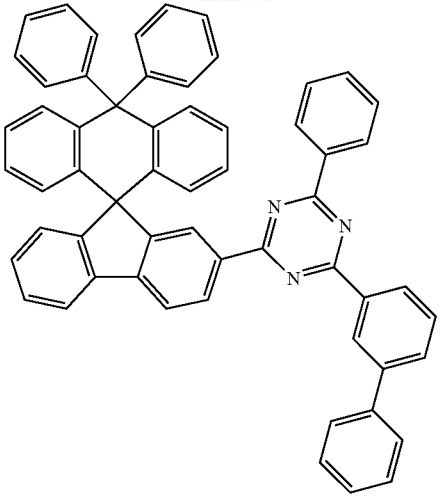
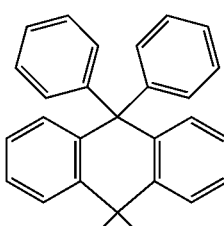
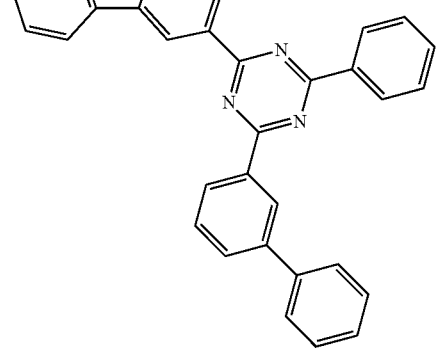
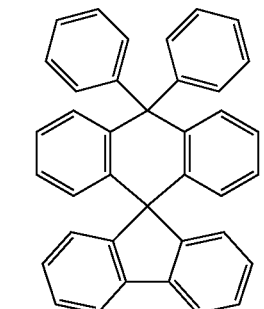
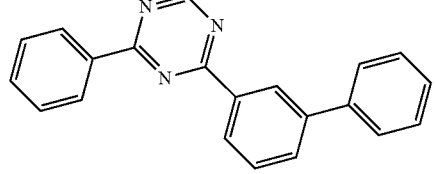

57
-continued
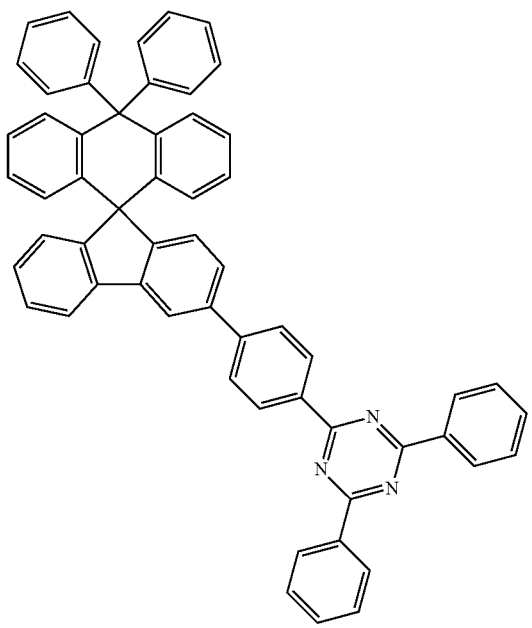
58
-continued
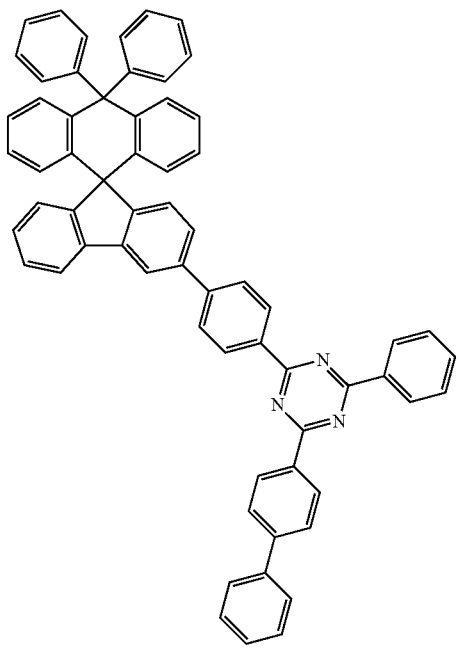
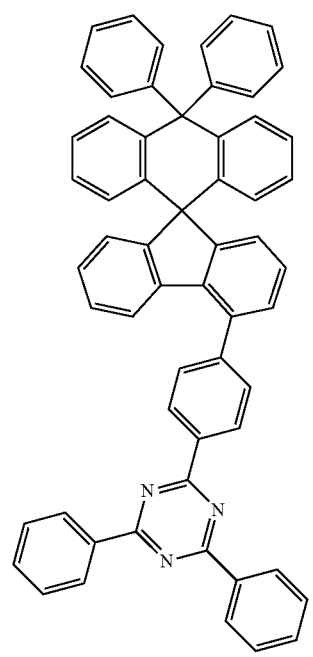
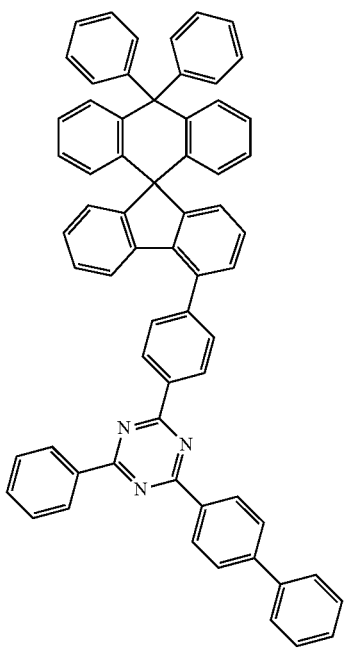

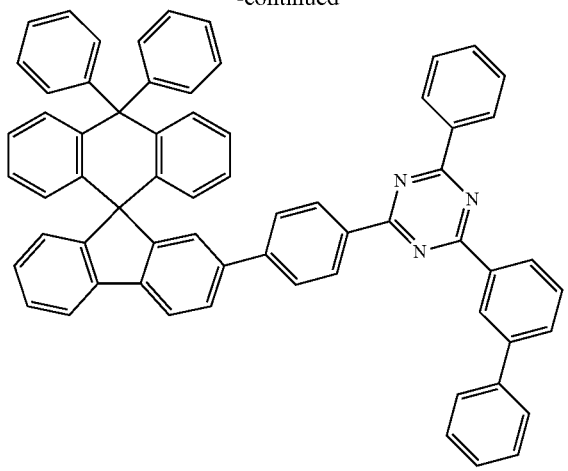
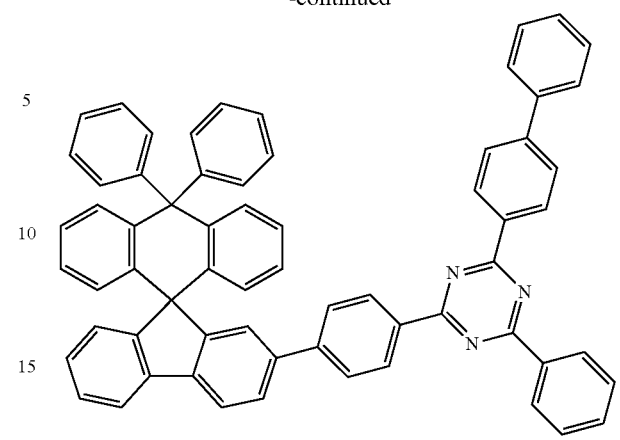
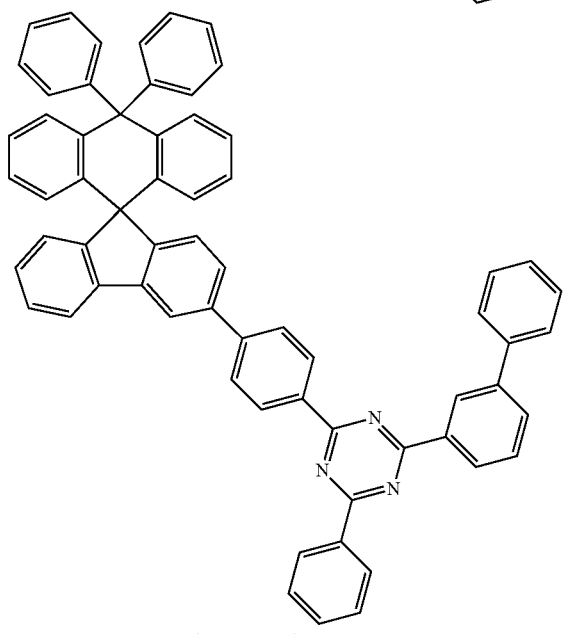
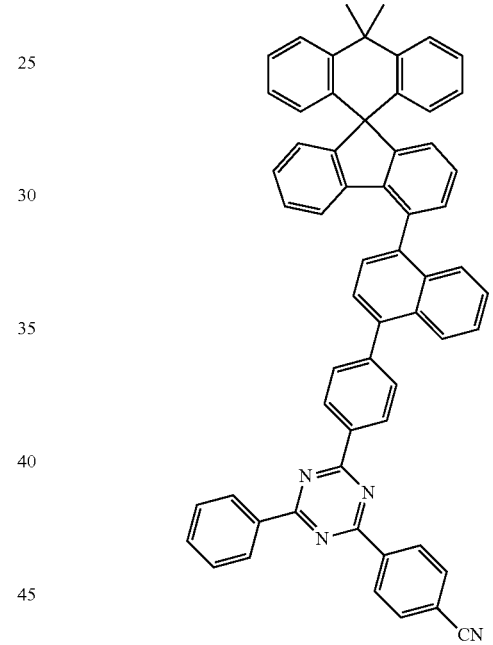
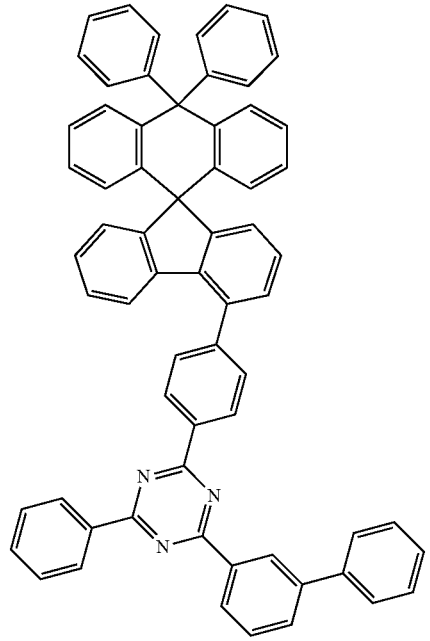
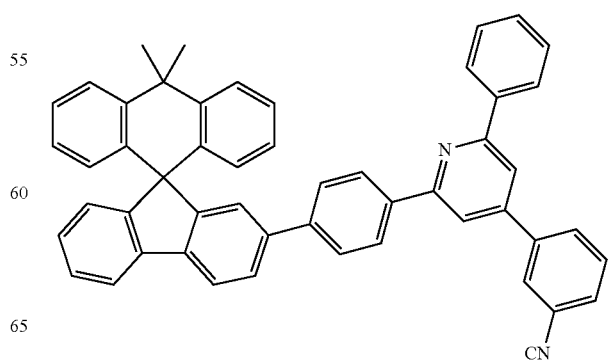

61
-continued
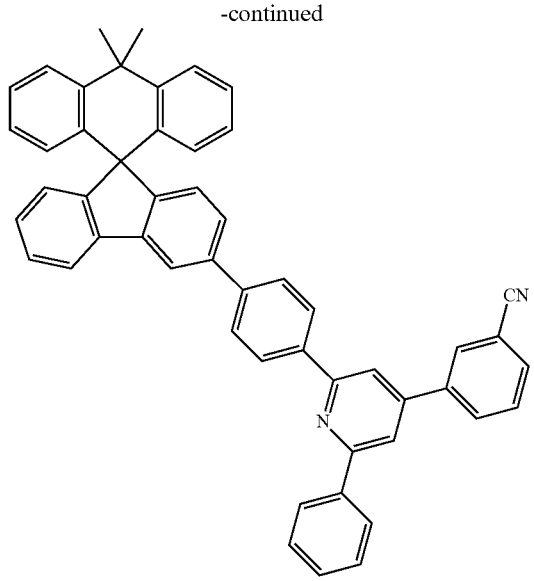
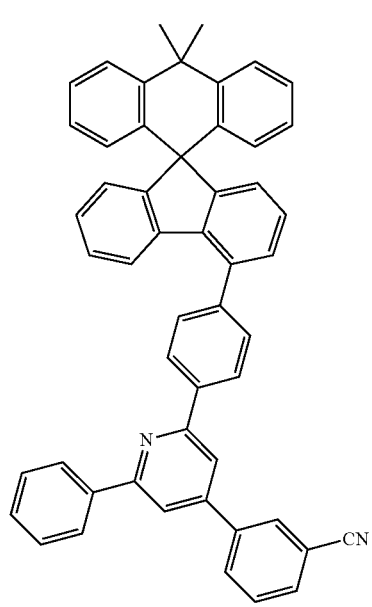
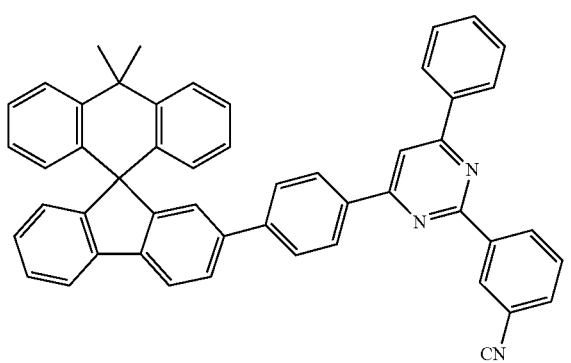
62
-continued
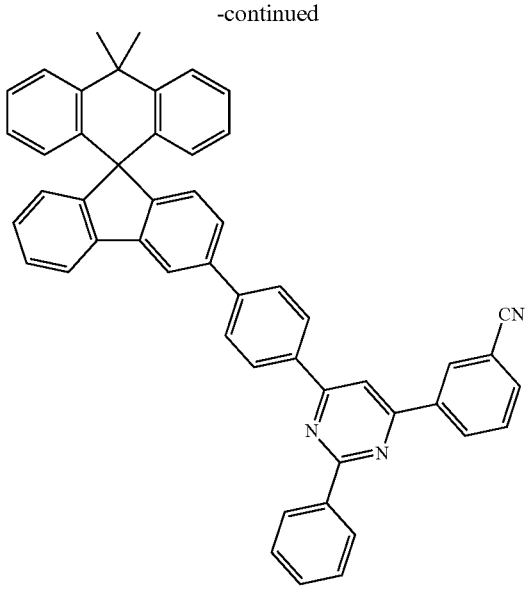
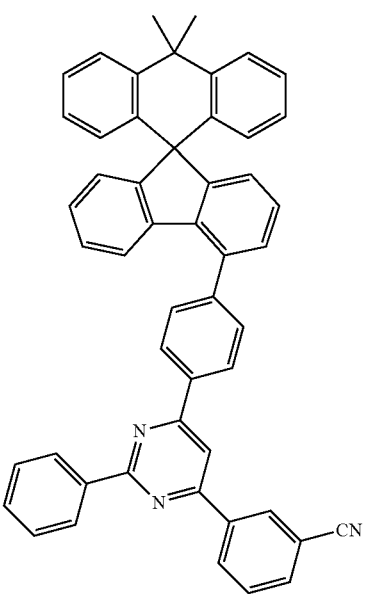
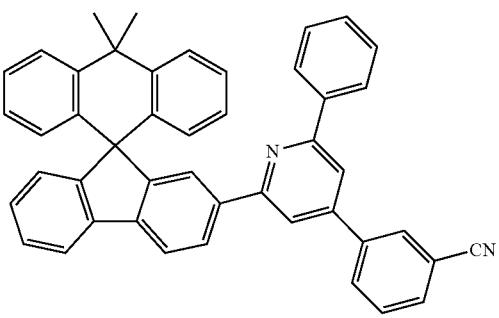

63
-continued
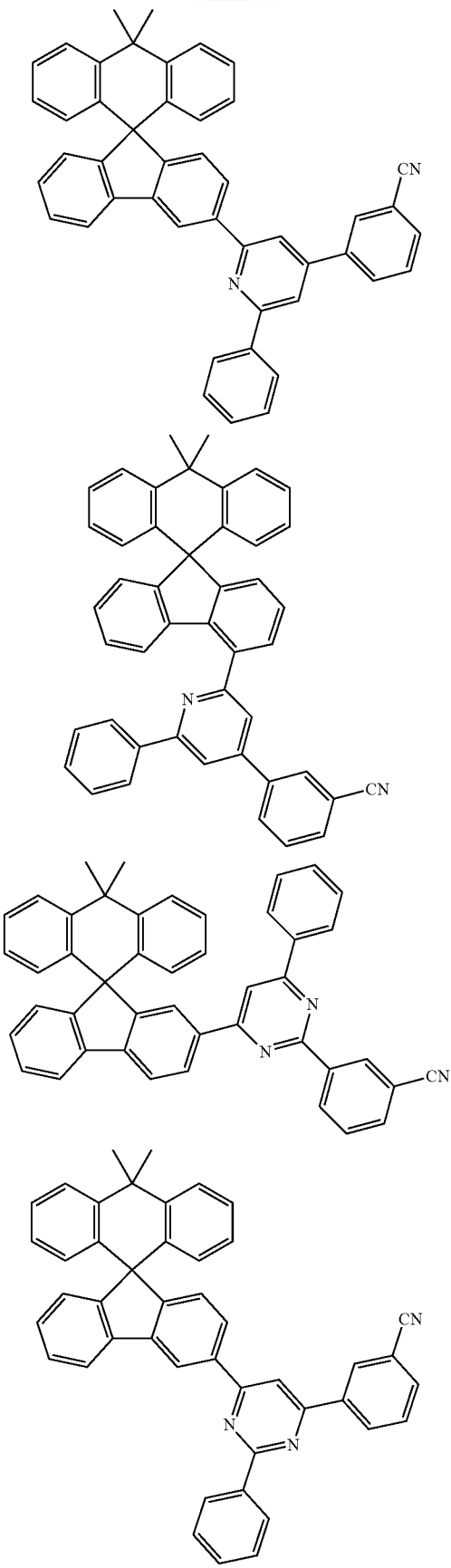
64
-continued
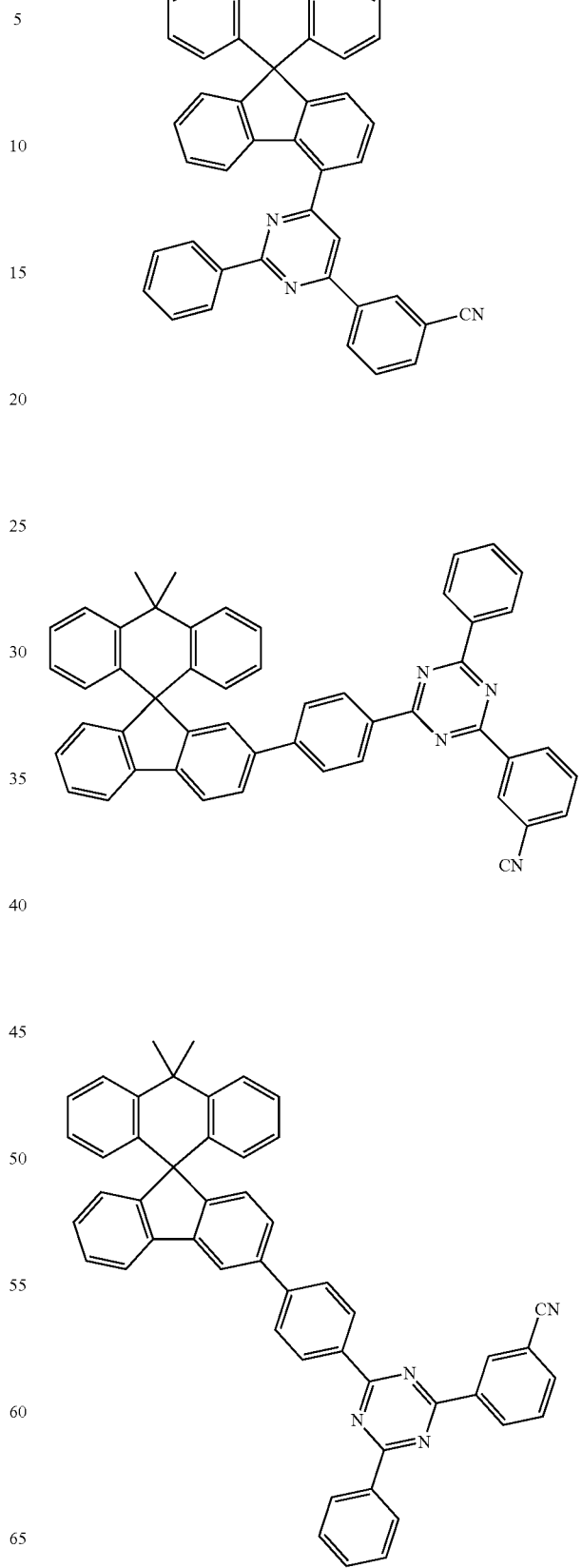

65
-continued
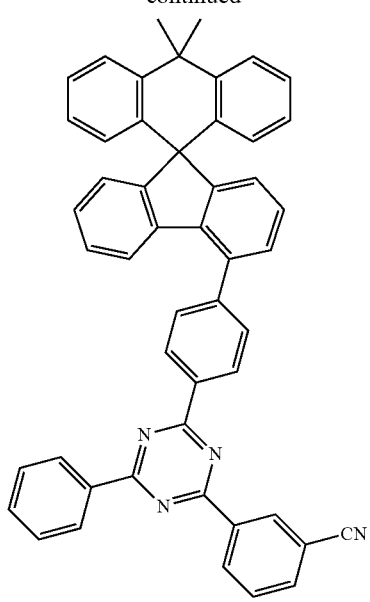
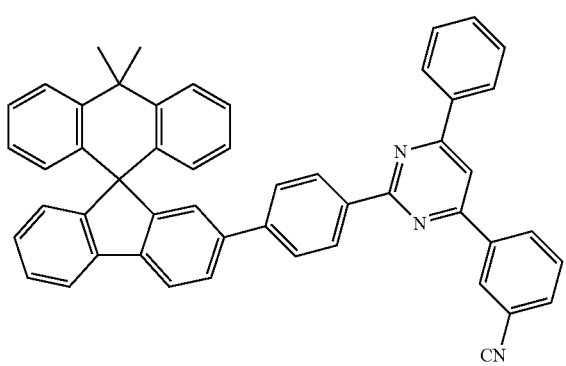
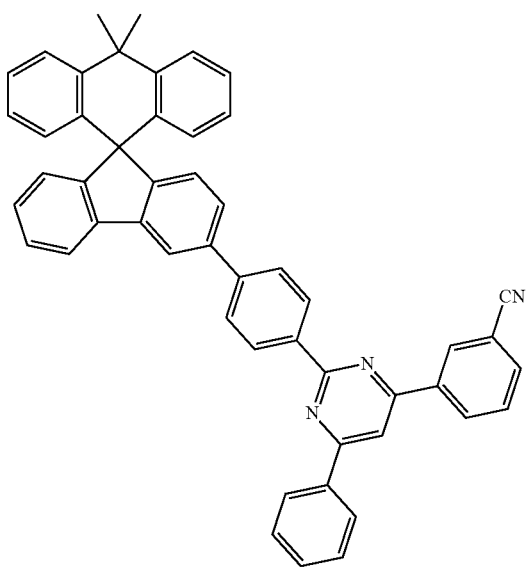
66
-continued
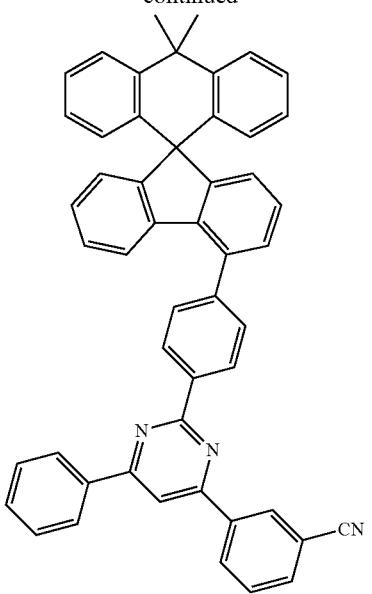
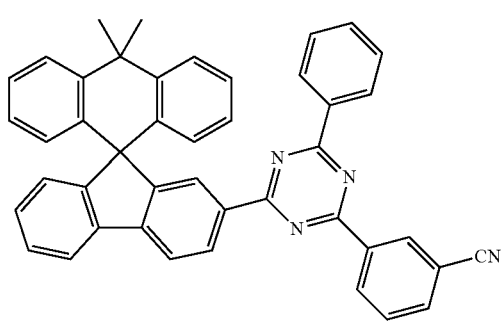
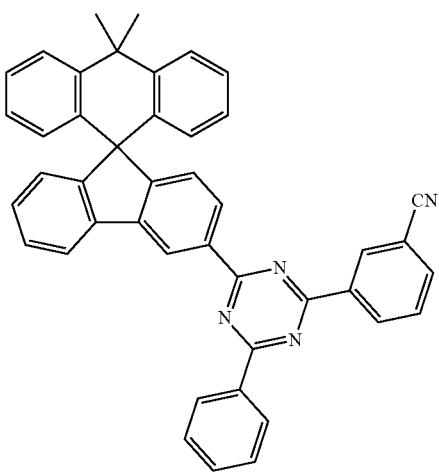

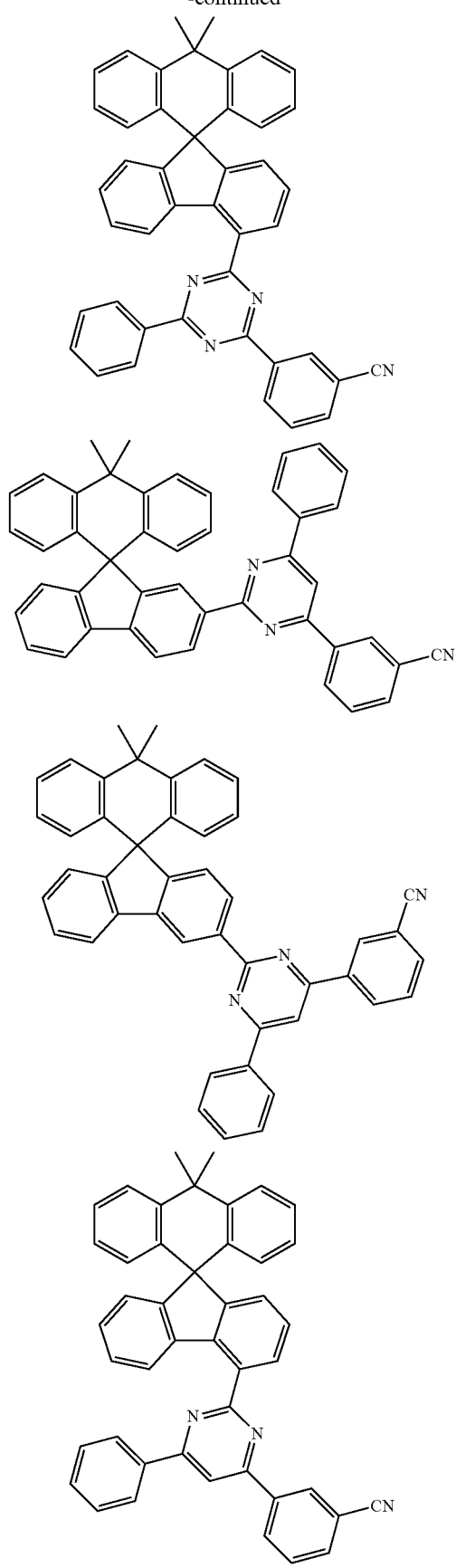
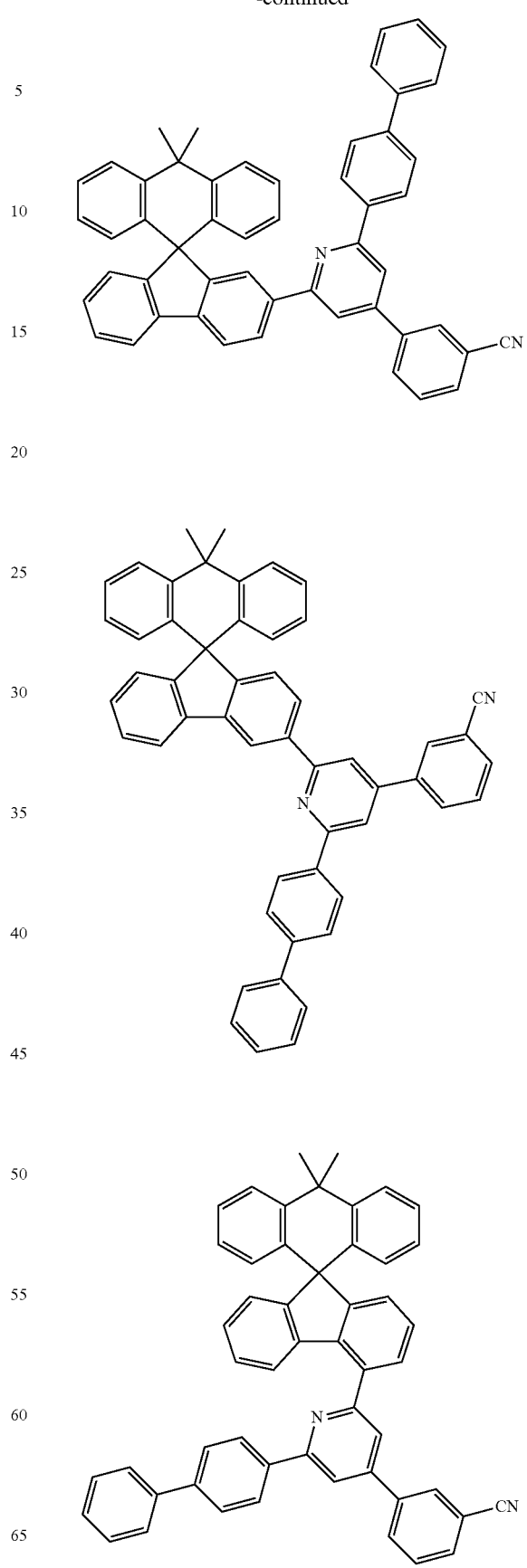

69
-continued
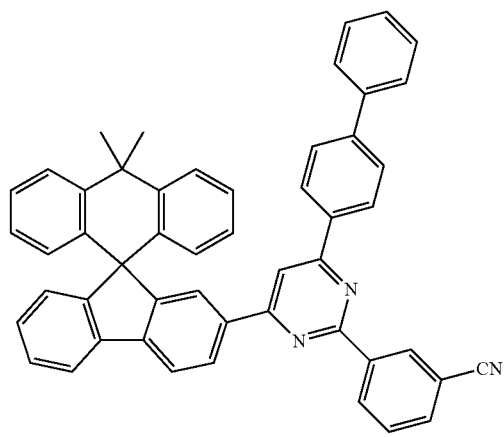
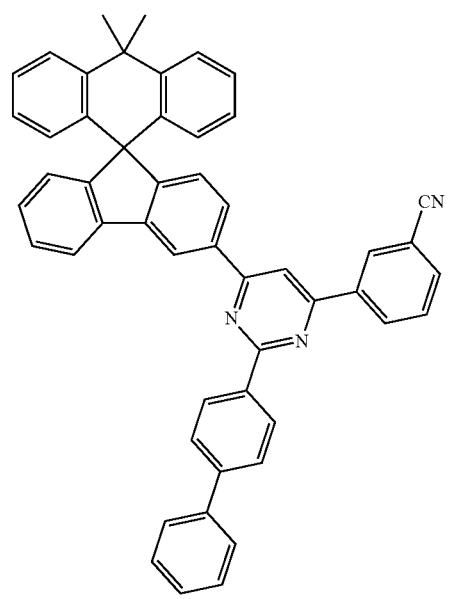
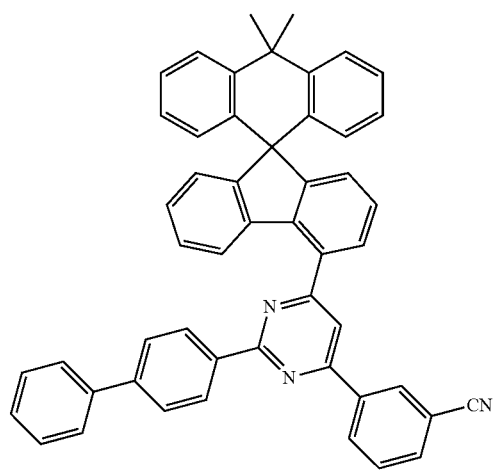
70
-continued
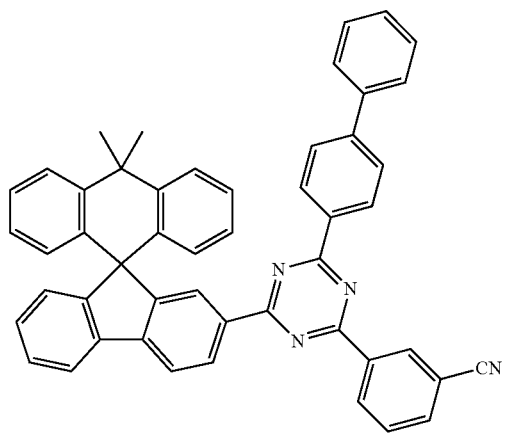
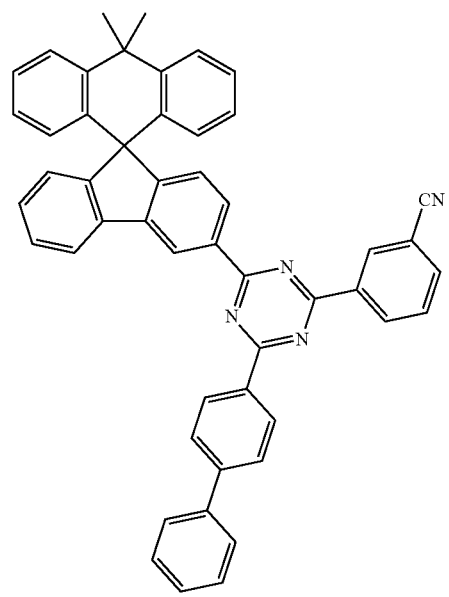
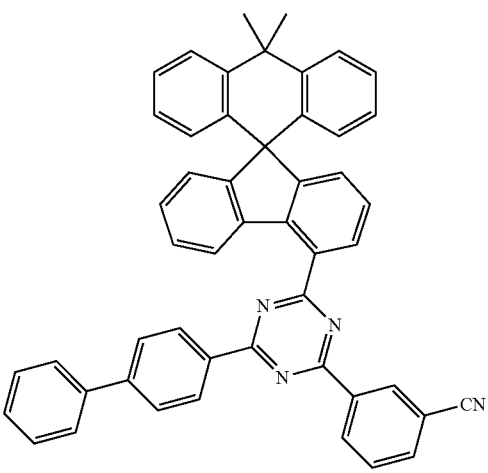

71
-continued
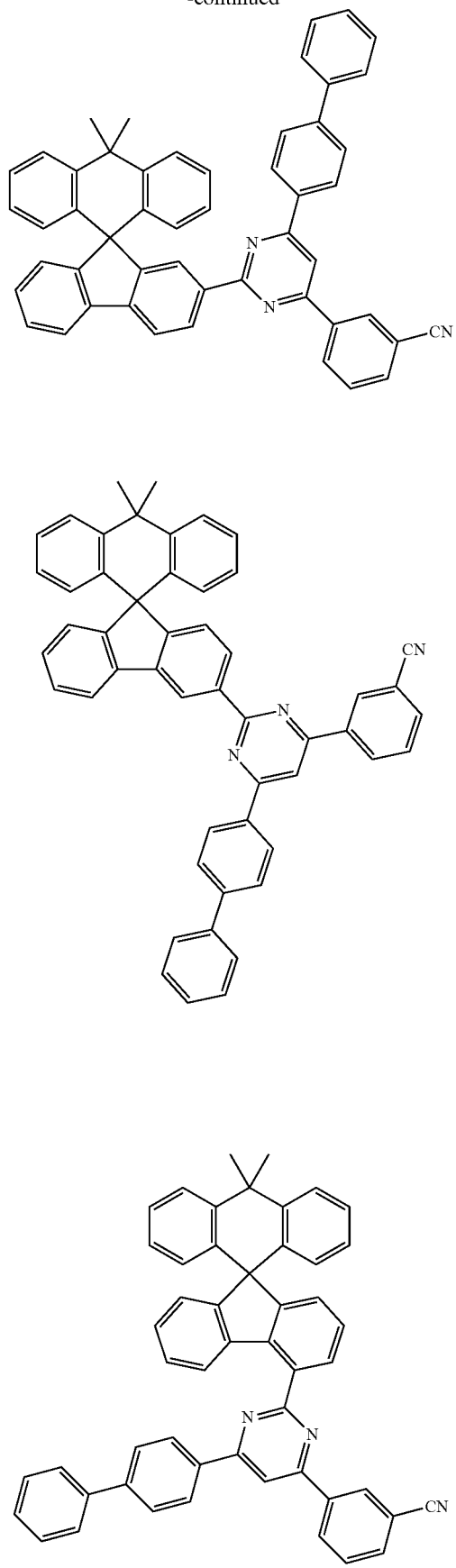
72
-continued
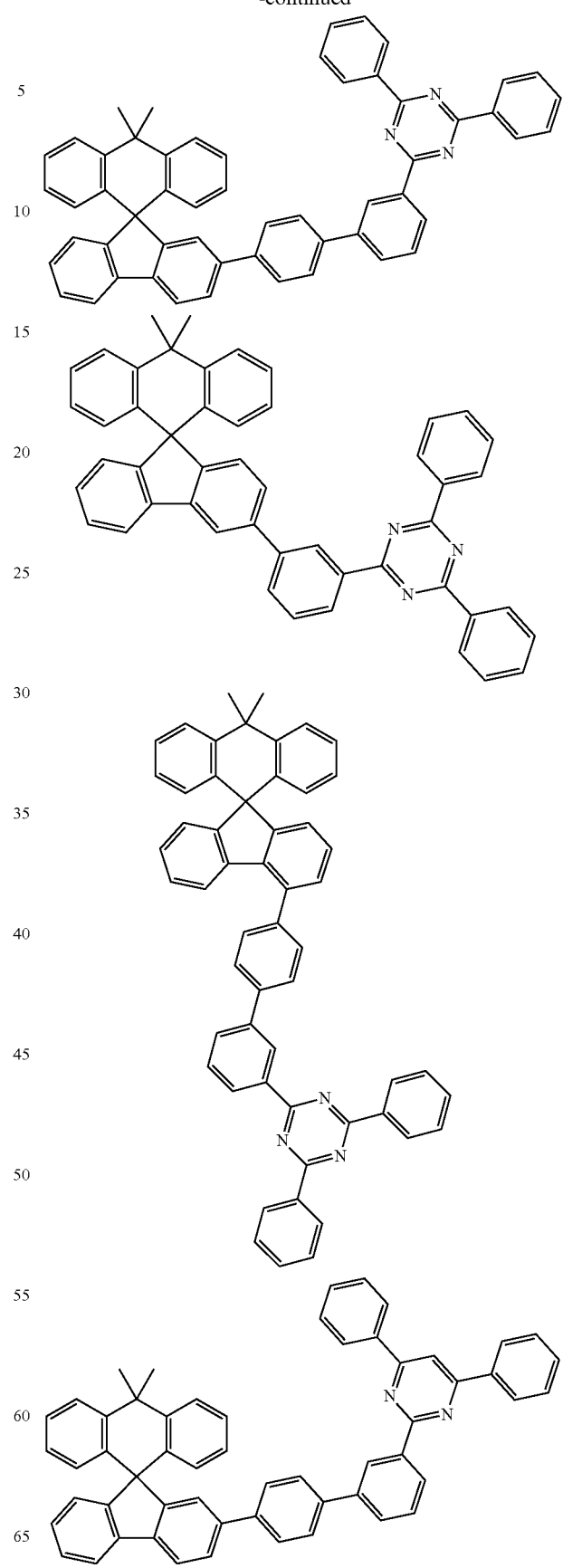

73
-continued
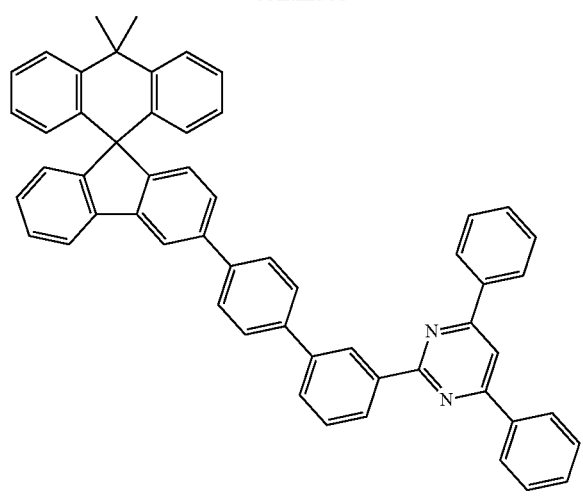
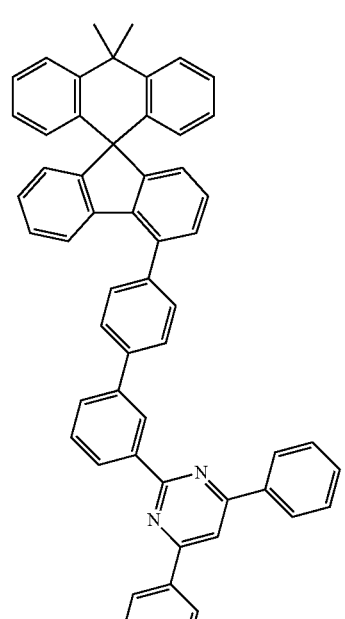
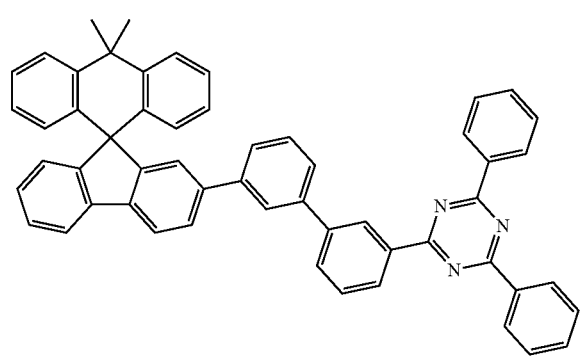
74
-continued
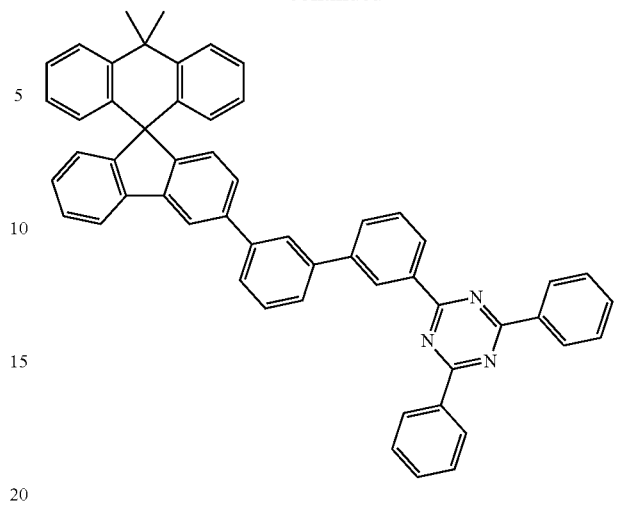
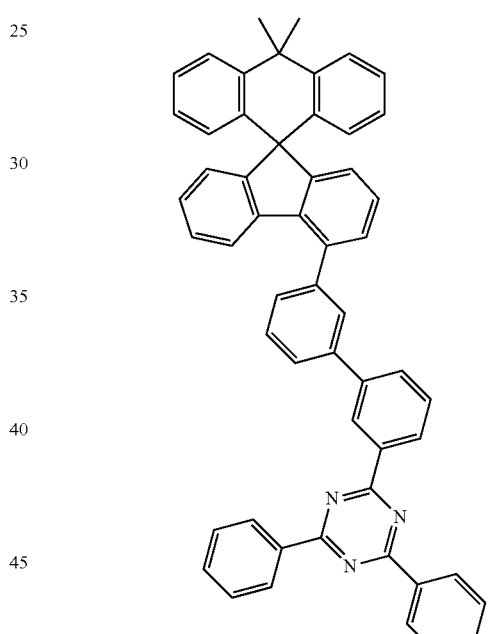
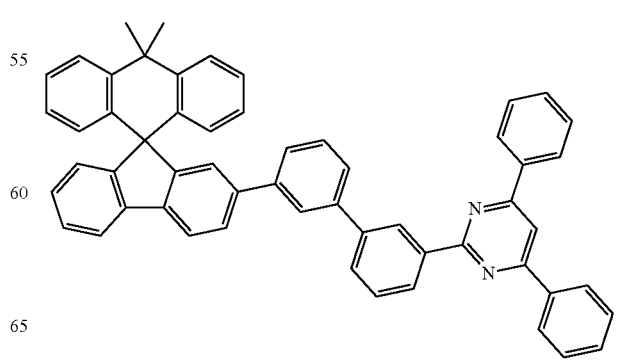

75
-continued
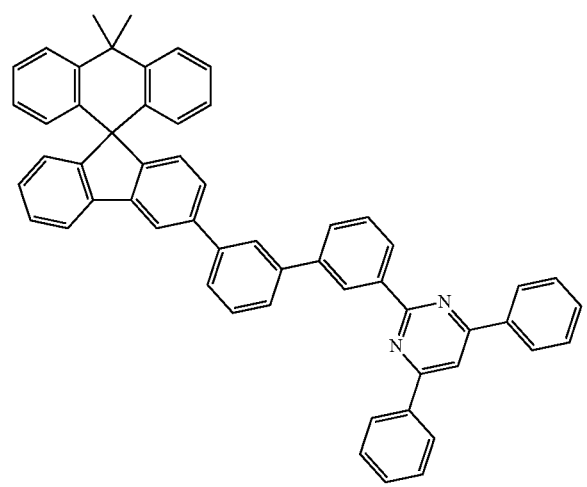
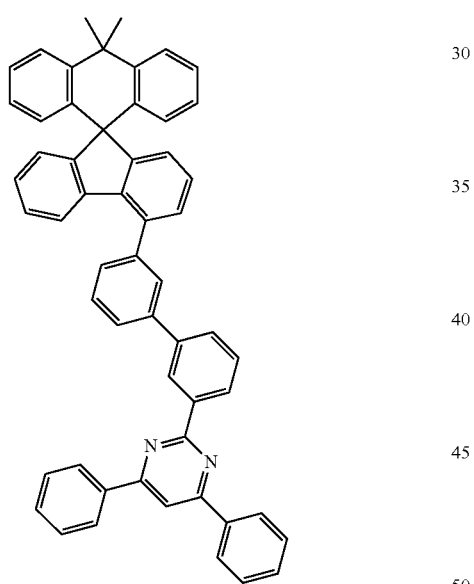
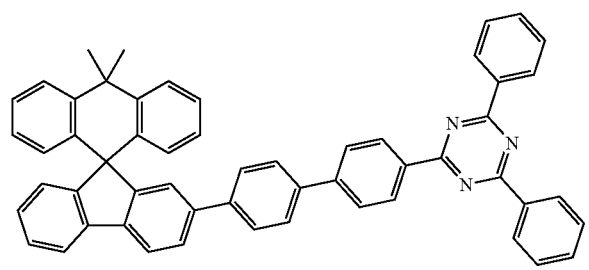
76
-continued
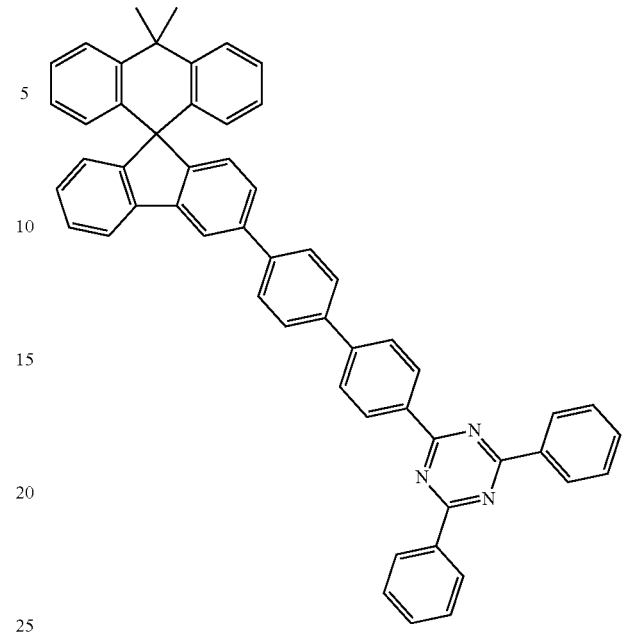
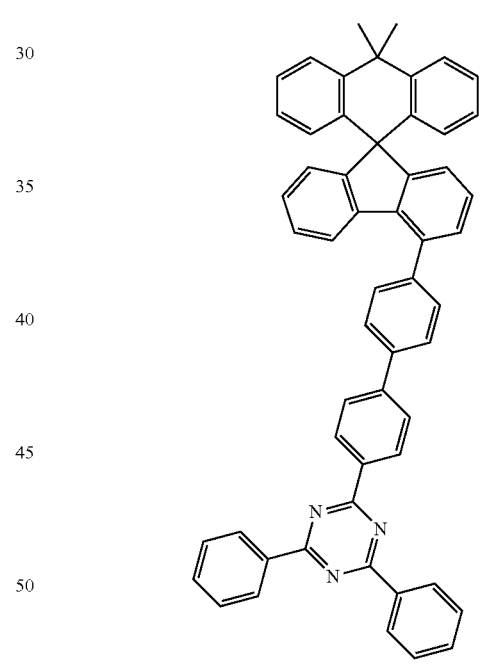
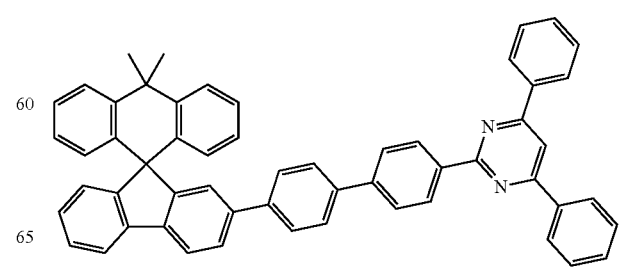

77
-continued
78
-continued
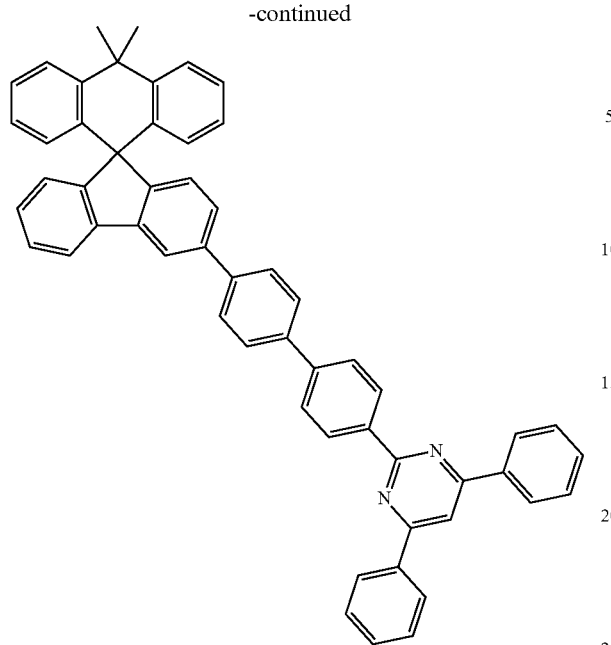
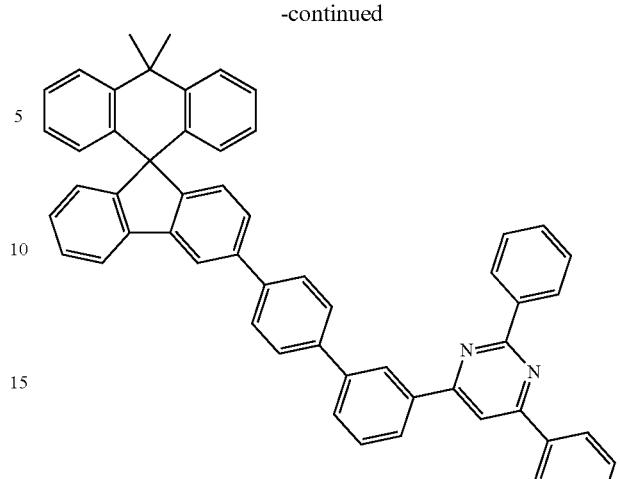
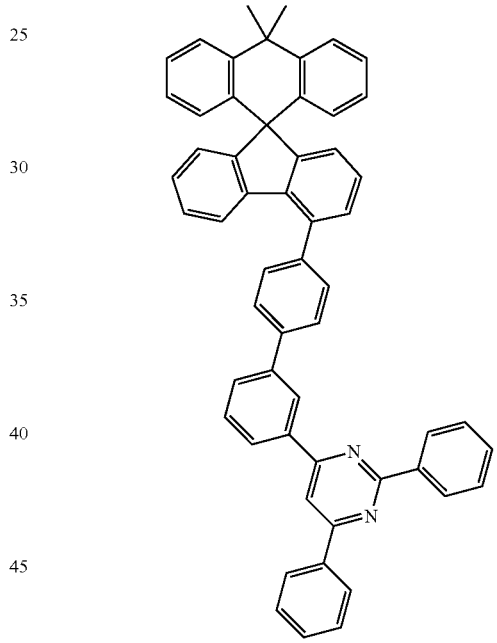
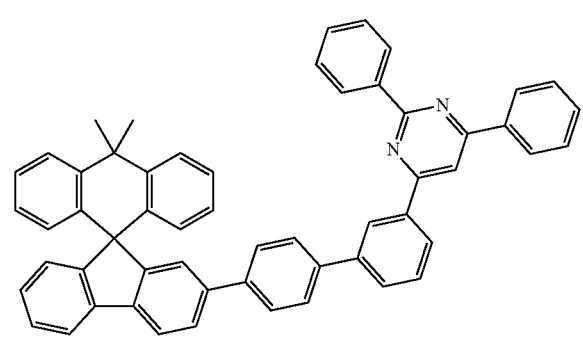
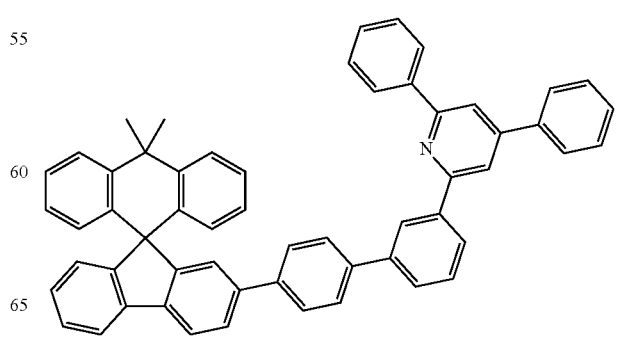

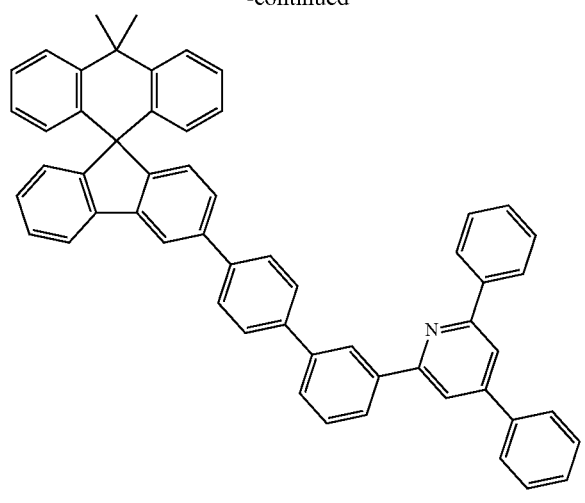
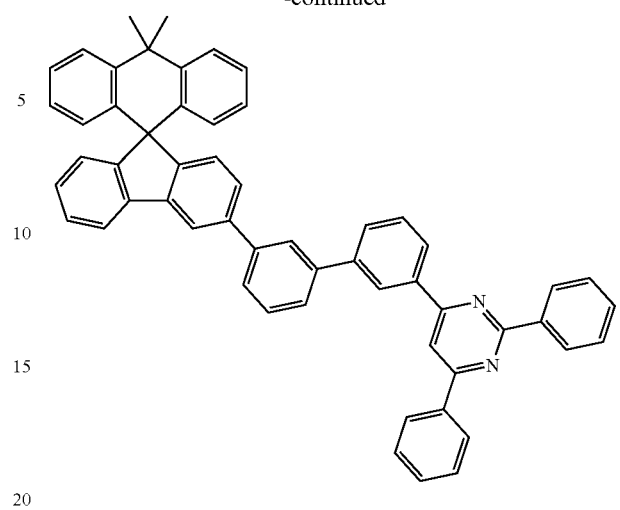
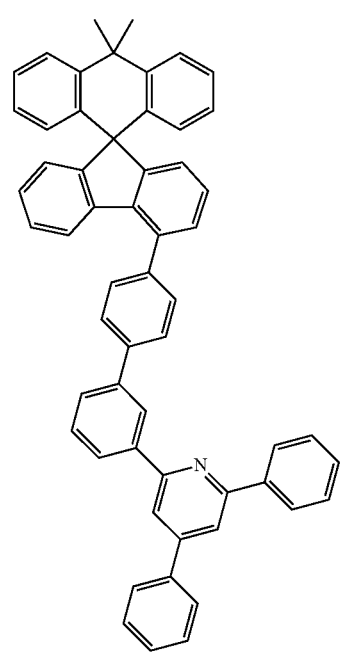
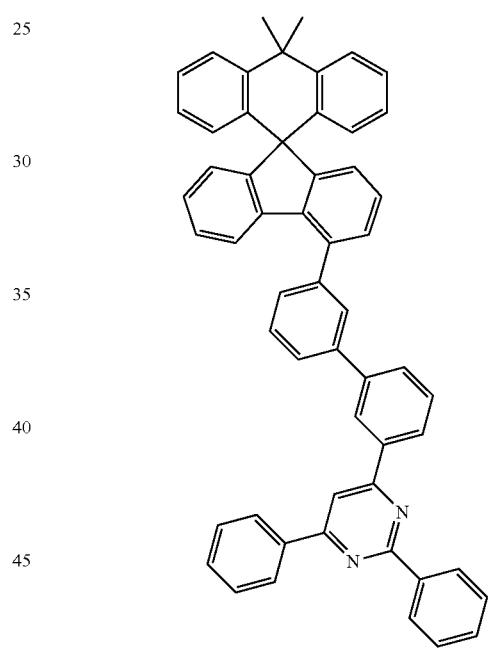
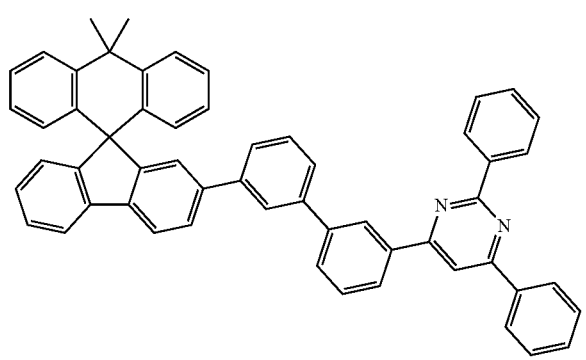
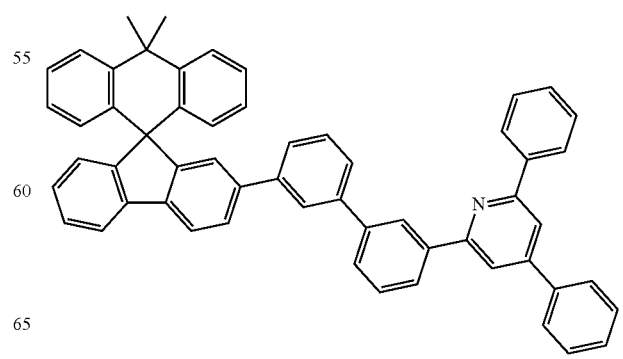

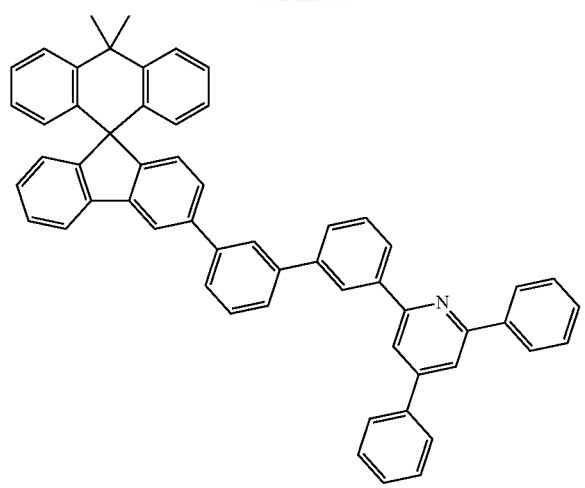
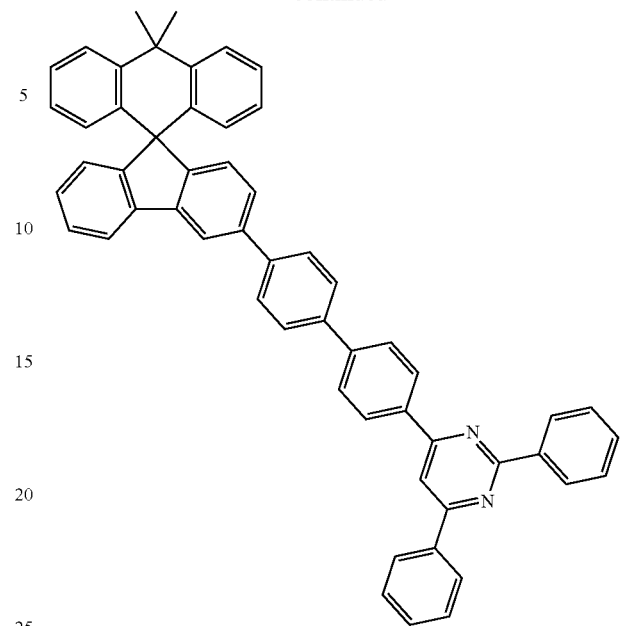
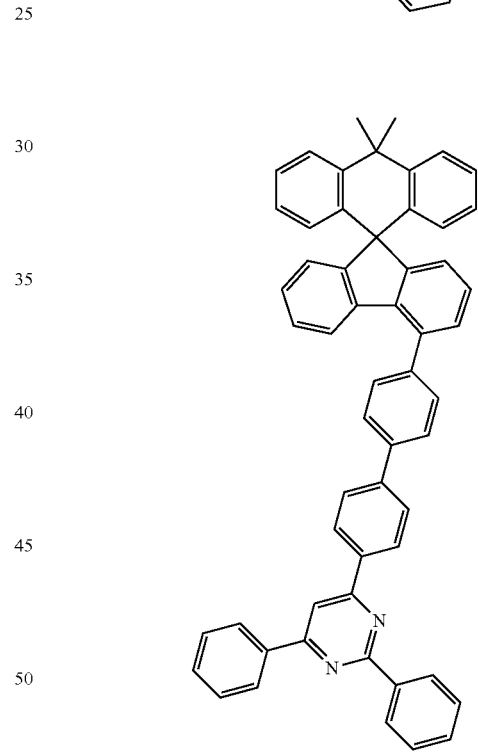
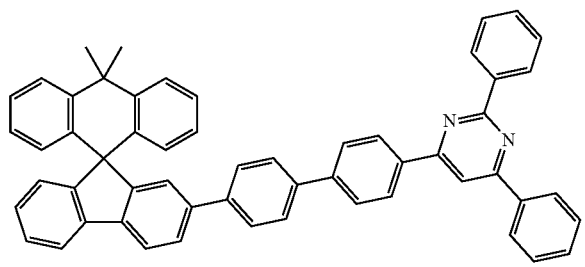
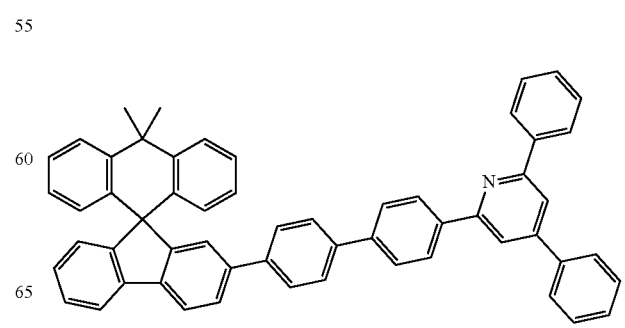

83
-continued
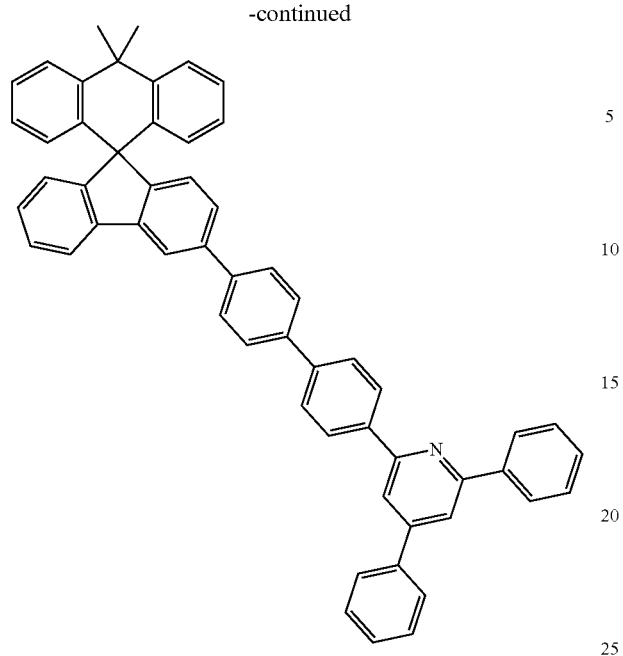
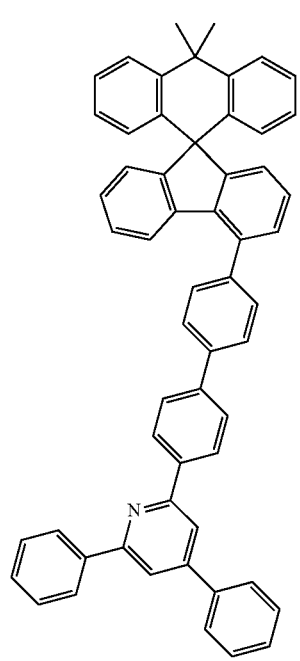
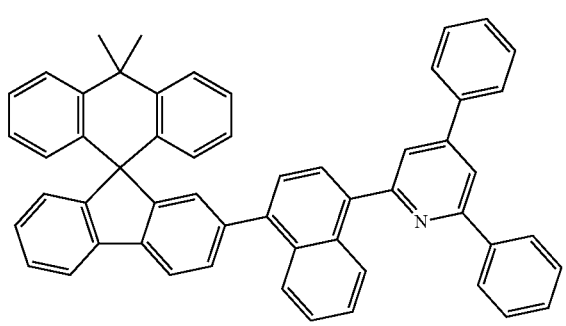
84
-continued
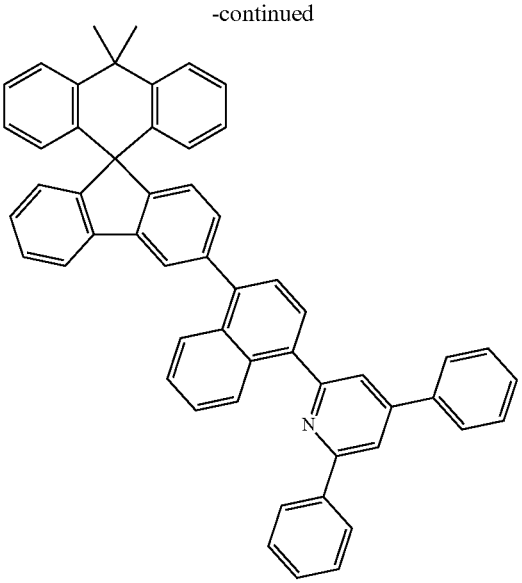
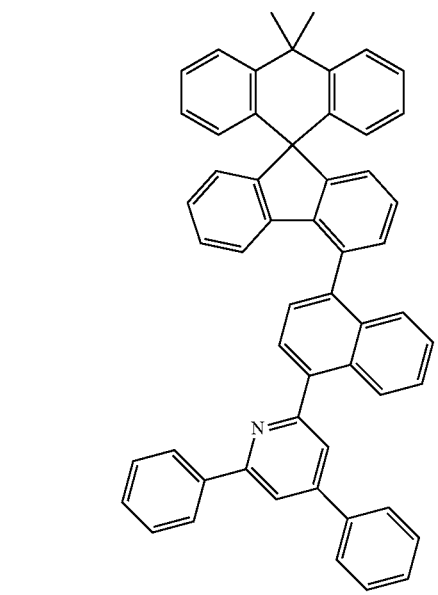
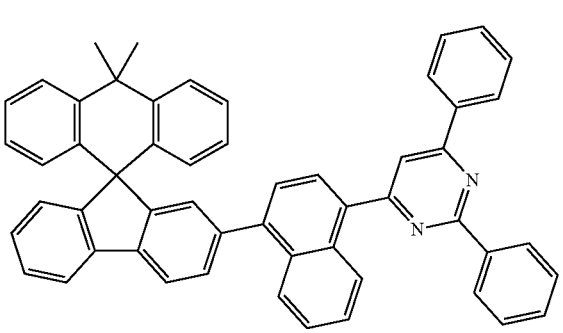

85
-continued
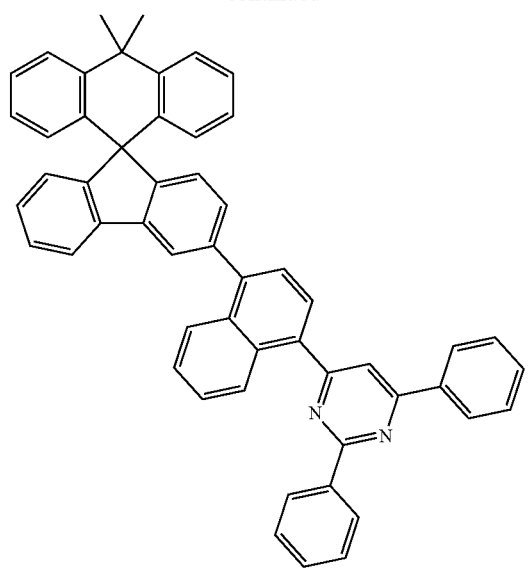
86
-continued
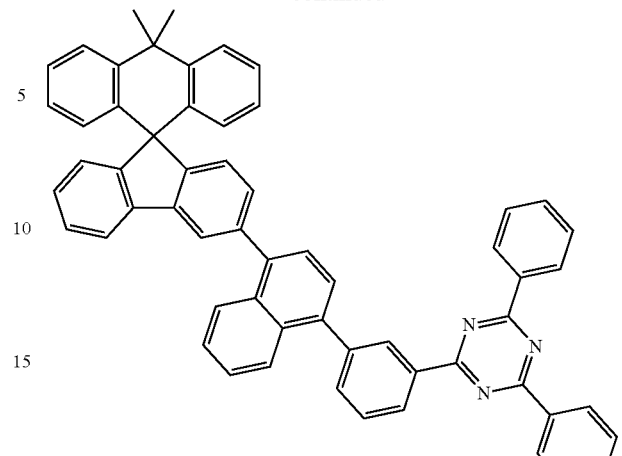
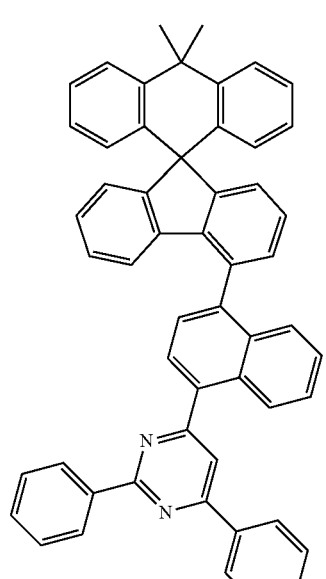
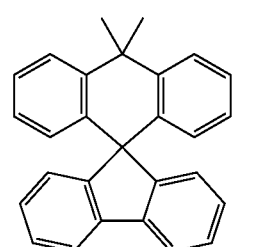
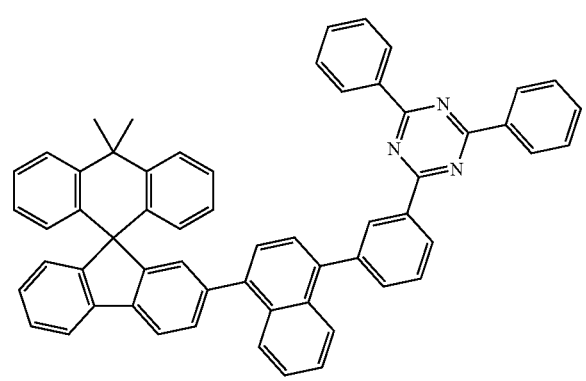
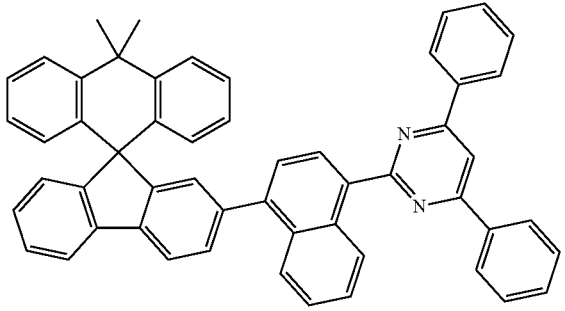

87
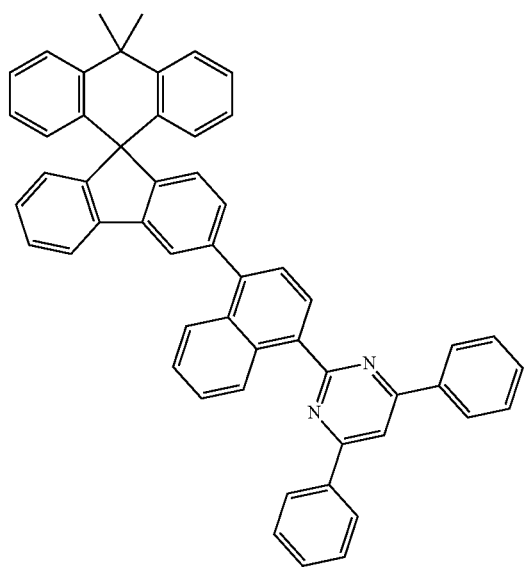
88
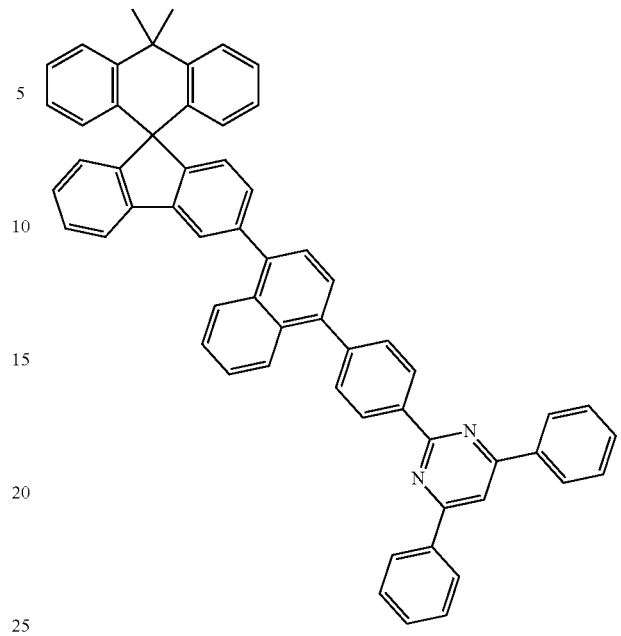
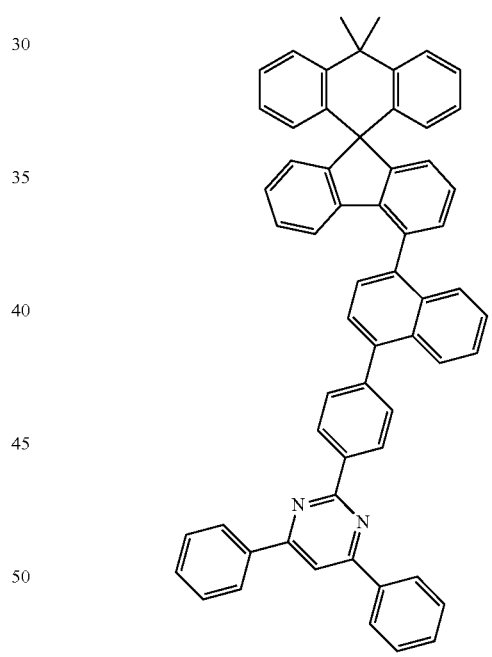
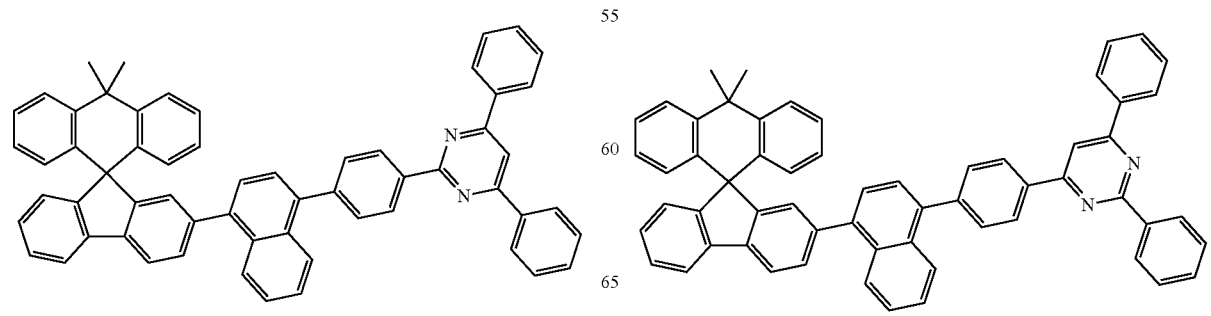

89
-continued
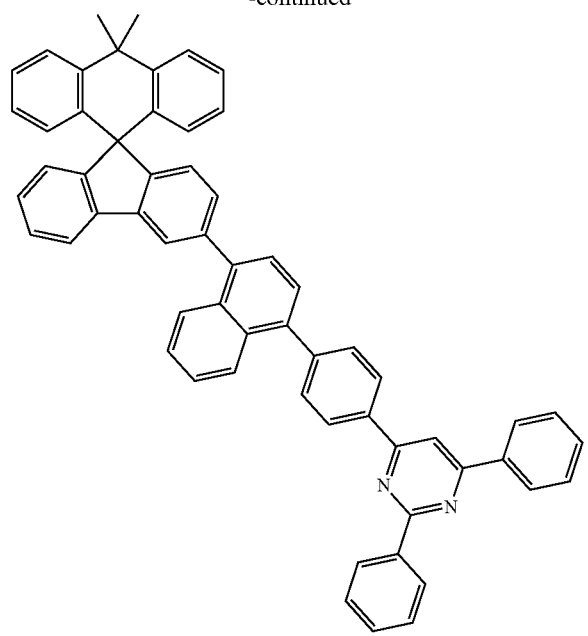
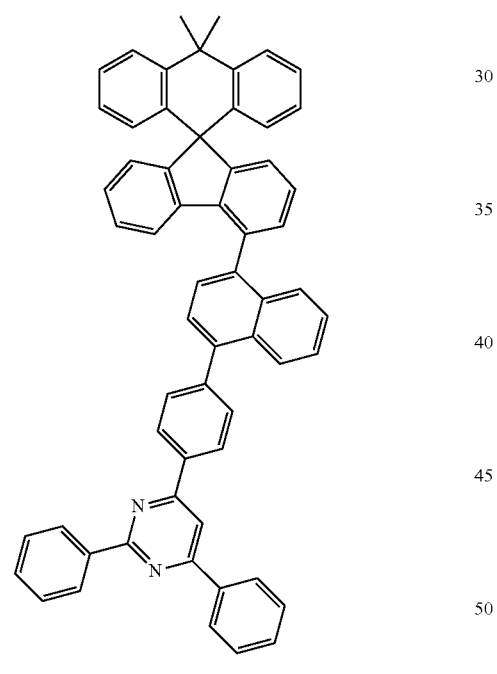
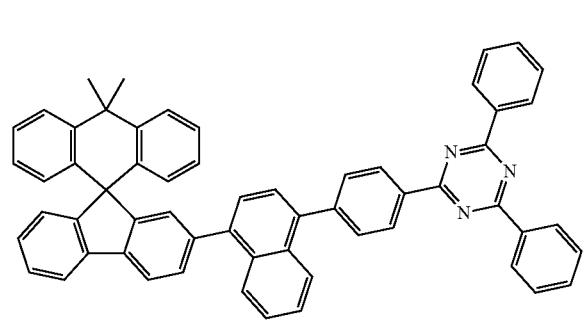
90
-continued
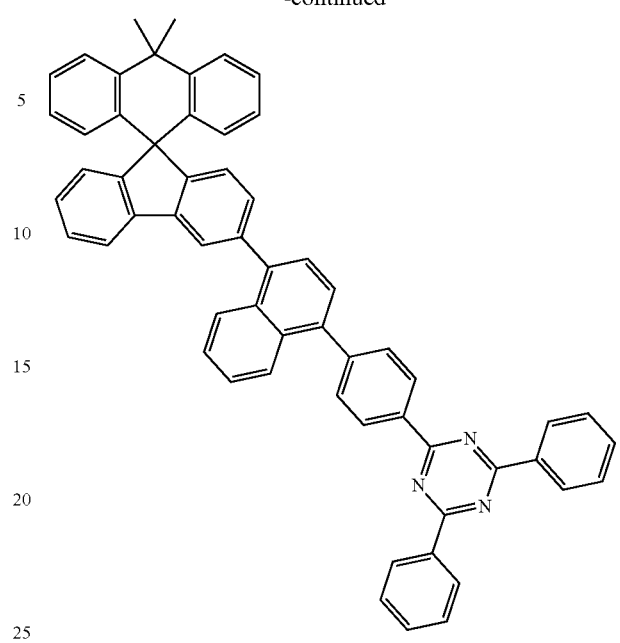
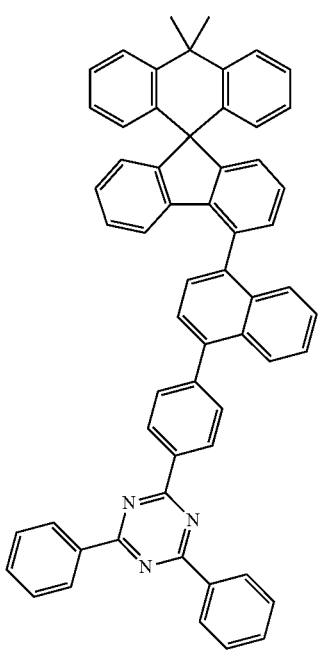
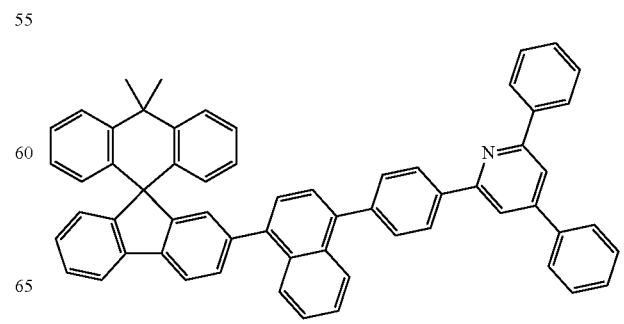

91
-continued
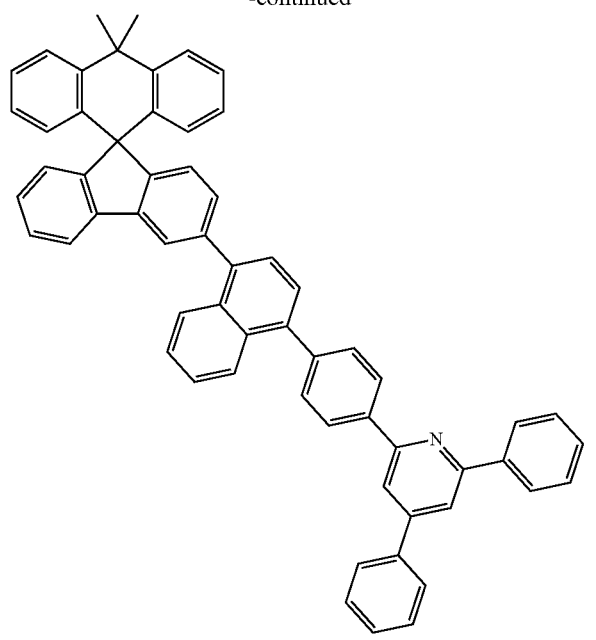
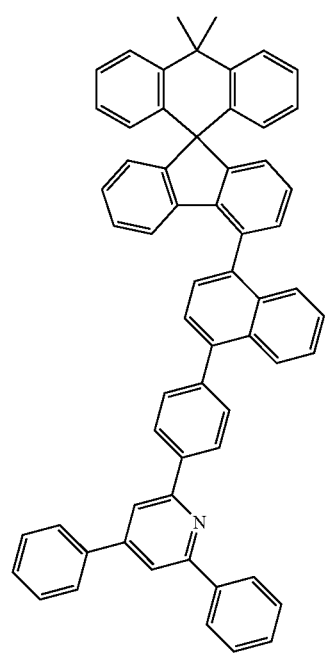
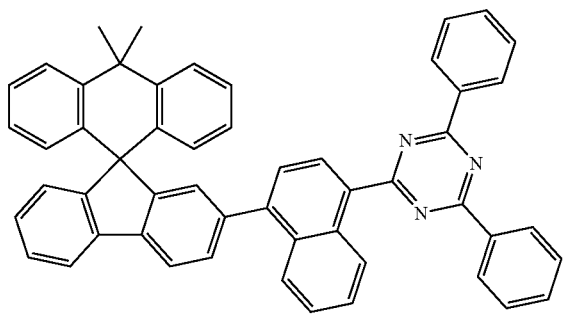
92
-continued
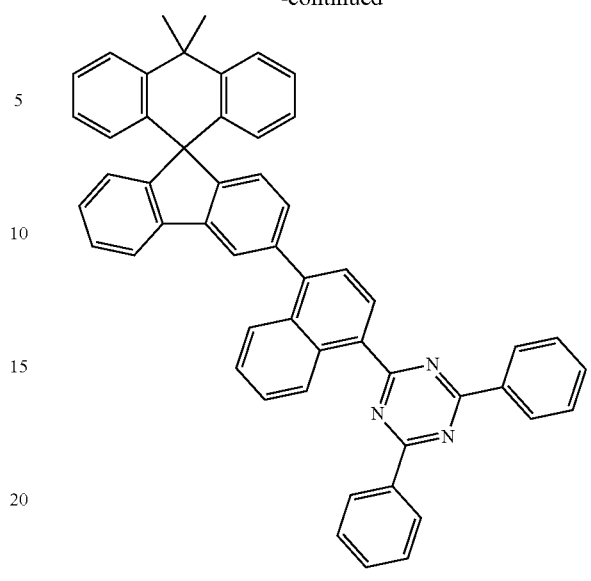
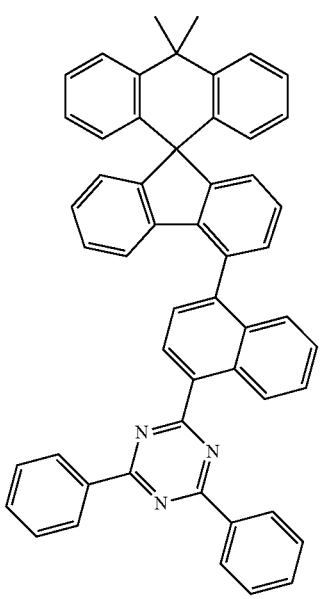
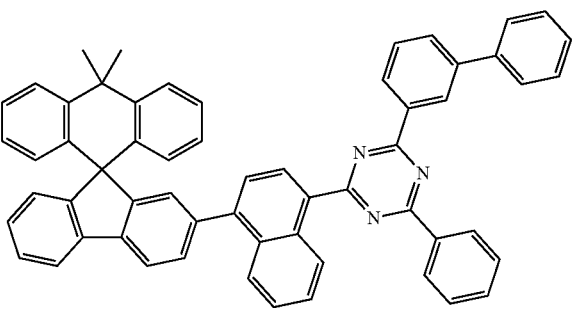

93
-continued
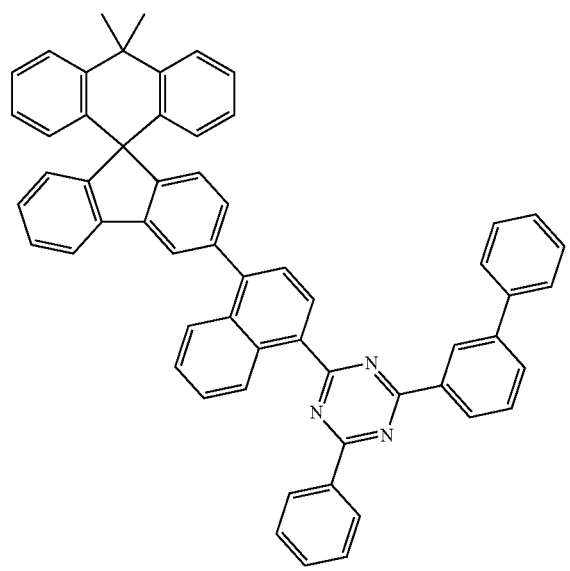
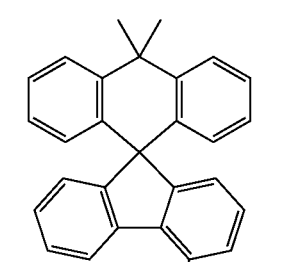
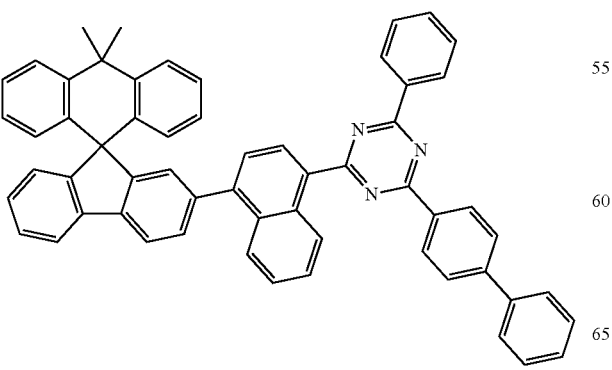
94
-continued
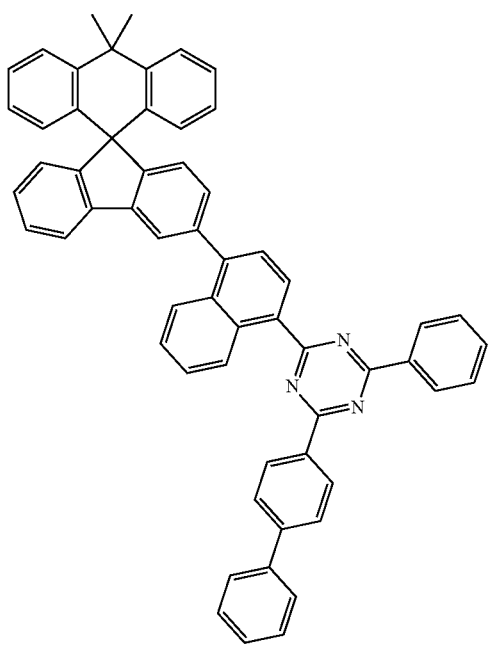
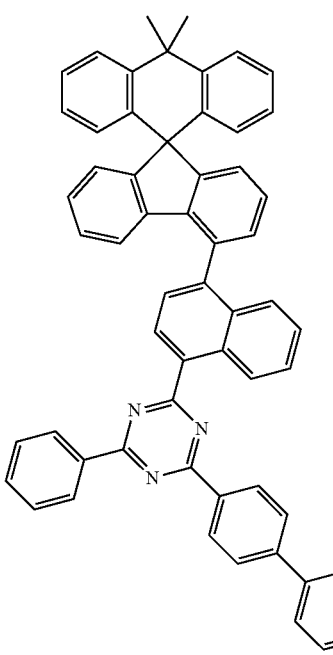

95
-continued
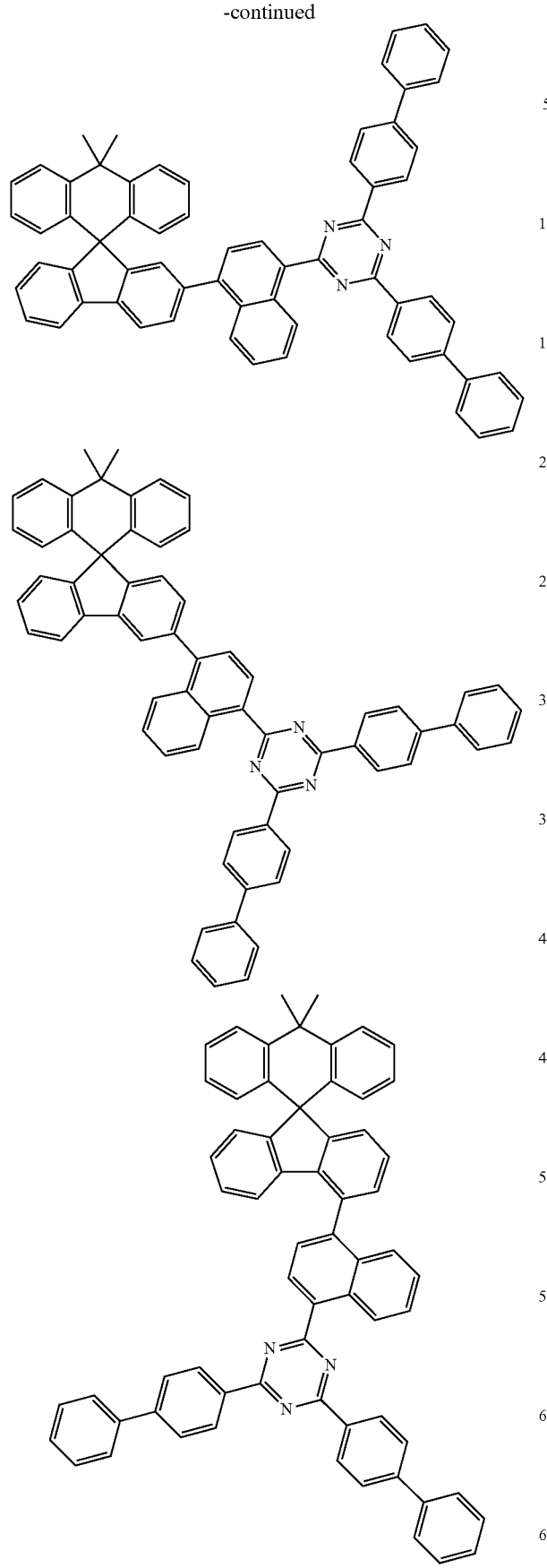
96
-continued
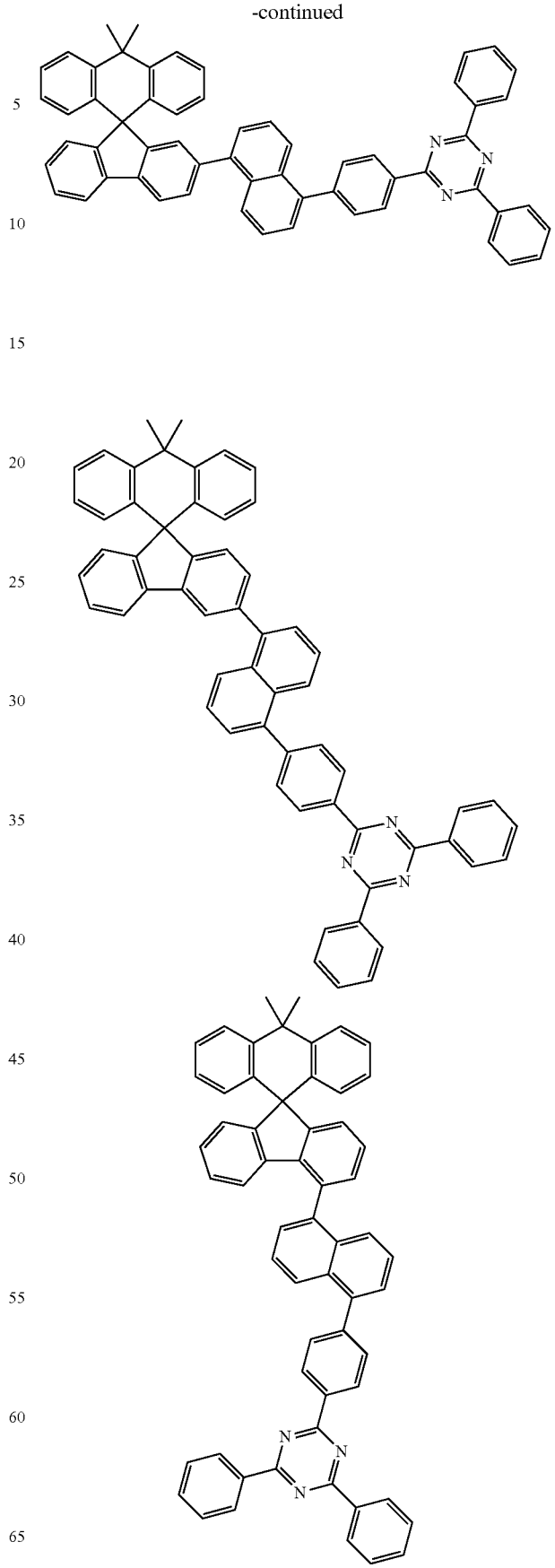

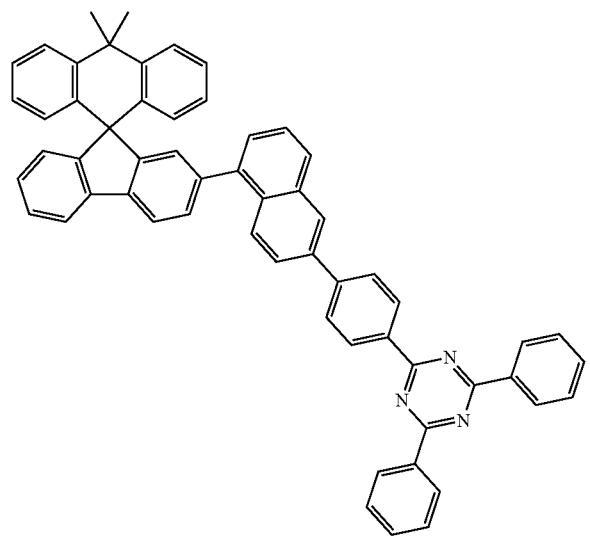
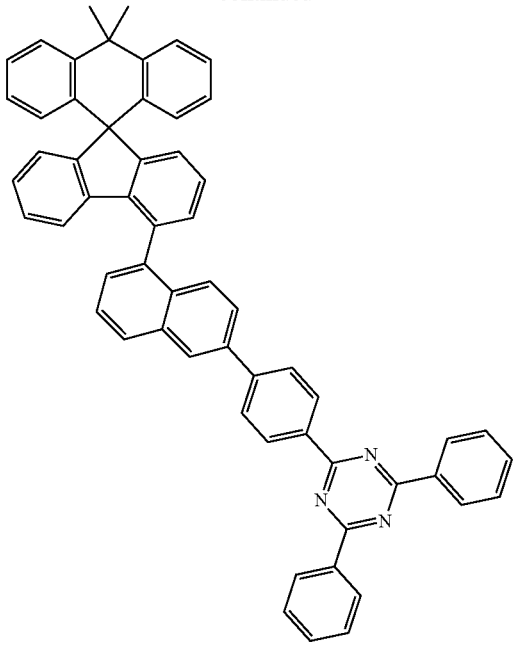
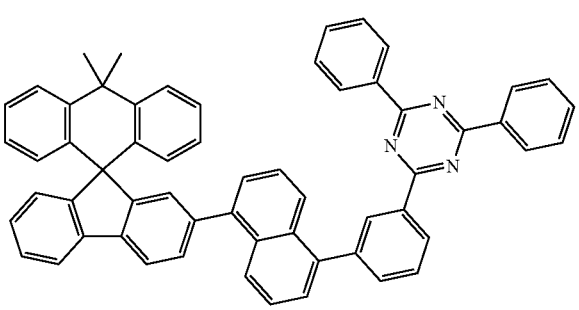
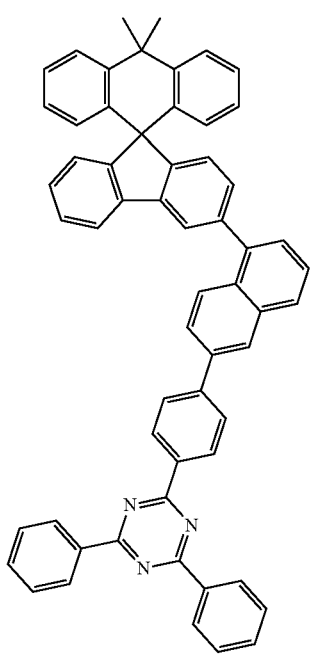
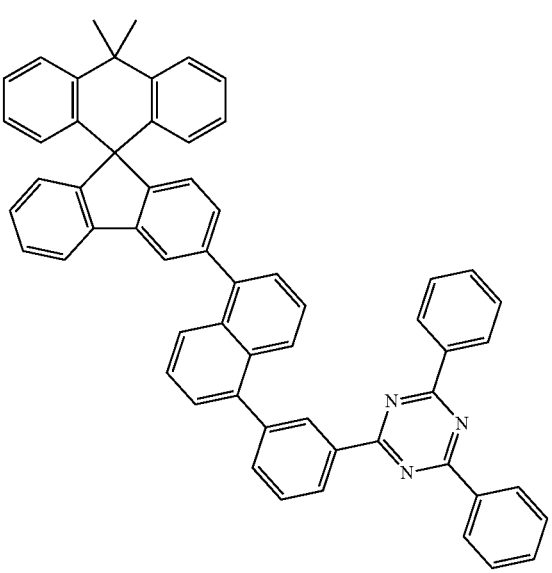

99
-continued
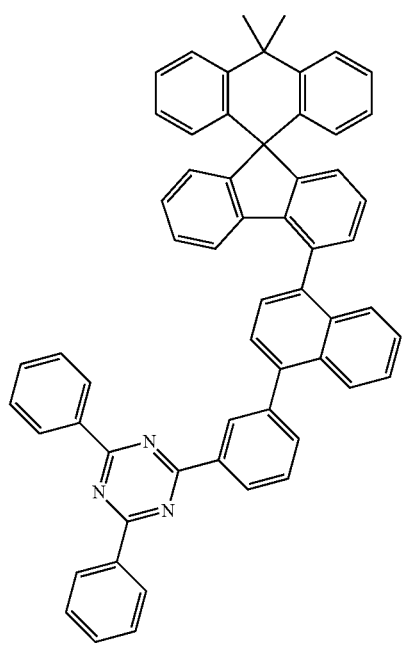
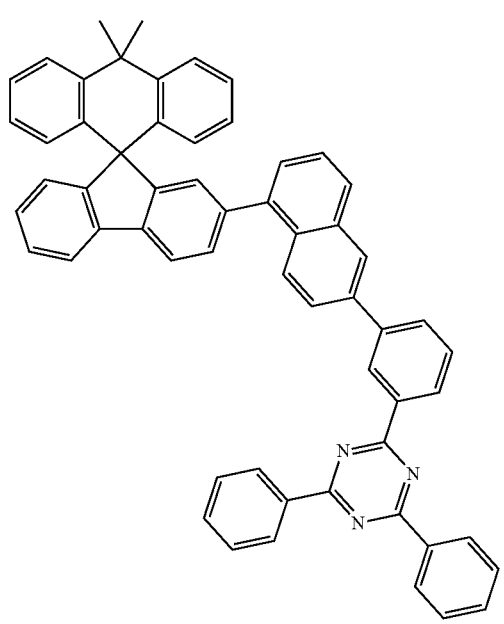
100
-continued
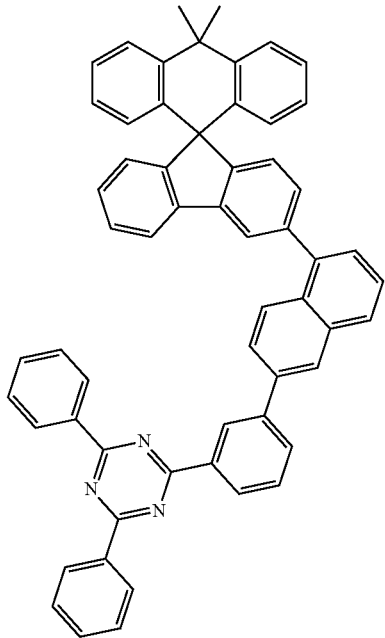
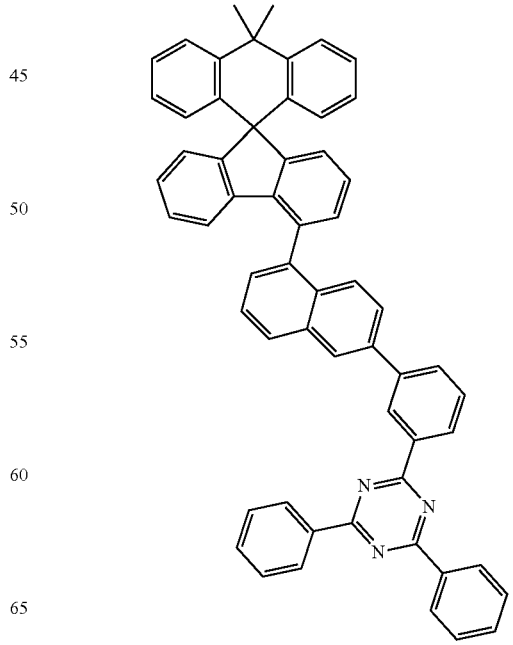

101
-continued
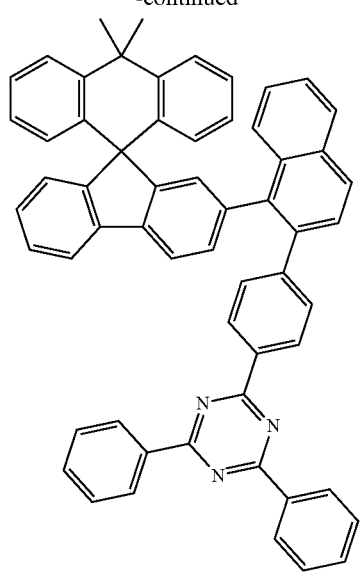
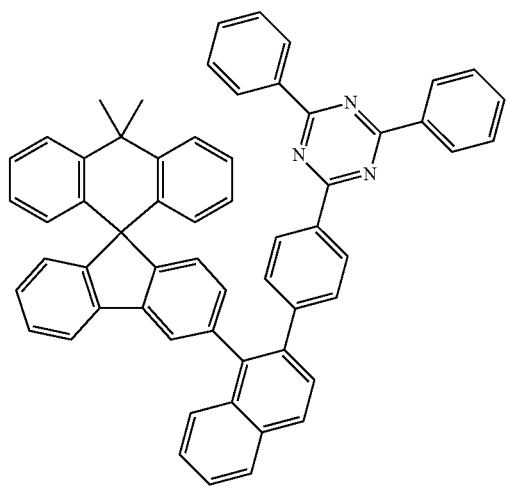
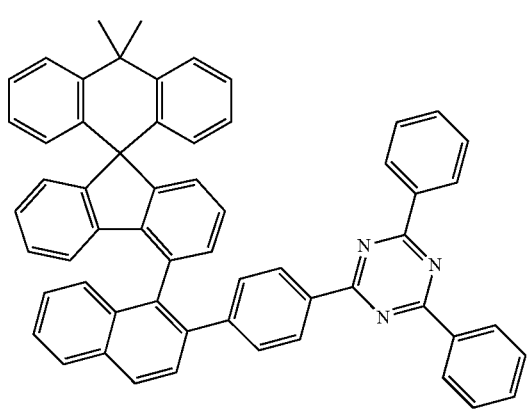
102
-continued
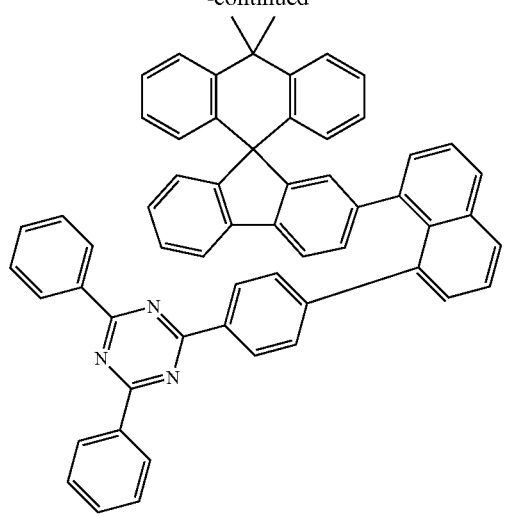
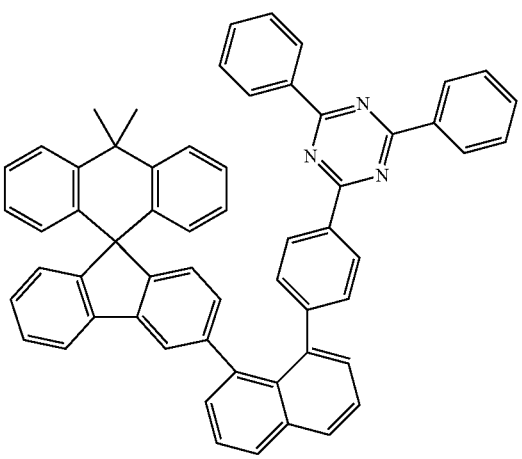
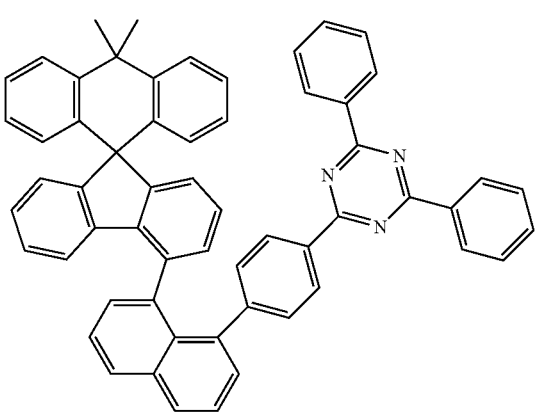

103
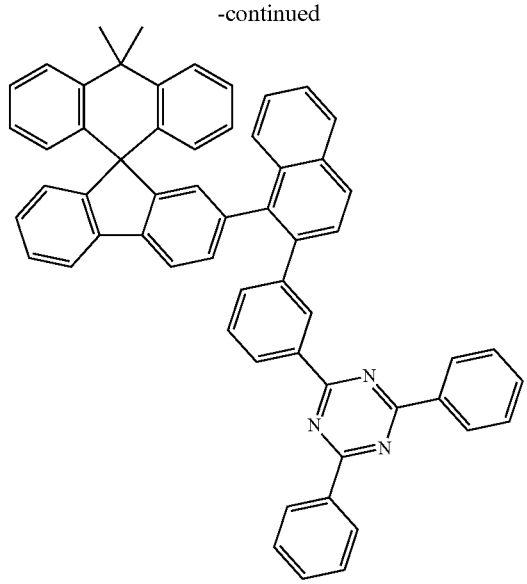
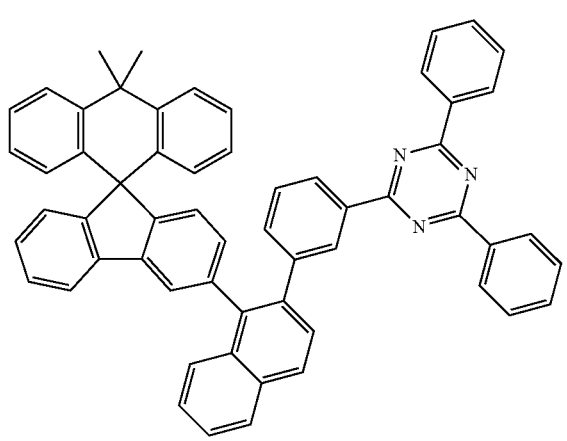
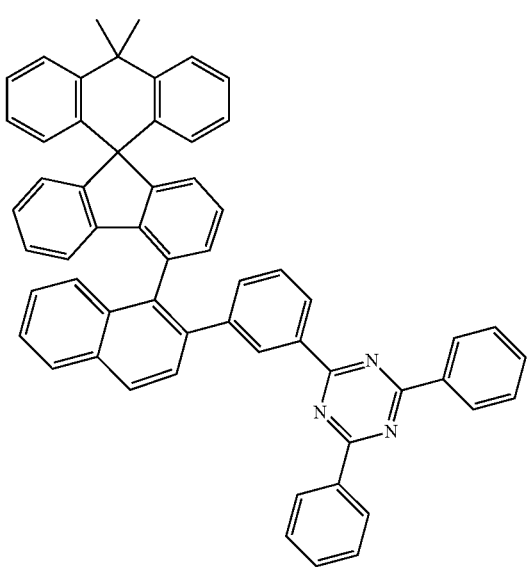
104
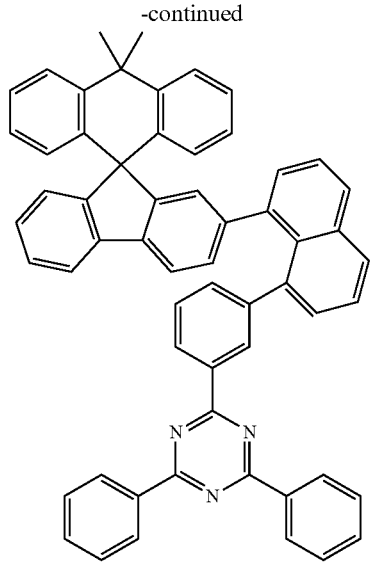
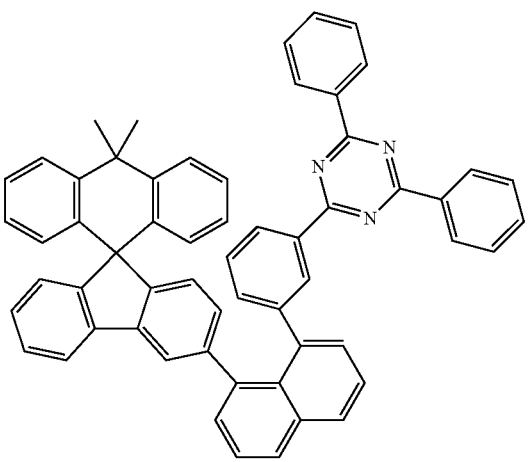
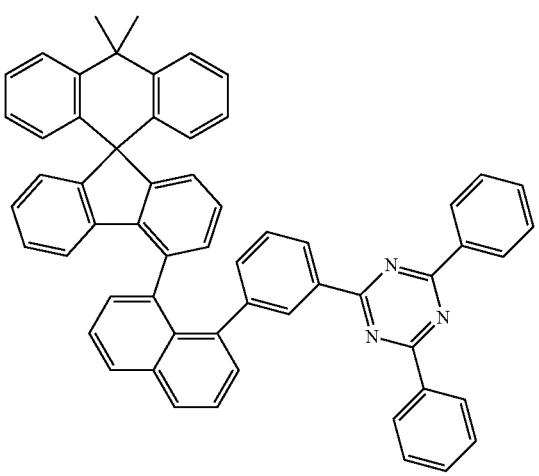

105
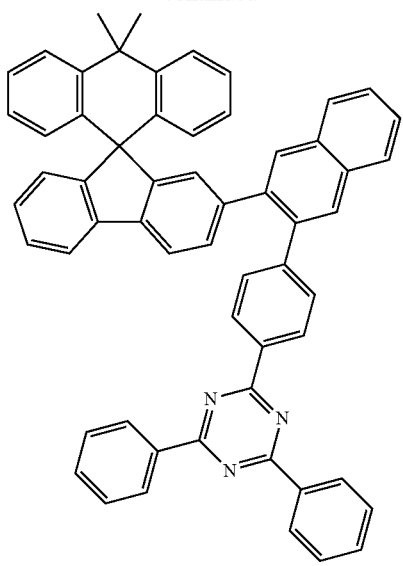
106
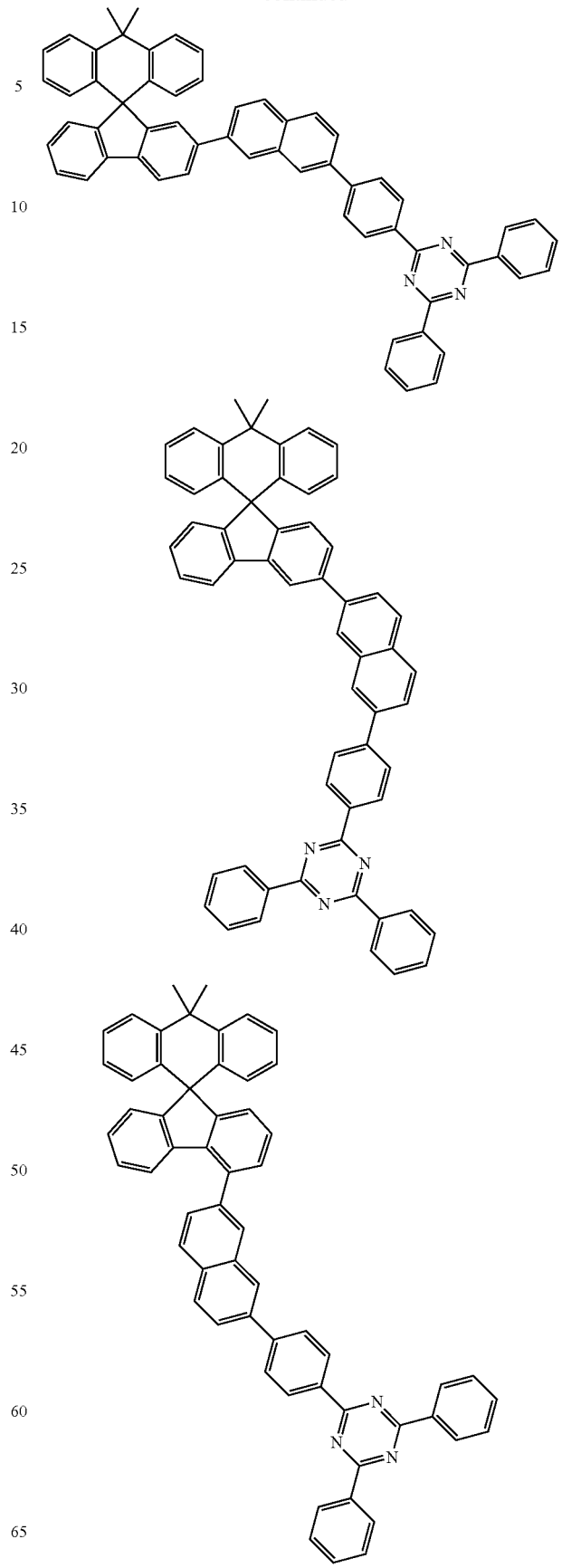

107
-continued
108
-continued
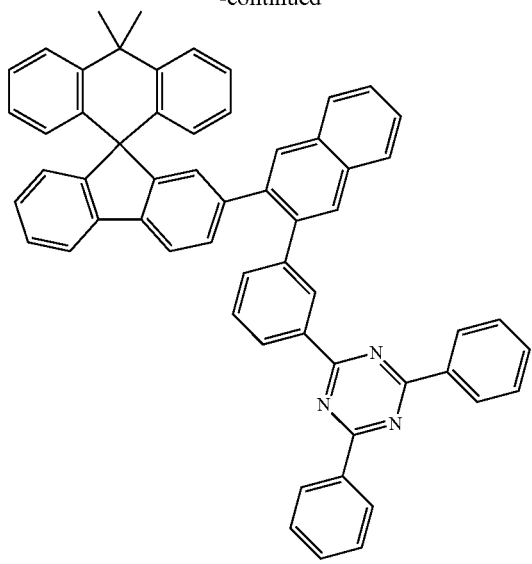
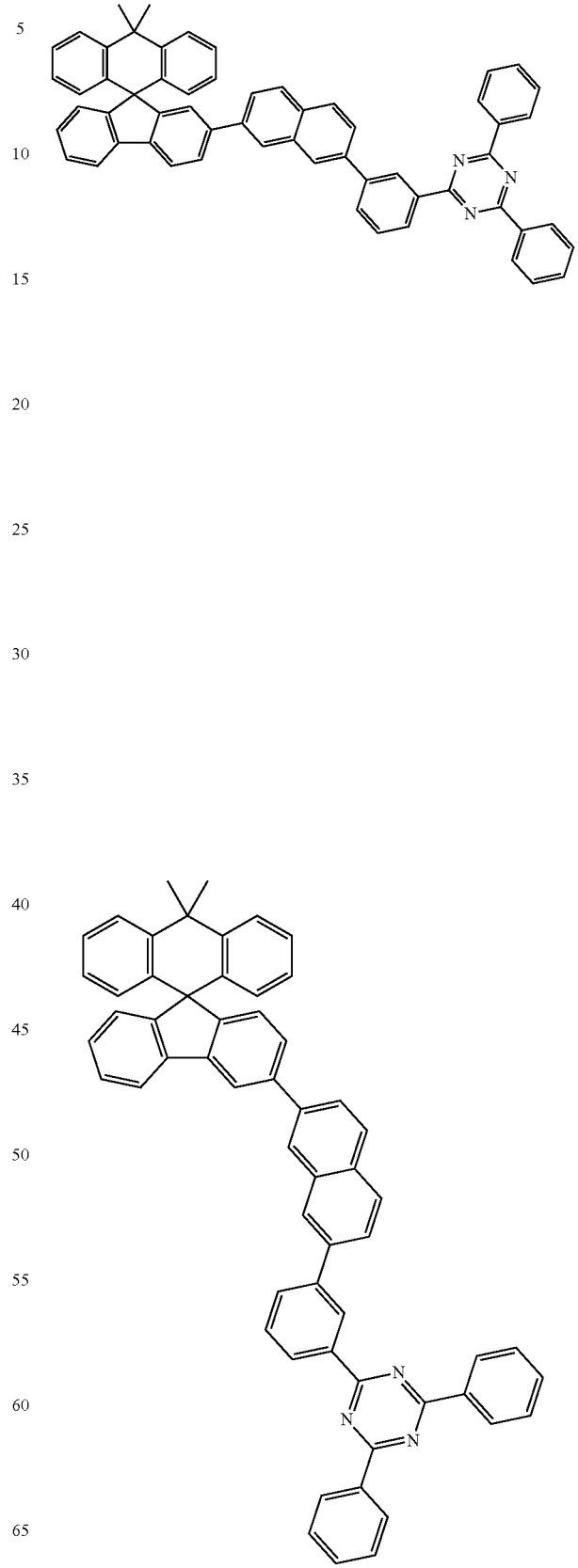

109
-continued
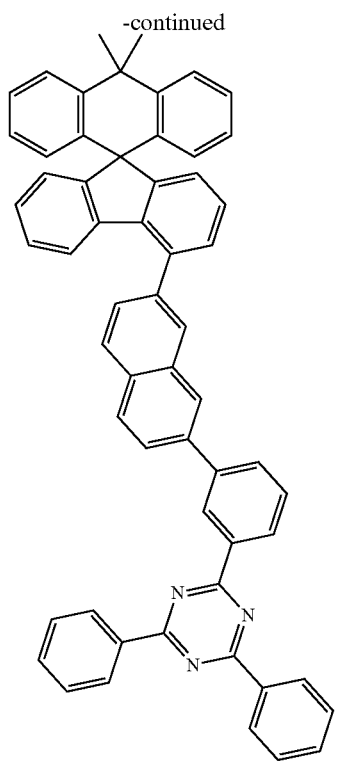
110
-continued
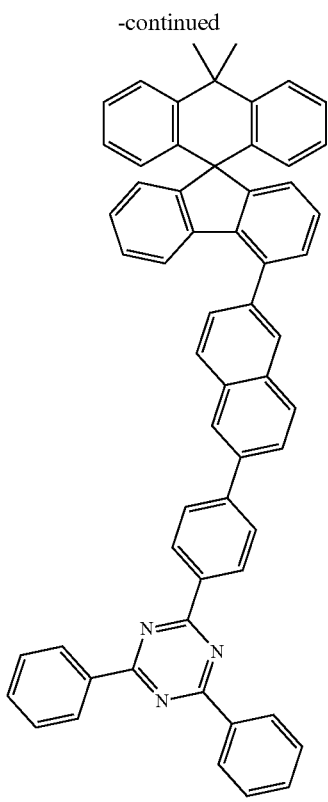
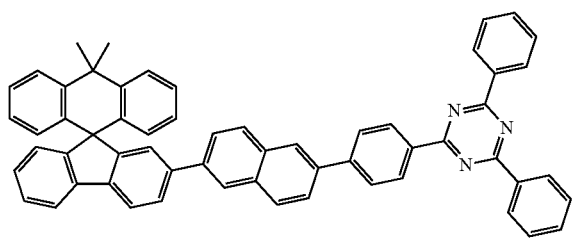
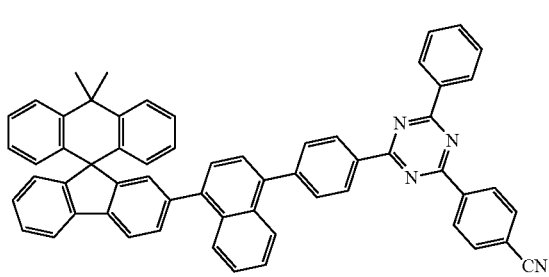
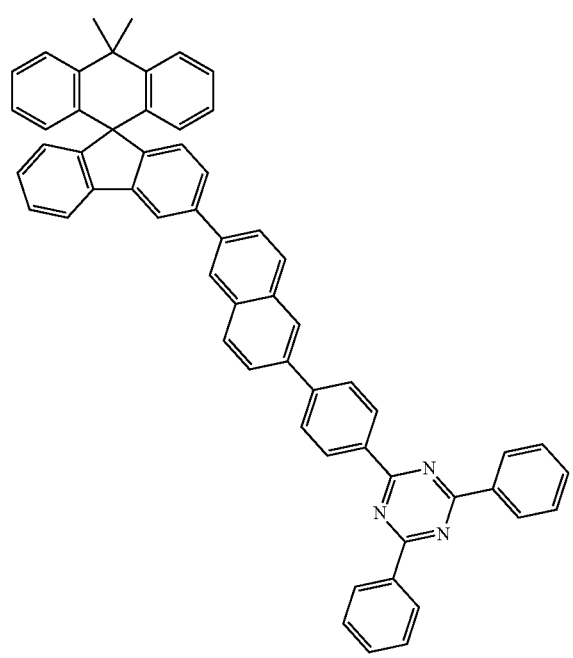
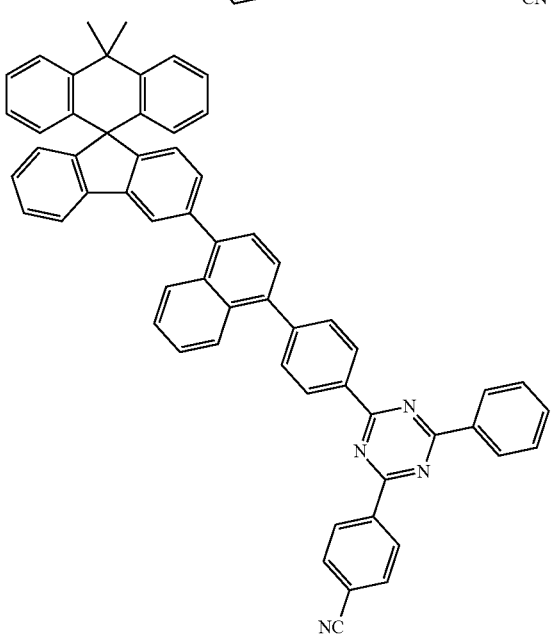

111
-continued
112
-continued
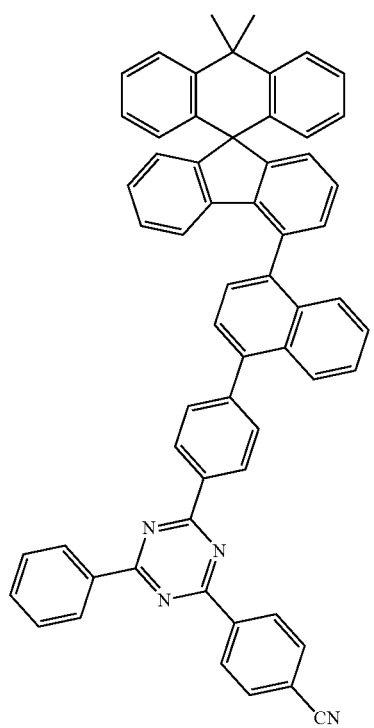 [SMILES: CC1(C)c2ccccc2C2(c3ccccc3-c3c(-c4ccc(-c5ccc(-c6nc(-c7ccccc7)nc(-c7ccc(C#N)cc7)n6)cc5)c5ccccc45)cccc32)c2ccccc21]
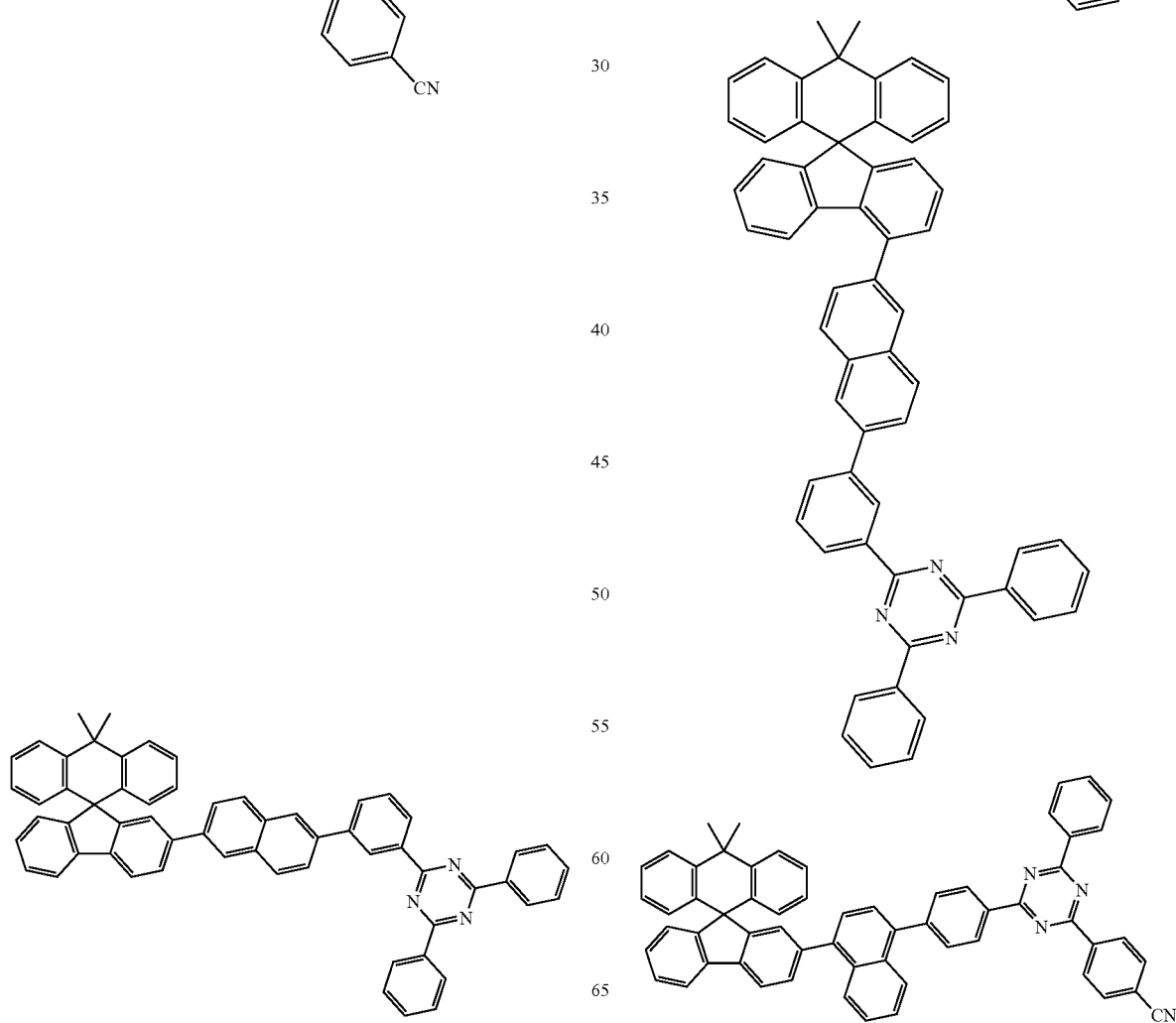

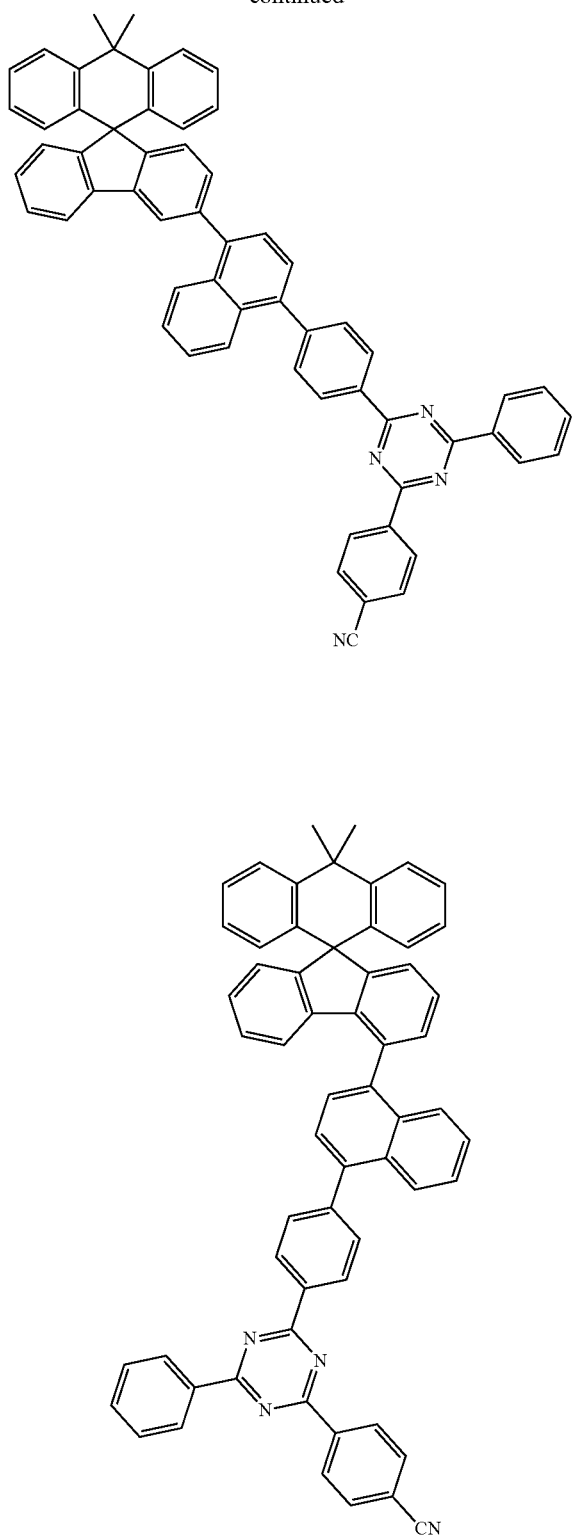
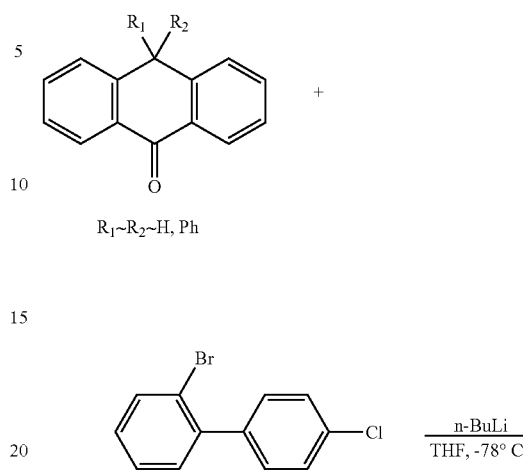
[Reaction Scheme 1-1]
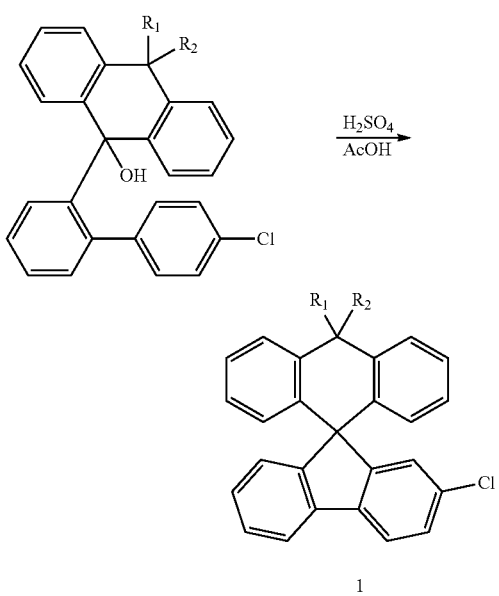
[Reaction Scheme 1-2]
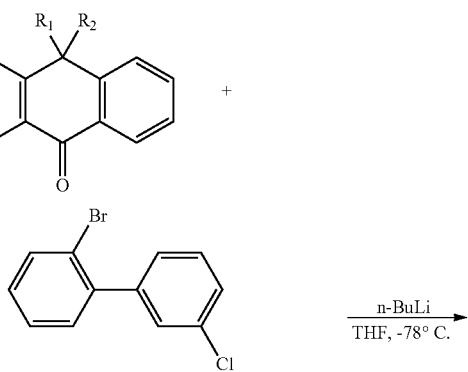
The compound represented by Chemical Formula 1 can be prepared through the following Reaction Schemes 1 to 4. The above preparation method can be further specified in preparation examples described hereinafter.
First, the first intermediates 1, 2, and 3 may be prepared according to the following Reaction Schemes 1-1 to 1-3.

115
-continued

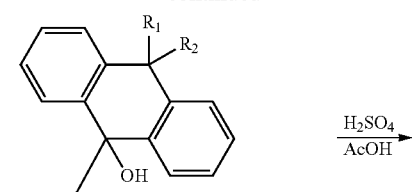

$\xrightarrow{\text{H}_2\text{SO}_4}{\text{AcOH}}$

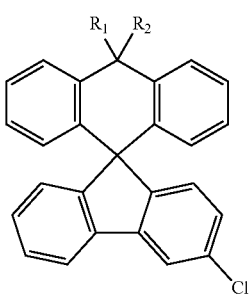

2

[Reaction Scheme 1-3]

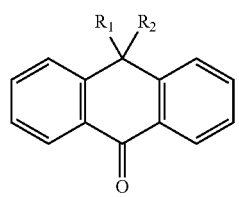
+

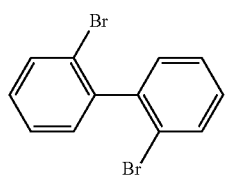
$\xrightarrow[\text{THF, -78° C.}]{\text{n-BuLi}}$

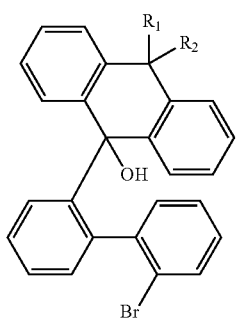
$\xrightarrow{\text{H}_2\text{SO}_4}{\text{AcOH}}$

116
-continued

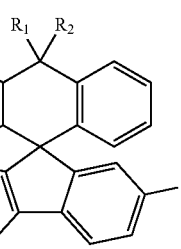

3

Next, the second intermediates 4, 5, and 6 may be prepared according to the following Reaction Scheme 2 by using the first intermediates 1, 2, and 3 as reactants.

[Reaction Scheme 2]

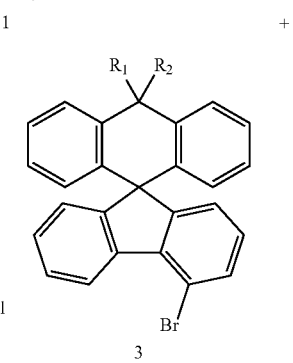

1
+

2    3

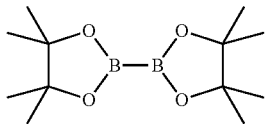
$\xrightarrow[\substack{\text{Dioxane}\\\text{Reflux}}]{\substack{\text{Pd(bda)2/ PCy3}\\\text{KOAc}}}$

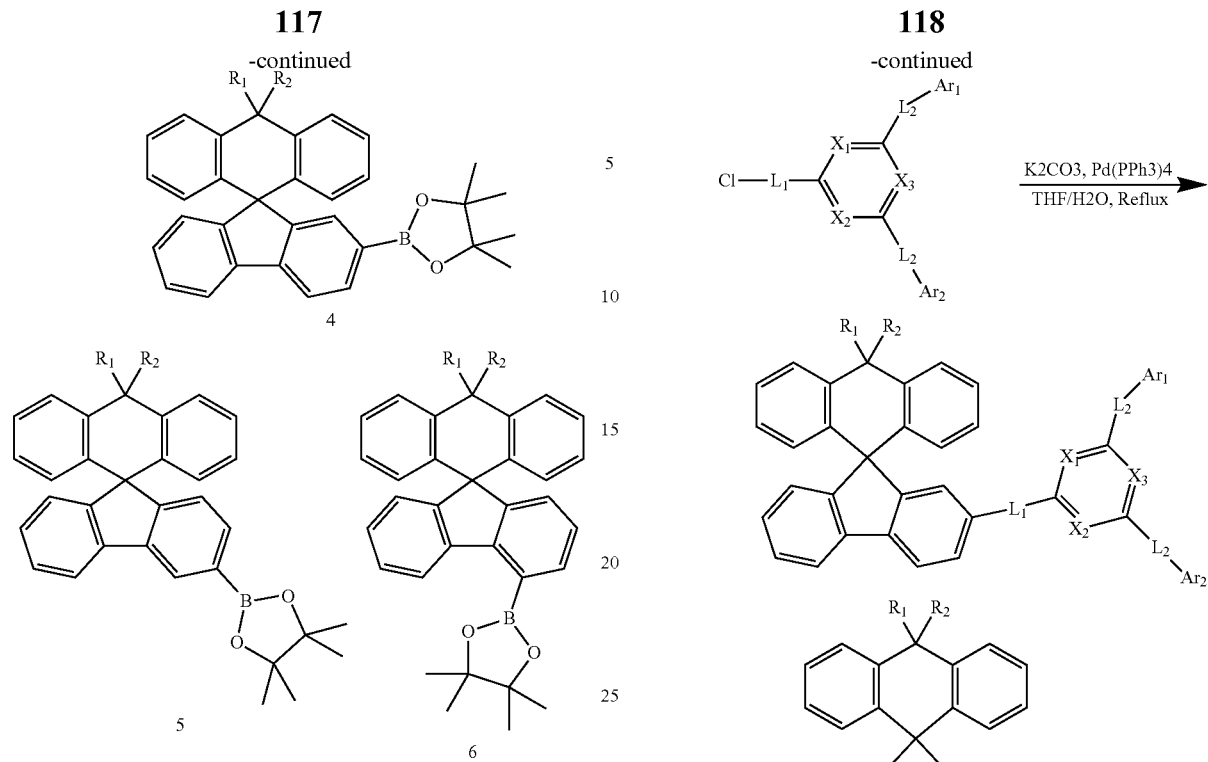

Finally, the compound of Chemical Formula 1 of the present disclosure can be prepared according to the following Reaction Scheme 3 by using the second intermediates 4, 5, and 6 as reactants.

[Reaction Scheme 3]

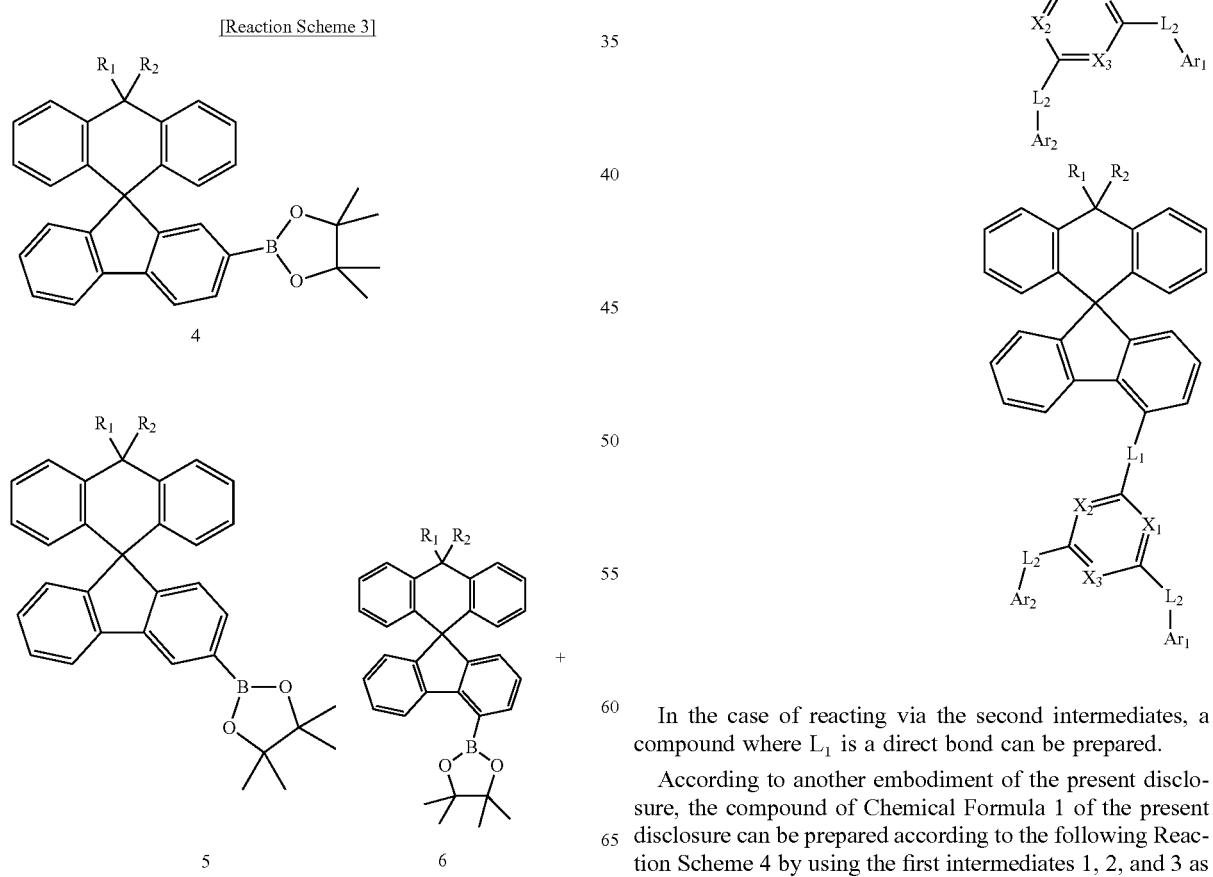

In the case of reacting via the second intermediates, a compound where $L_1$ is a direct bond can be prepared.

According to another embodiment of the present disclosure, the compound of Chemical Formula 1 of the present disclosure can be prepared according to the following Reaction Scheme 4 by using the first intermediates 1, 2, and 3 as reactants.

[Reaction Scheme 4]

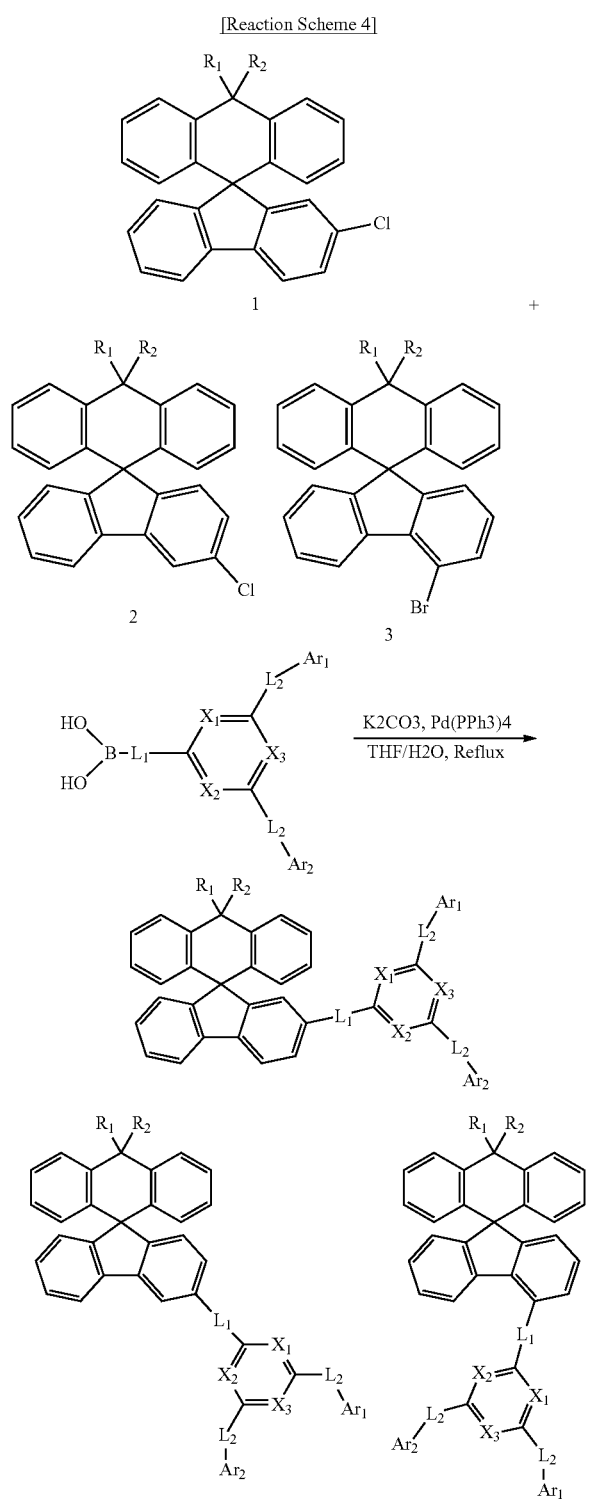

In Reaction Schemes 1-1 to 1-3 and Reaction Schemes 2, 3, and 4, $R_1$, $R_2$, $L_1$, $L_2$, $Ar_1$, and $Ar_2$ are the same as defined above.

In addition, the present disclosure provides an organic light emitting device including the compound represented by Chemical Formula 1. In one example, the present disclosure provides an organic light emitting device including: a first electrode; a second electrode provided opposite to the first electrode; and at least one layer of the organic material layers provided between the first electrode and the second electrode, wherein the at least one layer of the organic material layers includes a compound represented by Chemical Formula 1.

The organic material layer of the organic light emitting device of the present disclosure may have a single layer structure, or it may have a multilayered structure in which two or more organic material layers are stacked. For example, the organic light emitting device of the present disclosure may have a structure including a hole injection layer, a hole transport layer, a light emitting layer, an electron transport layer, an electron injection layer, and the like as the organic material layer. However, the structure of the organic light emitting device is not limited thereto, and it may include a smaller number of organic layers.

The organic material layer may include a hole injection layer, a hole transport layer, and a layer simultaneously performing hole injection and transport, wherein the hole injection layer, the hole transport layer, and the layer simultaneously performing hole injection and transport include a compound represented by Chemical Formula 1.

The organic material layer may include a light emitting layer, wherein the light emitting layer may include a compound represented by Chemical Formula 1.

The organic material layer may include an electron transport layer or an electron injection layer, wherein the electron transport layer or the electron injection layer includes a compound represented by Chemical Formula 1.

The electron transport layer, the electron injection layer, or a layer simultaneously performing electron transport and electron injection includes a compound represented by Chemical Formula 1.

The organic material layer includes a light emitting layer and an electron transport layer, wherein the electron transport layer may include a compound represented by Chemical Formula 1.

The organic light emitting device according to the present disclosure may be a normal type of organic light emitting device in which an anode, at least one organic material layer, and a cathode are sequentially stacked on a substrate. The organic light emitting device according to the present disclosure may be an inverted type of organic light emitting device in which a cathode, at least one organic material layer, and an anode are sequentially stacked on a substrate. For example, the structure of an organic light emitting device according to an embodiment of the present disclosure is illustrated in FIGS. 1 and 2.

FIG. 1 shows an example of an organic light emitting device including a substrate 1, an anode 2, a light emitting layer 3, and a cathode 4. In such a structure, the compound represented by Chemical Formula 1 may be included in the light emitting layer.

FIG. 2 shows an example of an organic light emitting device including a substrate 1, an anode 2, a hole injection layer 5, a hole transport layer 6, a light emitting layer 7, an electron transport layer 8, and a cathode 4. In such a structure, the compound represented by Chemical Formula 1 may be included in at least one layer of the hole injection layer, the hole transport layer, the light emitting layer, and the electron transport layer.

The organic light emitting device according to the present disclosure may be manufactured by materials and methods known in the art, except that at least one layer of the organic material layers includes the compound represented by Chemical Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer, and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer, and an anode material on a substrate.

In addition, the compound represented by Chemical Formula 1 may be formed into an organic layer by a solution coating method as well as a vacuum deposition method at the time of manufacturing an organic light emitting device. Herein, the solution coating method means a method of spin coating, dip coating, doctor blading, inkjet printing, screen printing, a spraying, roll coating, or the like, but is not limited thereto.

In addition to such a method, the organic light emitting device may be manufactured by sequentially depositing a cathode material, an organic material layer, and an anode material on a substrate (International Publication WO2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al and SnO$_2$:Sb; conductive polymers such as poly(3-methylthiophene), poly[3,4-(ethylene-1,2-dioxy)thiophene] (PEDOT), polypyrrole, and polyaniline; and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al and LiO$_2$/Al; and the like, but are not limited thereto.

The hole injection layer is a layer for injecting holes from the electrode, and the hole injection material is preferably a compound which has an ability to transport the holes, thus has a hole injecting effect in the anode and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrilehexaazatriphenylene-based organic material, a quinacridone-based organic material, a perylene-based organic material, anthraquinone, polyaniline, a polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, while having good quantum efficiency to fluorescence or phosphorescence. Specific examples thereof include: an 8-hydroxy-quinoline aluminum complex (Alq$_3$); a carbazole-based compound; a dimerized styryl compound; BAlq; a 10-hydroxybenzoquinoline-metal compound; a benzoxazole, benzothiazole, and benzimidazole-based compound; a poly(p-phenylene vinylene) (PPV)-based polymer; a spiro compound; polyfluorene; lubrene; and the like, but are not limited thereto.

The light emitting layer may include a host material and a dopant material. The host material may be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, fluoranthene compounds, and the like. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a stearylamine compound, a boron complex, a fluoranthene compound, a metal complex, and the like. Specific examples of the aromatic amine derivatives include substituted or unsubstituted fused aromatic ring derivatives having an arylamino group, and examples thereof include pyrene, anthracene, chrysene, periflanthene and the like, which have an arylamino group, and the stearylamine compound is a compound where at least one aryl vinyl group is substituted in a substituted or unsubstituted arylamine, in which one or more substituent groups selected from the group consisting of an aryl group, a silyl group, an alkyl group, a cycloalkyl group, and an arylamino group are substituted or unsubstituted. Specific examples thereof include styryl amine, styryl diamine, styryl triamine, styryl tetraamine, and the like, but are not limited thereto. Further, examples of the metal complex include an iridium complex, a platinum complex, and the like, but are not limited thereto.

The electron transport layer is a layer which receives electrons from an electron injection layer and transports the electrons to a light emitting layer, and an electron transport material is suitably a material which may receive electrons well from a cathode and transfer the electrons to a light emitting layer, and has large mobility for electrons. Specific examples thereof include: an Al complex of 8-hydroxyquinoline; a complex including Alq₃; an organic radical compound; a hydroxyflavone-metal complex; and the like, but are not limited thereto. The electron transport layer may be used with any desired cathode material, as used according to the related art. In particular, appropriate examples of the cathode material are typical materials having a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chloro gallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the material used.

In addition, the compound represented by Chemical Formula 1 may be included in an organic solar cell or an organic transistor in addition to an organic light emitting device.

The preparation of the compound represented by Chemical Formula 1 and the organic light emitting device including the same will be described in detail in the following examples. However, these examples are presented for illustrative purposes only, and the scope of the present disclosure is not limited thereto.

Preparation Example 1

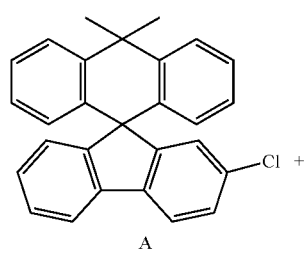

A

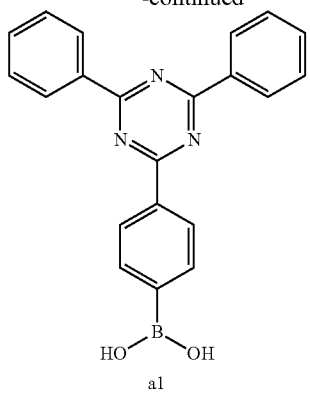

a1

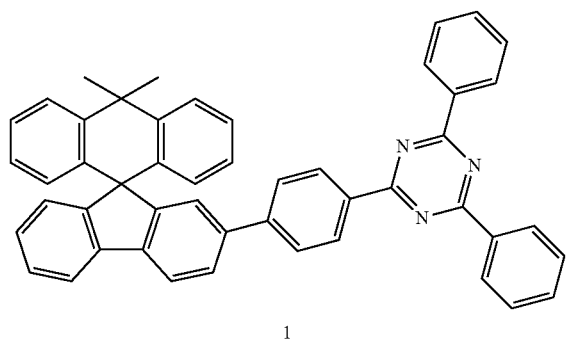

1

Compound A (8.64 g, 22.04 mmol) and Compound a1 (8.56 g, 24.24 mmol) were completely dissolved in 220 ml of tetrahydrofuran in a 500 ml-round bottom flask under a nitrogen atmosphere, and then a 2 M aqueous potassium carbonate solution (110 ml) was added thereto, tetrakis-(triphenylphosphine)palladium (0.76 g, 0.66 mmol) was added thereto, and the resulting mixture was heated and stirred for 4 hours. The temperature was lowered to room temperature, the aqueous layer was removed, and the resulting product was dried over anhydrous magnesium sulfate, and then concentrated under reduced pressure and recrystallized from 200 ml of tetrahydrofuran to give Compound 1 (12.46 g, 85%).

MS[M+H]⁺=666

Preparation Example 2

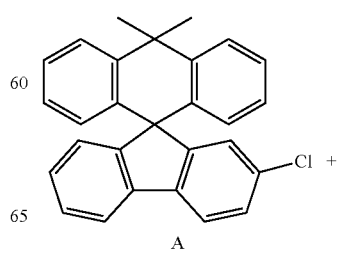

A

-continued

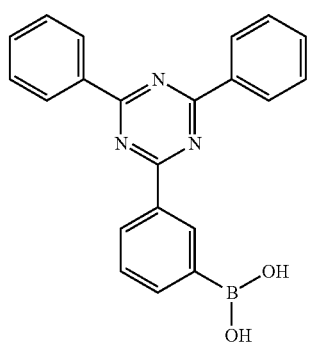

a2

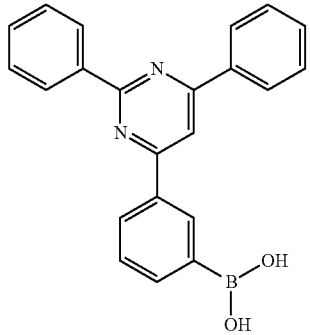

a3

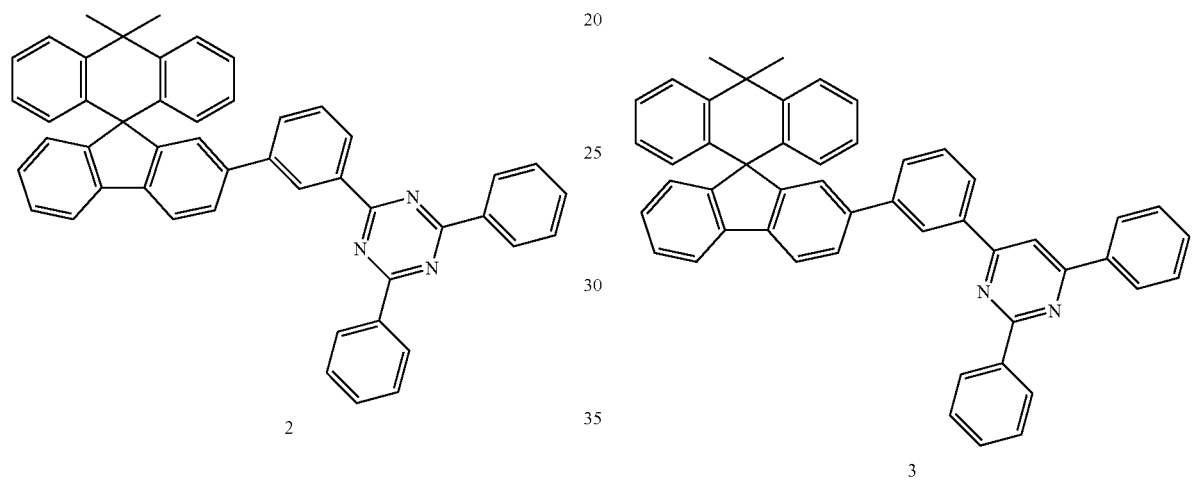

Compound A (7.15 g, 18.24 mmol) and Compound a2 were completely dissolved in 220 ml of tetrahydrofuran in a 500 ml-round bottom flask under a nitrogen atmosphere, and then a 2 M aqueous potassium carbonate solution (100 ml) was added thereto, tetrakis-(triphenylphosphine)palladium (0.63 g, 0.55 mmol) was added thereto, and the resulting mixture was heated and stirred for 3 hours. The temperature was lowered to room temperature, the aqueous layer was removed, and the resulting product was dried over anhydrous magnesium sulfate, and then concentrated under reduced pressure and recrystallized from 200 ml of ethyl acetate to give Compound 2 (8.26 g, 68%).

MS[M+H]$^+$=666

Preparation Example 3

Compound A (6.44 g, 16.43 mmol) and Compound a3 were completely dissolved in 220 ml of tetrahydrofuran in a 500 ml-round bottom flask under a nitrogen atmosphere, and then a 2 M aqueous potassium carbonate solution (110 ml) was added thereto, tetrakis-(triphenylphosphine)palladium (0.57 g, 0.49 mmol) was added thereto, and the resulting mixture was heated and stirred for 2 hours. The temperature was lowered to room temperature, the aqueous layer was removed, and the resulting product was dried over anhydrous magnesium sulfate, and then concentrated under reduced pressure and recrystallized from 230 ml of ethyl acetate to give Compound 3 (8.26 g, 68%).

MS[M+H]$^+$=665

Preparation Example 4

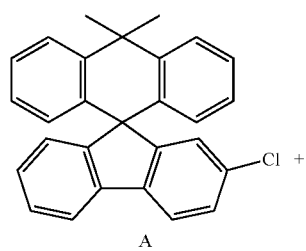

A

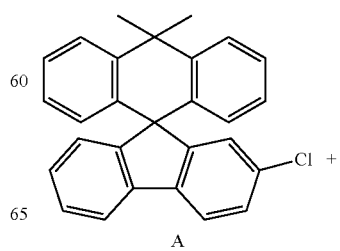

A

-continued

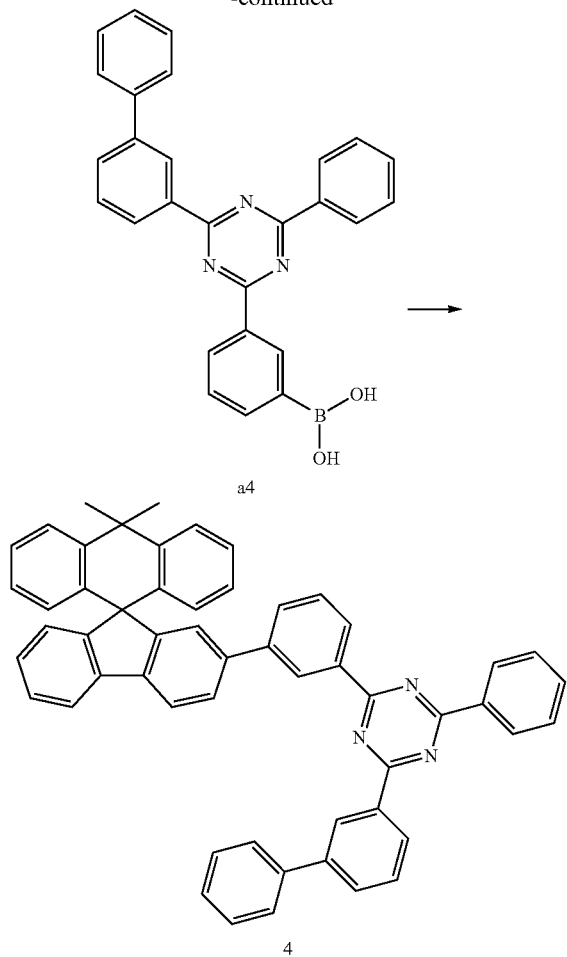

a4

4

Compound A (5.26 g, 13.42 mmol) and Compound a4 (6.33 g, 14.76 mmol) were completely dissolved in 180 ml of tetrahydrofuran in a 500 ml-round bottom flask under a nitrogen atmosphere, and then a 2 M aqueous potassium carbonate solution (90 ml) was added thereto, tetrakis-(triphenylphosphine)palladium (0.47 g, 0.40 mmol) was added thereto, and the resulting mixture was heated and stirred for 6 hours. The temperature was lowered to room temperature, the aqueous layer was removed, and the resulting product was dried over anhydrous magnesium sulfate, and then concentrated under reduced pressure and recrystallized from 420 ml of acetonitrile to give Compound 4 (7.78 g, 78%).
MS[M+H]$^+$=742

Preparation Example 5

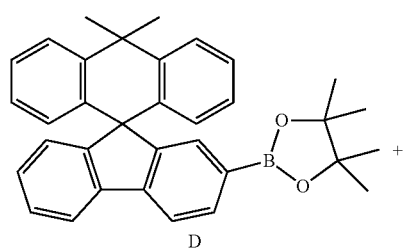

D

-continued

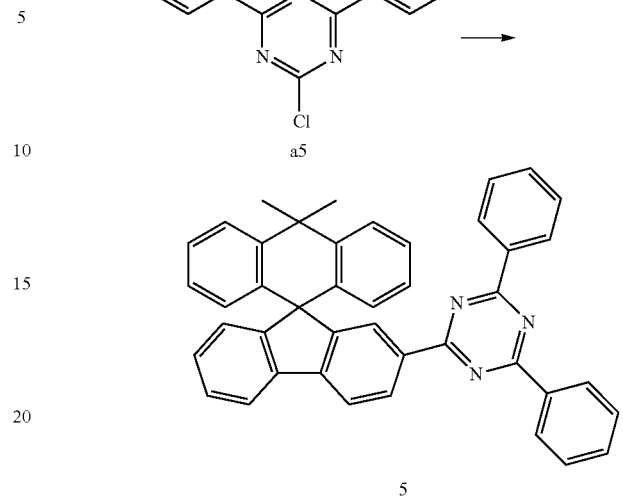

a5

5

Compound D (6.33 g, 14.76 mmol) and Compound a5 (5.26 g, 13.42 mmol) were completely dissolved in 180 ml of tetrahydrofuran in a 500 ml-round bottom flask under a nitrogen atmosphere, and then a 2 M aqueous potassium carbonate solution (90 ml) was added thereto, bis(tri-t-butylphosphine)palladium (0.47 g, 0.40 mmol) was added thereto, and the resulting mixture was heated and stirred for 6 hours. The temperature was lowered to room temperature, the aqueous layer was removed, and the resulting product was dried over anhydrous magnesium sulfate, and then concentrated under reduced pressure and recrystallized from 420 ml of acetonitrile to give Compound 5 (10.07 g, 69%).
MS[M+H]$^+$=590

Preparation Example 6

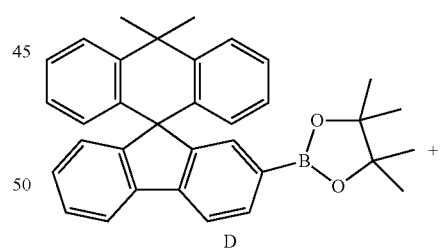

D

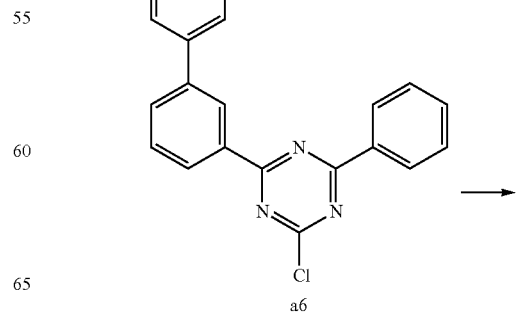

a6

-continued

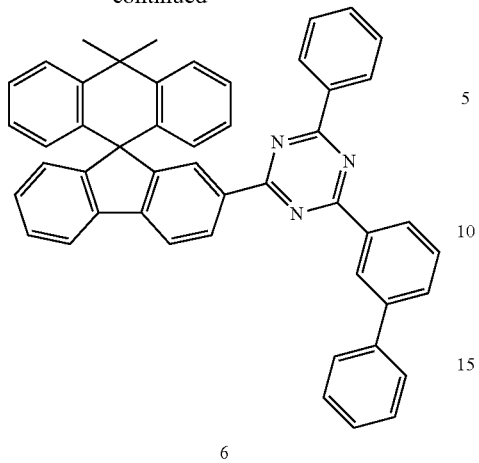

6

Compound D (8.15 g, 16.84 mmol) and Compound a6 (6.08 g, 17.73 mmol) were completely dissolved in 200 ml of tetrahydrofuran in a 500 ml-round bottom flask under a nitrogen atmosphere, and then a 2 M aqueous potassium carbonate solution (100 ml) was added thereto, bis(tri-t-butylphosphine)palladium (0.61 g, 0.53 mmol) was added thereto, and the resulting mixture was heated and stirred for 3 hours. The temperature was lowered to room temperature, the aqueous layer was removed, and the resulting product was dried over anhydrous magnesium sulfate, and then concentrated under reduced pressure and recrystallized from 320 ml of ethyl acetate to give Compound 6 (7.65 g, 65%).

MS[M+H]$^{30}$ =666

Preparation Example 7

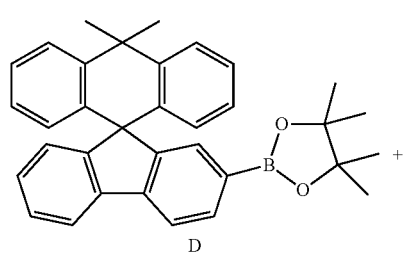

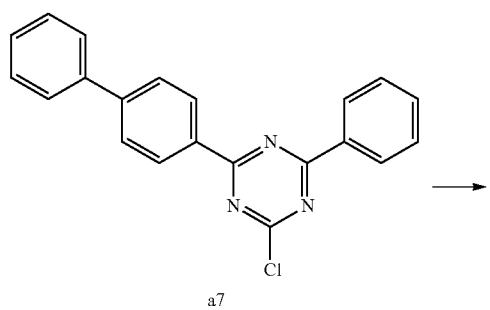

-continued

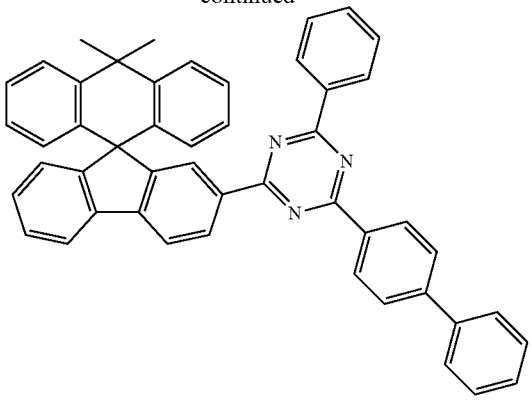

7

Compound D (7.32 g, 15.12 mmol) and Compound a7 (5.46 g, 15.92 mmol) were completely dissolved in 220 ml of tetrahydrofuran in a 500 ml-round bottom flask under a nitrogen atmosphere, and then a 2 M aqueous potassium carbonate solution (110 ml) was added thereto, bis(tri-t-butylphosphine)palladium (0.55 g, 0.48 mmol) was added thereto, and the resulting mixture was heated and stirred for 6 hours. The temperature was lowered to room temperature, the aqueous layer was removed, and the resulting product was dried over anhydrous magnesium sulfate, and then concentrated under reduced pressure and recrystallized from 260 ml of acetonitrile to give Compound 7 (8.12 g, 77%).

MS[M+H]$^+$=666

Preparation Example 8

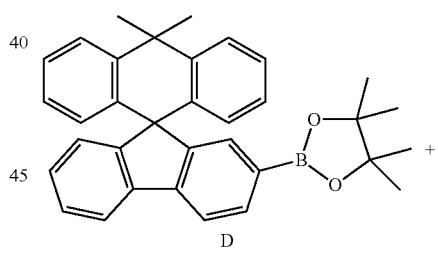

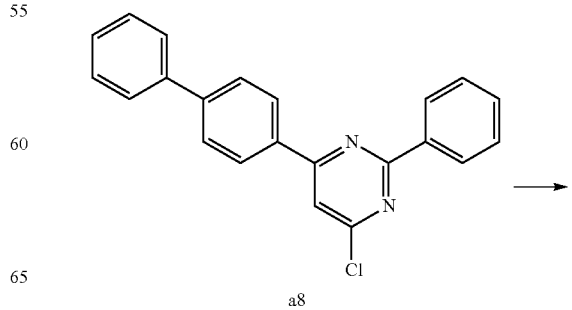

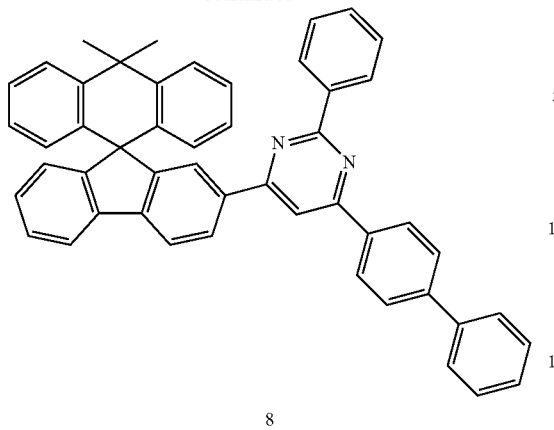

8

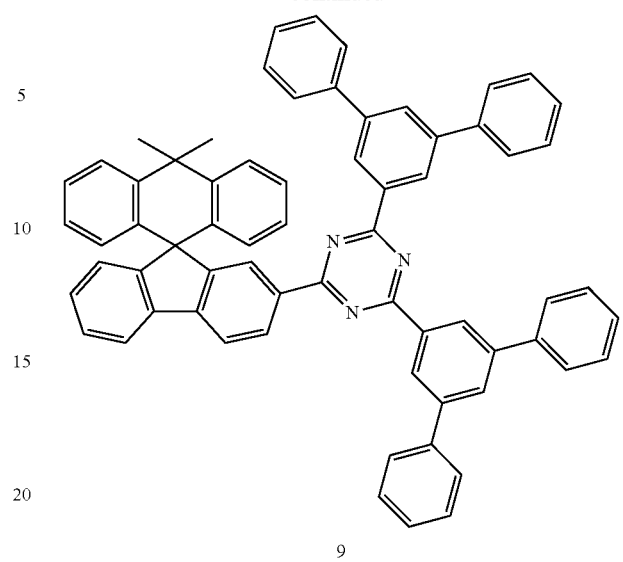

9

Compound D (10.15 g, 20.97 mmol) and Compound a8 (7.55 g, 22.08 mmol) were completely dissolved in 240 ml of tetrahydrofuran in a 500 ml-round bottom flask under a nitrogen atmosphere, and then a 2 M aqueous potassium carbonate solution (120 ml) was added thereto, bis(tri-t-butylphosphine)palladium (0.77 g, 0.66 mmol) was added thereto, and the resulting mixture was heated and stirred for 4 hours. The temperature was lowered to room temperature, the aqueous layer was removed, and the resulting product was dried over anhydrous magnesium sulfate, and then concentrated under reduced pressure and recrystallized from 280 ml of acetonitrile to give Compound 8 (11.16 g, 76%).

MS[M+H]$^+$=665

Preparation Example 9

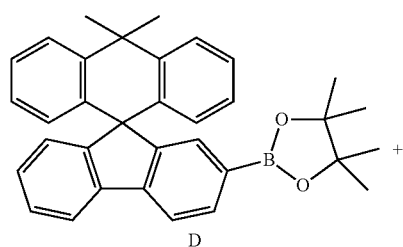

D

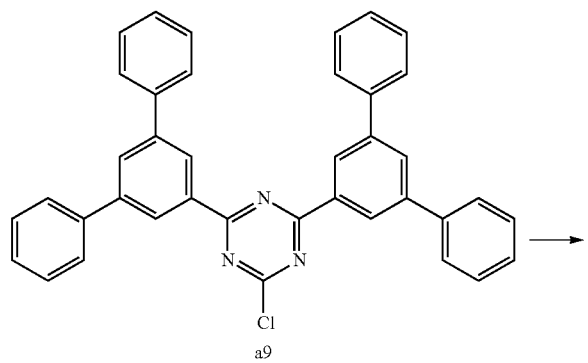

a9

Compound D (3.85 g, 7.96 mmol) and Compound a9 (4.79 g, 8.37 mmol) were completely dissolved in 120 ml of tetrahydrofuran in a 500 ml-round bottom flask under a nitrogen atmosphere, and then a 2 M aqueous potassium carbonate solution (60 ml) was added thereto, bis(tri-t-butylphosphine)palladium (0.47 g, 0.40 mmol) was added thereto, and the resulting mixture was heated and stirred for 11 hours. The temperature was lowered to room temperature, the aqueous layer was removed, and the resulting product was dried over anhydrous magnesium sulfate, and then concentrated under reduced pressure and recrystallized from 320 ml of acetonitrile to give Compound 9 (5.07 g, 68%).

MS[M+H]$^+$=894

Preparation Example 10

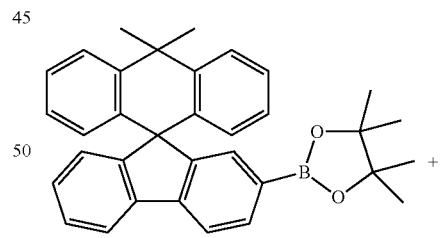

D

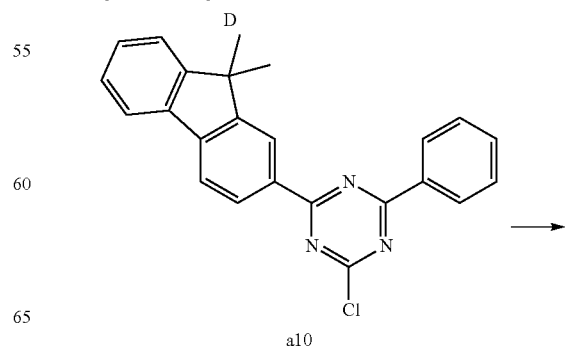

a10

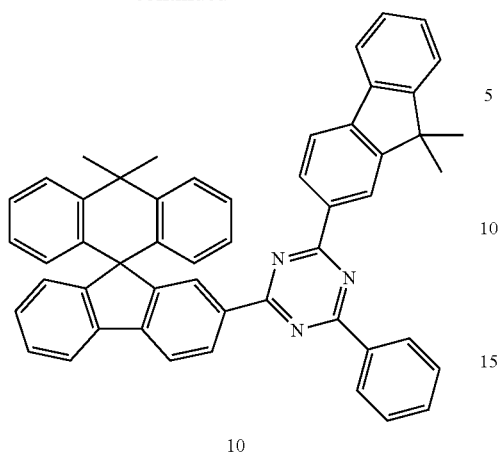

10

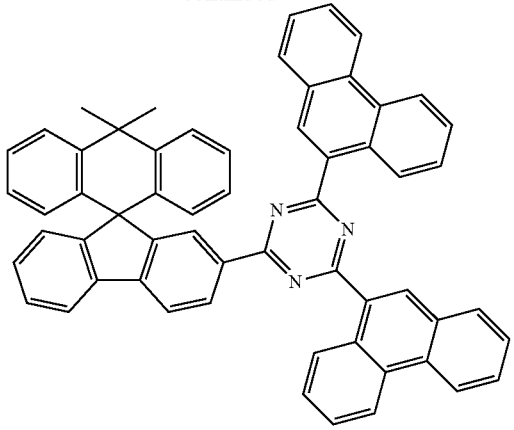

11

Compound D (6.31 g, 13.04 mmol) and Compound a10 (5.27 g, 13.72 mmol) were completely dissolved in 160 ml of tetrahydrofuran in a 500 ml-round bottom flask under a nitrogen atmosphere, and then a 2 M aqueous potassium carbonate solution (80 ml) was added thereto, bis(tri-t-butylphosphine)palladium (0.48 g, 0.41 mmol) was added thereto, and the resulting mixture was heated and stirred for 4 hours. The temperature was lowered to room temperature, the aqueous layer was removed, and the resulting product was dried over anhydrous magnesium sulfate, and then concentrated under reduced pressure and recrystallized from 290 ml of ethyl acetate to give Compound 10 (6.62 g, 68%).

MS[M+H]$^+$=706

Compound D (4.56 g, 9.42 mmol) and Compound a11 (4.63 g, 9.91 mmol) were completely dissolved in 180 ml of tetrahydrofuran in a 500 ml-round bottom flask under a nitrogen atmosphere, and then a 2 M aqueous potassium carbonate solution (90 ml) was added thereto, bis(tri-t-butylphosphine)palladium (0.34 g, 0.30 mmol) was added thereto, and the resulting mixture was heated and stirred for 9 hours. The temperature was lowered to room temperature, the aqueous layer was removed, and the resulting product was dried over anhydrous magnesium sulfate, and then concentrated under reduced pressure and recrystallized from 260 ml of ethyl acetate to give Compound 11 (5.88 g, 75%).

MS[M+H]$^+$=790

Preparation Example 11

Preparation Example 12

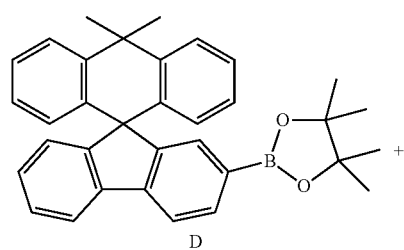

D

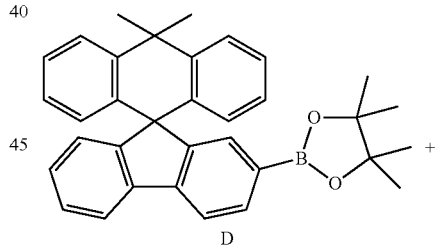

D

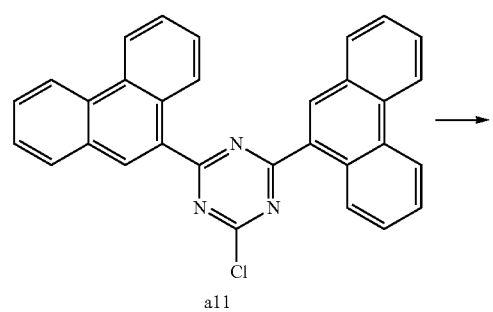

a11

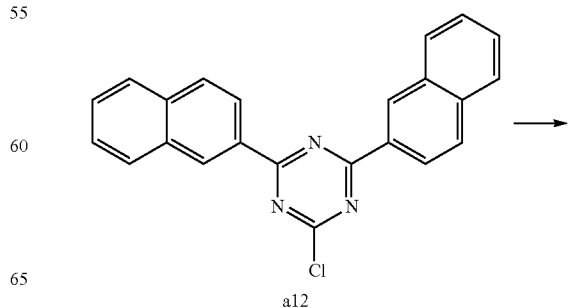

a12

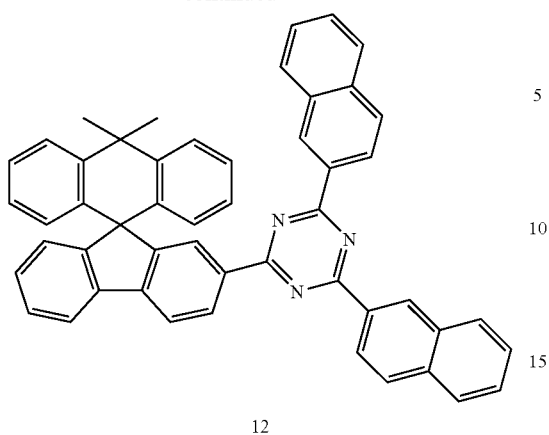

12

Compound D (6.55 g, 13.54 mmol) and Compound a12 (5.23 g, 14.25 mmol) were completely dissolved in 180 ml of tetrahydrofuran in a 500 ml-round bottom flask under a nitrogen atmosphere, and then a 2 M aqueous potassium carbonate solution (90 ml) was added thereto, bis(tri-t-butylphosphine)palladium (0.49 g, 0.43 mmol) was added thereto, and the resulting mixture was heated and stirred for 6 hours. The temperature was lowered to room temperature, the aqueous layer was removed, and the resulting product was dried over anhydrous magnesium sulfate, and then concentrated under reduced pressure and recrystallized from 280 ml of ethyl acetate to give Compound 12 (7.52 g, 76%).

MS[M+H]$^+$=690

Preparation Example 13

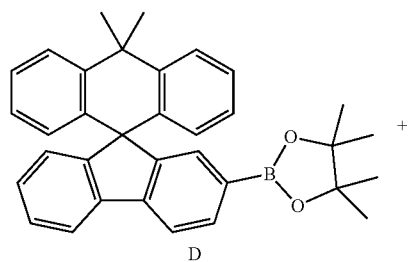

D

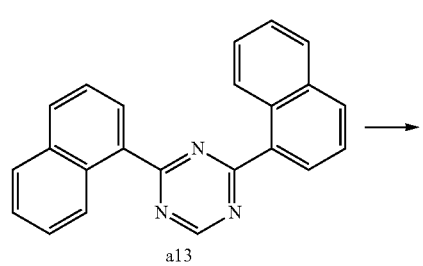

a13

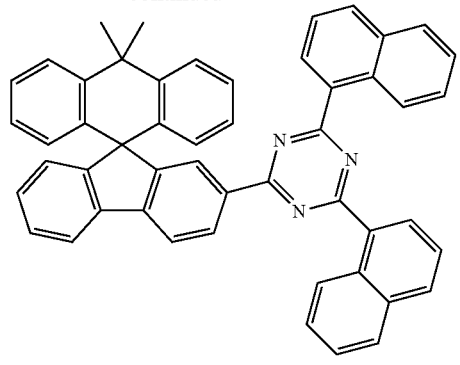

13

Compound D (5.99 g, 12.37 mmol) and Compound a13 (4.78 g, 13.02 mmol) were completely dissolved in 200 ml of tetrahydrofuran in a 500 ml-round bottom flask under a nitrogen atmosphere, and then a 2 M aqueous potassium carbonate solution (100 ml) was added thereto, bis(tri-t-butylphosphine)palladium (0.45 g, 0.39 mmol) was added thereto, and the resulting mixture was heated and stirred for 7 hours. The temperature was lowered to room temperature, the aqueous layer was removed, and the resulting product was dried over anhydrous magnesium sulfate, and then concentrated under reduced pressure and recrystallized from 250 ml of ethyl acetate to give Compound 13 (6.42 g, 71%).

MS[M+H]$^+$=690

Preparation Example 14

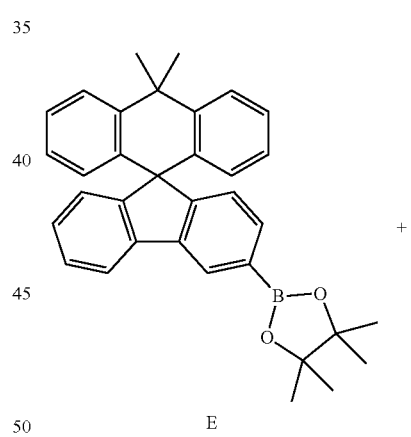

E

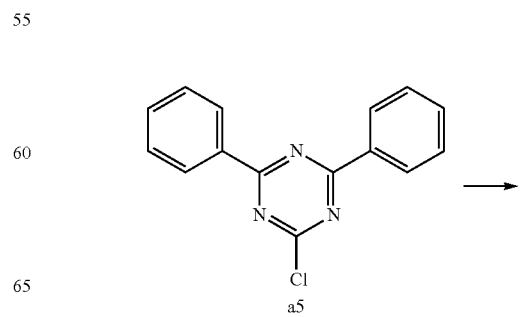

a5

-continued

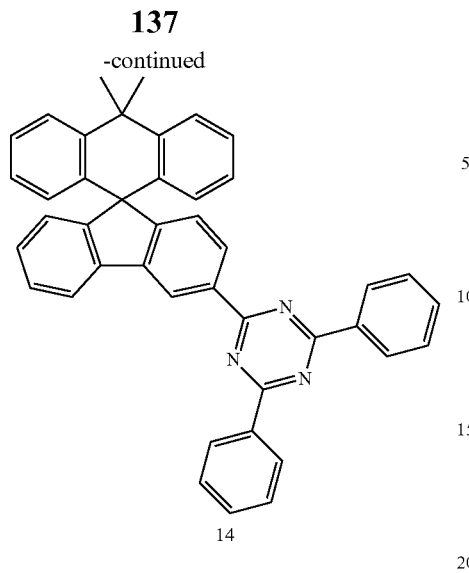

14

Compound E (6.33 g, 14.76 mmol) and Compound a5 (5.26 g, 13.42 mmol) were completely dissolved in 180 ml of tetrahydrofuran in a 500 ml-round bottom flask under a nitrogen atmosphere, and then a 2 M aqueous potassium carbonate solution (90 ml) was added thereto, bis(tri-t-butylphosphine)palladium (0.47 g, 0.40 mmol) was added thereto, and the resulting mixture was heated and stirred for 6 hours. The temperature was lowered to room temperature, the aqueous layer was removed, and the resulting product was dried over anhydrous magnesium sulfate, and then concentrated under reduced pressure and recrystallized from 420 ml of acetonitrile to give Compound 14 (10.07 g, 69%).

MS[M+H]$^+$=590

Preparation Example 15

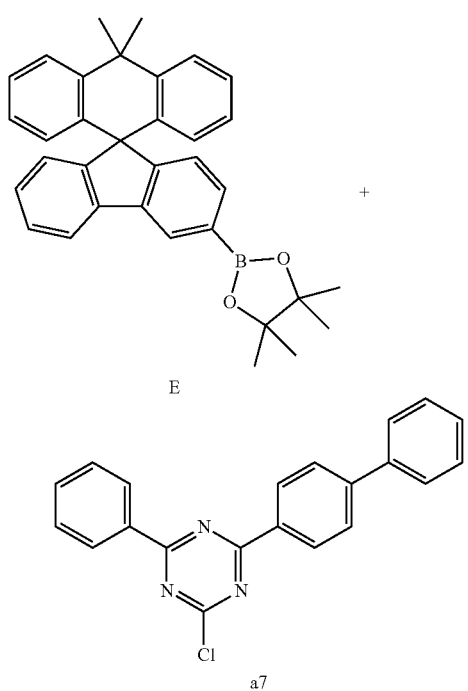

-continued

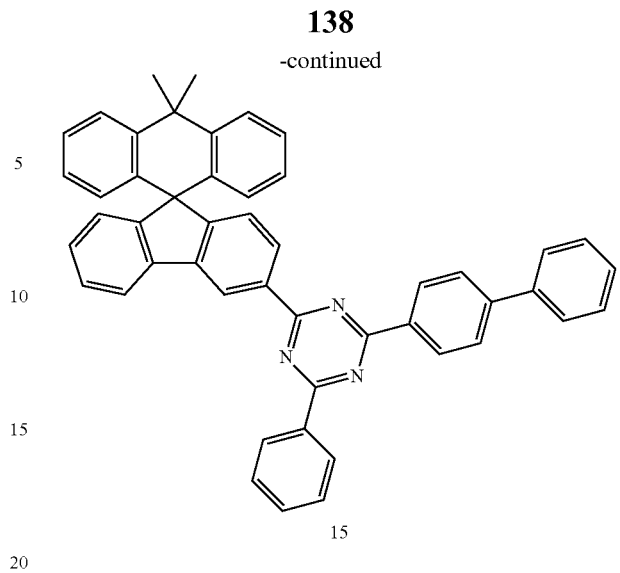

15

Compound E (6.92 g, 14.29 mmol) and Compound a7 (5.16 g, 15.04 mmol) were completely dissolved in 140 ml of tetrahydrofuran in a 500 ml-round bottom flask under a nitrogen atmosphere, and then a 2 M aqueous potassium carbonate solution (70 ml) was added thereto, bis(tri-t-butylphosphine)palladium (0.52 g, 0.45 mmol) was added thereto, and the resulting mixture was heated and stirred for 3 hours. The temperature was lowered to room temperature, the aqueous layer was removed, and the resulting product was dried over anhydrous magnesium sulfate, and then concentrated under reduced pressure and recrystallized from 250 ml of ethyl acetate to give Compound 15 (7.15 g, 71%).

MS[M+H]$^+$=666

Preparation Example 16

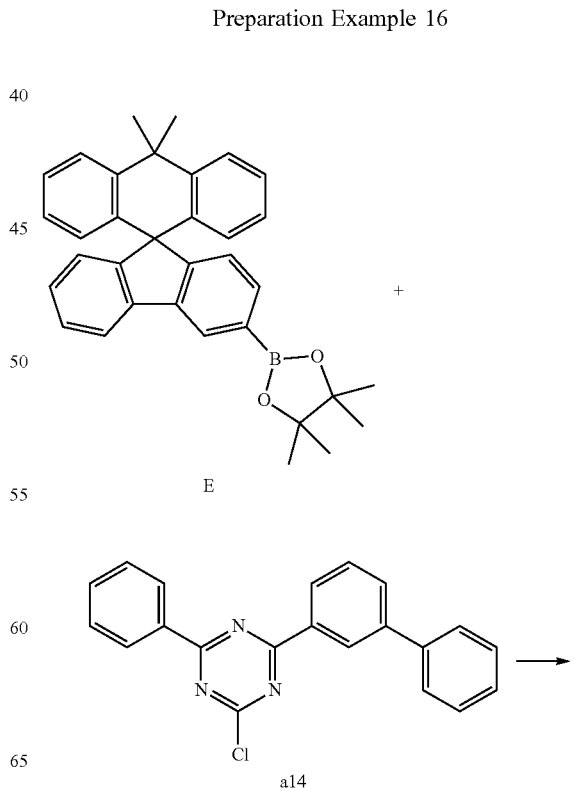

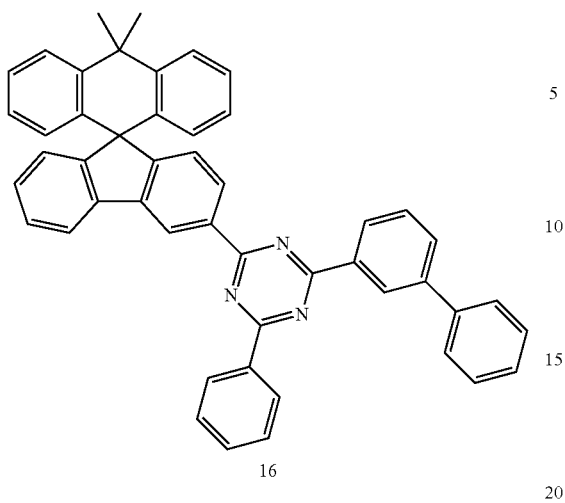

16

Compound E (6.39 g, 13.21 mmol) and Compound a14 (4.77 g, 13.91 mmol) were completely dissolved in 160 ml of tetrahydrofuran in a 500 ml-round bottom flask under a nitrogen atmosphere, and then a 2 M aqueous potassium carbonate solution (80 ml) was added thereto, bis(tri-t-butylphosphine)palladium (0.48 g, 0.42 mmol) was added thereto, and the resulting mixture was heated and stirred for 4 hours. The temperature was lowered to room temperature, the aqueous layer was removed, and the resulting product was dried over anhydrous magnesium sulfate, and then concentrated under reduced pressure and recrystallized from 280 ml of ethyl acetate to give Compound 16 (5.86 g, 63%).

MS[M+H]$^+$=666

Preparation Example 17

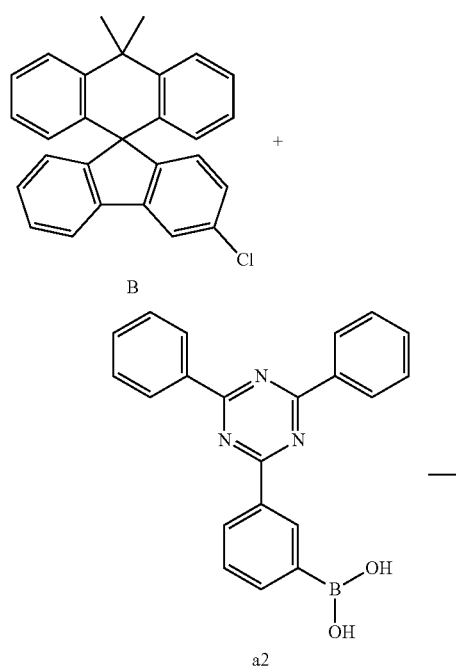

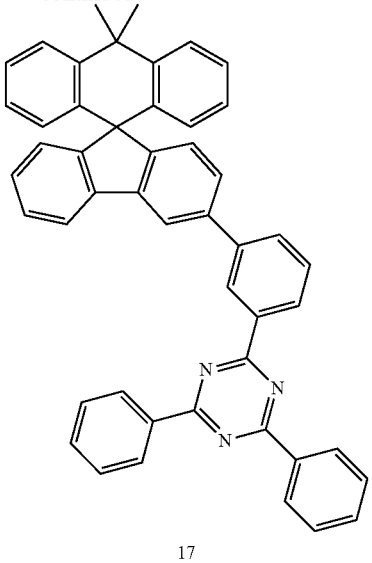

17

Compound B (6.12 g, 15.61 mmol) and Compound a2 (5.24 g, 14.83 mmol) were completely dissolved in 160 ml of tetrahydrofuran in a 500 ml-round bottom flask under a nitrogen atmosphere, and then a 2 M aqueous potassium carbonate solution (80 ml) was added thereto, tetrakis-(triphenylphosphine)palladium (0.54 g, 0.47 mmol) was added thereto, and the resulting mixture was heated and stirred for 2 hours. The temperature was lowered to room temperature, the aqueous layer was removed, and the resulting product was dried over anhydrous magnesium sulfate, and then concentrated under reduced pressure and recrystallized from 210 ml of ethyl acetate to give Compound 17 (6.25 g, 60%).

MS[M+H]$^+$=666

Preparation Example 18

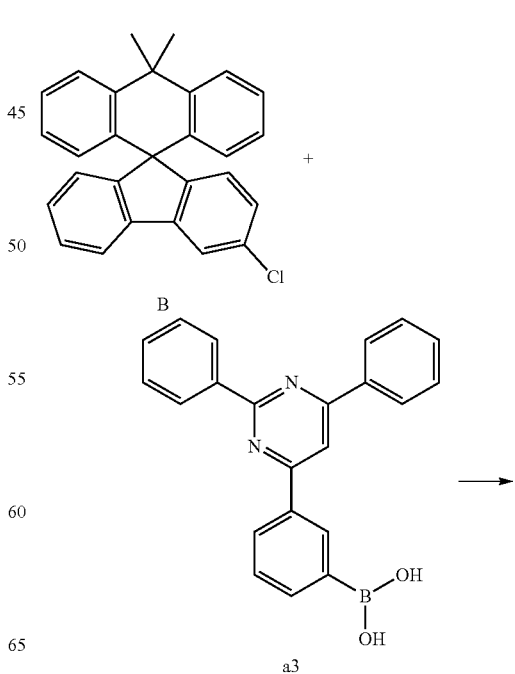

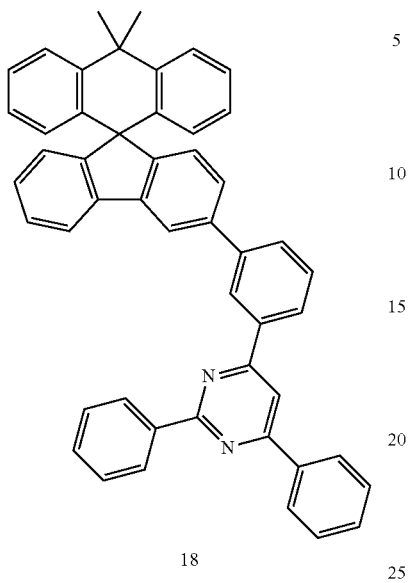

18

Compound B (5.86 g, 14.95 mmol) and Compound a3 (5.01 g, 14.20 mmol) were completely dissolved in 140 ml of tetrahydrofuran in a 500 ml-round bottom flask under a nitrogen atmosphere, and then a 2 M aqueous potassium carbonate solution (70 ml) was added thereto, tetrakis-(triphenylphosphine)palladium (0.52 g, 0.45 mmol) was added thereto, and the resulting mixture was heated and stirred for 3 hours. The temperature was lowered to room temperature, the aqueous layer was removed, and the resulting product was dried over anhydrous magnesium sulfate, and then concentrated under reduced pressure and recrystallized from 180 ml of ethyl acetate to give Compound 18 (5.29 g, 53).

MS[M+H]$^+$=666

Preparation Example 19

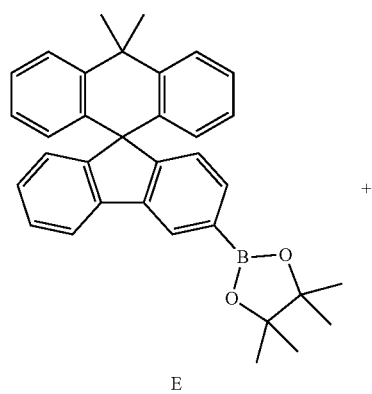

E

+

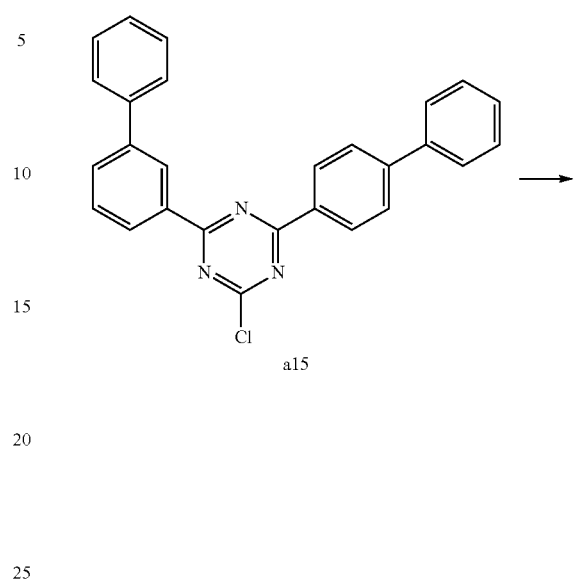

a15

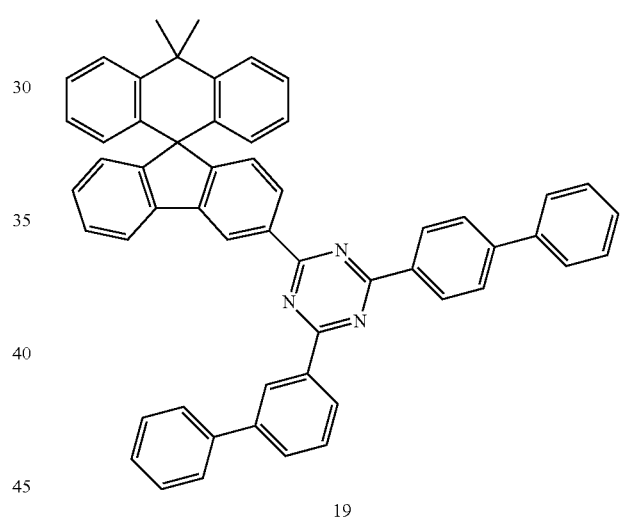

19

Compound E (5.45 g, 11.27 mmol) and Compound a15 (4.97 g, 11.86 mmol) were completely dissolved in 120 ml of tetrahydrofuran in a 500 ml-round bottom flask under a nitrogen atmosphere, and then a 2 M aqueous potassium carbonate solution (60 ml) was added thereto, bis(tri-t-butylphosphine)palladium (0.41 g, 0.36 mmol) was added thereto, and the resulting mixture was heated and stirred for 6 hours. The temperature was lowered to room temperature, the aqueous layer was removed, and the resulting product was dried over anhydrous magnesium sulfate, and then concentrated under reduced pressure and recrystallized from 230 ml of ethyl acetate to give Compound 19 (7.16 g, 81%).

MS[M+H]$^+$=666

Preparation Example 20

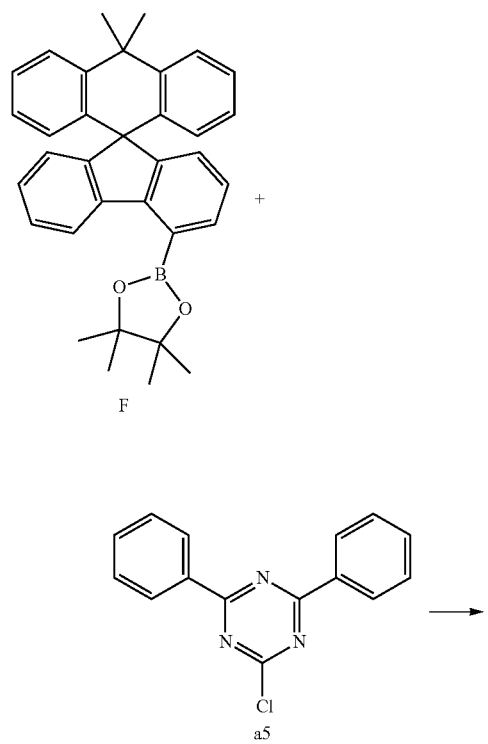

Compound F (7.39 g, 15.26 mmol) and Compound a5 (4.29 g, 16.07 mmol) were completely dissolved in 180 ml of tetrahydrofuran in a 500 ml-round bottom flask under a nitrogen atmosphere, and then a 2 M aqueous potassium carbonate solution (90 ml) was added thereto, bis(tri-t-butylphosphine)palladium (0.56 g, 0.48 mmol) was added thereto, and the resulting mixture was heated and stirred for 4 hours. The temperature was lowered to room temperature, the aqueous layer was removed, and the resulting product was dried over anhydrous magnesium sulfate, and then concentrated under reduced pressure and recrystallized from 290 ml of ethyl acetate to give Compound 20 (6.11 g, 64%).

MS[M+H]$^+$=590

Preparation Example 21

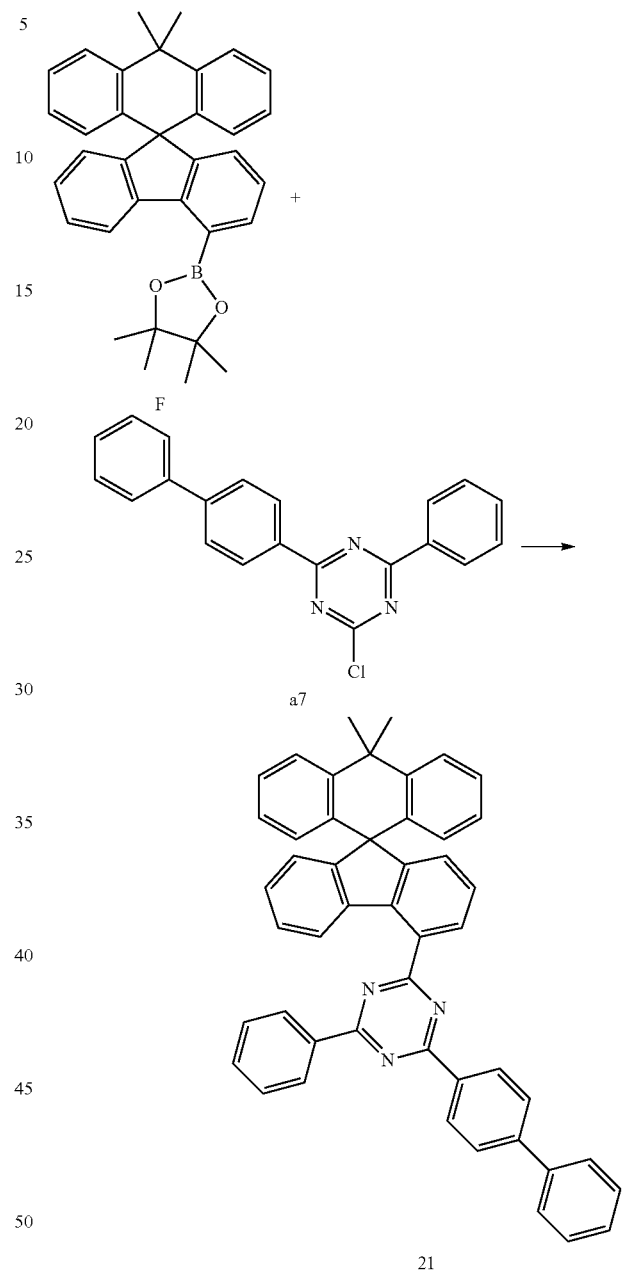

Compound F (8.15 g, 16.84 mmol) and Compound a7 (6.08 g, 17.73 mmol) were completely dissolved in 220 ml of tetrahydrofuran in a 500 ml-round bottom flask under a nitrogen atmosphere, and then a 2 M aqueous potassium carbonate solution (110 ml) was added thereto, bis(tri-t-butylphosphine)palladium (0.61 g, 0.53 mmol) was added thereto, and the resulting mixture was heated and stirred for 3 hours. The temperature was lowered to room temperature, the aqueous layer was removed, and the resulting product was dried over anhydrous magnesium sulfate, and then concentrated under reduced pressure and recrystallized from 230 ml of tetrahydrofuran to give Compound 21 (7.97 g, 68%).

MS[M+H]$^+$=666

Preparation Example 22

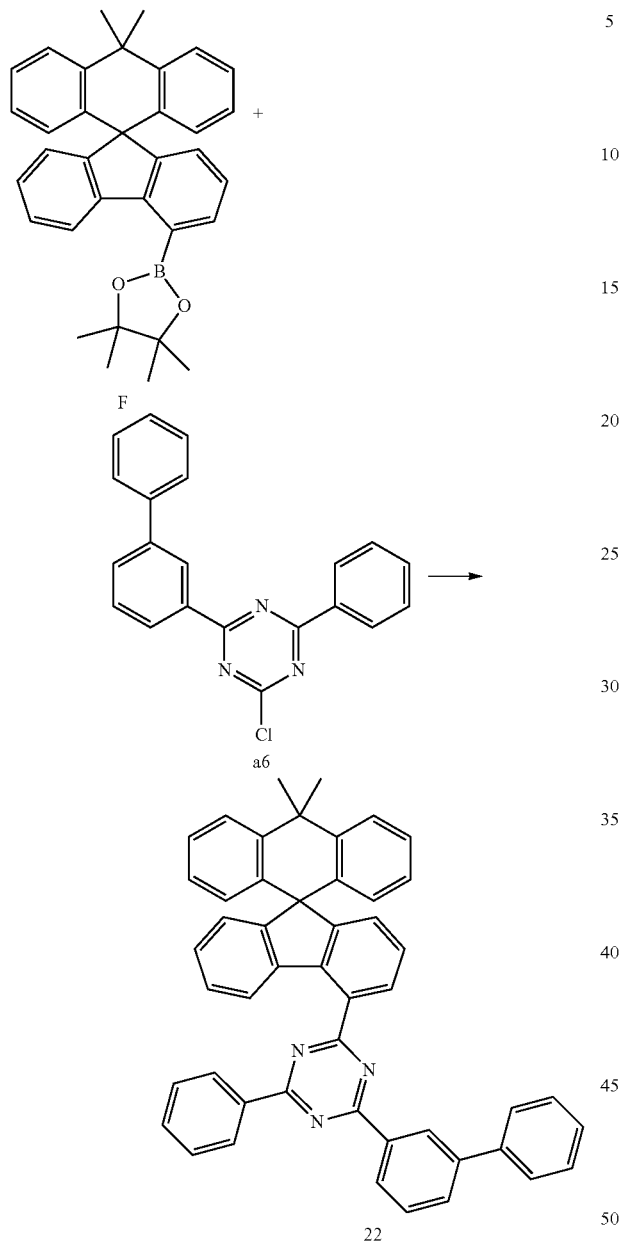

Compound F (4.47 g, 15.43 mmol) and Compound a6 (5.57 g, 16.24 mmol) were completely dissolved in 180 ml of tetrahydrofuran in a 500 ml-round bottom flask under a nitrogen atmosphere, and then a 2 M aqueous potassium carbonate solution (90 ml) was added thereto, bis(tri-t-butylphosphine)palladium (0.56 g, 0.49 mmol) was added thereto, and the resulting mixture was heated and stirred for 4 hours. The temperature was lowered to room temperature, the aqueous layer was removed, and the resulting product was dried over anhydrous magnesium sulfate, and then concentrated under reduced pressure and recrystallized from 190 ml of tetrahydrofuran to give Compound 22 (6.08 g, 56%).

MS[M+H]$^+$=666

Preparation Example 23

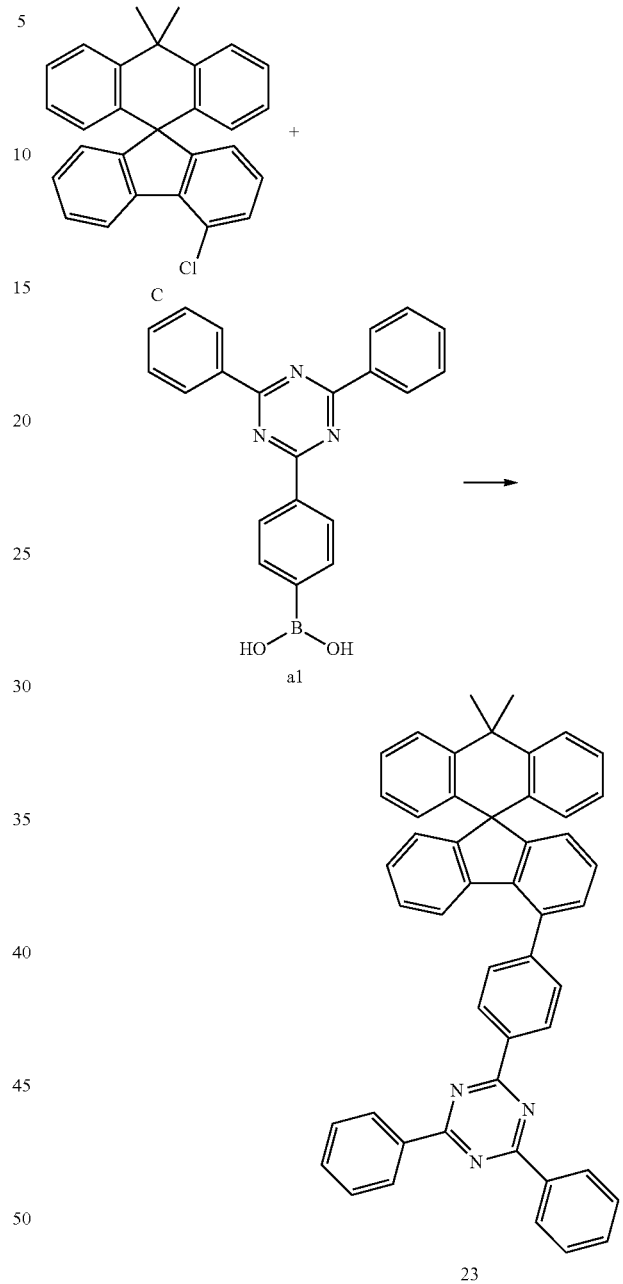

Compound C (6.13 g, 15.64 mmol) and Compound a1 (5.24 g, 14.86 mmol) were completely dissolved in 240 ml of tetrahydrofuran in a 500 ml-round bottom flask under a nitrogen atmosphere, and then a 2 M aqueous potassium carbonate solution (120 ml) was added thereto, tetrakis-(triphenylphosphine)palladium (0.54 g, 0.47 mmol) was added thereto, and the resulting mixture was heated and stirred for 7 hours. The temperature was lowered to room temperature, the aqueous layer was removed, and the resulting product was dried over anhydrous magnesium sulfate, and then concentrated under reduced pressure and recrystallized from 240 ml of tetrahydrofuran to give Compound 23 (8.82 g, 85%).

MS[M+H]$^+$=666

Preparation Example 24

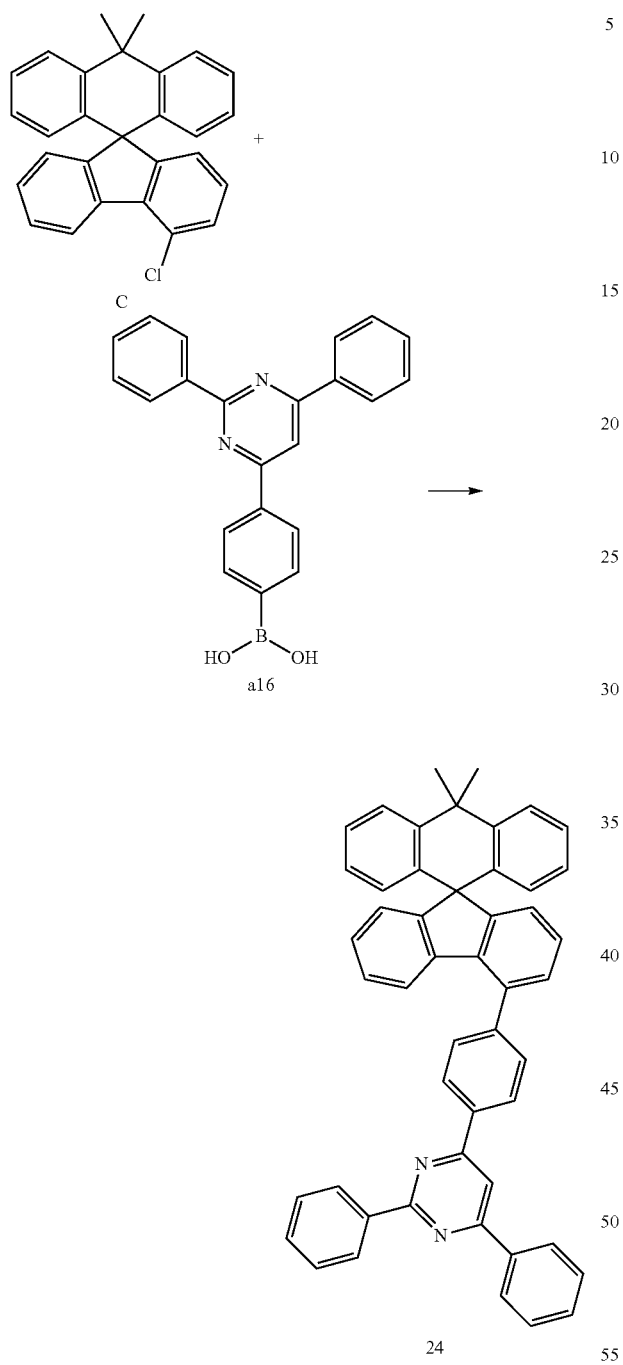

Compound C (6.13 g, 15.64 mmol) and Compound a16 (5.24 g, 14.86 mmol) were completely dissolved in 240 ml of tetrahydrofuran in a 500 ml-round bottom flask under a nitrogen atmosphere, and then a 2 M aqueous potassium carbonate solution (120 ml) was added thereto, tetrakis-(triphenylphosphine)palladium (0.54 g, 0.47 mmol) was added thereto, and the resulting mixture was heated and stirred for 7 hours. The temperature was lowered to room temperature, the aqueous layer was removed, and the resulting product was dried over anhydrous magnesium sulfate, and then concentrated under reduced pressure and recrystallized from 240 ml of tetrahydrofuran to give Compound 24 (8.82 g, 85%).

MS[M+H]$^+$=666

Preparation Example 25

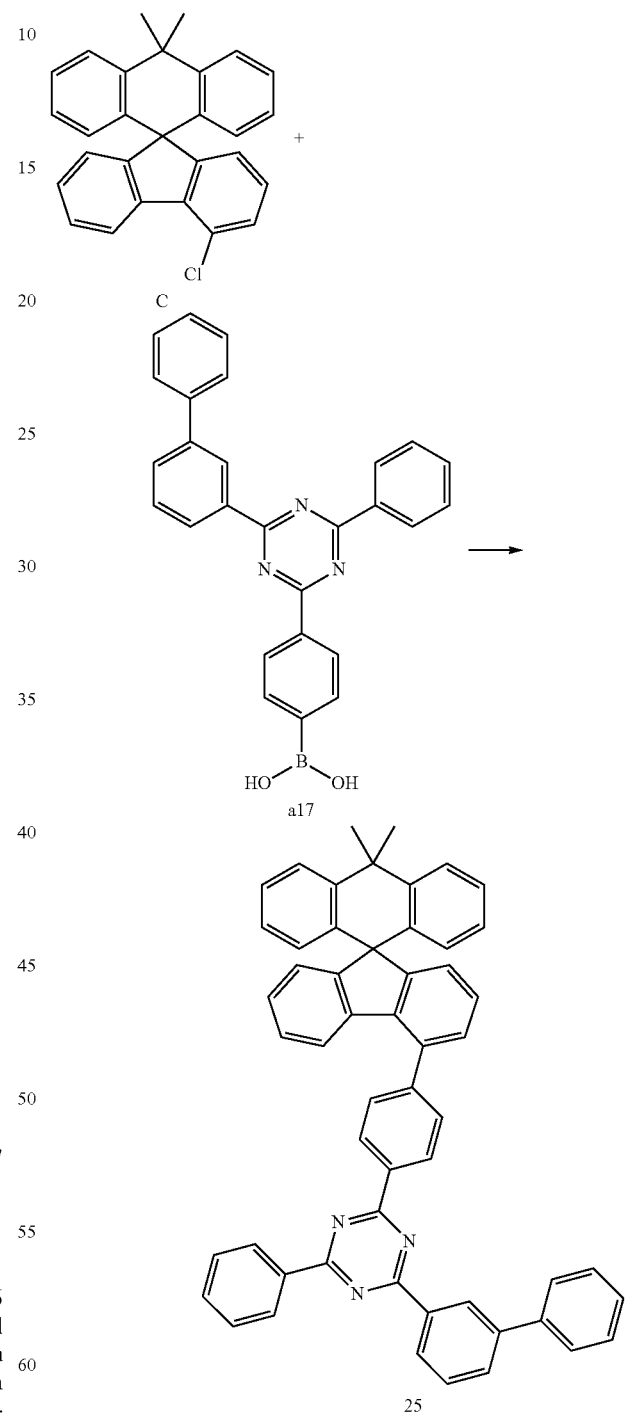

Compound C (5.71 g, 14.57 mmol) and Compound a17 (6.56 g, 15.29 mmol) were completely dissolved in 220 ml of tetrahydrofuran in a 500 ml-round bottom flask under a nitrogen atmosphere, and then a 2 M aqueous potassium carbonate solution (110 ml) was added thereto, tetrakis-(triphenylphosphine)palladium (0.50 g, 0.44 mmol) was added thereto, and the resulting mixture was heated and stirred for 5 hours. The temperature was lowered to room temperature, the aqueous layer was removed, and the resulting product was dried over anhydrous magnesium sulfate, and then concentrated under reduced pressure and recrystallized from 210 ml of tetrahydrofuran to give Compound 25 (7.59 g, 70%).

MS[M+H]$^+$=742

Preparation Example 26

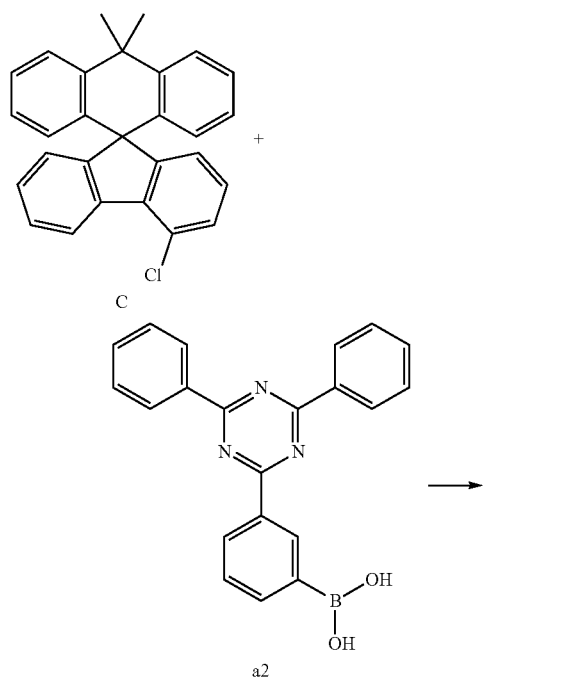

Compound C (4.88 g, 12.45 mmol) and Compound a2 (4.61 g, 13.07 mmol) were completely dissolved in 200 ml of tetrahydrofuran in a 500 ml-round bottom flask under a nitrogen atmosphere, and then a 2 M aqueous potassium carbonate solution (100 ml) was added thereto, tetrakis-(triphenylphosphine)palladium (0.43 g, 0.37 mmol) was added thereto, and the resulting mixture was heated and stirred for 4 hours. The temperature was lowered to room temperature, the aqueous layer was removed, and the resulting product was dried over anhydrous magnesium sulfate, and then concentrated under reduced pressure and recrystallized from 210 ml of tetrahydrofuran to give Compound 26 (6.66 g, 80%).

MS[M+H]$^+$=666

Preparation Example 27

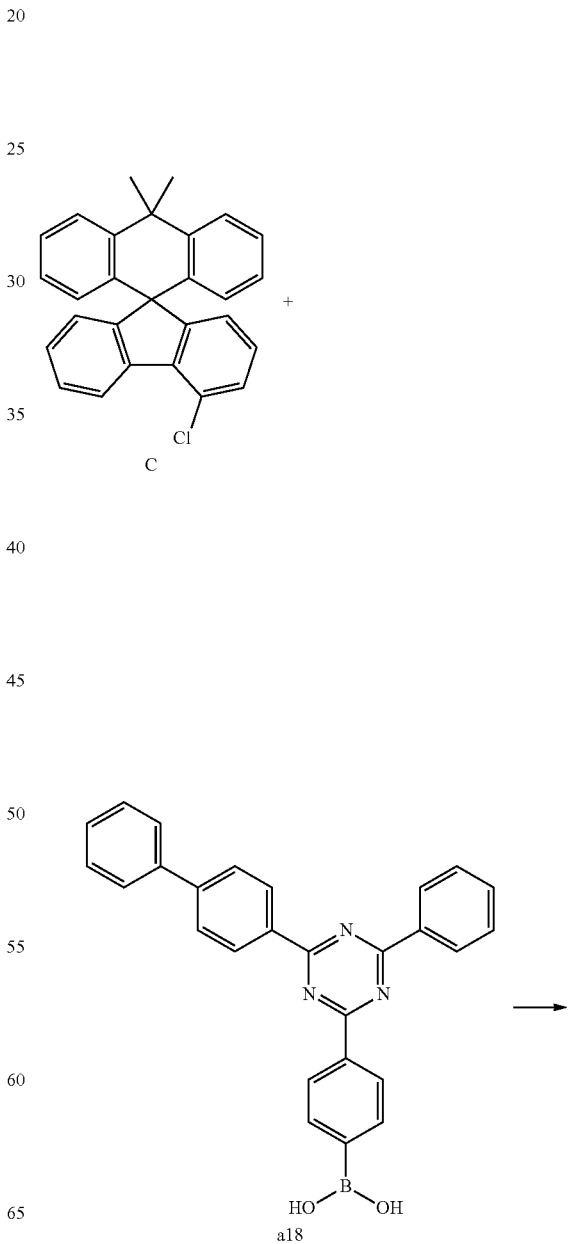

151

-continued

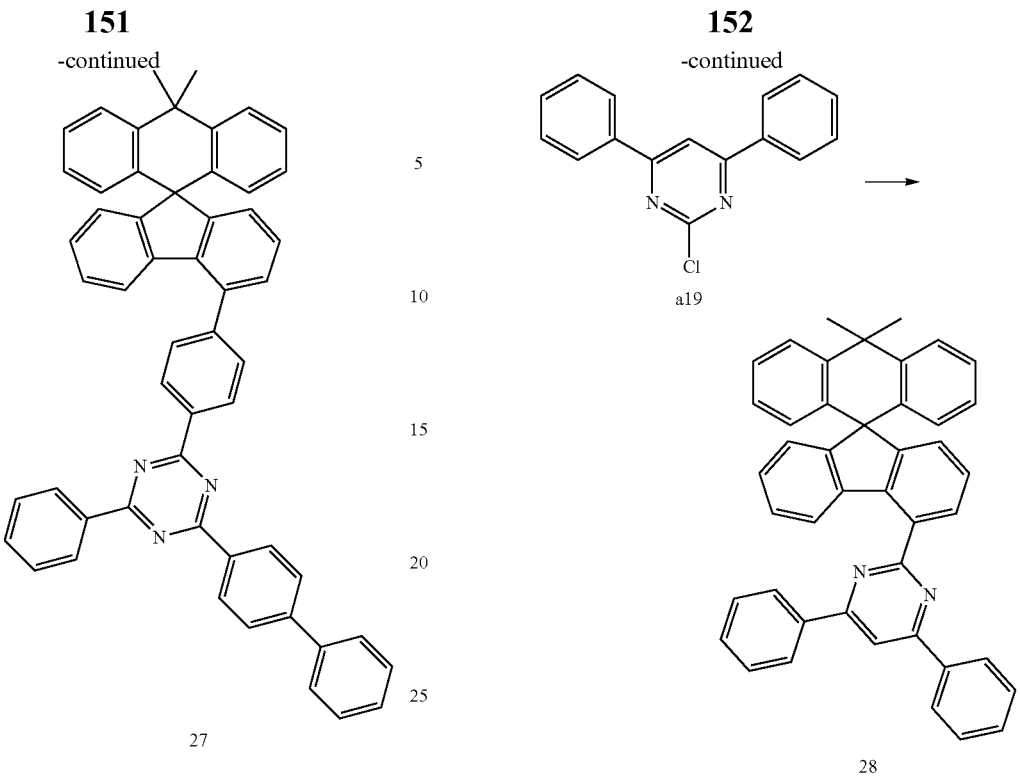

27

Compound C (5.34 g, 13.62 mmol) and Compound a18 (6.14 g, 14.30 mmol) were completely dissolved in 240 ml of tetrahydrofuran in a 500 ml-round bottom flask under a nitrogen atmosphere, and then a 2 M aqueous potassium carbonate solution (120 ml) was added thereto, tetrakis-(triphenylphosphine)palladium (0.47 g, 0.41 mmol) was added thereto, and the resulting mixture was heated and stirred for 4 hours. The temperature was lowered to room temperature, the aqueous layer was removed, and the resulting product was dried over anhydrous magnesium sulfate, and then concentrated under reduced pressure and recrystallized from 190 ml of tetrahydrofuran to give Compound 27 (8.63 g, 85%).

MS[M+H]$^+$=742

Preparation Example 28

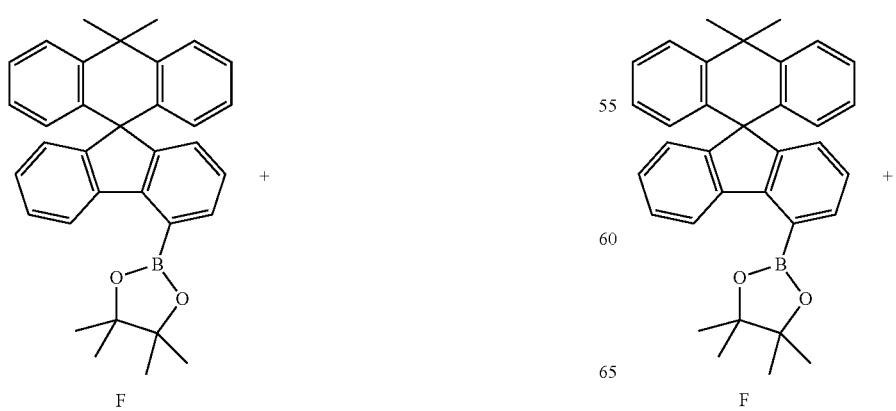

152

-continued

28

Compound F (9.08 g, 18.75 mmol) and Compound a19 (4.75 g, 17.86 mmol) were completely dissolved in 260 ml of tetrahydrofuran in a 500 ml-round bottom flask under a nitrogen atmosphere, and then a 2 M aqueous potassium carbonate solution (130 ml) was added thereto, bis(tri-t-butylphosphine)palladium (0.62 g, 0.54 mmol) was added thereto, and the resulting mixture was heated and stirred for 4 hours. The temperature was lowered to room temperature, the aqueous layer was removed, and the resulting product was dried over anhydrous magnesium sulfate, and then concentrated under reduced pressure and recrystallized from 220 ml of ethyl acetate to give Compound 28 (7.49 g, 71%).

MS[M+H]$^+$=589

Preparation Example 29

153

-continued

154

-continued

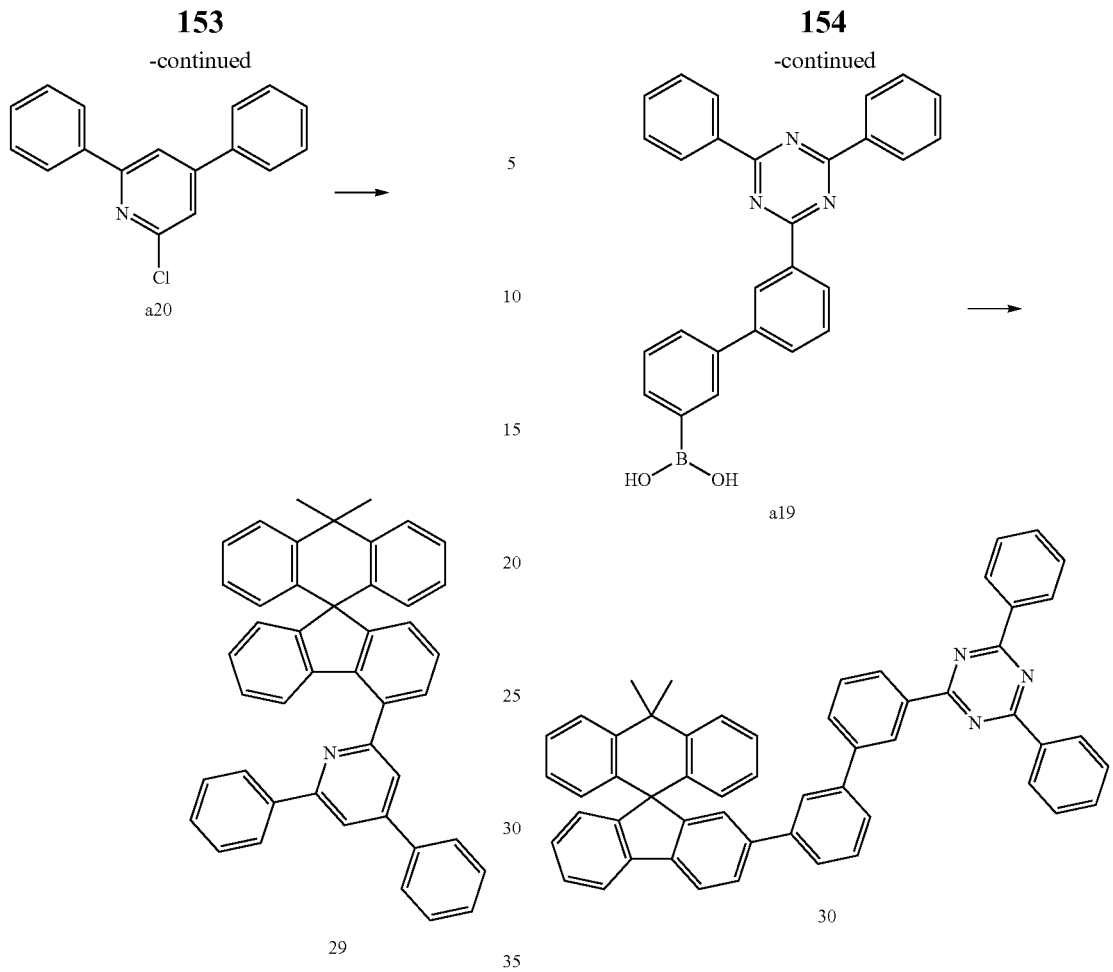

Compound F (8.54 g, 17.64 mmol) and Compound a20 (4.47 g, 16.80 mmol) were completely dissolved in 220 ml of tetrahydrofuran in a 500 ml-round bottom flask under a nitrogen atmosphere, and then a 2 M aqueous potassium carbonate solution (110 ml) was added thereto, bis(tri-t-butylphosphine)palladium (0.58 g, 0.50 mmol) was added thereto, and the resulting mixture was heated and stirred for 4 hours. The temperature was lowered to room temperature, the aqueous layer was removed, and the resulting product was dried over anhydrous magnesium sulfate, and then concentrated under reduced pressure and recrystallized from 150 ml of ethyl acetate to give Compound 29 (7.11 g, 72%).

MS[M+H]$^+$=588

Compound A (5.47 g, 13.95 mmol) and Compound a19 (6.29 g, 14.65 mmol) were completely dissolved in 180 ml of tetrahydrofuran in a 500 ml-round bottom flask under a nitrogen atmosphere, and then a 2 M aqueous potassium carbonate solution (90 ml) was added thereto, tetrakis-(triphenylphosphine)palladium (0.48 g, 0.42 mmol) was added thereto, and the resulting mixture was heated and stirred for 3 hours. The temperature was lowered to room temperature, the aqueous layer was removed, and the resulting product was dried over anhydrous magnesium sulfate, and then concentrated under reduced pressure and recrystallized from 210 ml of tetrahydrofuran to give Compound 30 (8.49 g, 82%).

MS[M+H]$^+$=742

Preparation Example 30

Preparation Example 31

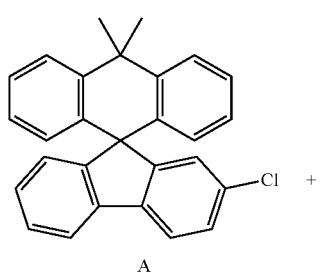

A

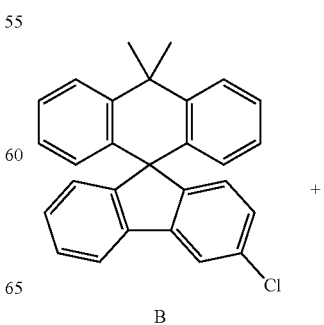

B

-continued

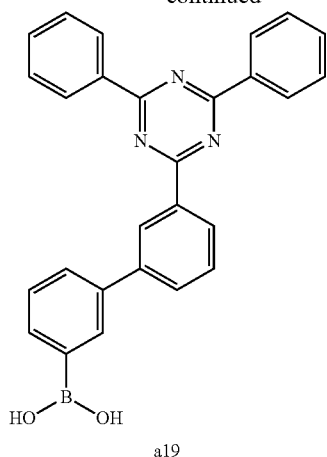

a19

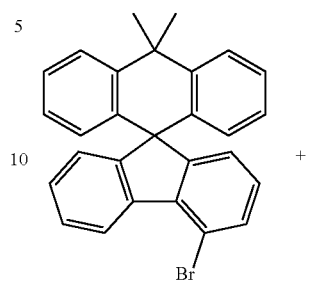

31

Compound B (5.24 g, 13.37 mmol) and Compound a19 (6.02 g, 14.04 mmol) were completely dissolved in 180 ml of tetrahydrofuran in a 500 ml-round bottom flask under a nitrogen atmosphere, and then a 2 M aqueous potassium carbonate solution (90 ml) was added thereto, tetrakis-(triphenylphosphine)palladium (0.46 g, 0.40 mmol) was added thereto, and the resulting mixture was heated and stirred for 2 hours. The temperature was lowered to room temperature, the aqueous layer was removed, and the resulting product was dried over anhydrous magnesium sulfate, and then concentrated under reduced pressure and recrystallized from 180 ml of tetrahydrofuran to give Compound 31 (7.77 g, 78%).

MS[M+H]⁺=742

Preparation Example 32

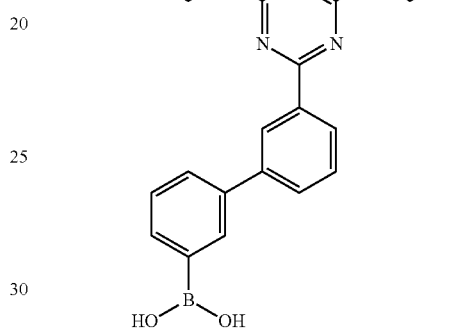

a19

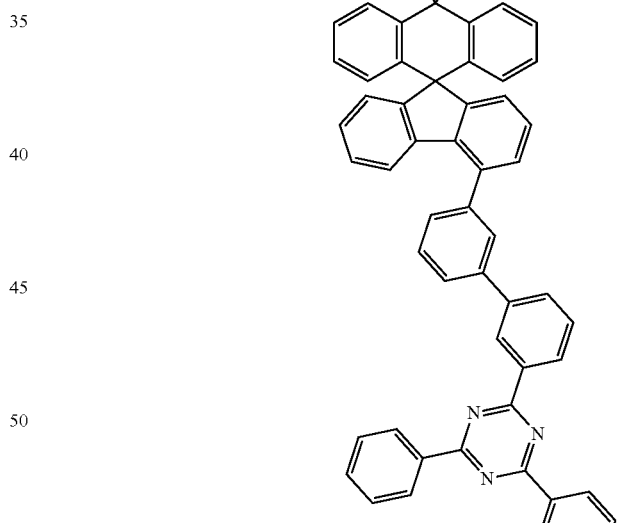

32

Compound C (4.85 g, 12.37 mmol) and Compound a19 (5.57 g, 12.99 mmol) were completely dissolved in 160 ml of tetrahydrofuran in a 500 ml-round bottom flask under a nitrogen atmosphere, and then a 2 M aqueous potassium carbonate solution (80 ml) was added thereto, tetrakis-(triphenylphosphine)palladium (0.43 g, 0.37 mmol) was added thereto, and the resulting mixture was heated and stirred for 5 hours. The temperature was lowered to room temperature, the aqueous layer was removed, and the resulting product was dried over anhydrous magnesium sulfate, and then concentrated under reduced pressure and recrystallized from 220 ml of tetrahydrofuran to give Compound 32 (8.05 g, 88%).

MS[M+H]⁺=742

Preparation Example 33

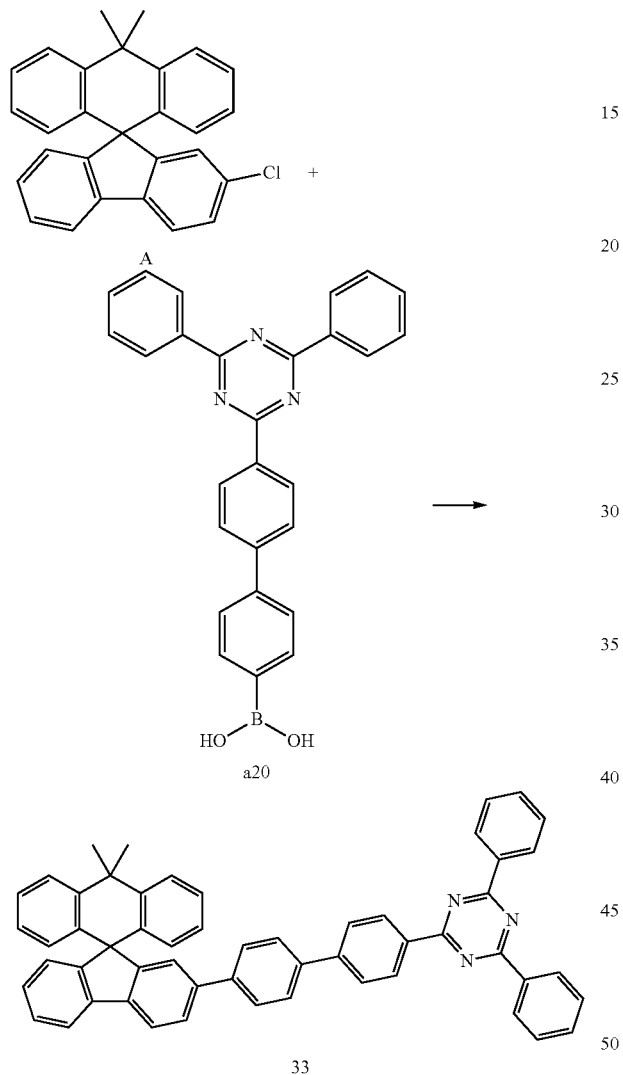

Compound A (4.29 g, 10.94 mmol) and Compound a20 (4.93 g, 11.49 mmol) were completely dissolved in 160 ml of tetrahydrofuran in a 500 ml-round bottom flask under a nitrogen atmosphere, and then a 2 M aqueous potassium carbonate solution (80 ml) was added thereto, tetrakis-(triphenylphosphine)palladium (0.38 g, 0.32 mmol) was added thereto, and the resulting mixture was heated and stirred for 2 hours. The temperature was lowered to room temperature, the aqueous layer was removed, and the resulting product was dried over anhydrous magnesium sulfate, and then concentrated under reduced pressure and recrystallized from 260 ml of tetrahydrofuran to give Compound 33 (6.95 g, 86%).

MS[M+H]⁺=742

Preparation Example 34

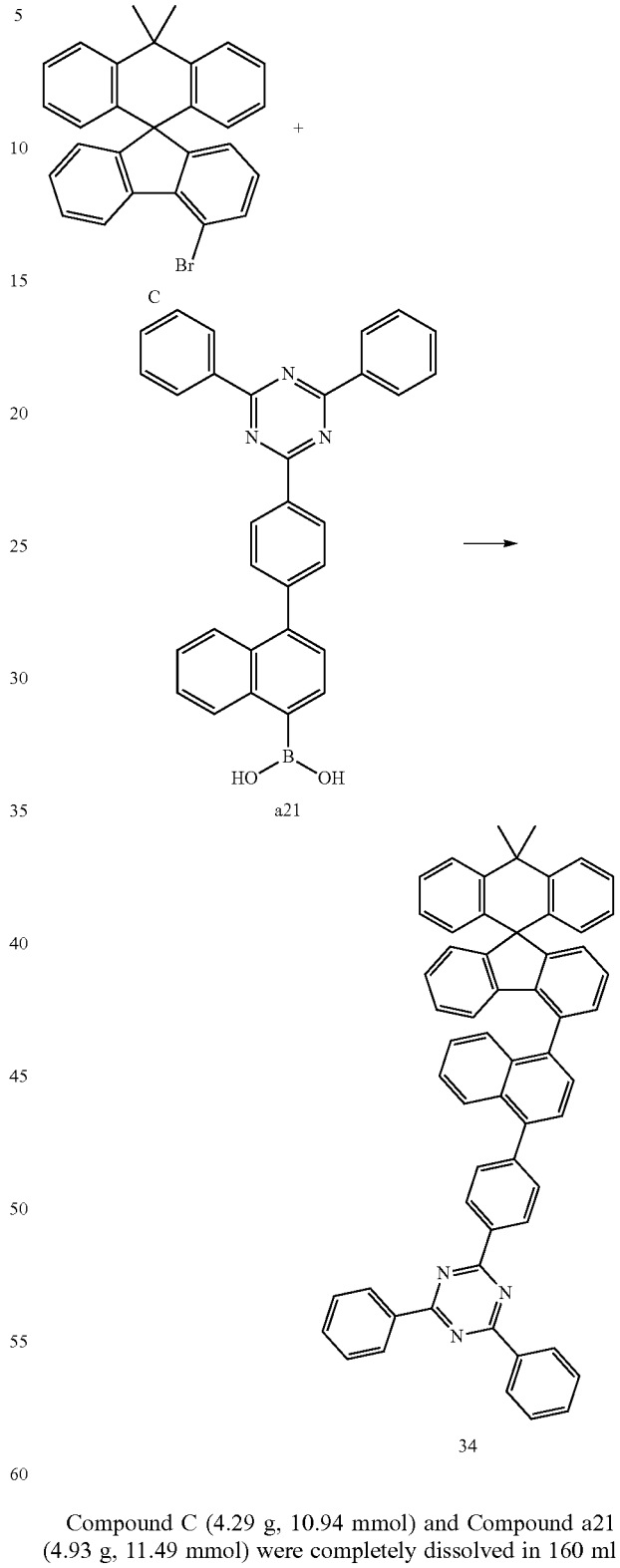

Compound C (4.29 g, 10.94 mmol) and Compound a21 (4.93 g, 11.49 mmol) were completely dissolved in 160 ml of tetrahydrofuran in a 500 ml-round bottom flask under a nitrogen atmosphere, and then a 2 M aqueous potassium carbonate solution (80 ml) was added thereto, tetrakis-(triphenylphosphine)palladium (0.38 g, 0.32 mmol) was added thereto, and the resulting mixture was heated and stirred for 2 hours. The temperature was lowered to room temperature, the aqueous layer was removed, and the resulting product was dried over anhydrous magnesium sulfate, and then concentrated under reduced pressure and recrystallized from 260 ml of tetrahydrofuran to give Compound 34 (5.47 g, 70%).

MS[M+H]$^+$=792

Preparation Example 35

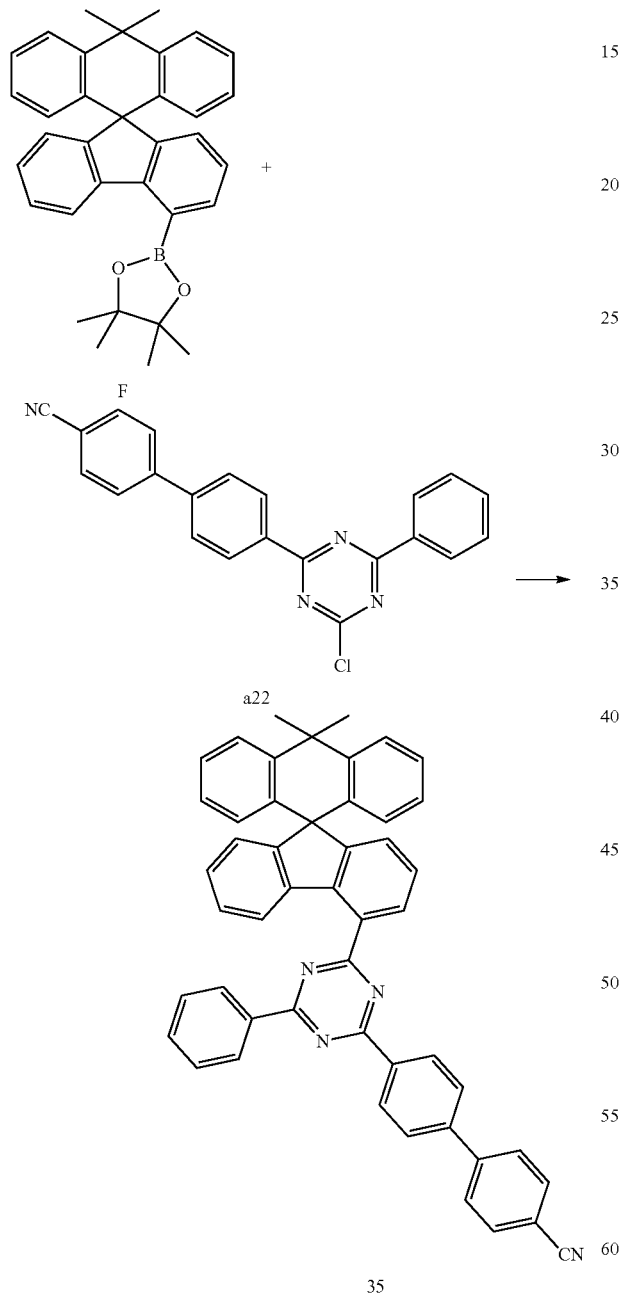

Compound F (7.92 g, 16.36 mmol) and Compound a22 (6.02 g, 16.36 mmol) were completely dissolved in 240 ml of tetrahydrofuran in a 500 ml-round bottom flask under a nitrogen atmosphere, and then a 2 M aqueous potassium carbonate solution (120 ml) was added thereto, bis(tri-t-butylphosphine)palladium (0.57 g, 0.49 mmol) was added thereto, and the resulting mixture was heated and stirred for 4 hours. The temperature was lowered to room temperature, the aqueous layer was removed, and the resulting product was dried over anhydrous magnesium sulfate, and then concentrated under reduced pressure and recrystallized from 230 ml of tetrahydrofuran to give Compound 35 (8.95 g, 79%).

MS[M+H]$^+$=691

Preparation Example 36

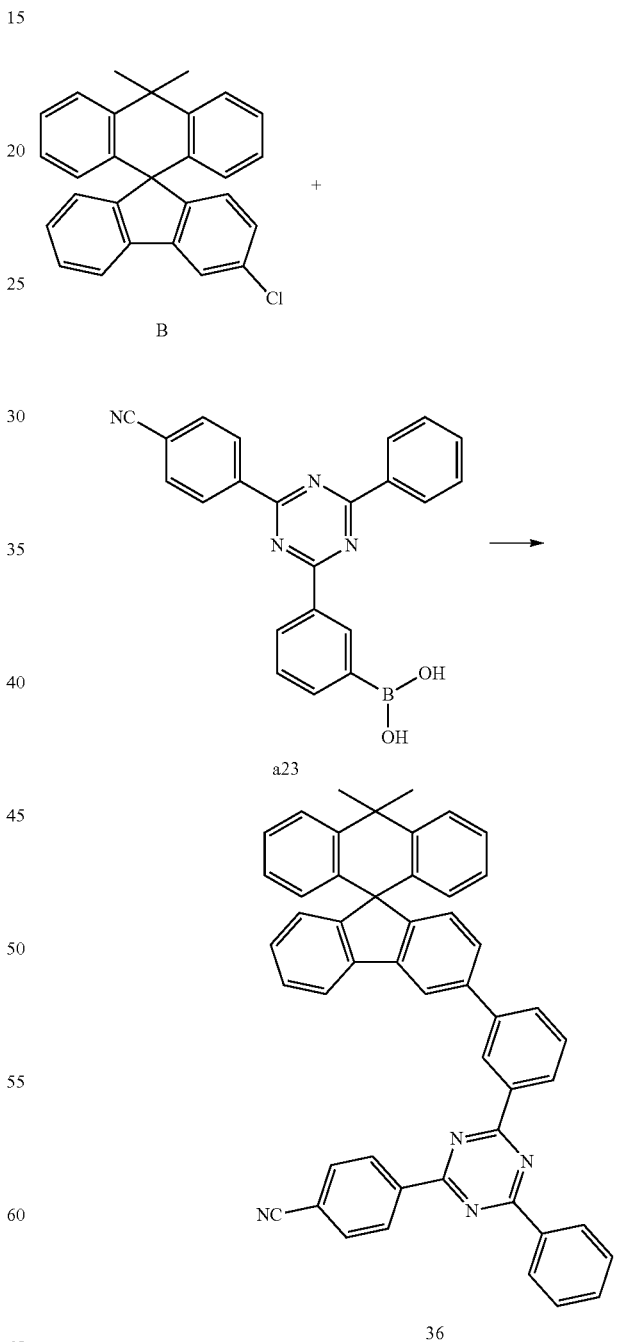

Compound B (6.35 g, 17.26 mmol) and Compound a23 (8.35 g, 17.26 mmol) were completely dissolved in 200 ml of tetrahydrofuran in a 500 ml-round bottom flask under a nitrogen atmosphere, and then a 2 M aqueous potassium carbonate solution (100 ml) was added thereto, tetrakis-(triphenylphosphine)palladium (0.60 g, 0.52 mmol) was added thereto, and the resulting mixture was heated and stirred for 3 hours. The temperature was lowered to room temperature, the aqueous layer was removed, and the resulting product was dried over anhydrous magnesium sulfate, and then concentrated under reduced pressure and recrystallized from 240 ml of ethyl acetate to give Compound 36 (7.74 g, 65%).

MS[M+H]⁺=691

Preparation Example 37

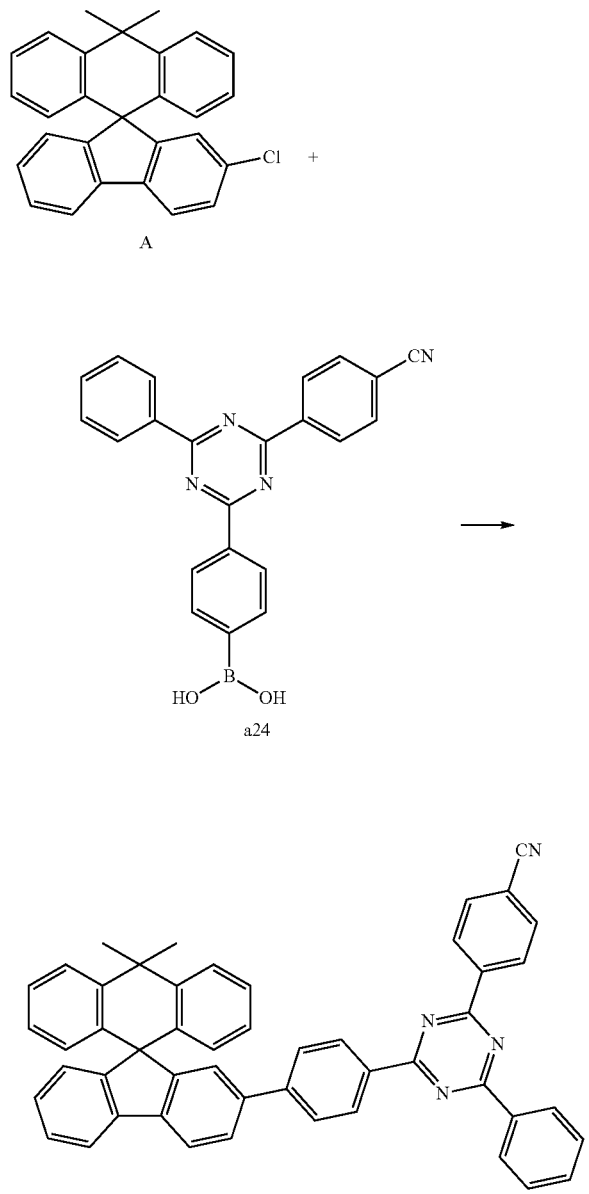

Compound A (7.16 g, 19.46 mmol) and Compound a24 (9.42 g, 19.46 mmol) were completely dissolved in 260 ml of tetrahydrofuran in a 500 ml-round bottom flask under a nitrogen atmosphere, and then a 2 M aqueous potassium carbonate solution (130 ml) was added thereto, tetrakis-(triphenylphosphine)palladium (0.67 g, 0.58 mmol) was added thereto, and the resulting mixture was heated and stirred for 5 hours. The temperature was lowered to room temperature, the aqueous layer was removed, and the resulting product was dried over anhydrous magnesium sulfate, and then concentrated under reduced pressure and recrystallized from 250 ml of tetrahydrofuran to give Compound 37 (11.08 g, 82%).

MS[M+H]⁺=691

Example 1-1

A glass substrate on which ITO (indium tin oxide) was coated at a thickness of 1000 Å was put into distilled water in which a detergent was dissolved, and ultrasonically washed. In this case, a product manufactured by Fischer Co., was used as the detergent, and distilled water that was filtered twice using a filter manufactured by Millipore Co. was used as the distilled water. After the ITO substrate was washed for 30 minutes, ultrasonic washing was conducted twice using distilled water for 10 minutes. After the washing using distilled water was completed, ultrasonic washing was conducted using solvents of isopropyl alcohol, acetone, and methanol, and then dried, after which it was transferred to a plasma cleaner. In addition, the substrate was cleaned for 5 minutes using oxygen plasma, and then transferred to a vacuum depositor.

On the ITO electrode prepared as above, a compound represented by the following Chemical Formula HAT was thermally vacuum-deposited at a thickness of 100 Å to form a hole injection layer. A compound (1250 Å) represented by the following Chemical Formula HT1, which is a material for transporting holes, was vacuum-deposited on the hole injection layer to form a hole transport layer. Then, a compound represented by the following Chemical Formula EB1 was vacuum-deposited on the hole transport layer to form an electron blocking layer. Subsequently, a compound represented by the following Chemical Formula BH and a compound represented by the following Chemical Formula BD were vacuum-deposited at a weight ratio of 25:1 on the electron blocking layer to a thickness of 200 Å to form a light emitting layer. Compound 1 of Preparation Example 1 previously prepared was vacuum-deposited on the light emitting layer to a thickness of 50 Å to form a hole blocking layer. Then, a compound represented by the following Chemical Formula ET1 and a compound represented by the following Chemical Formula LiQ were vacuum-deposited at a weight ratio of 1:1 on the hole blocking layer to form an electron transport layer with a thickness of 310 Å. Lithium fluoride (LiF) at a thickness of 12 Å and aluminum at a thickness of 1000 Å were sequentially deposited on the electron transport layer to form a cathode

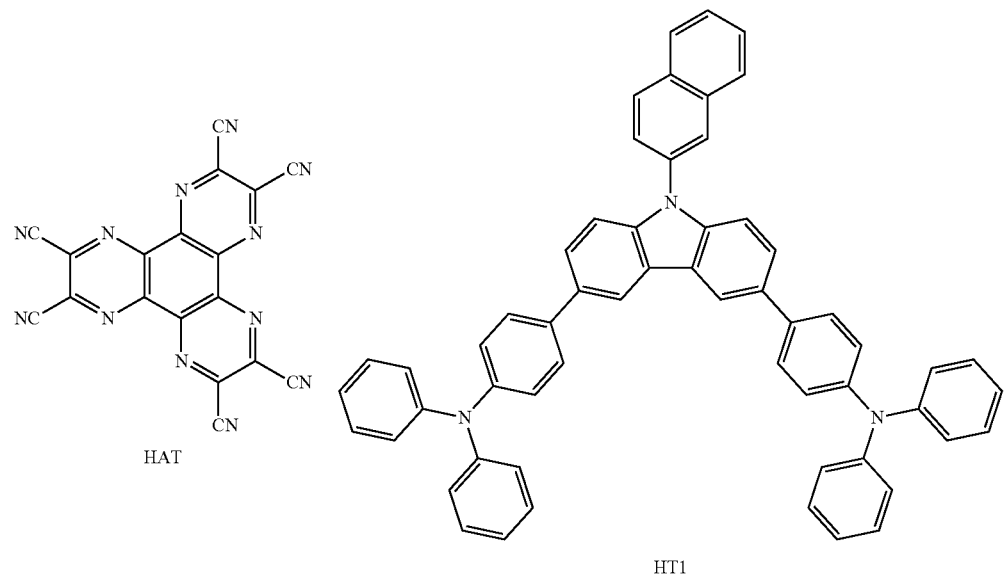
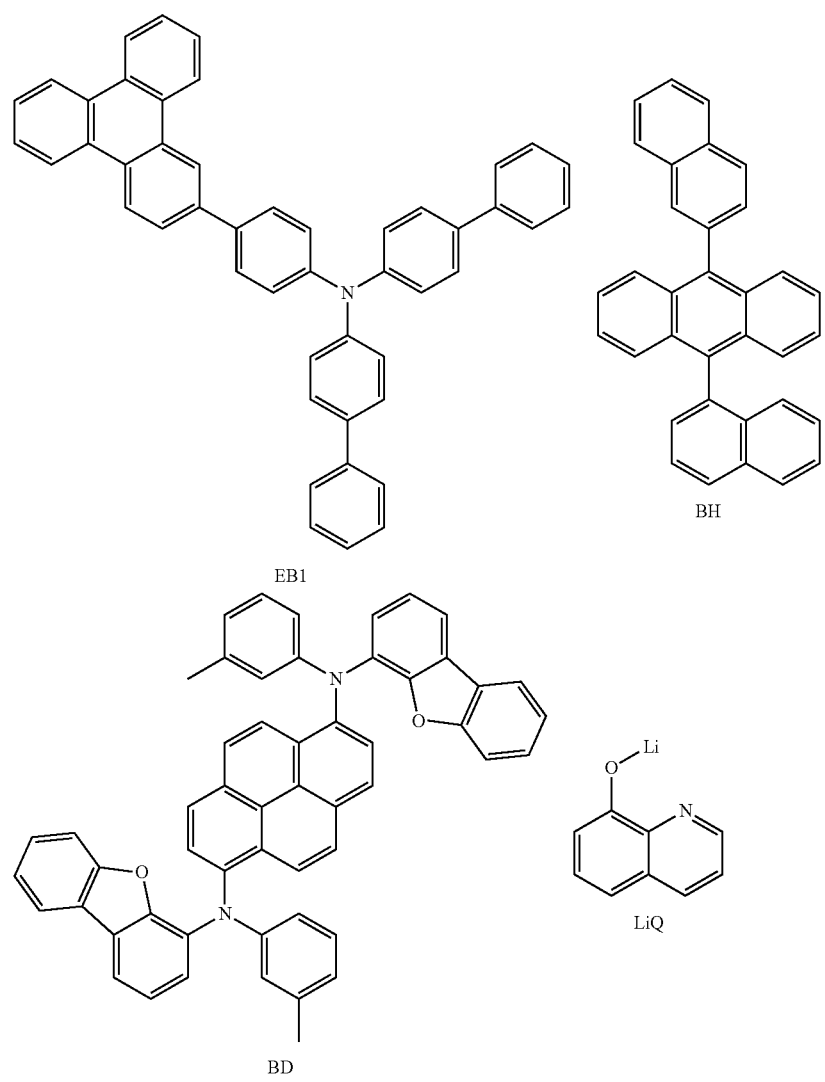

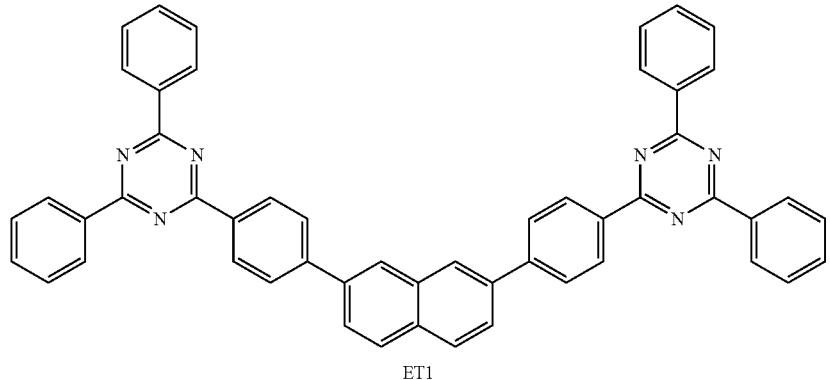 [SMILES: c1ccc(-c2nc(-c3ccccc3)nc(-c3ccc(-c4ccc5ccc(-c6ccc(-c7nc(-c8ccccc8)nc(-c8ccccc8)n7)cc6)cc5c4)cc3)n2)cc1]

ET1

In the above process, the vapor deposition rate of the organic material was maintained at 0.4 to 0.7 Å/s, the vapor deposition rate of lithium fluoride of the cathode was maintained at 0.3 Å/s, the vapor deposition rate of aluminum was maintained at 2 Å/sec, and the degree of vacuum during vapor deposition was maintained at $2\times10^{-7}$~$5\times10^{-6}$ Torr, thereby manufacturing an organic light emitting device.

Examples 1-2 to 1-14

An organic light emitting device was manufactured in the same manner as in Example 1-1, except that the compounds shown in Table 1 below were used instead of Compound 1.

Comparative Examples 1-1 to 1-3

An organic light emitting device was manufactured in the same manner as in Example 1-1, except that the compounds shown in Table 1 below were used instead of Compound 1. The compounds HB1, HB2, and HB3 used in Table 1 below are as follows.

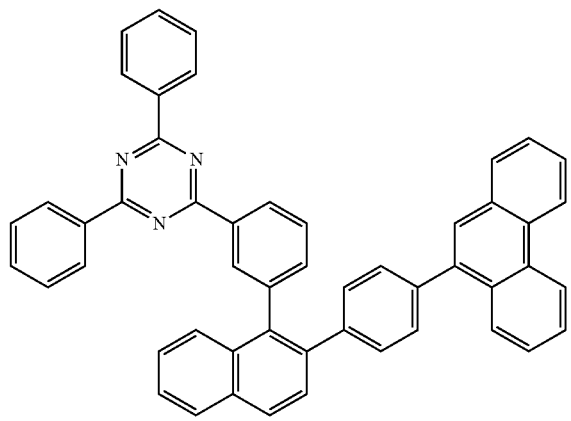

HB1

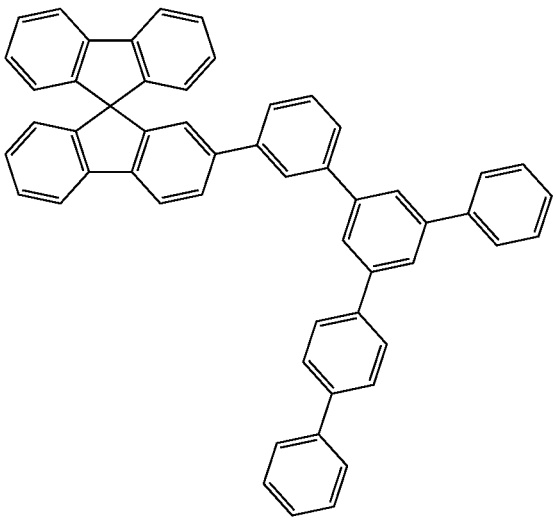

HB2

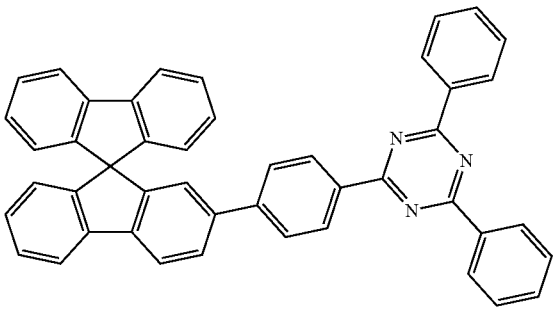

HB3

Experimental Example 1

When currents were applied to the organic light emitting devices manufactured in the examples and comparative examples, the voltage, efficiency, color coordinates, and lifetime were measured, and the results are shown in Table 1 below. T95 means the time required for the luminance to decrease to 95% of its initial value (1600 nit).

TABLE 1

|  | Compound (Hole blocking layer) | Voltage (V @10 mA/cm$^2$) | Efficiency (cd/A @10 mA/cm$^2$) | Color coordinates (x, y) | T95 (h) |
|---|---|---|---|---|---|
| Example 1-1 | Compound 1 | 4.60 | 46.31 | (0.140, 0.046) | 270 |
| Example 1-2 | Compound 2 | 4.43 | 46.53 | (0.141, 0.045) | 275 |
| Example 1-3 | Compound 3 | 4.76 | 46.24 | (0.142, 0.047) | 285 |
| Example 1-4 | Compound 4 | 4.50 | 46.45 | (0.142, 0.044) | 295 |
| Example 1-5 | Compound 17 | 4.63 | 46.36 | (0.140, 0.044) | 275 |
| Example 1-6 | Compound 18 | 4.76 | 46.27 | (0.139, 0.047) | 285 |
| Example 1-7 | Compound 23 | 4.66 | 46.34 | (0.141, 0.047) | 280 |
| Example 1-8 | Compound 24 | 4.74 | 46.23 | (0.138, 0.046) | 260 |
| Example 1-9 | Compound 25 | 4.51 | 46.40 | (0.138, 0.045) | 280 |
| Example 1-10 | Compound 26 | 4.52 | 46.43 | (0.138, 0.044) | 275 |
| Example 1-11 | Compound 27 | 4.53 | 46.45 | (0.142, 0.044) | 275 |
| Example 1-12 | Compound 30 | 4.62 | 46.42 | (0.142, 0.043) | 285 |
| Example 1-13 | Compound 32 | 4.48 | 46.44 | (0.142, 0.044) | 280 |
| Example 1-14 | Compound 34 | 4.40 | 46.67 | (0.142, 0.045) | 270 |
| Comparative Example 1-1 | HB 1 | 5.07 | 46.02 | (0.141, 0.045) | 235 |
| Comparative Example 1-2 | HB 2 | 4.92 | 45.81 | (0.141, 0.045) | 240 |
| Comparative Example 1-3 | HB 3 | 4.85 | 45.43 | (0.143, 0.048) | 220 |

As shown in Table 1, in the case of the organic light emitting device manufactured by using the compound of the present disclosure as a hole blocking layer, it exhibits excellent characteristics in terms of efficiency, driving voltage, and/or stability of the organic light emitting device. In particular, the organic light emitting devices manufactured using the compound of the present disclosure as the hole blocking layer show low voltage, high efficiency, and long lifetime characteristics, as compared with the organic light emitting devices manufactured using the compound of Comparative Examples 1-2 of a spirobifluorene core and the compound of Comparative Example 1-3 of a 9,10-dimethylfluorene core as a hole blocking layer. Specifically, the core of the compound of the present disclosure has a relatively higher electron content than the spirobifluorene and 9,10-dimethyfluorene cores, and when used as a hole blocking layer, it shows the advantages in voltage and efficiency without decreasing the lifetime. From the results shown in Table 1, it could be confirmed that the compound according to the present disclosure is excellent in hole blocking ability and can be applied to organic light emitting devices.

Examples 2-1 to 2-35

An organic light emitting device was manufactured in the same manner as in Comparative Example 1-1, except that the compound described in Table 2 below was used instead of ET 1 as the electron transport layer in Comparative Example 1-1.

Comparative Example 2-1 and Comparative Example 2-2

An organic light emitting device was manufactured in the same manner as in Comparative Example 1-1, except that the compounds represented by the following ET2 and ET3 were used instead of the compound ET1.

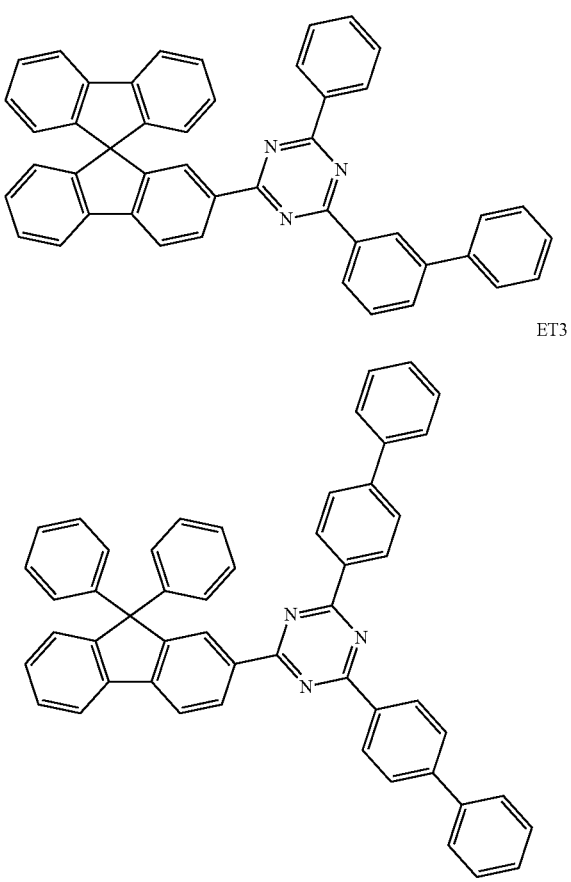

Experimental Example 2

When currents were applied to the organic light emitting devices manufactured in the examples and comparative examples, the voltage, efficiency, color coordinates, and lifetime were measured, and the results are shown in Table 2 below. T95 means the time required for the luminance to decrease to 95% of its initial value (1600 nit).

TABLE 2

| | Compound (Electron transport layer) | Voltage (V @10 mA/cm$^2$) | Efficiency (cd/A @10 mA/cm$^2$) | Color coordinates (x, y) | T95 (h) |
|---|---|---|---|---|---|
| Example 2-1 | Compound 1 | 4.60 | 46.51 | (0.140, 0.045) | 290 |
| Example 2-2 | Compound 2 | 4.53 | 46.43 | (0.141, 0.046) | 295 |
| Example 2-3 | Compound 3 | 4.71 | 46.34 | (0.142, 0.047) | 305 |
| Example 2-4 | Compound 4 | 4.62 | 46.55 | (0.142, 0.045) | 315 |
| Example 2-5 | Compound 5 | 4.61 | 46.66 | (0.140, 0.046) | 295 |
| Example 2-6 | Compound 6 | 4.72 | 46.47 | (0.139, 0.044) | 305 |
| Example 2-7 | Compound 7 | 4.76 | 46.53 | (0.138, 0.047) | 280 |
| Example 2-8 | Compound 8 | 4.57 | 46.60 | (0.144, 0.045) | 300 |
| Example 2-9 | Compound 9 | 4.68 | 46.43 | (0.138, 0.046) | 295 |
| Example 2-10 | Compound 10 | 4.56 | 46.55 | (0.142, 0.047) | 295 |
| Example 2-11 | Compound 11 | 4.67 | 45.71 | (0.141, 0.045) | 260 |
| Example 2-12 | Compound 12 | 4.55 | 46.55 | (0.142, 0.044) | 295 |
| Example 2-13 | Compound 13 | 4.64 | 45.61 | (0.141, 0.046) | 260 |
| Example 2-14 | Compound 14 | 4.53 | 46.70 | (0.143, 0.045) | 300 |
| Example 2-15 | Compound 15 | 4.55 | 46.53 | (0.138, 0.044) | 295 |
| Example 2-16 | Compound 16 | 4.51 | 46.45 | (0.142, 0.045) | 295 |
| Example 2-17 | Compound 17 | 4.46 | 45.61 | (0.141, 0.046) | 260 |
| Example 2-18 | Compound 18 | 4.58 | 46.50 | (0.141, 0.045) | 295 |
| Example 2-19 | Compound 19 | 4.55 | 46.43 | (0.138, 0.044) | 295 |
| Example 2-20 | Compound 20 | 4.54 | 46.45 | (0.142, 0.044) | 295 |
| Example 2-21 | Compound 21 | 4.62 | 45.85 | (0.141, 0.045) | 260 |
| Example 2-22 | Compound 22 | 4.58 | 46.45 | (0.142, 0.045) | 295 |
| Example 2-23 | Compound 23 | 4.52 | 45.81 | (0.141, 0.046) | 270 |
| Example 2-24 | Compound 24 | 4.55 | 46.45 | (0.142, 0.045) | 285 |
| Example 2-25 | Compound 25 | 4.44 | 45.82 | (0.141, 0.046) | 275 |
| Example 2-26 | Compound 26 | 4.53 | 46.65 | (0.142, 0.044) | 285 |
| Example 2-27 | Compound 27 | 4.53 | 46.65 | (0.142, 0.044) | 285 |
| Example 2-28 | Compound 30 | 4.55 | 46.43 | (0.140, 0.044) | 290 |
| Example 2-29 | Compound 31 | 4.53 | 45.84 | (0.142, 0.045) | 275 |
| Example 2-30 | Compound 32 | 4.64 | 45.94 | (0.141, 0.046) | 275 |
| Example 2-31 | Compound 33 | 4.57 | 46.73 | (0.142, 0.045) | 265 |
| Example 2-32 | Compound 34 | 4.58 | 46.61 | (0.141, 0.045) | 275 |
| Example 2-30 | Compound 32 | 4.64 | 45.94 | (0.141, 0.046) | 275 |
| Example 2-31 | Compound 33 | 4.57 | 46.73 | (0.142, 0.045) | 265 |
| Example 2-32 | Compound 34 | 4.58 | 46.61 | (0.141, 0.045) | 275 |
| Example 2-33 | Compound 35 | 4.68 | 46.26 | (0.141, 0.045) | 305 |
| Example 2-34 | Compound 36 | 4.66 | 46.30 | (0.142, 0.044) | 315 |
| Example 2-35 | Compound 37 | 4.72 | 46.08 | (0.142, 0.045) | 320 |
| Comparative Example 2-1 | ET 2 | 4.85 | 44.91 | (0.143, 0.047) | 235 |
| Comparative Example 2-2 | ET 3 | 4.92 | 45.13 | (0.143, 0.045) | 215 |

As shown in Table 2, in the case of the organic light emitting devices manufactured by using the compound of the present disclosure as an electron transport layer, it exhibits excellent characteristics in terms of efficiency, driving voltage, and/or stability of the organic light emitting device. In particular, the organic light emitting devices manufactured using the compound of the present disclosure as the electron transport layer show low voltage, high efficiency, and long lifetime characteristics, as compared with the organic light emitting devices manufactured using the compound of Comparative Examples 2-1 of a spirobifluorene core and the compound of Comparative Example 2-2 of a 9,10-dimethylfluorene core as an electron transport layer. Specifically, the core of the compound of the present disclosure has a relatively higher electron content than the spirobifluorene and 9,10-dimethylfluorene cores, and when used as an electron transport layer, it shows the advantages in voltage and efficiency while increasing the lifetime by 20%-30%. From the results shown in Table 2, it could be confirmed that the compounds according to the present disclosure are excellent in electron transport ability and can be applied to organic light emitting devices.

DESCRIPTION OF REFERENCE CHARACTERS

1: substrate
2: anode
3: light emitting layer
4: cathode
5: hole injection layer
6: hole transport layer
7: light emitting layer
8: electron transport layer

What is claimed is:

1. A compound represented by the following Chemical Formula 1:

[Chemical Formula 1]

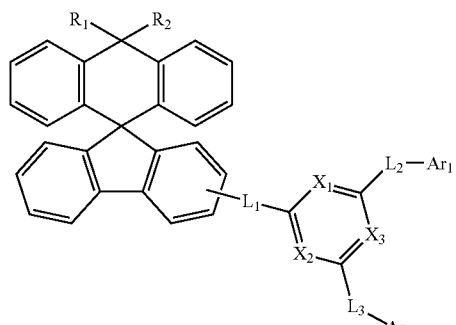

wherein, in Chemical Formula 1, $R_1$ and $R_2$ are each independently a substituted or unsubstituted $C_{1-60}$ alkyl, or a substituted or unsubstituted $C_{6-60}$ aryl, $L_1$, $L_2$, and $L_3$ are each independently a direct bond, a substituted or unsubstituted $C_{6-60}$ arylene, or a $C_{2-60}$ heteroarylene containing at least one heteroatom selected from the group consisting of O, N, S, and Si, $X_1$ to $X_3$ are each independently N or CR', and at least one of X1 to X3 is N, R' is hydrogen or a substituted or unsubstituted $C_{1-60}$ alkyl, and $Ar_1$ and $Ar_2$ are each independently a substituted or unsubstituted $C_{6-60}$ aryl.

2. The compound of claim 1, wherein

Chemical Formula 1 is any one selected from compounds represented by the following Chemical Formulas 1-1 to 1-5:

[Chemical Formula 1-1]

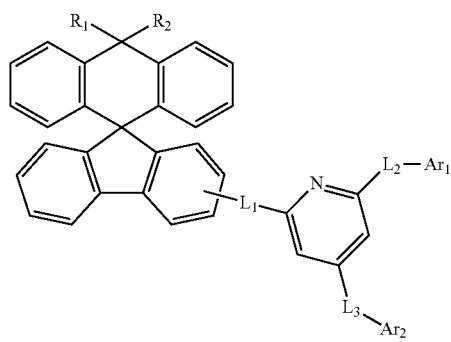

[Chemical Formula 1-2]

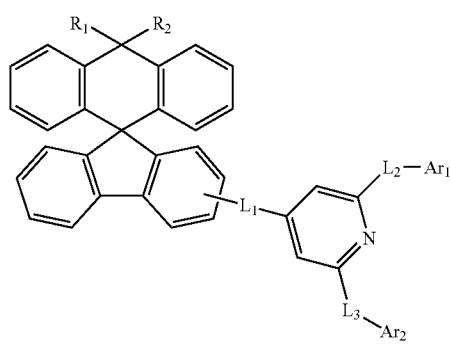

[Chemical Formula 1-3]

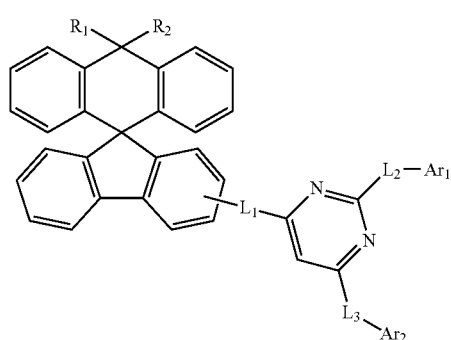

[Chemical Formula 1-4]

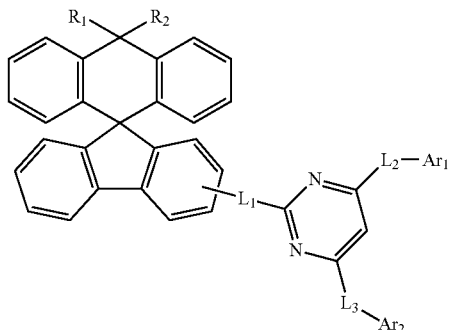

[Chemical Formula 1-5]

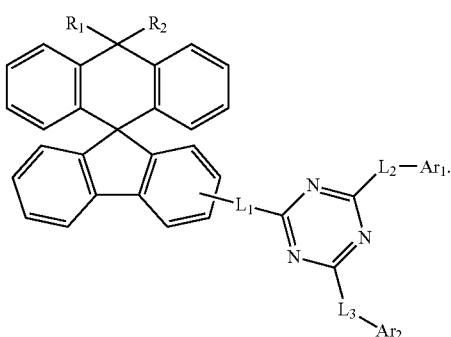

3. The compound of claim 1, wherein $R_1$ and $R_2$ are each independently methyl or phenyl.

4. The compound of claim 1, wherein $L_1$, $L_2$, and $L_3$ are each independently a direct bond or any one selected from the group consisting of the following:

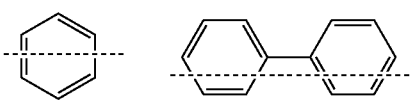

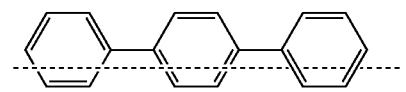

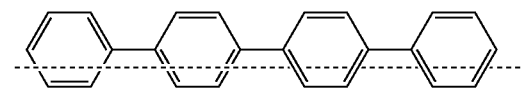

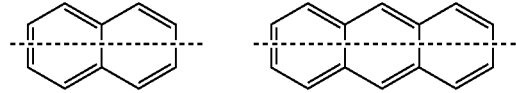

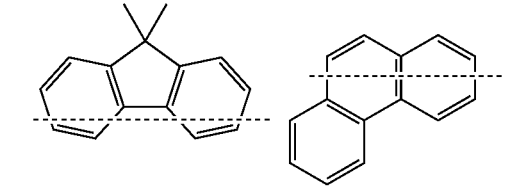

-continued
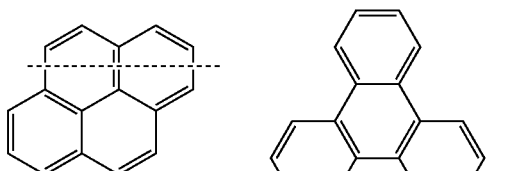
5. The compound of claim 1, wherein
L₁, L₂, and L₃ are each independently a direct bond or
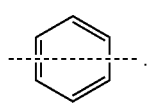
6. The compound of claim 1, wherein
Ar₁ and Ar₂ are each independently selected from the group consisting of the following:
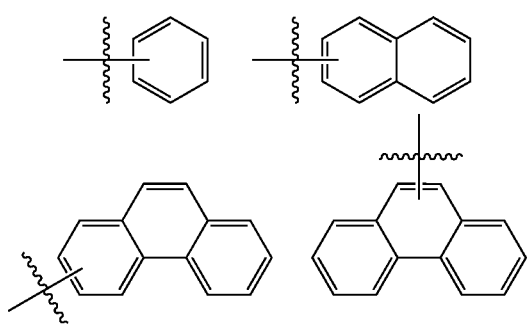
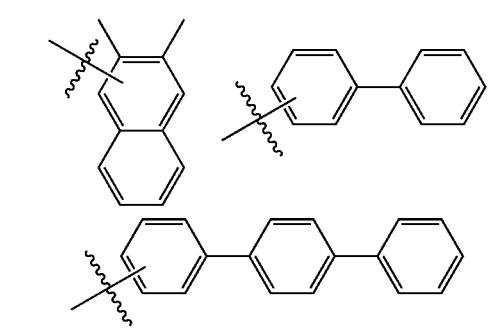
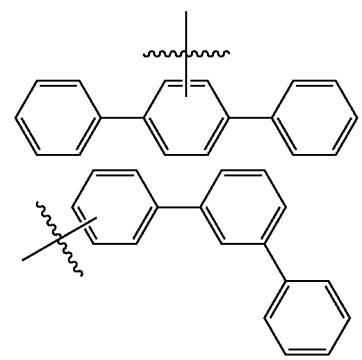
-continued
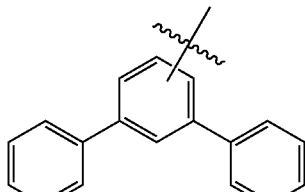
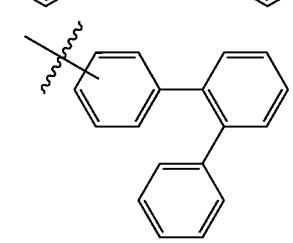
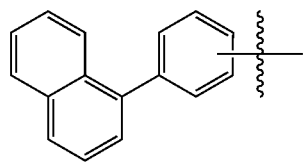
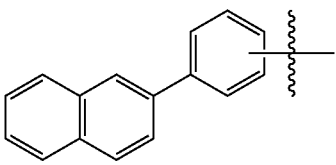
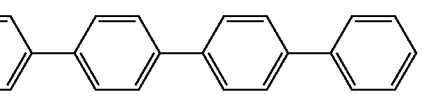
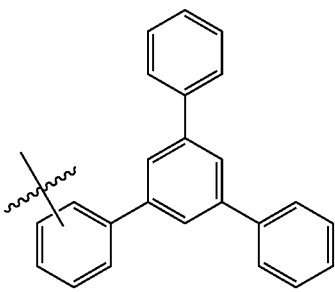
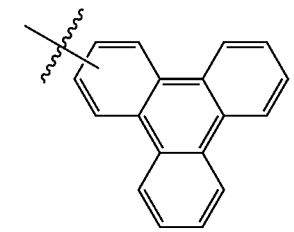
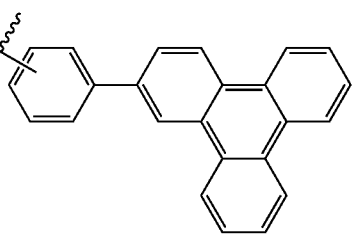

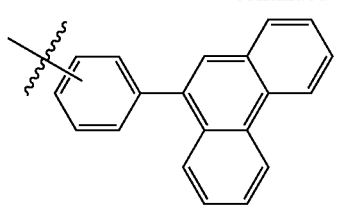
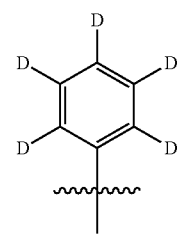
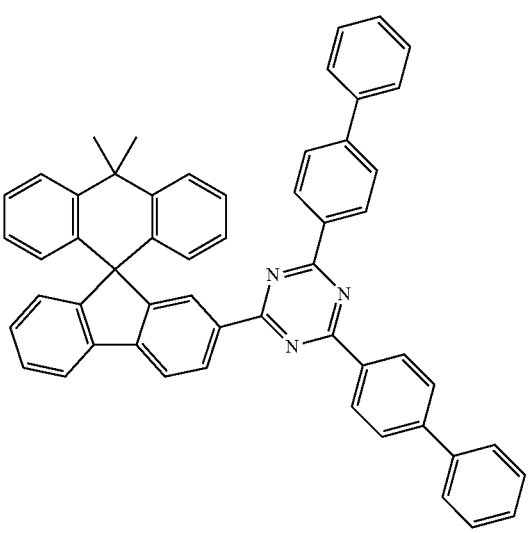
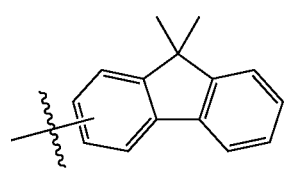
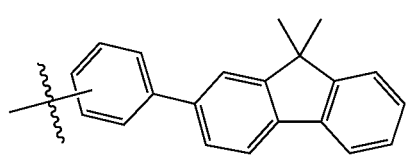
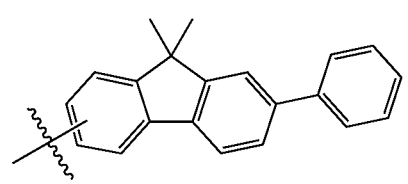
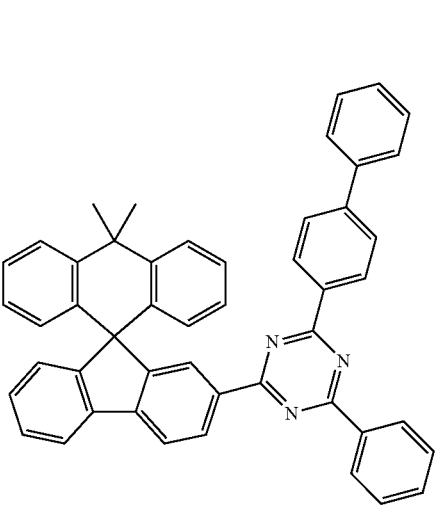
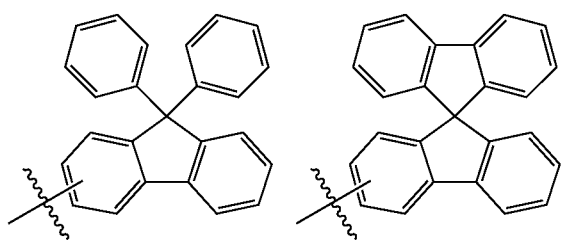
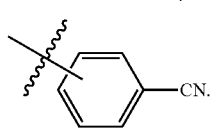
7. The compound of claim 1, wherein
the compound represented by Chemical Formula 1 is any one selected from the group consisting of the following:

177
-continued
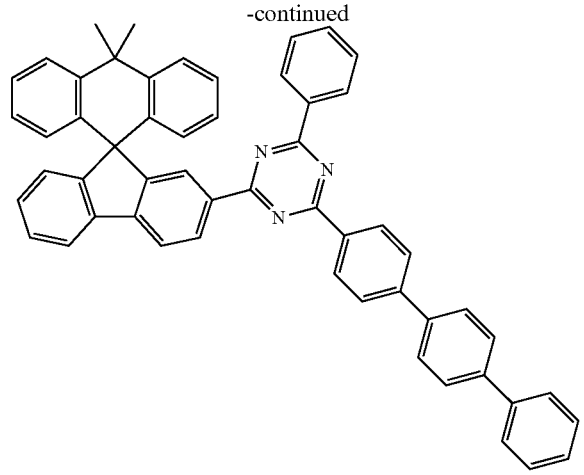
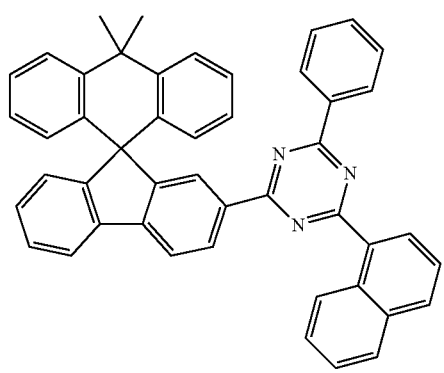
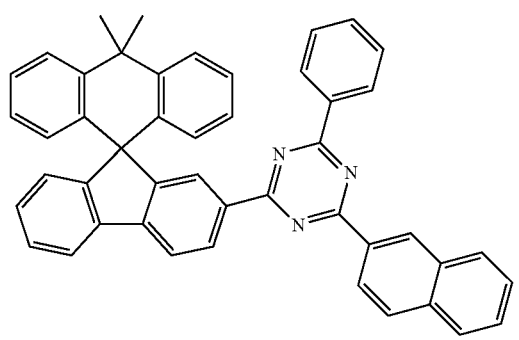
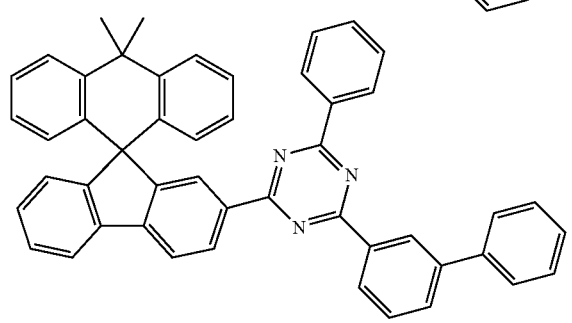
178
-continued
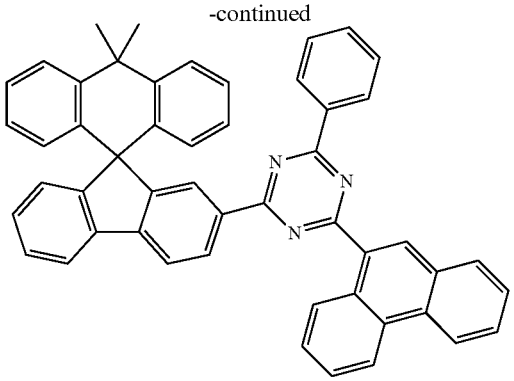
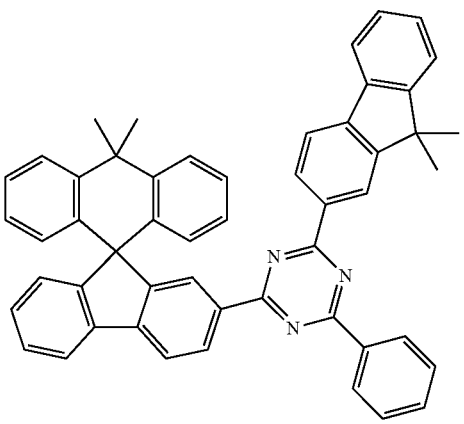
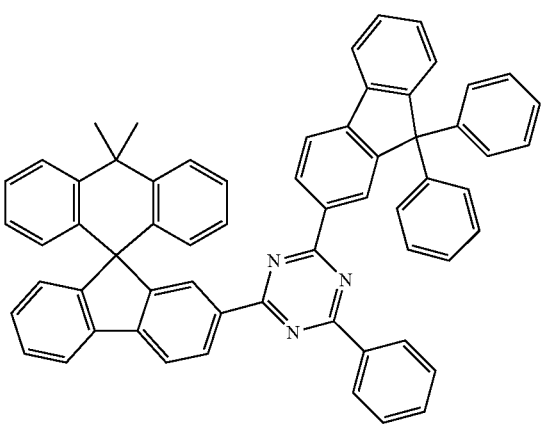
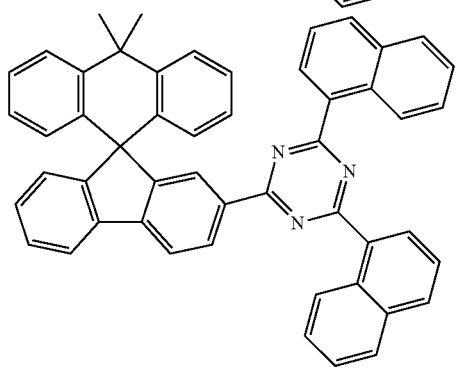

179
-continued
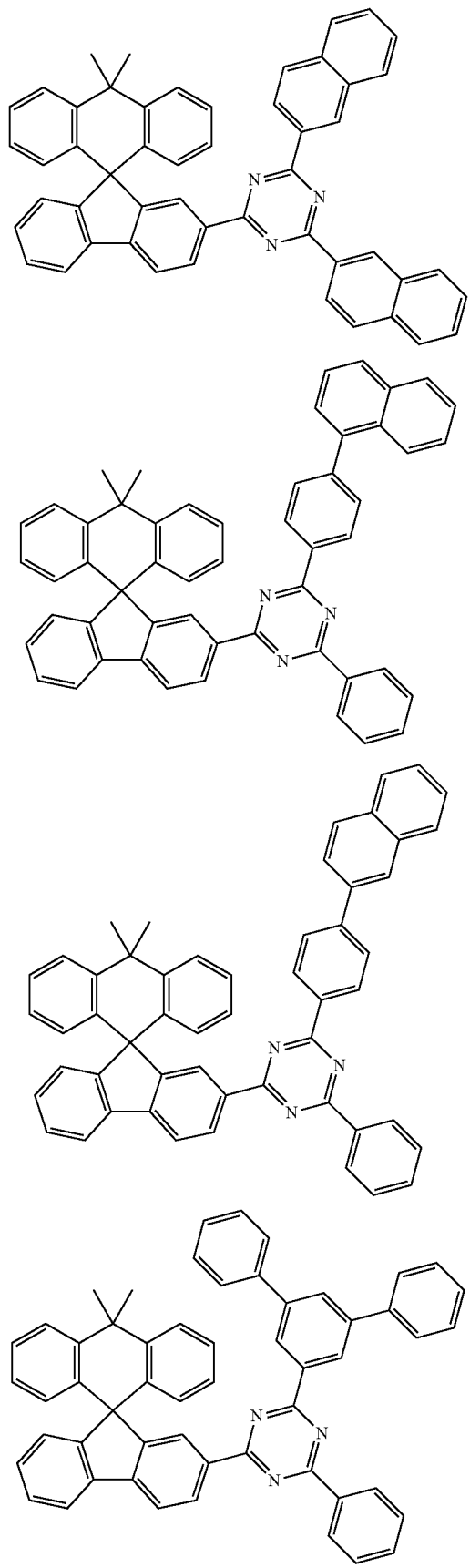
180
-continued
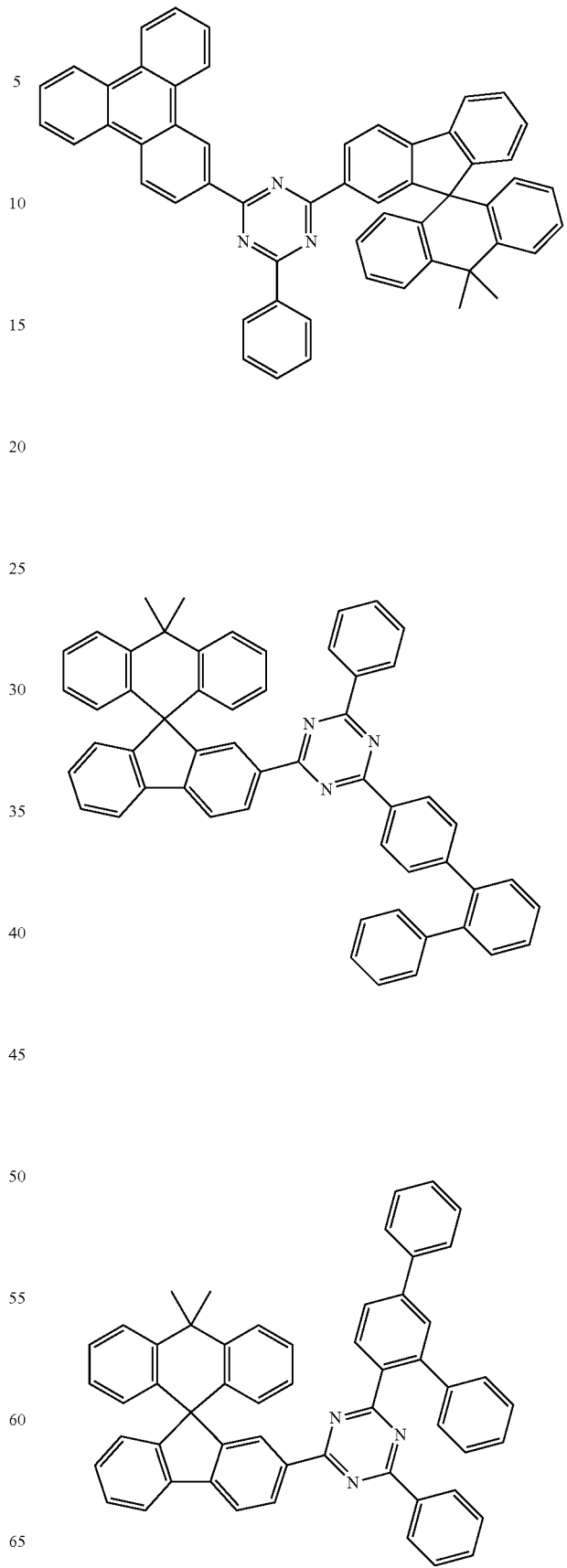

181
-continued
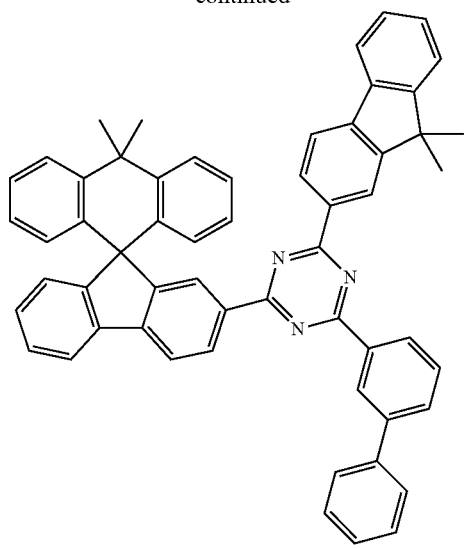
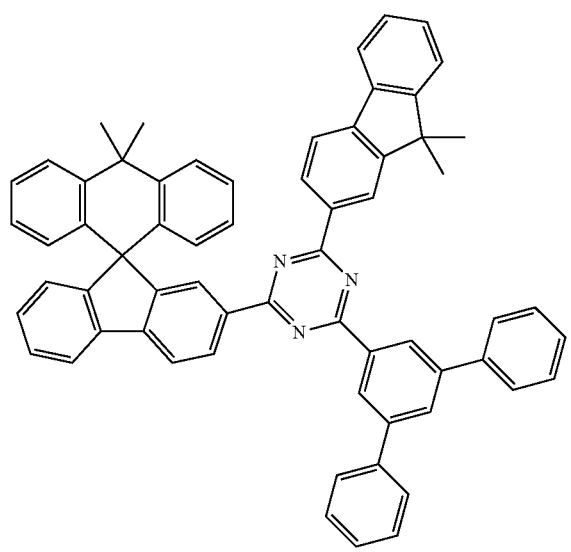
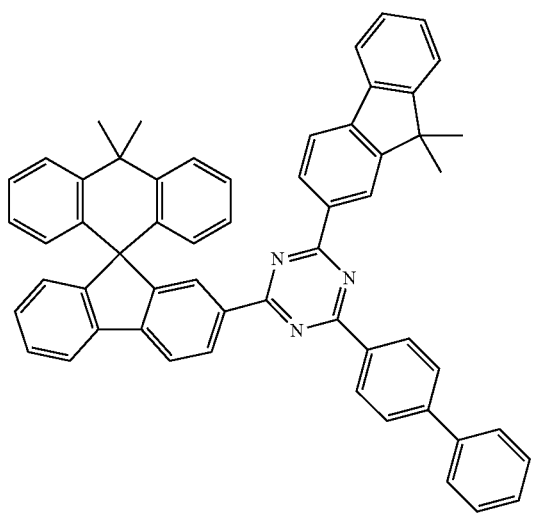
182
-continued
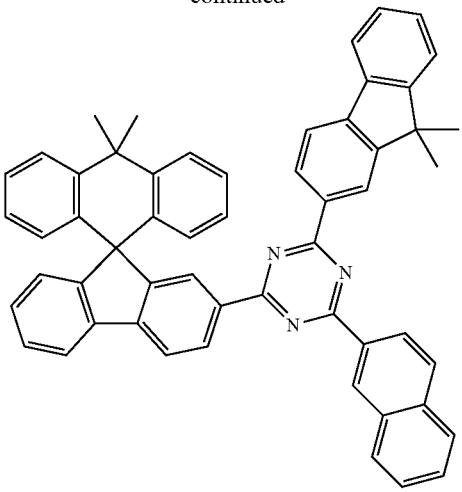
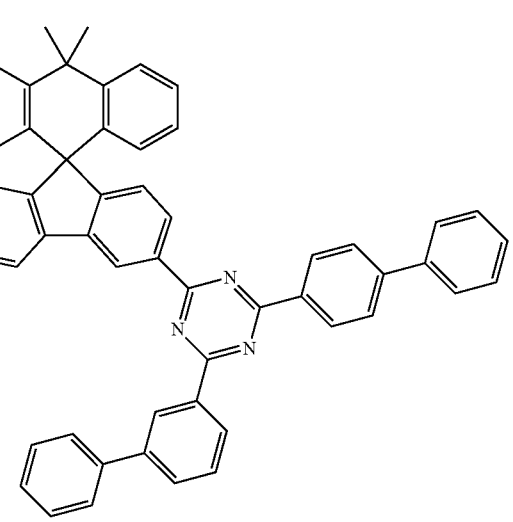

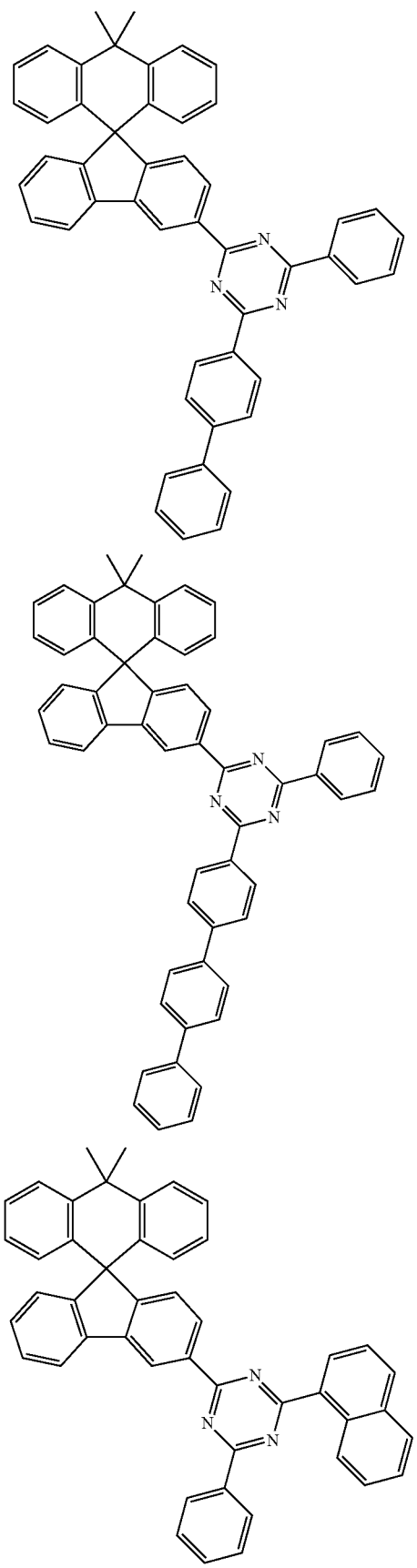
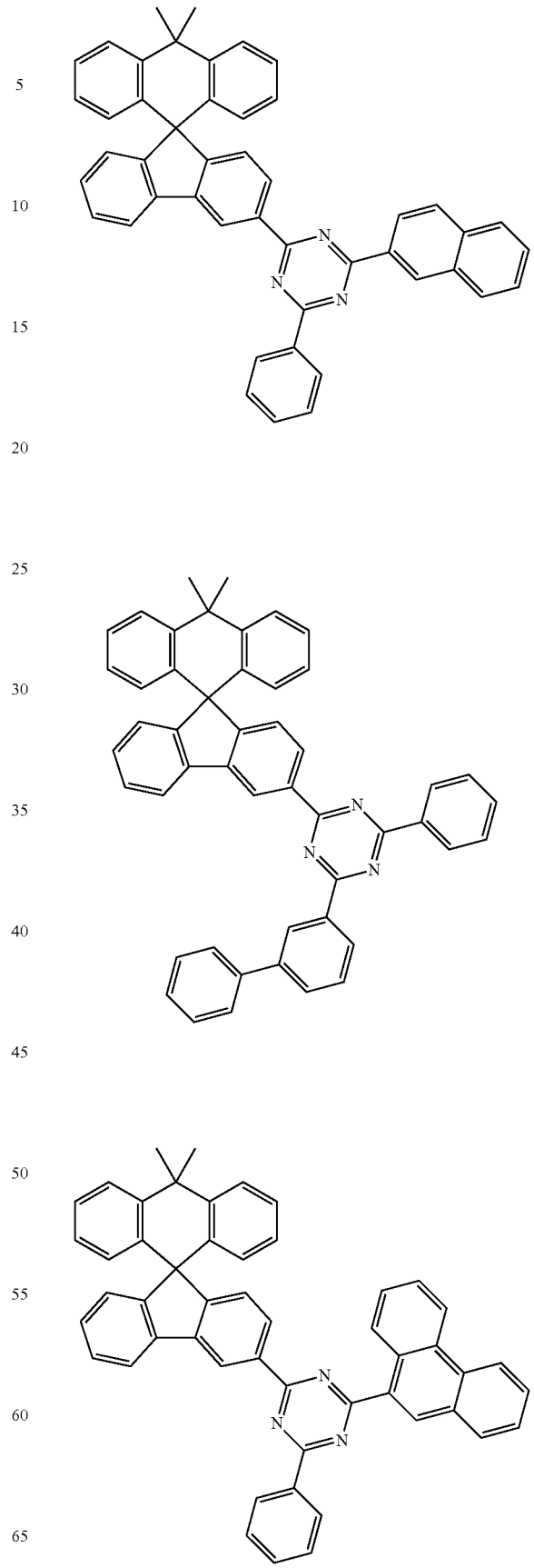

185
-continued
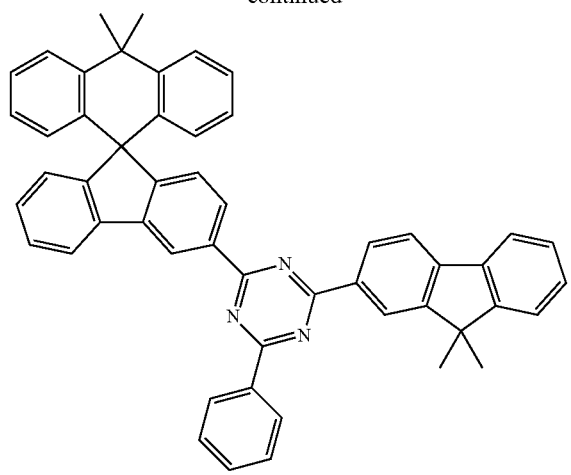
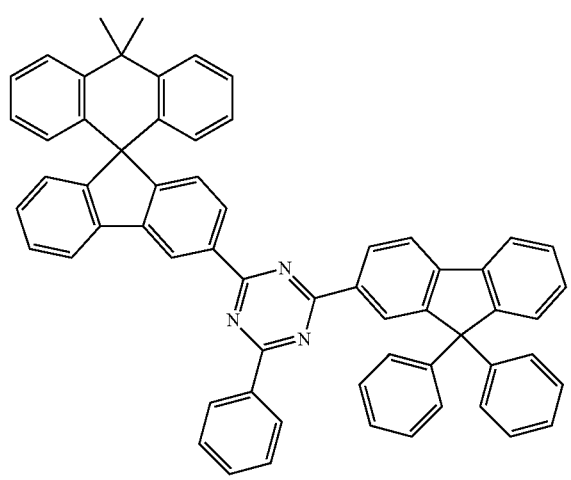
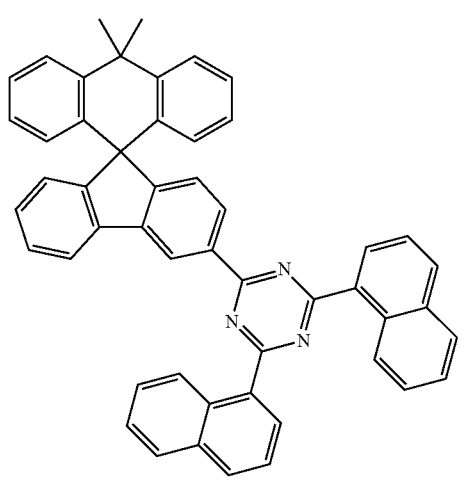
186
-continued
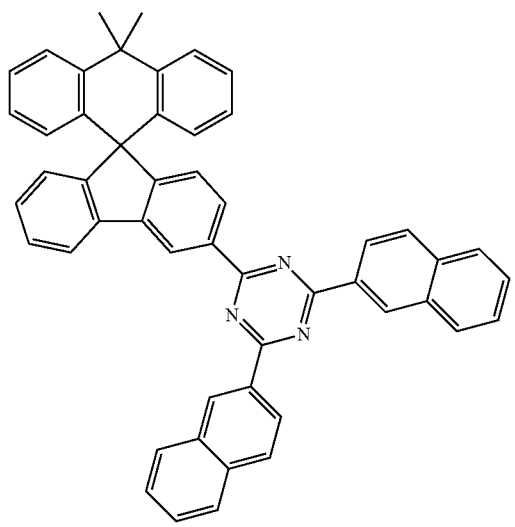
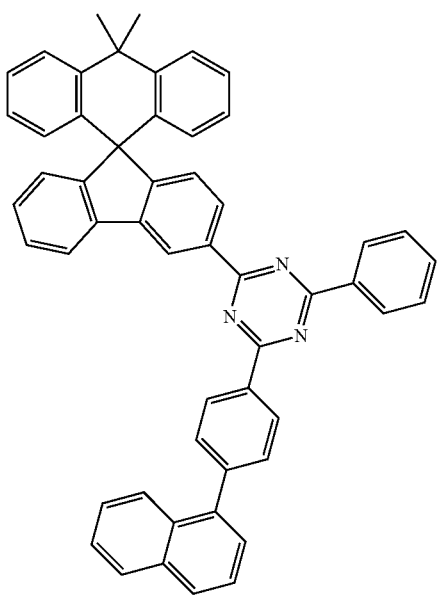

187
-continued
188
-continued
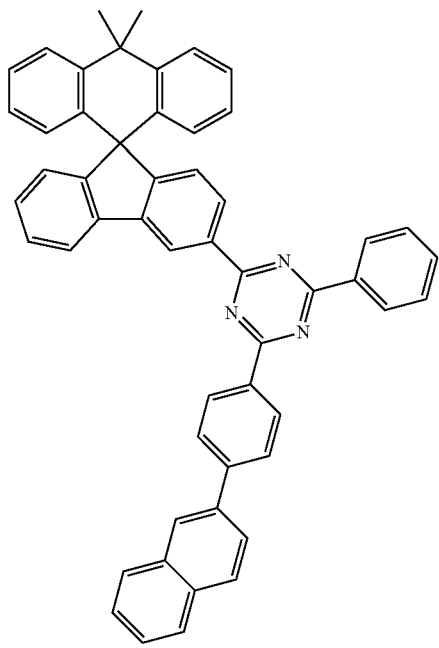
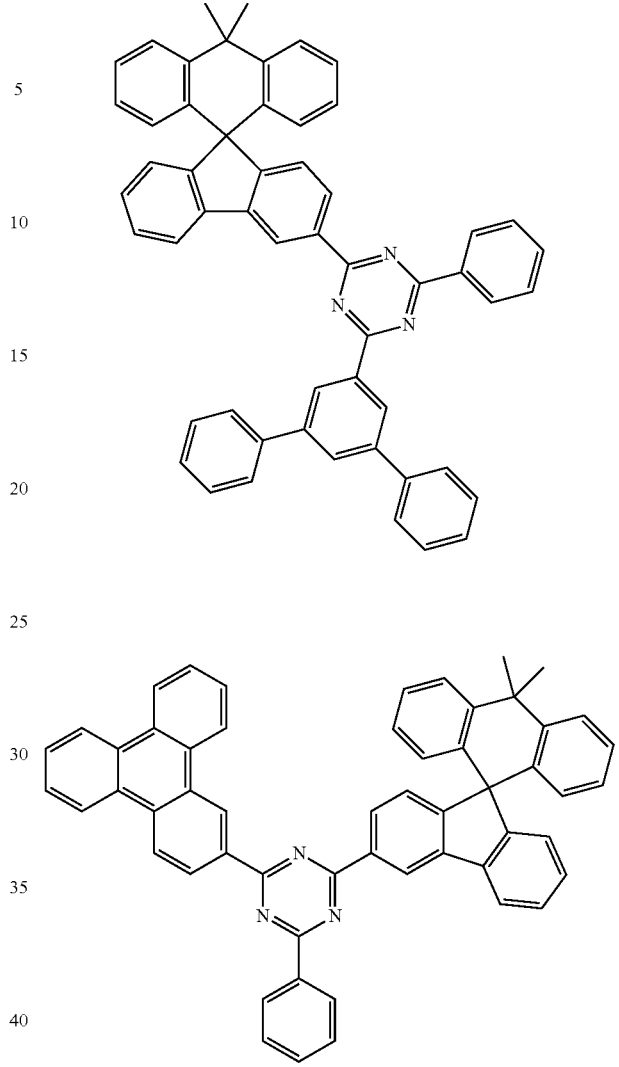
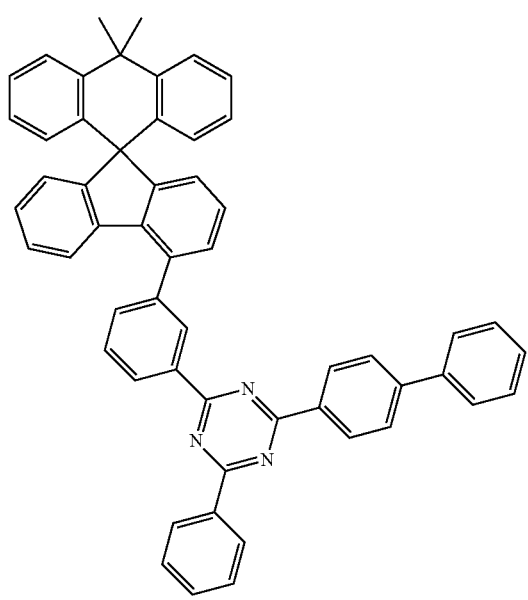
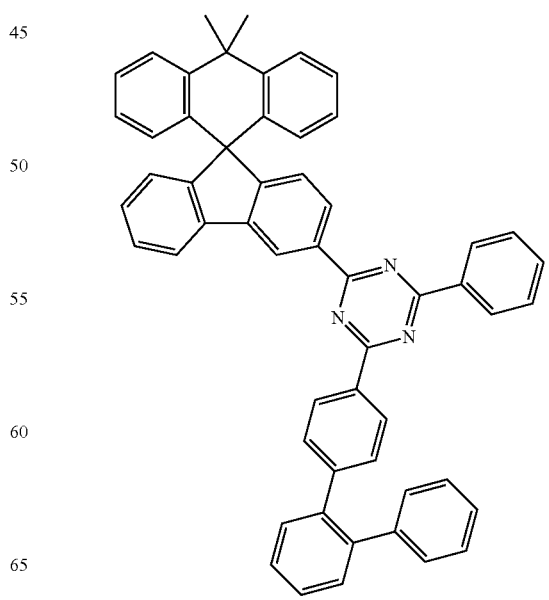

189
-continued
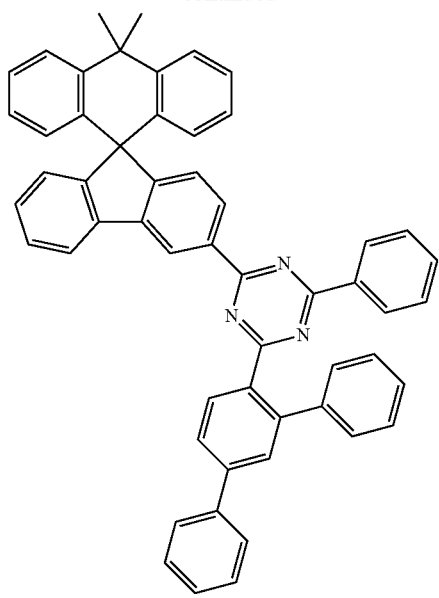
190
-continued
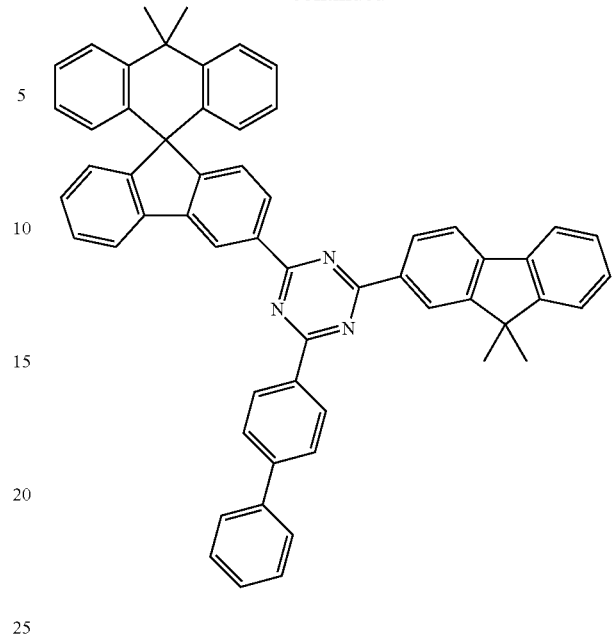
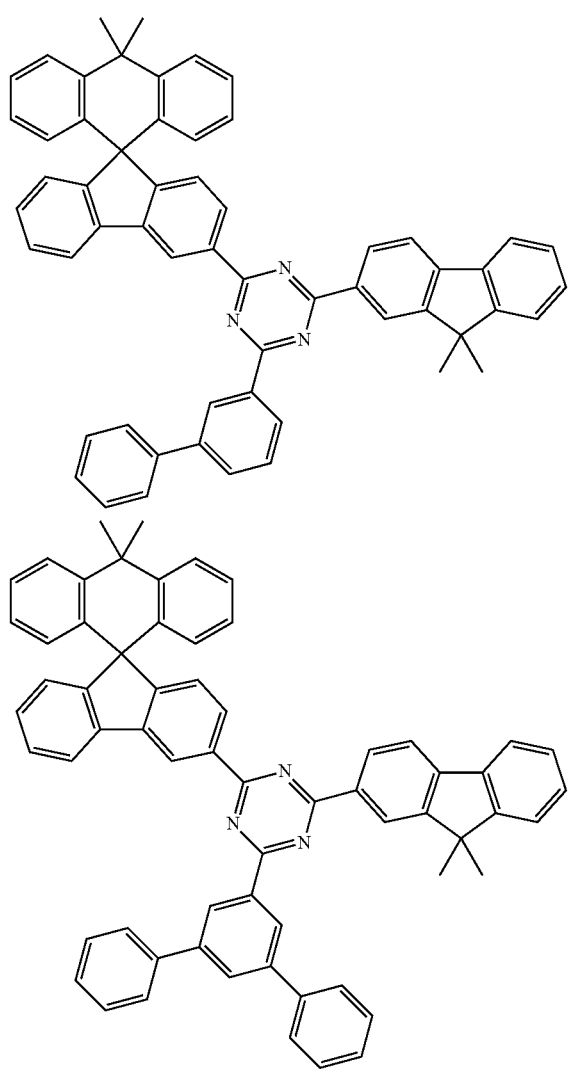
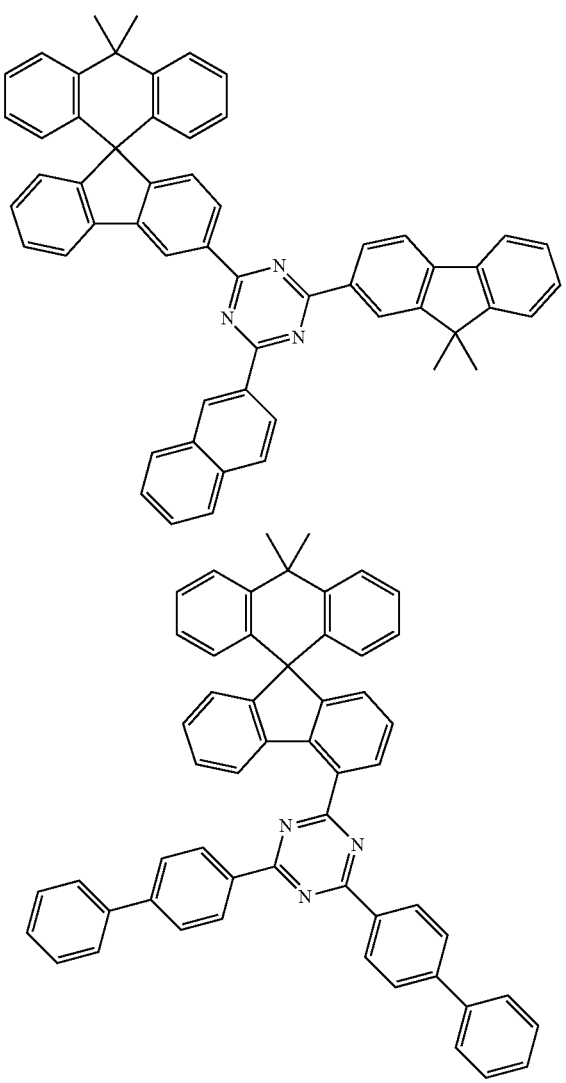

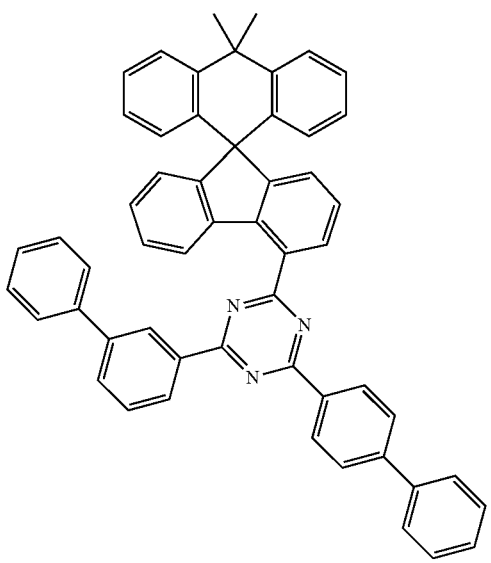
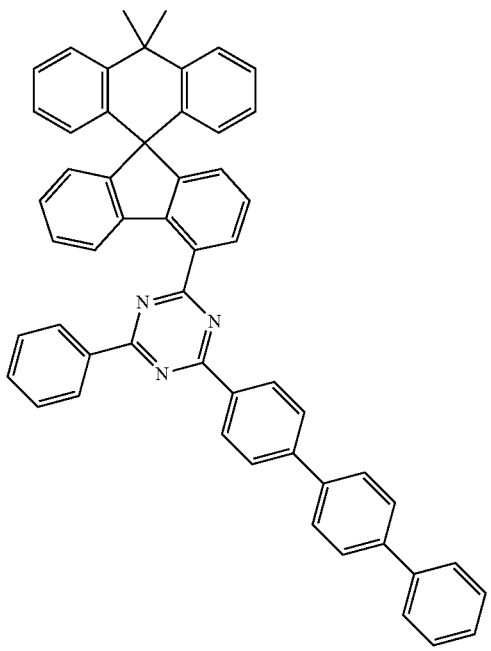
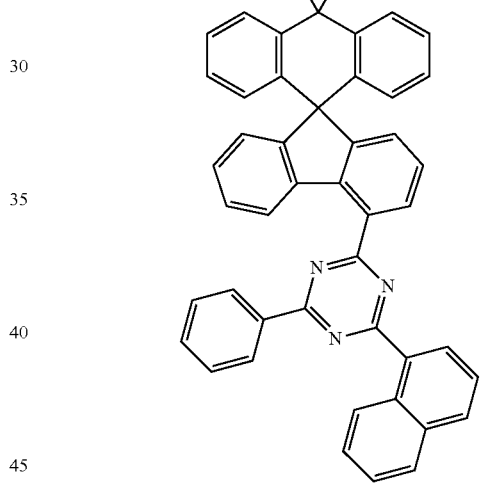
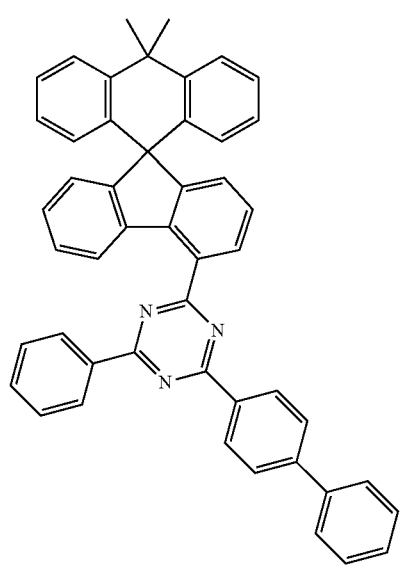
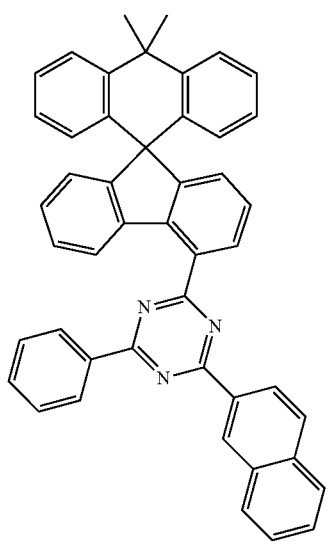

193
-continued
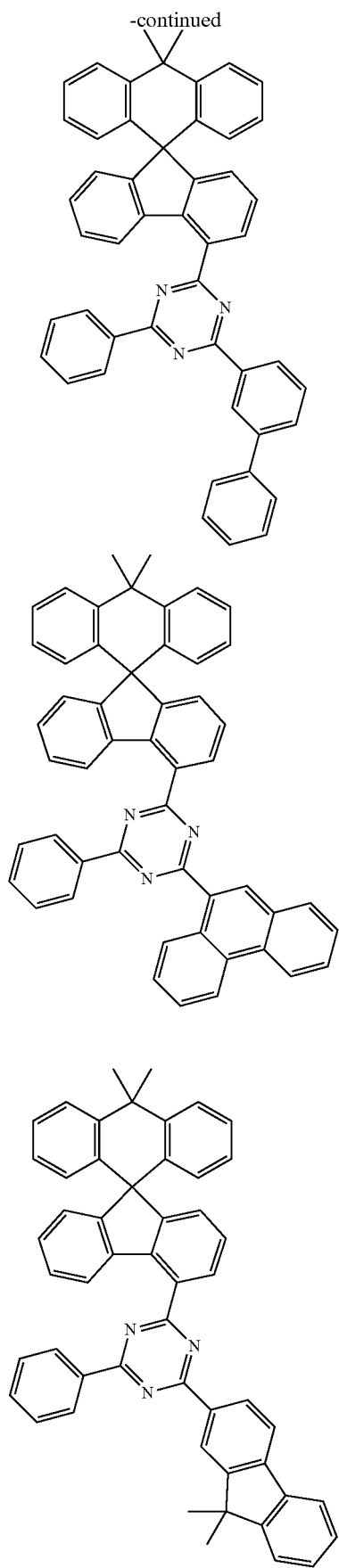
194
-continued
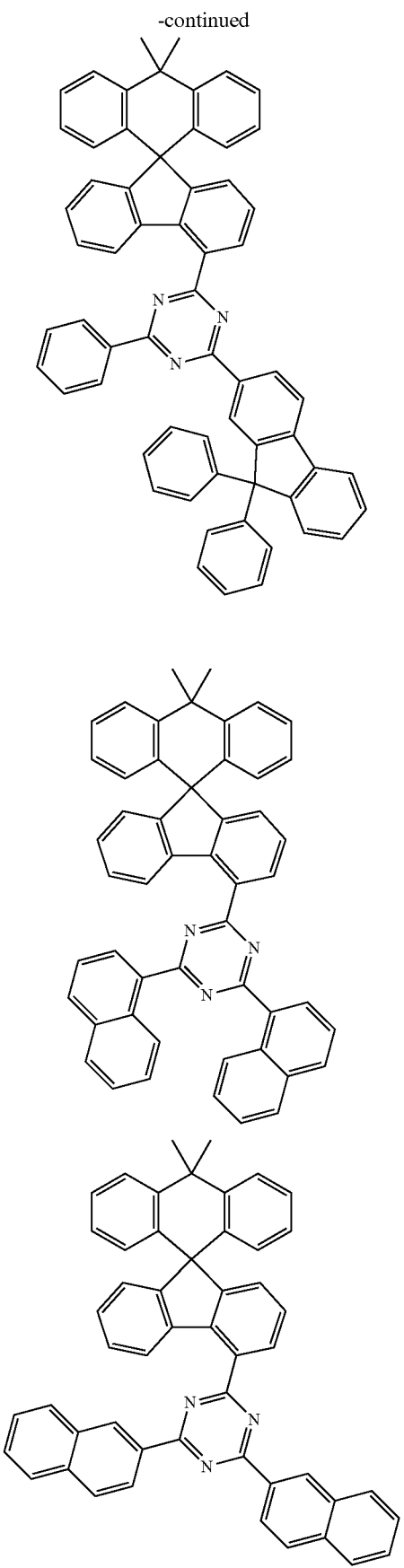

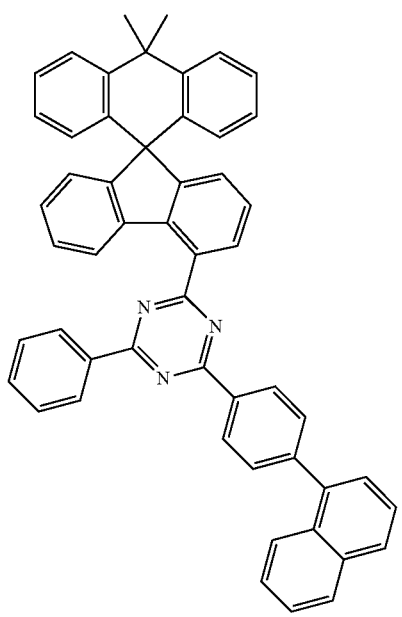
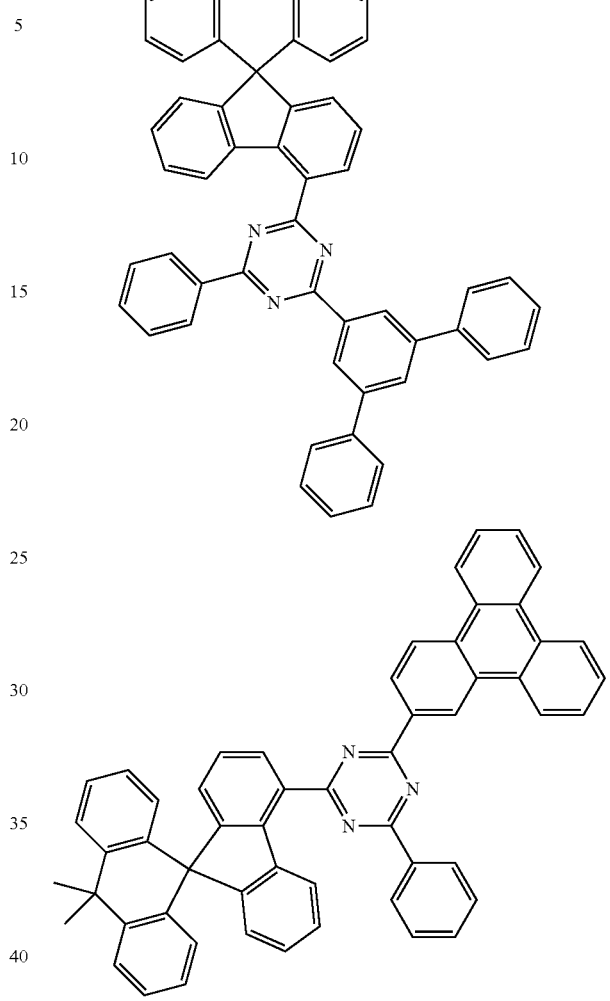
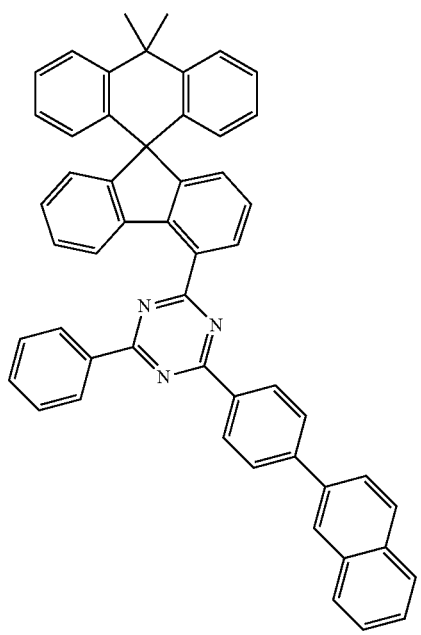
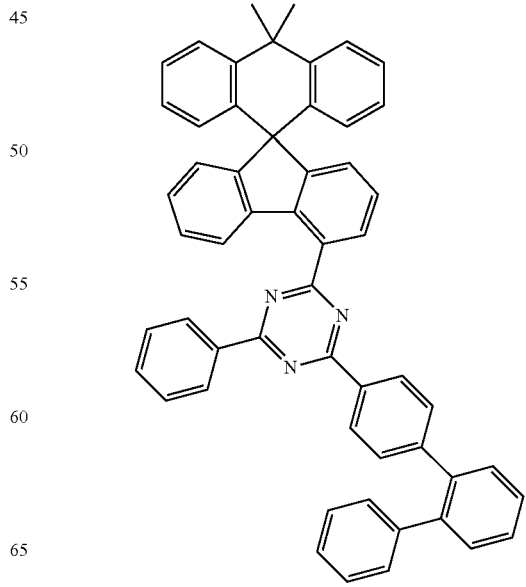

197
-continued
198
-continued
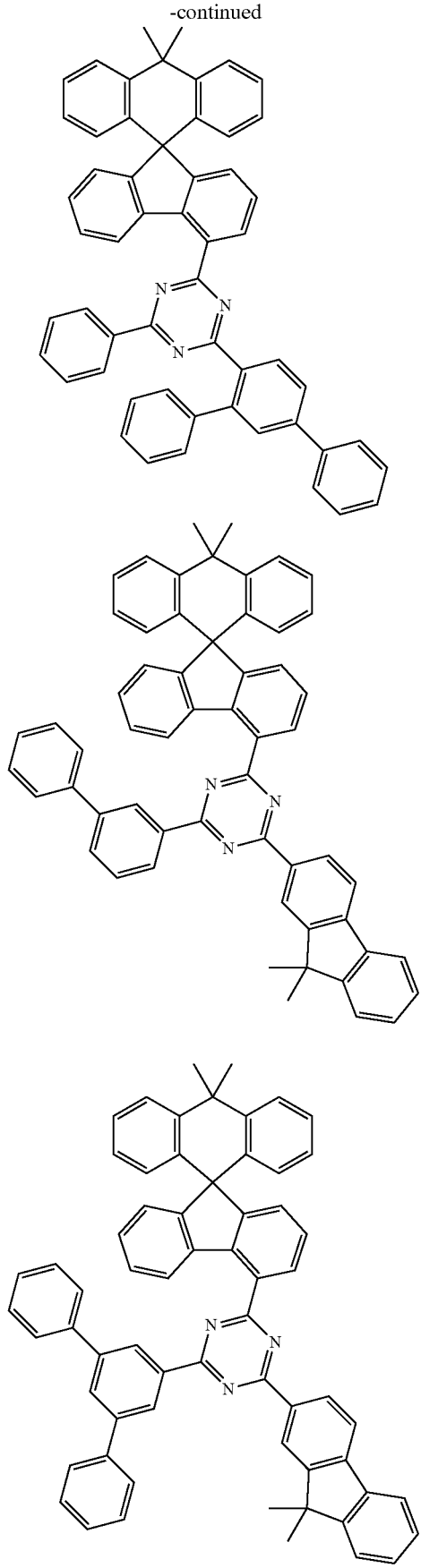
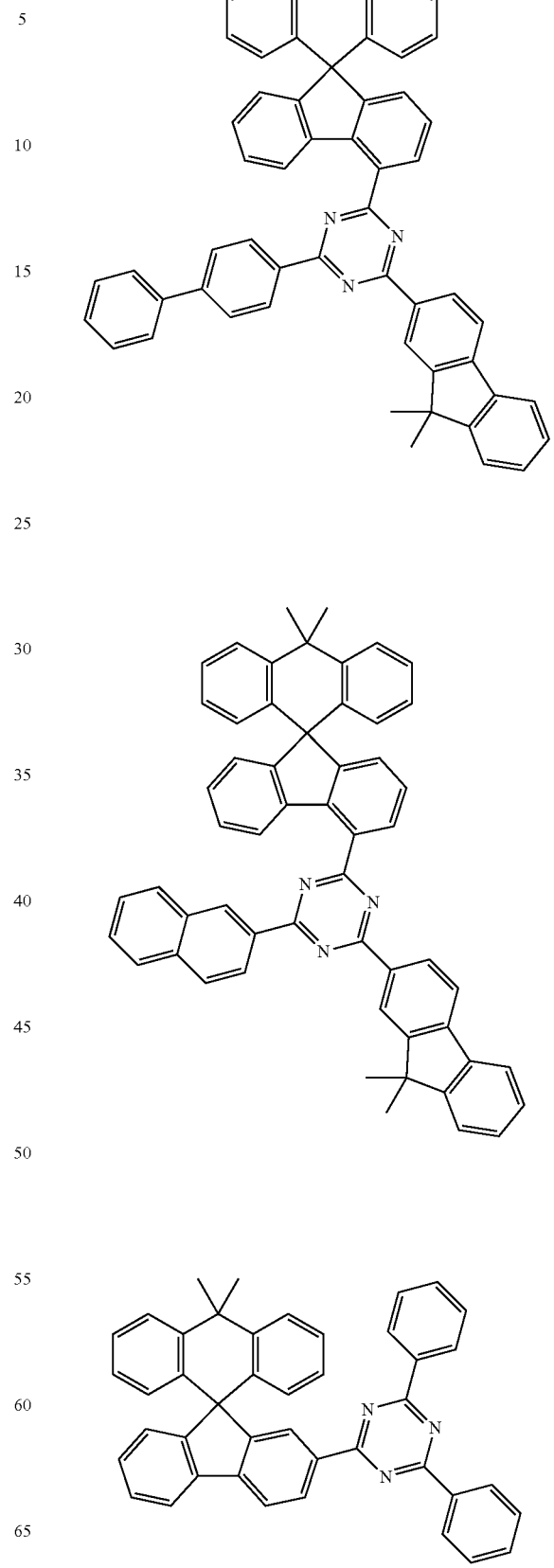

199
-continued
200
-continued
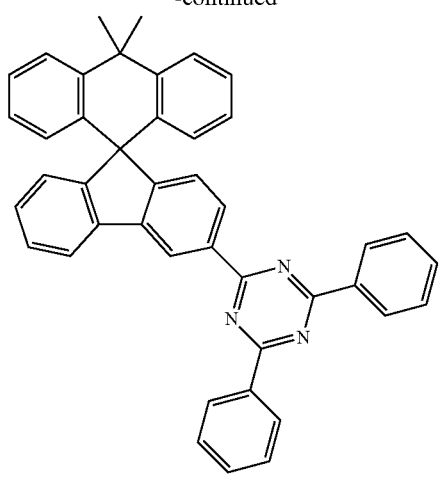
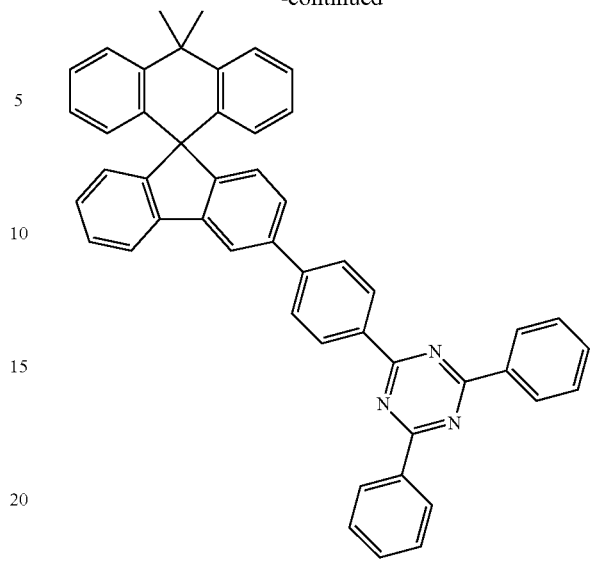
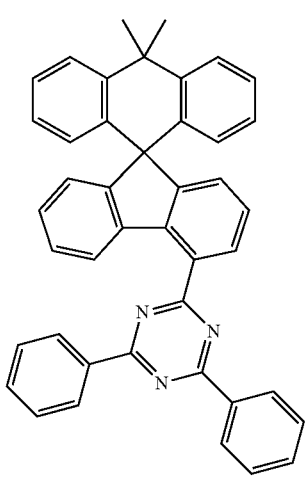
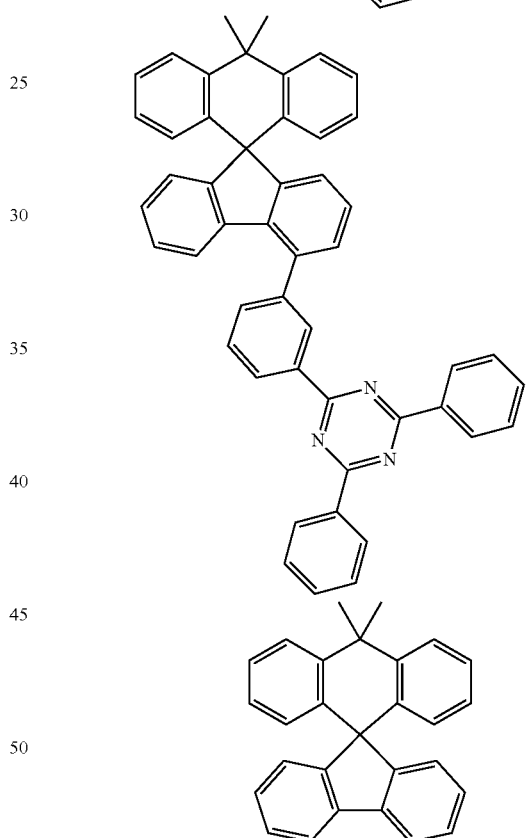
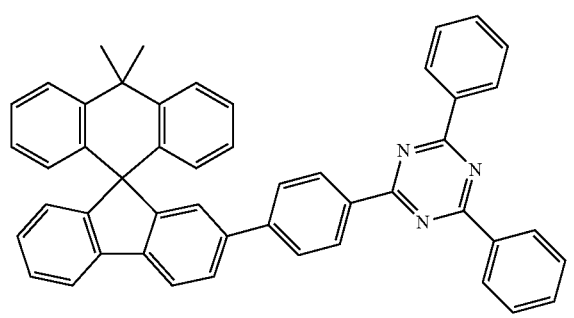

201
-continued
202
-continued
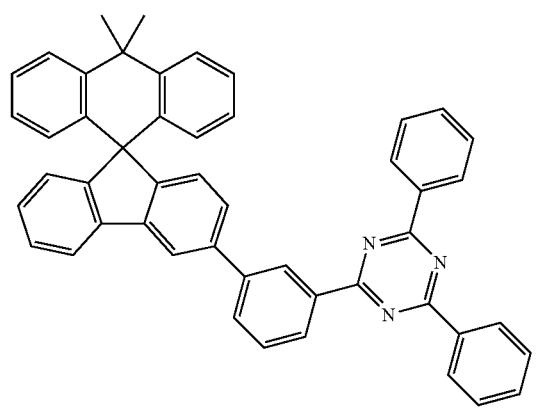
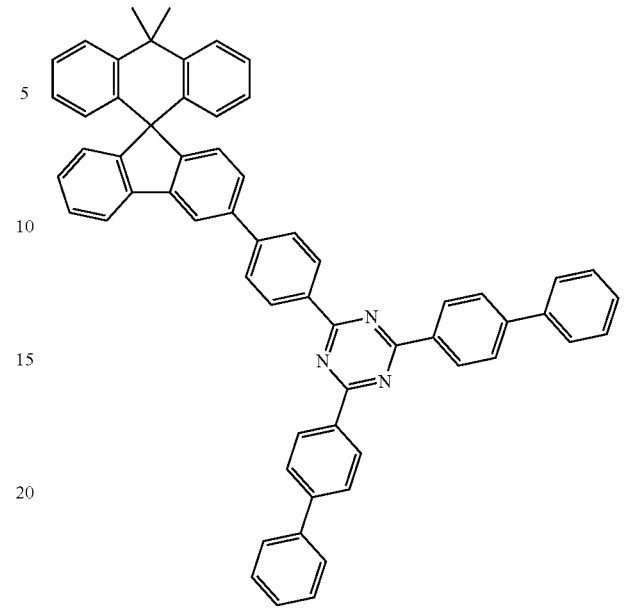
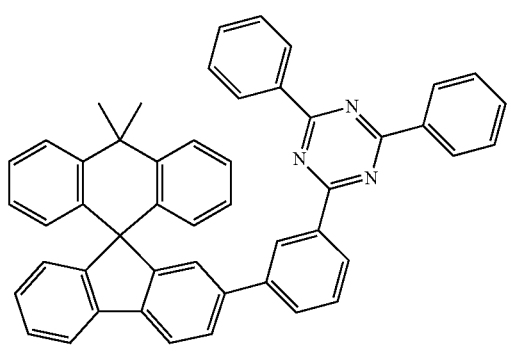
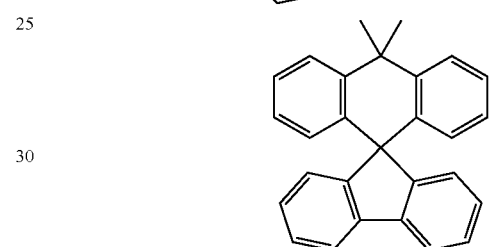
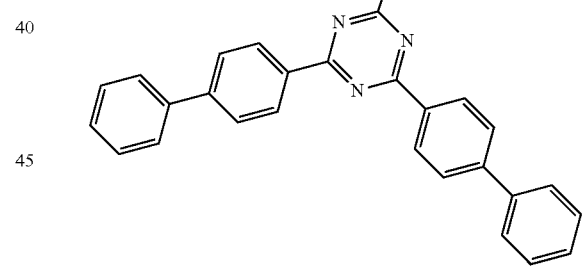
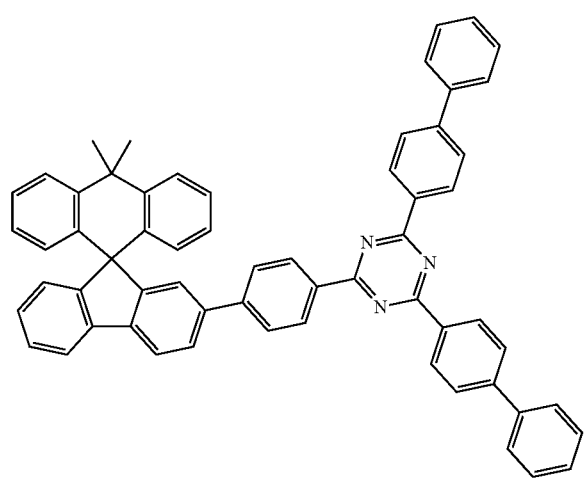
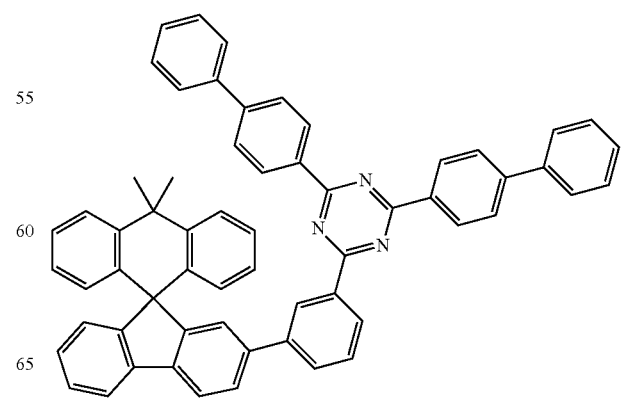

203
-continued
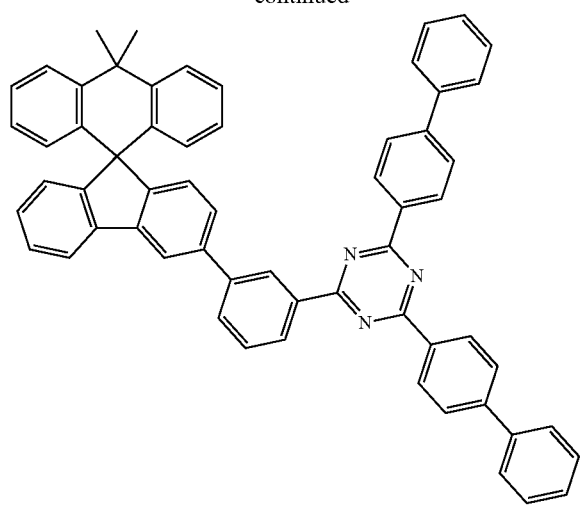
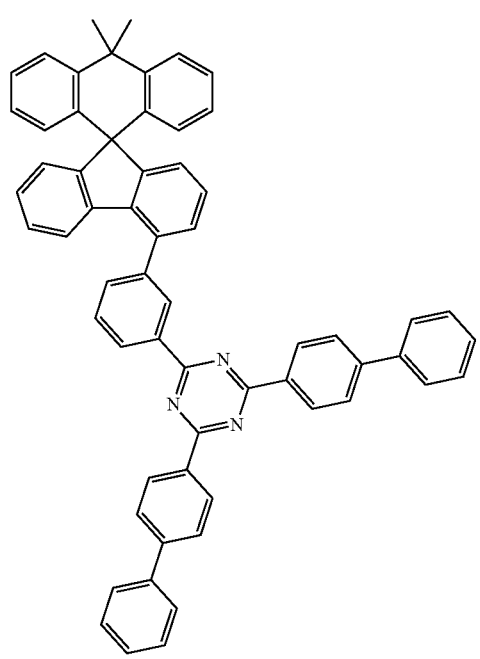
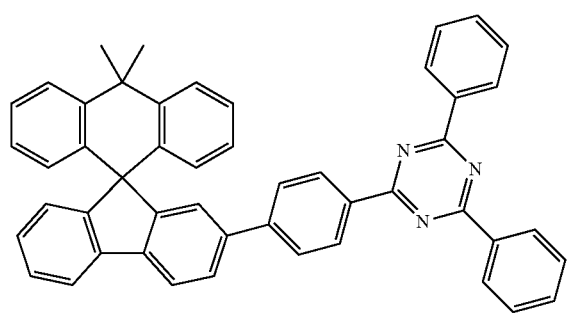
204
-continued
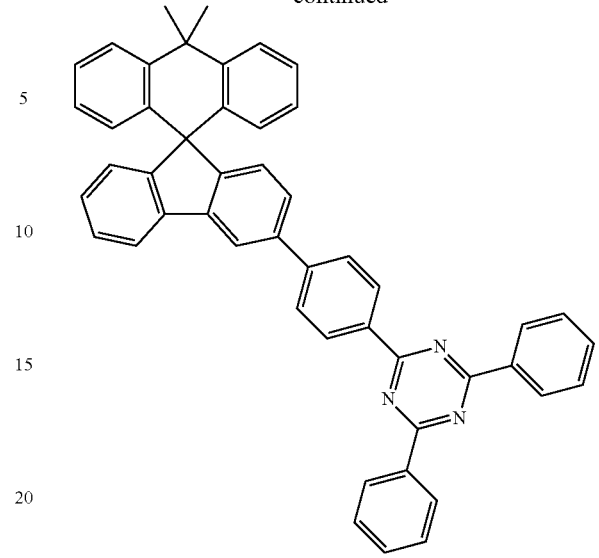
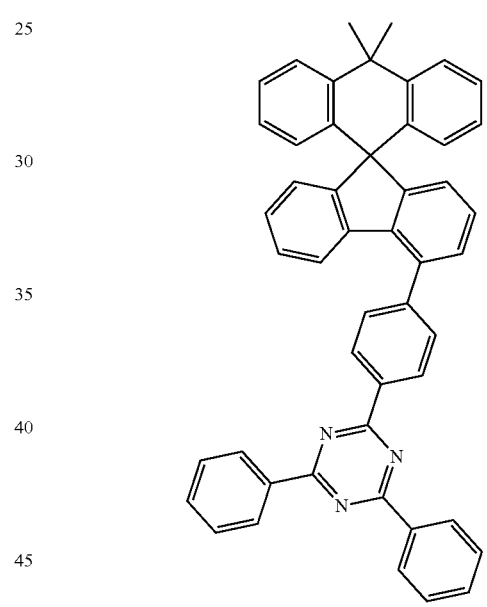
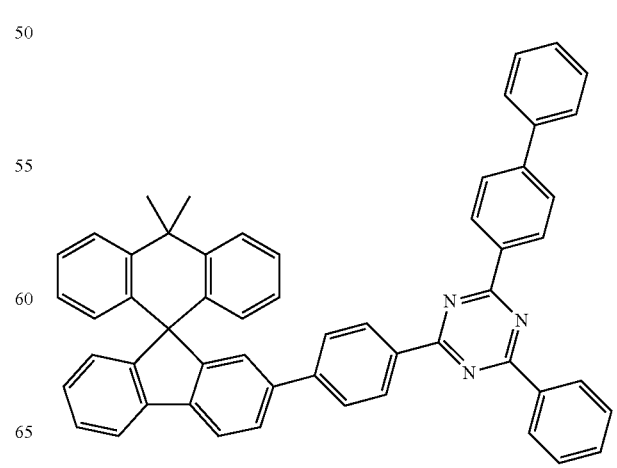

205
-continued
206
-continued
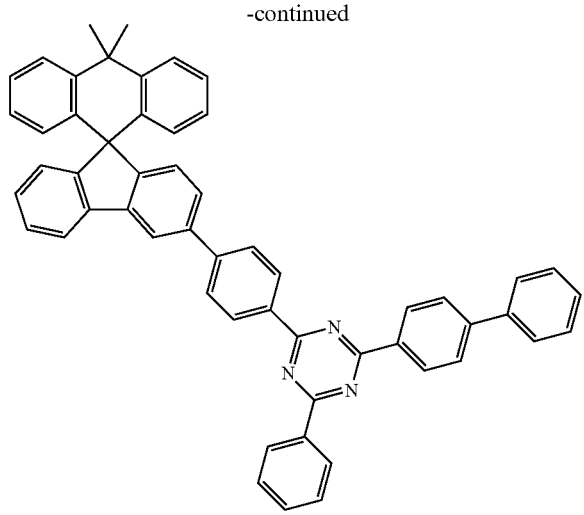
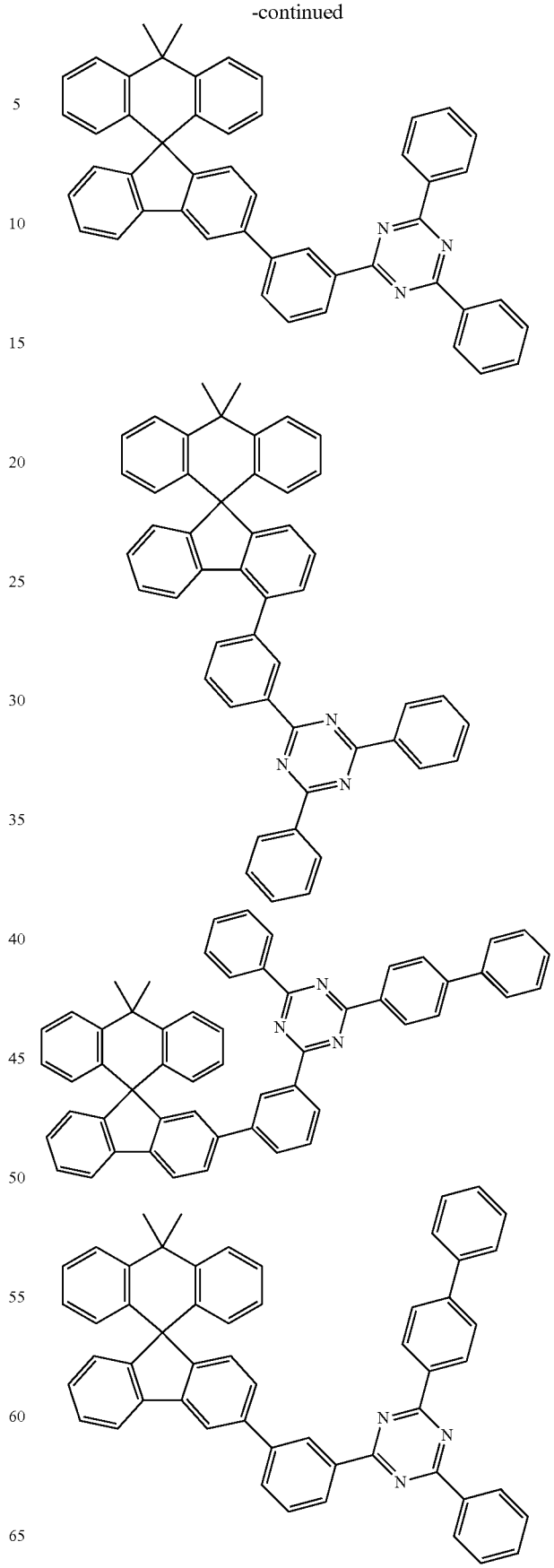

207
-continued
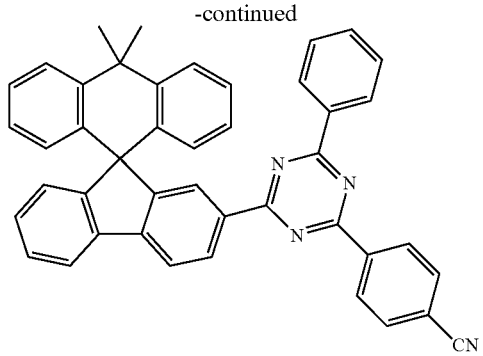
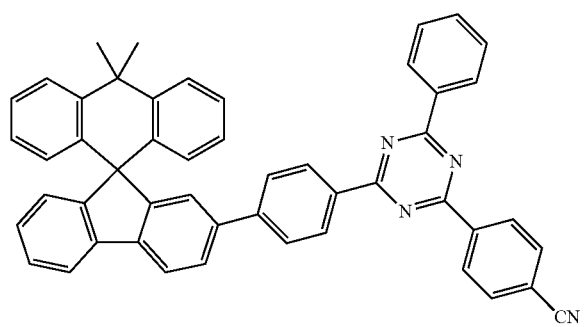
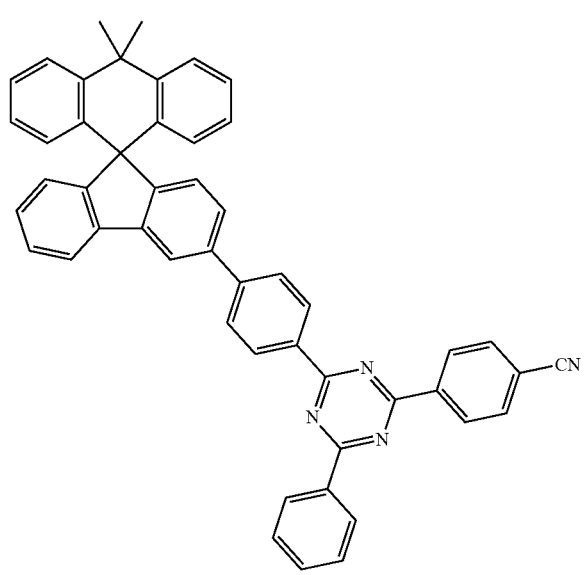
208
-continued
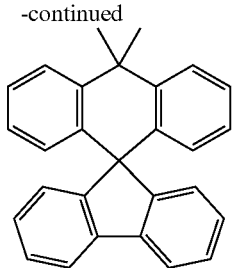
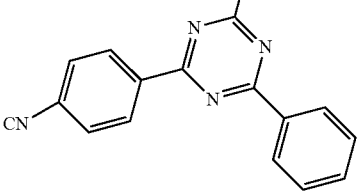
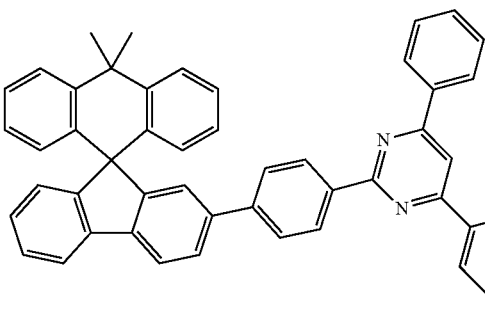
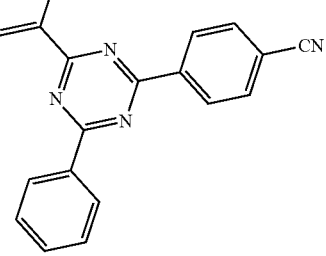

209
-continued
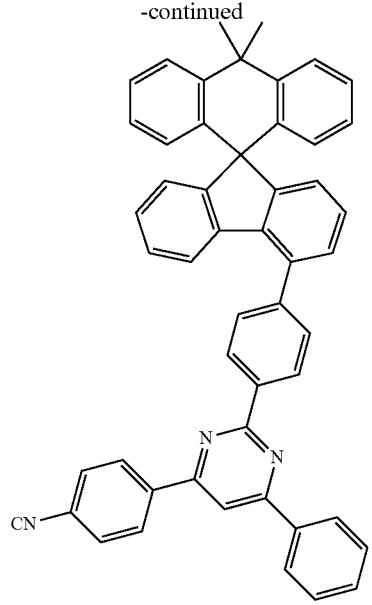
210
-continued
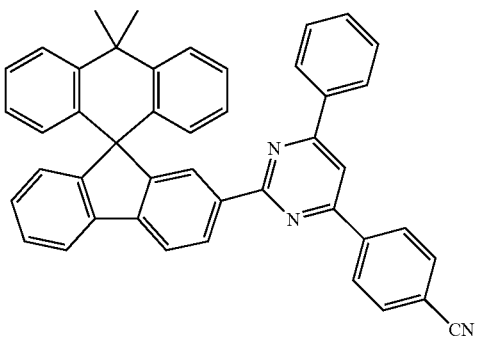
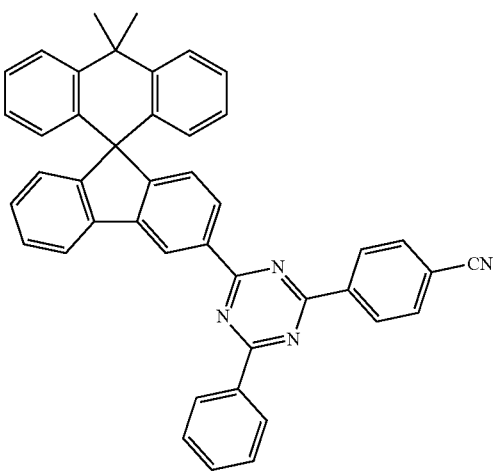
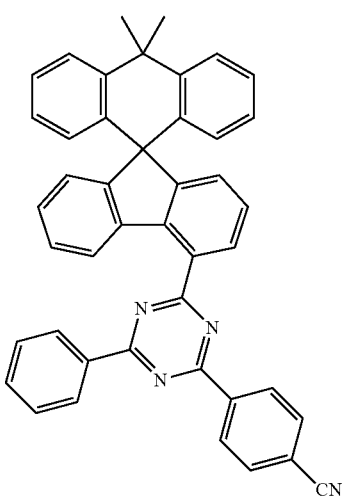
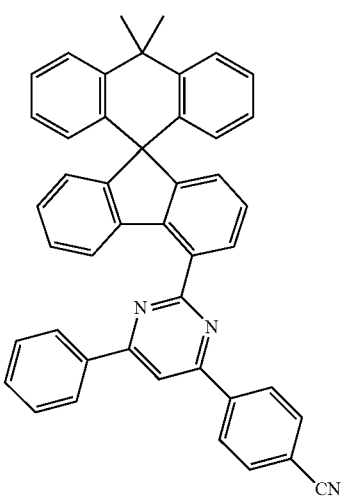

211
-continued
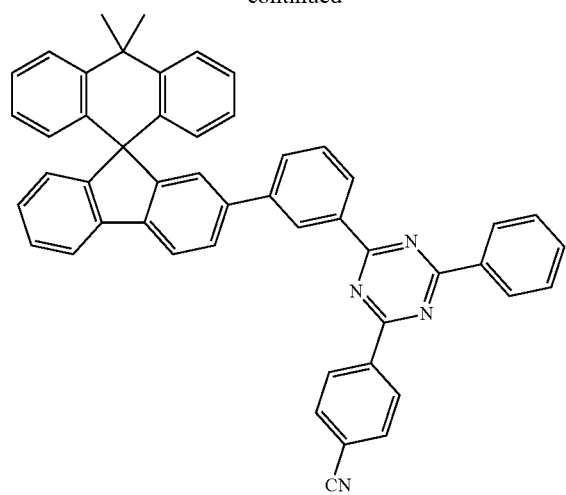
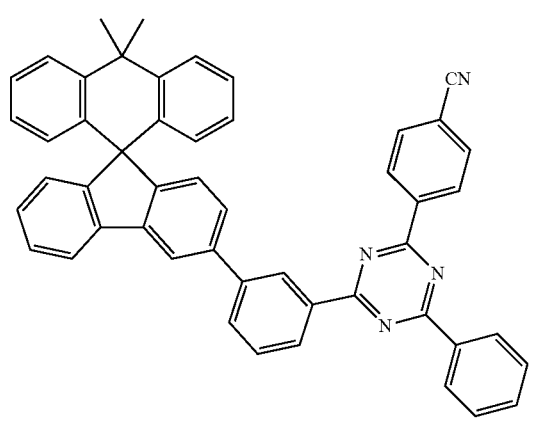
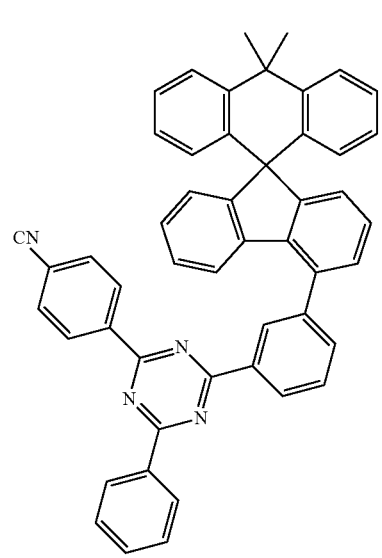
212
-continued
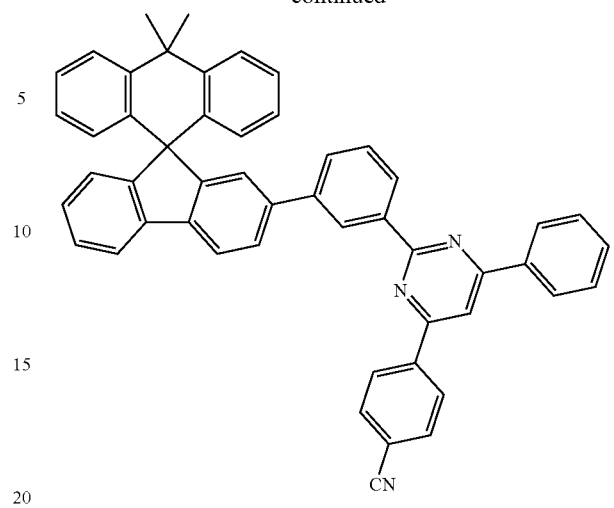
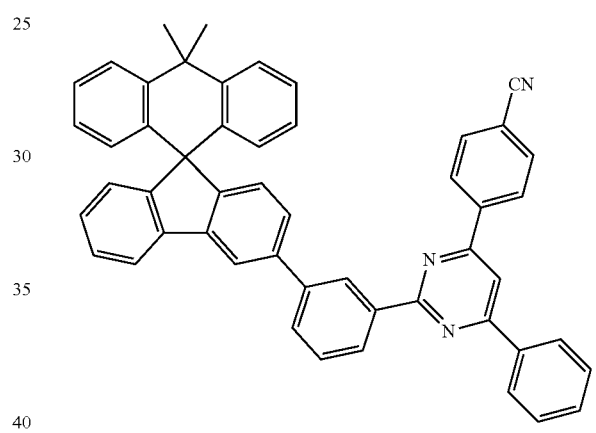
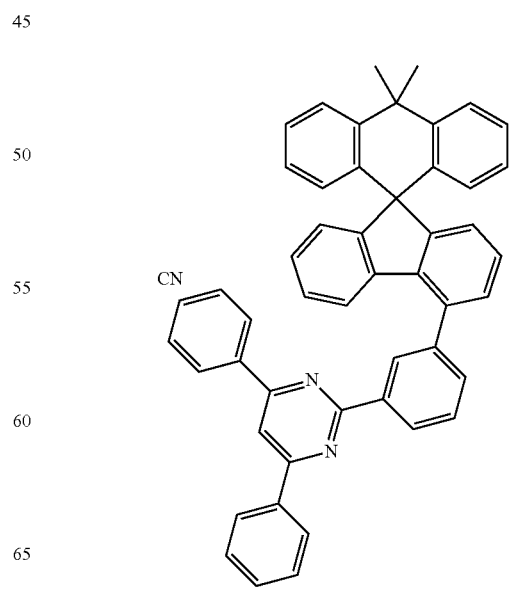

213
-continued
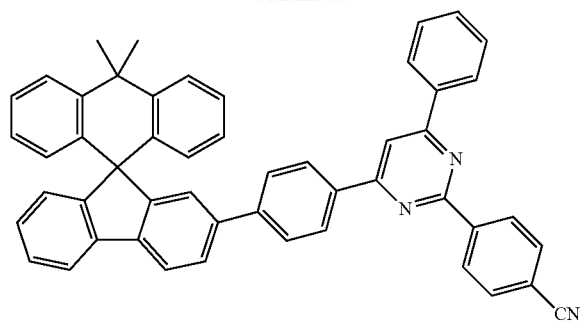
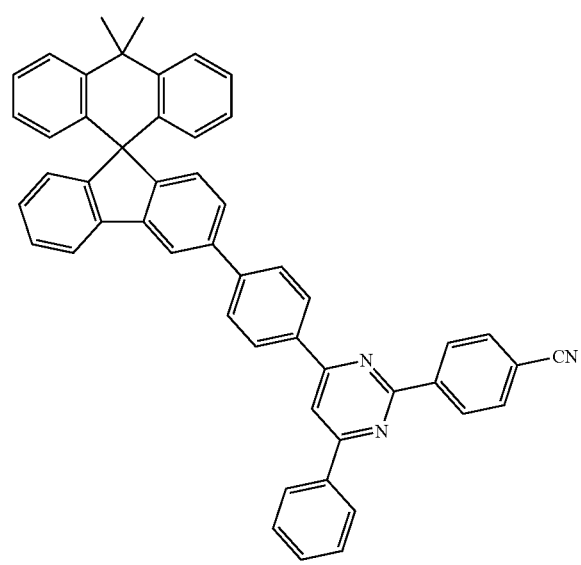
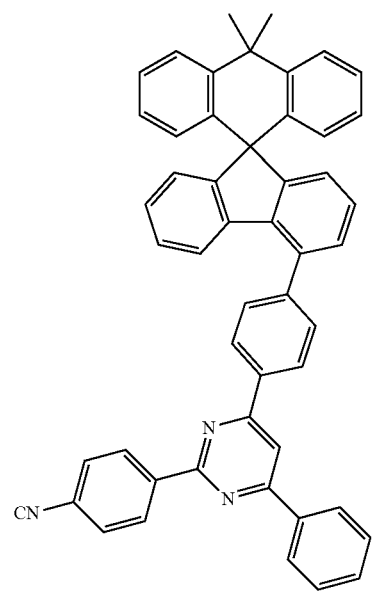
214
-continued
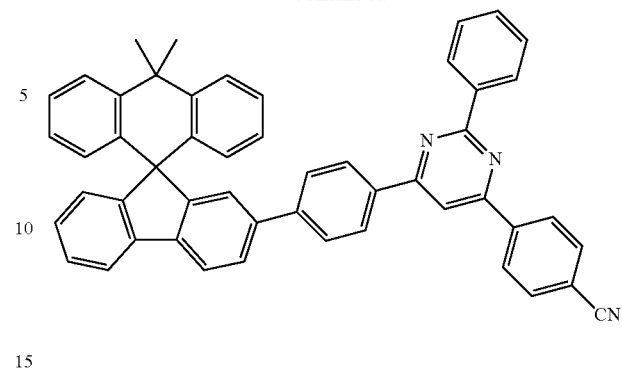
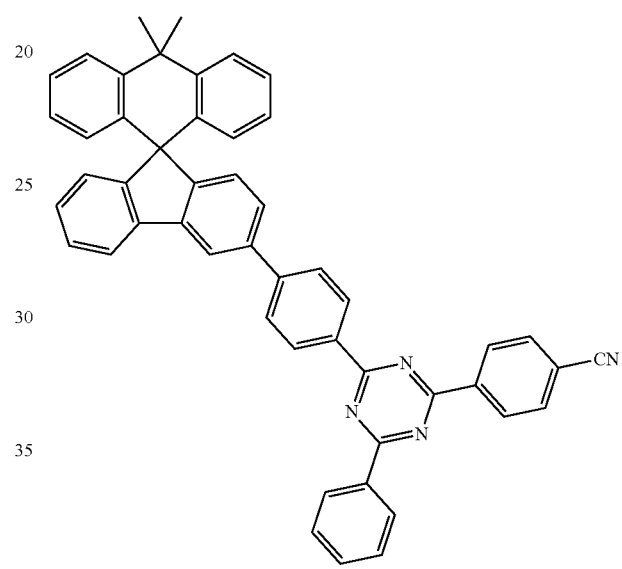
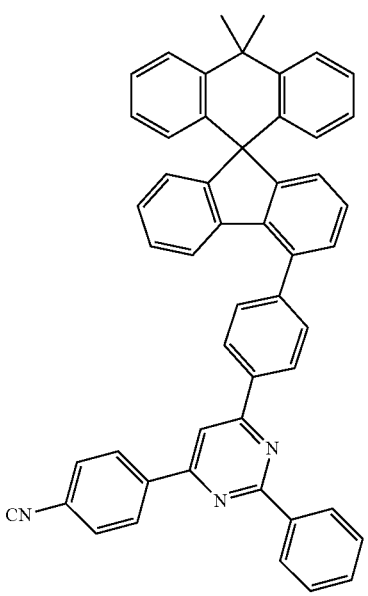

215
-continued
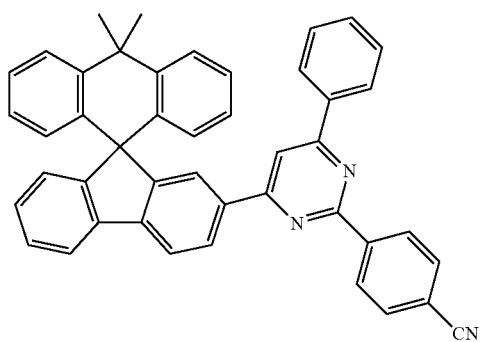
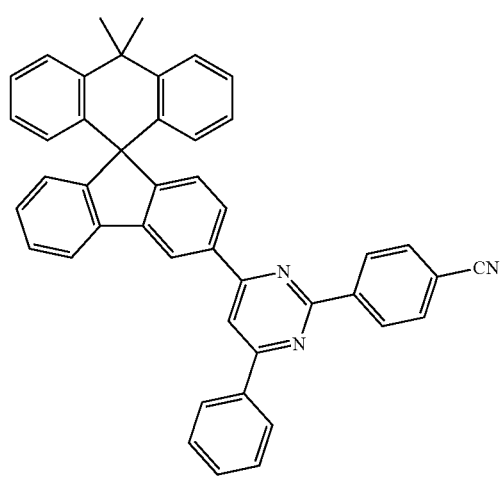
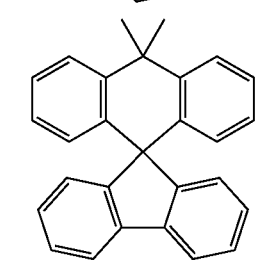
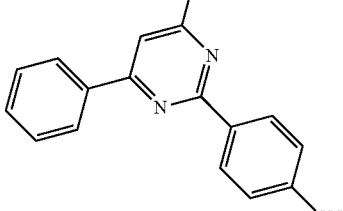
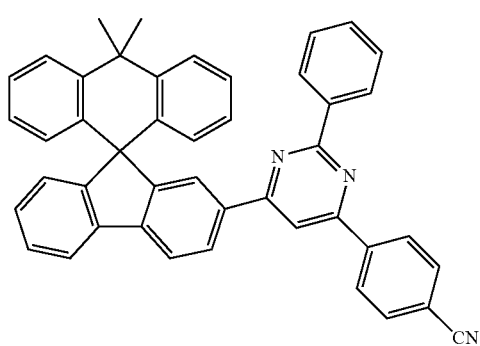
216
-continued
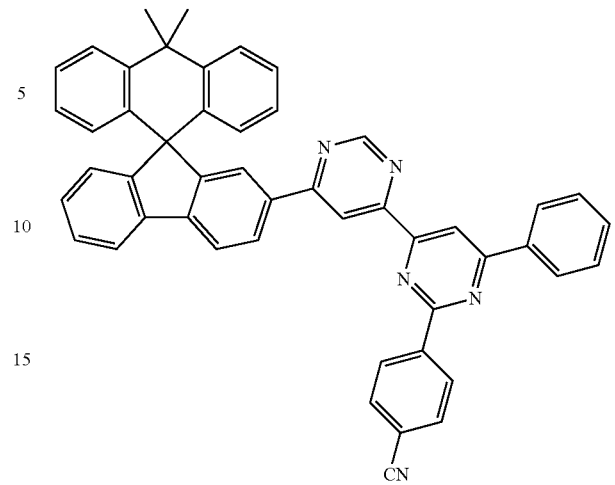
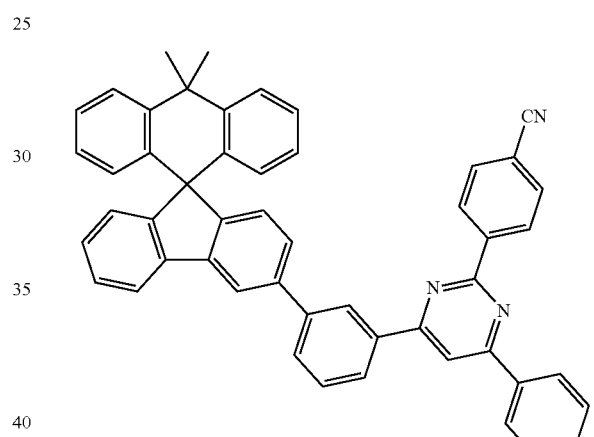
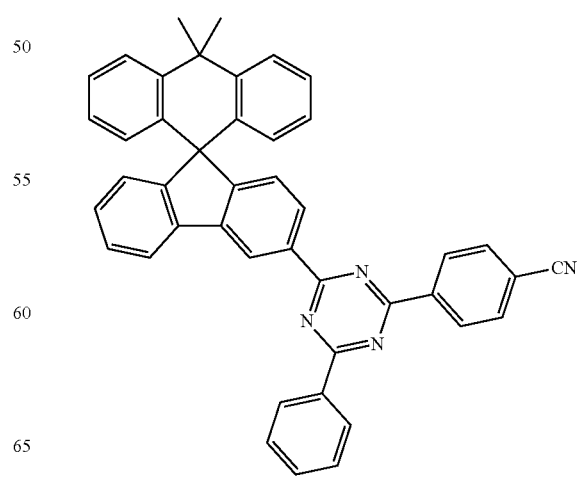

217
-continued
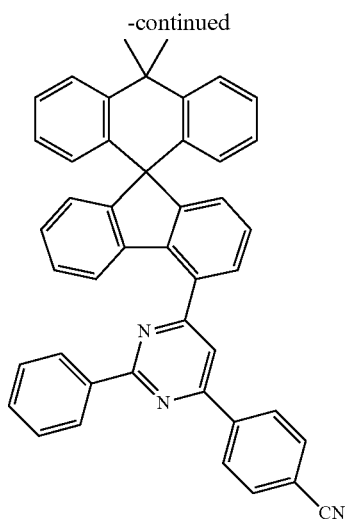
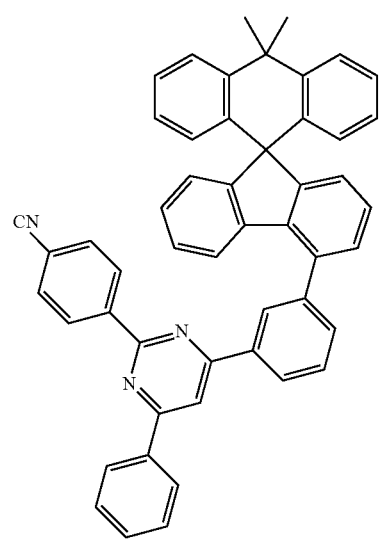
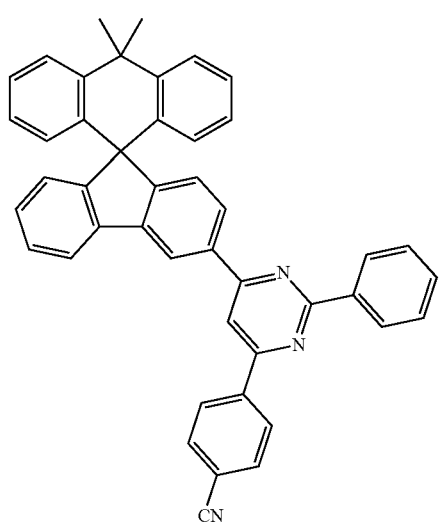
218
-continued
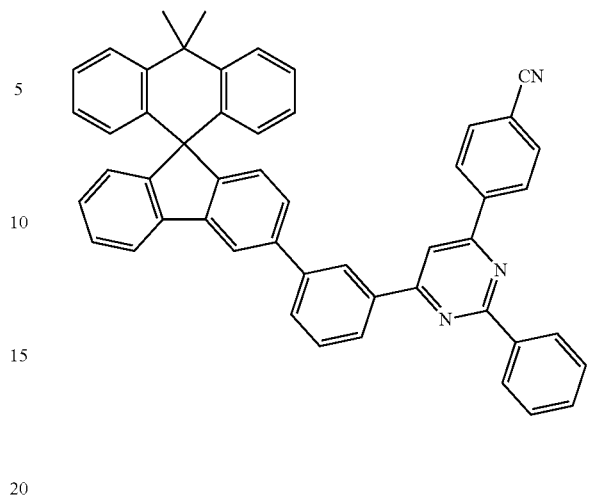
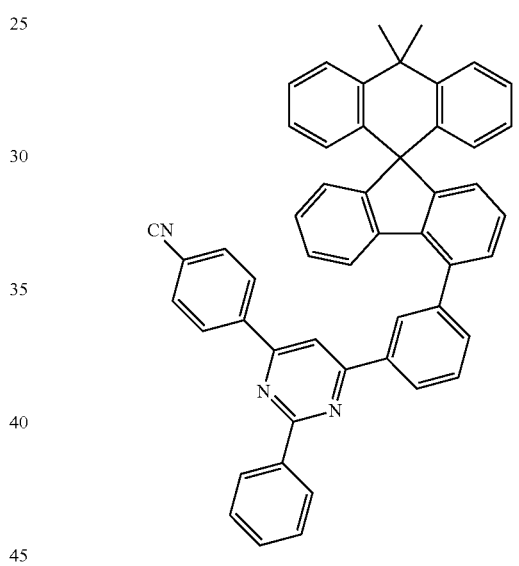
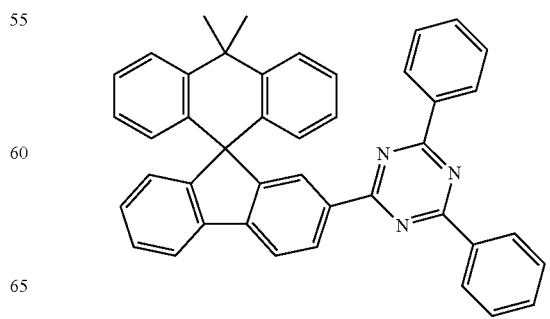

| 219 | 220 |
|---|---|
| -continued | -continued |
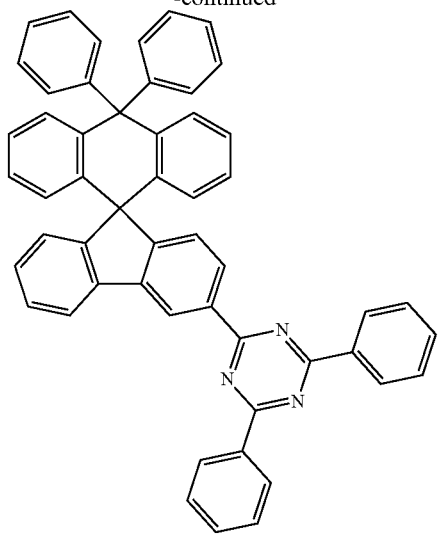
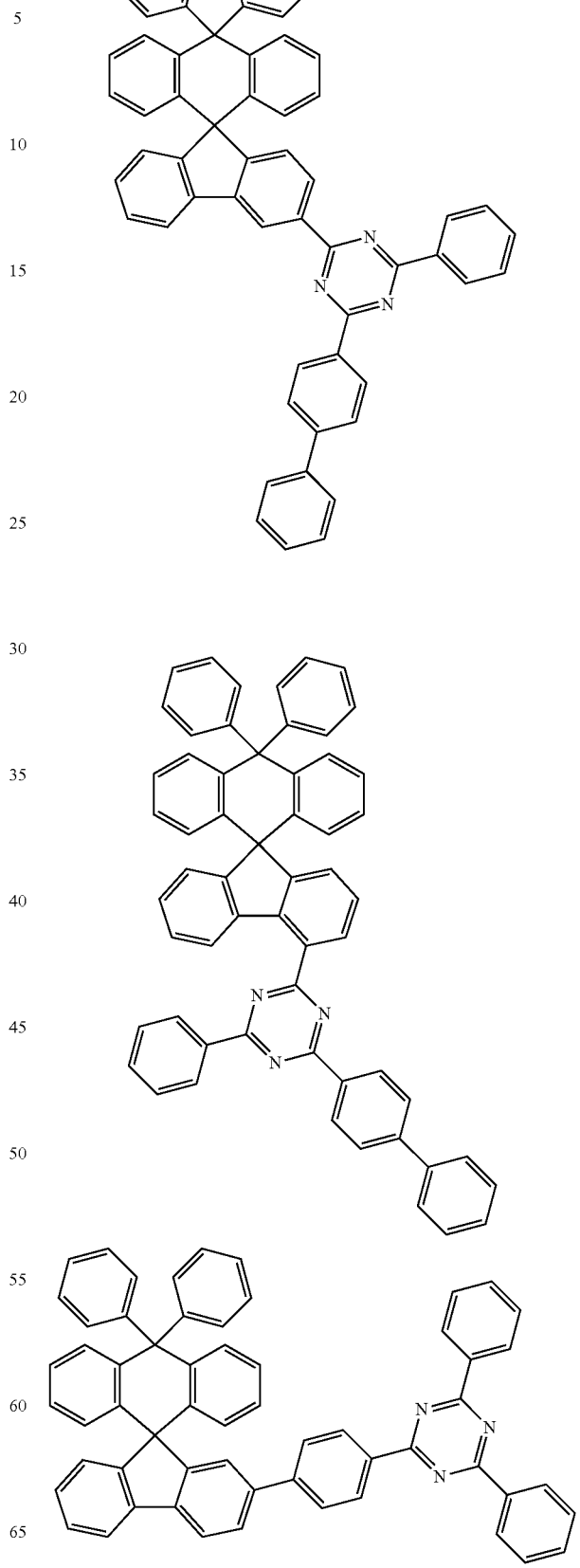

221
-continued
222
-continued
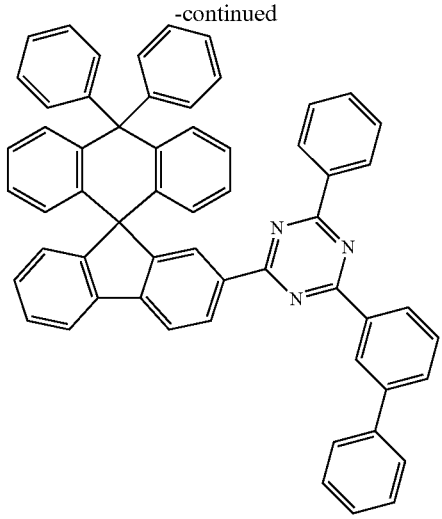
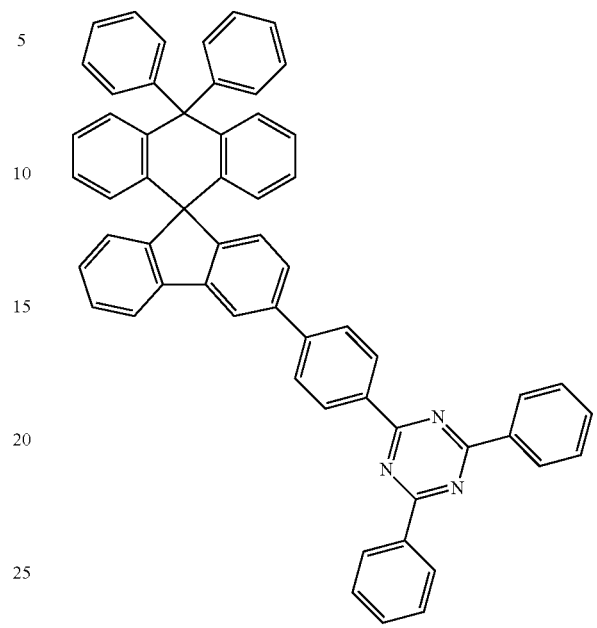
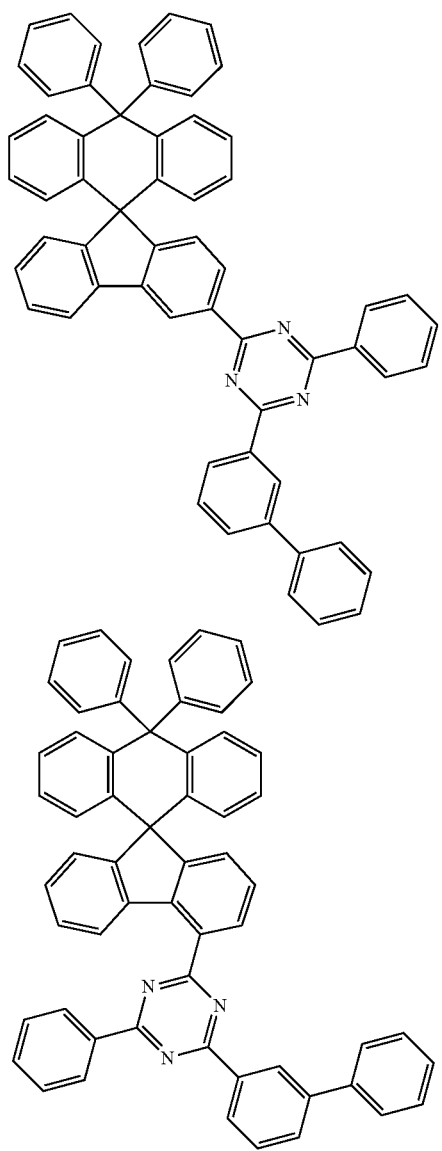
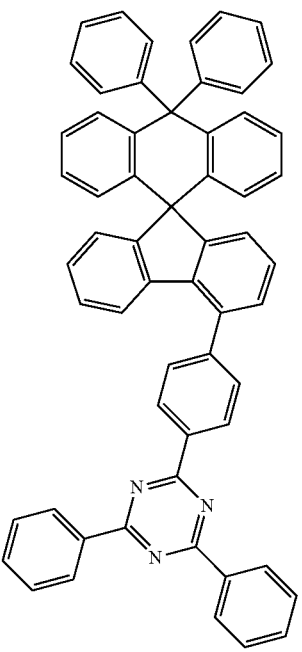

223
-continued
224
-continued
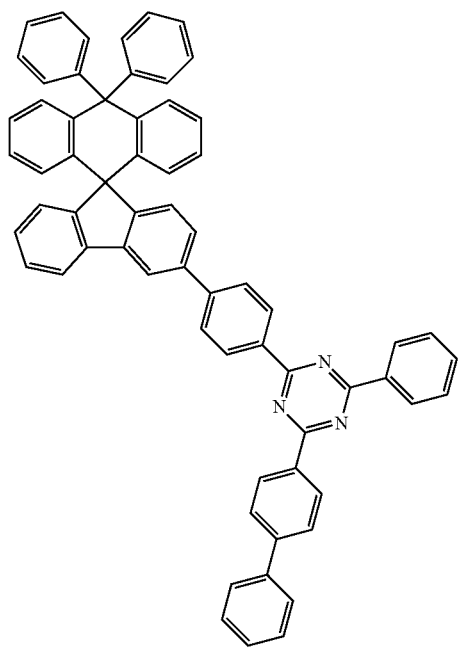
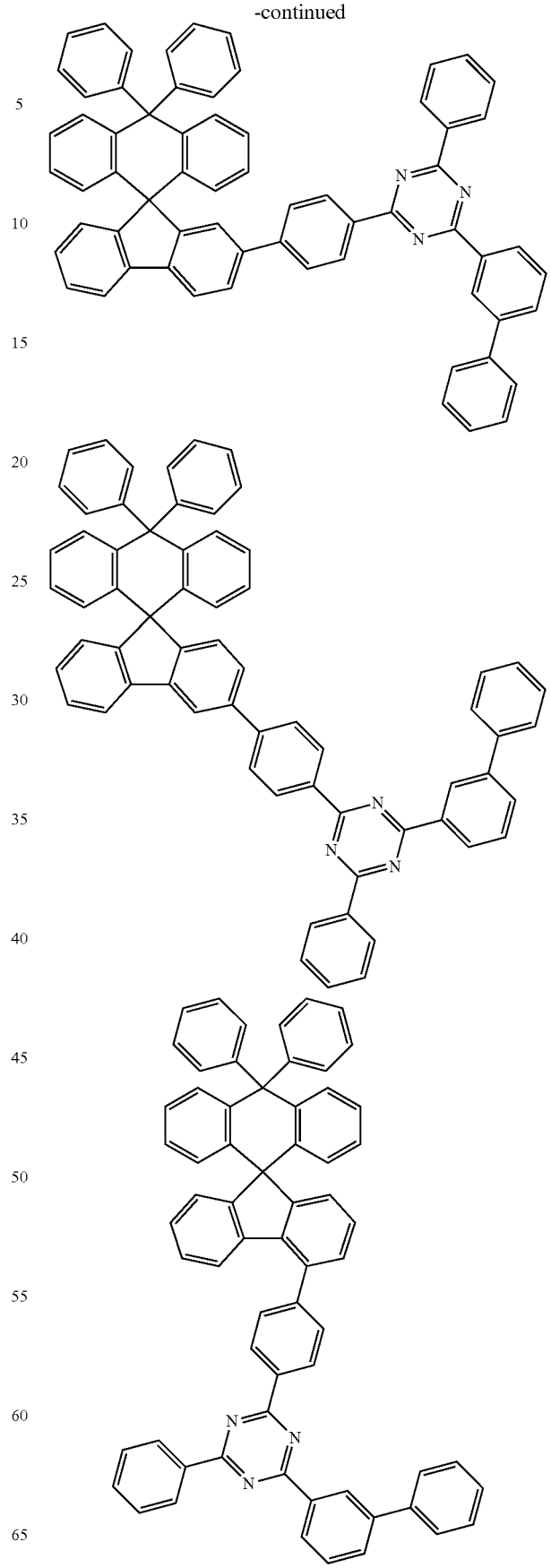

225
-continued
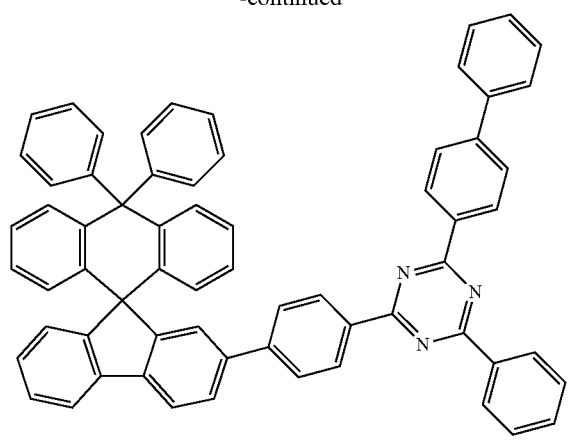
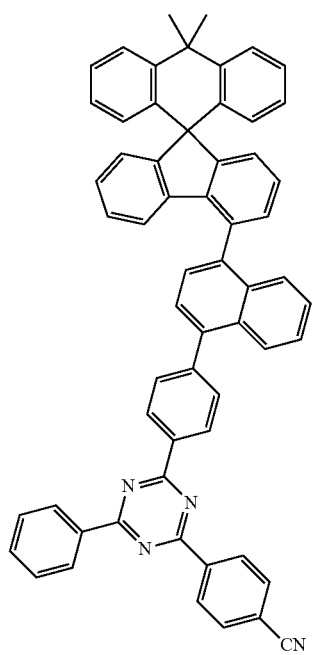
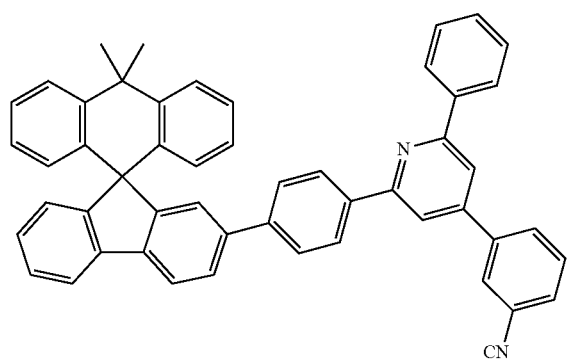
226
-continued
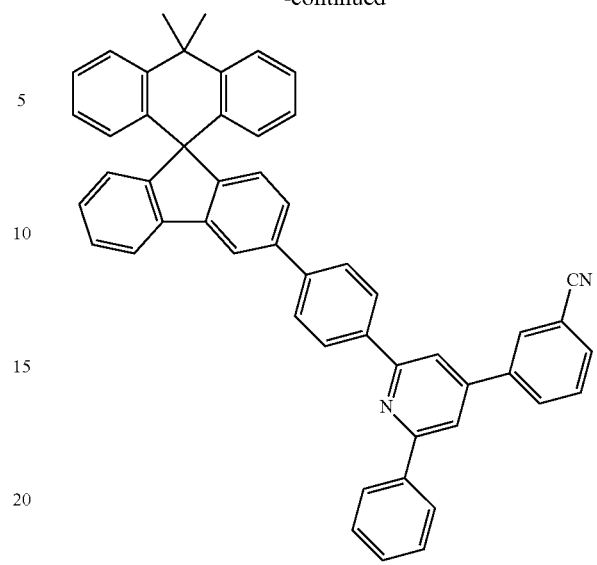
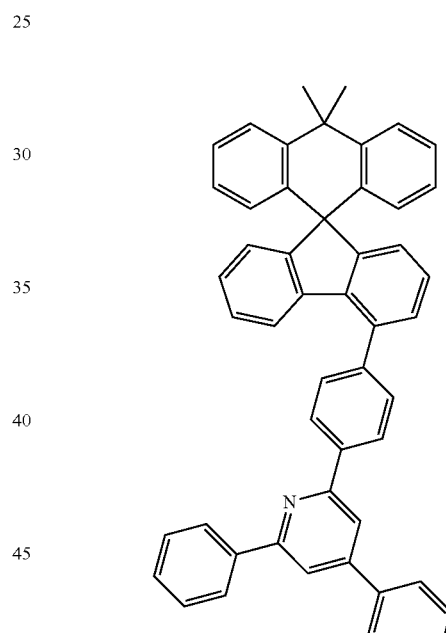
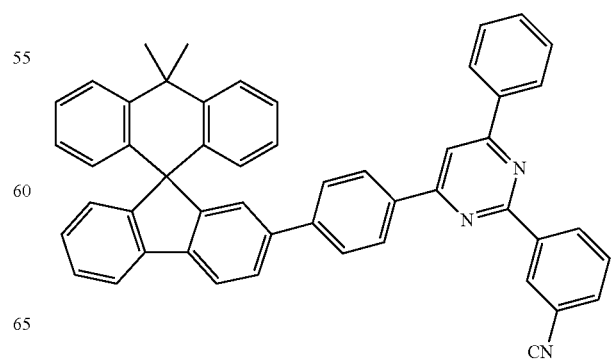

227
-continued
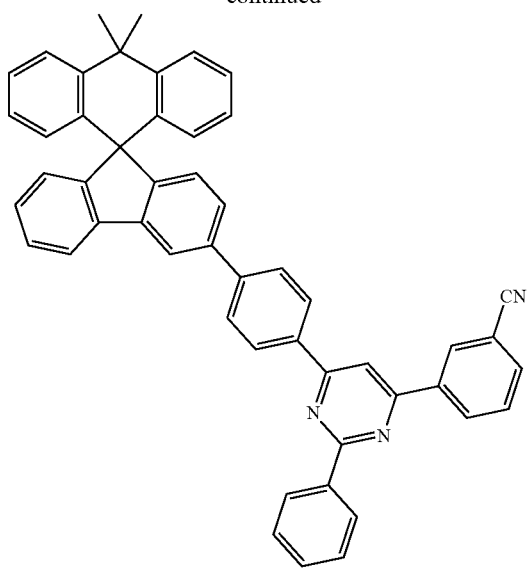
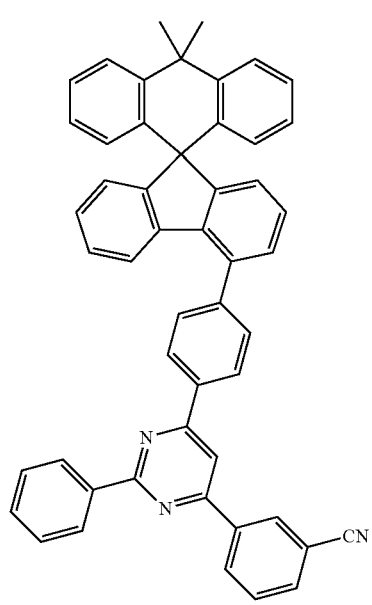
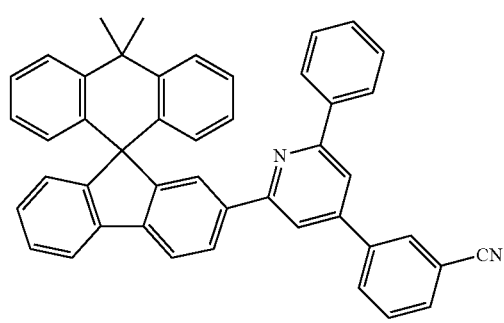
228
-continued
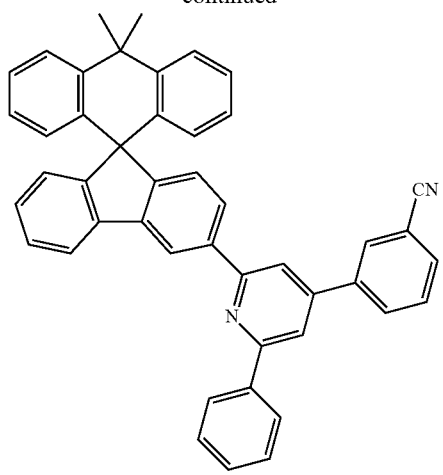
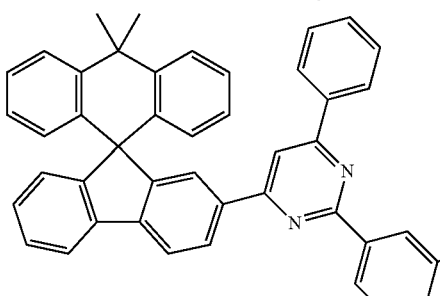
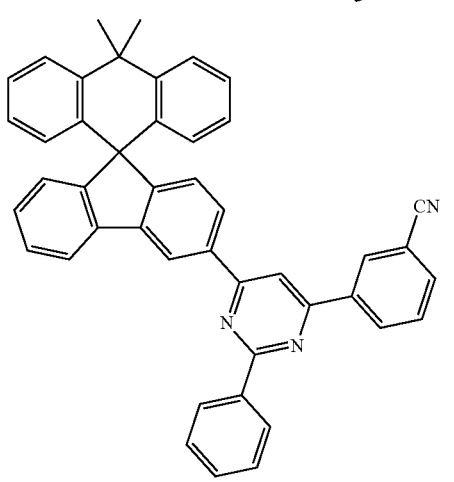

229
-continued
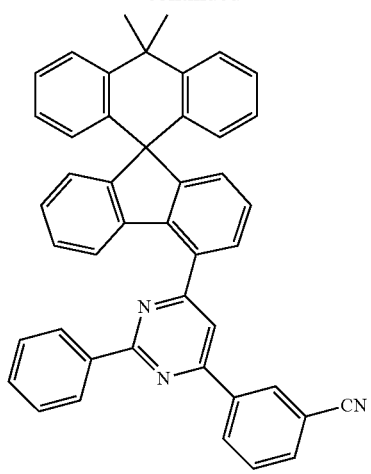
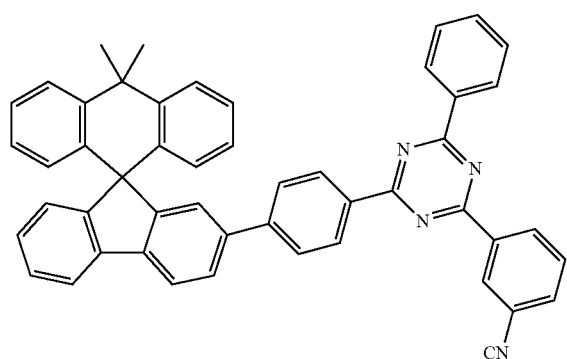
230
-continued
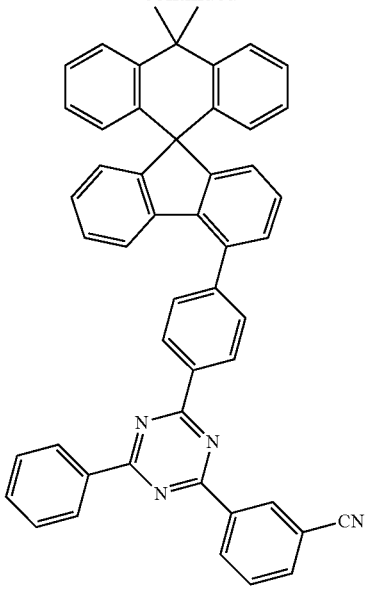
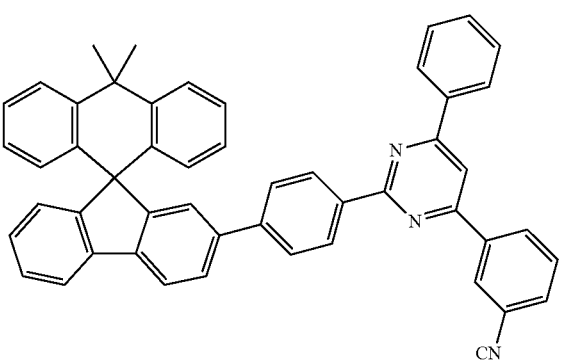
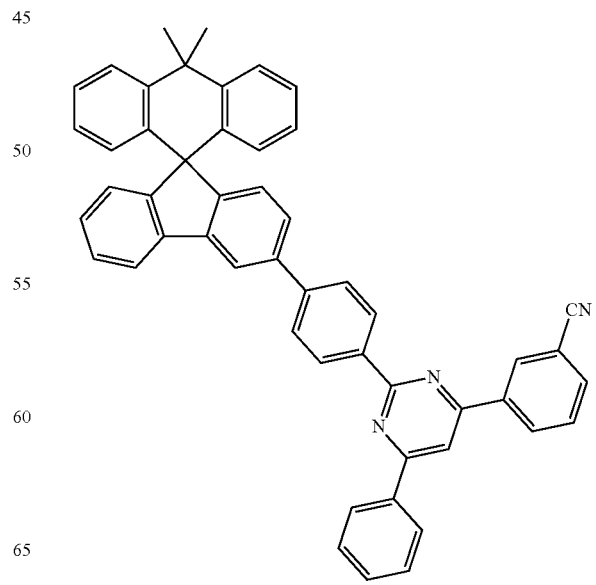

231
-continued
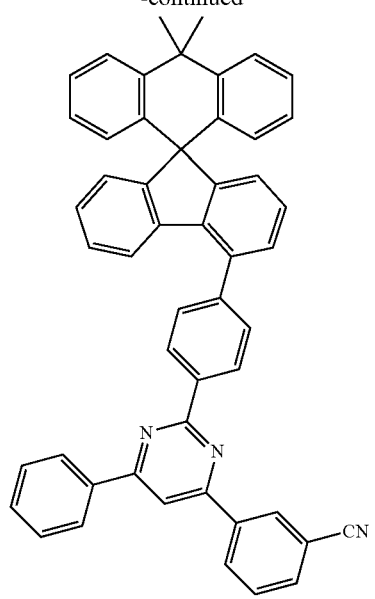
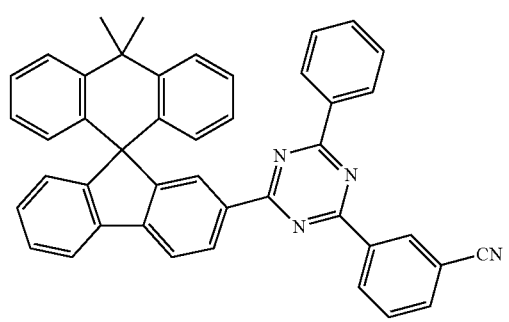
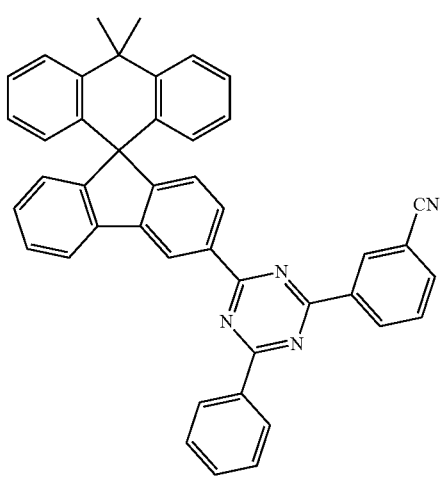
232
-continued
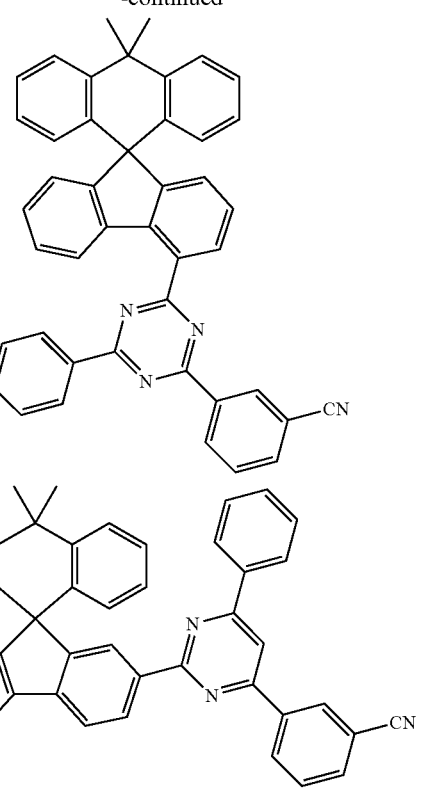
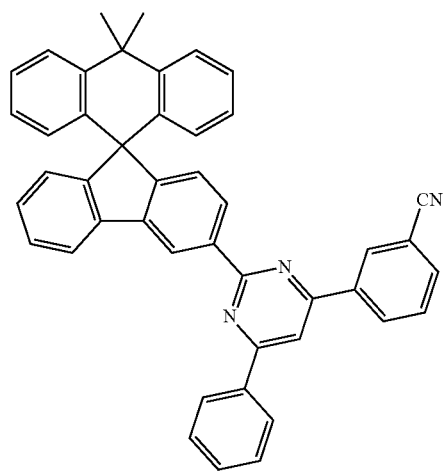
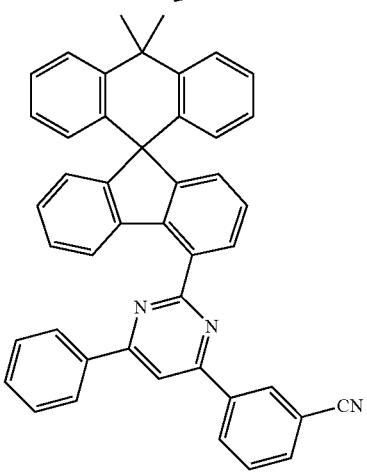

233
-continued
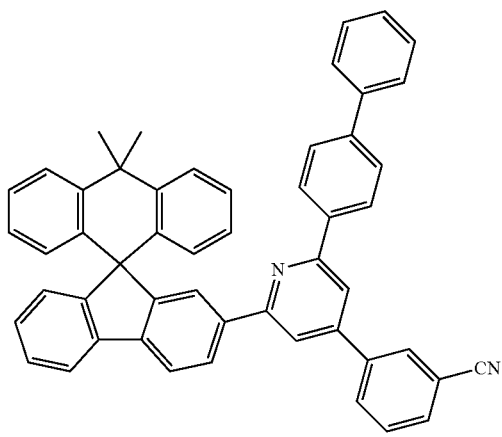
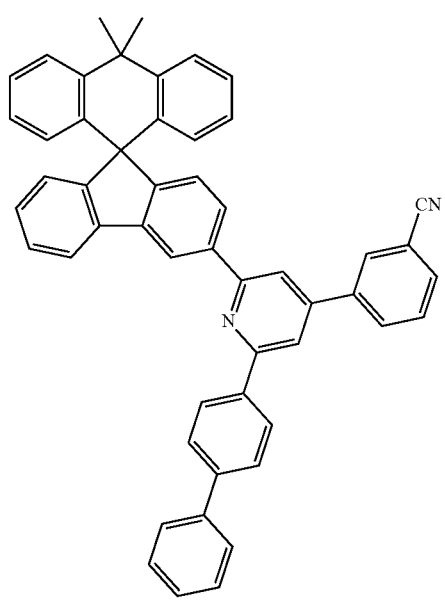
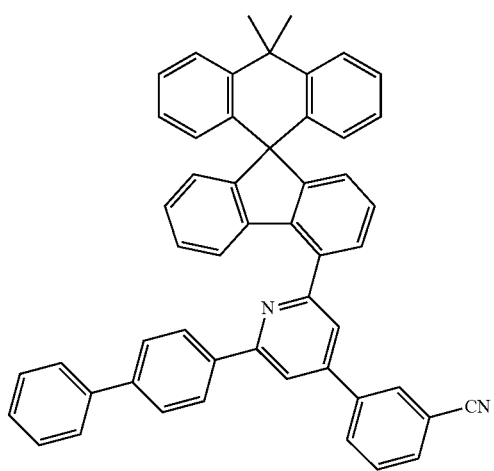
234
-continued
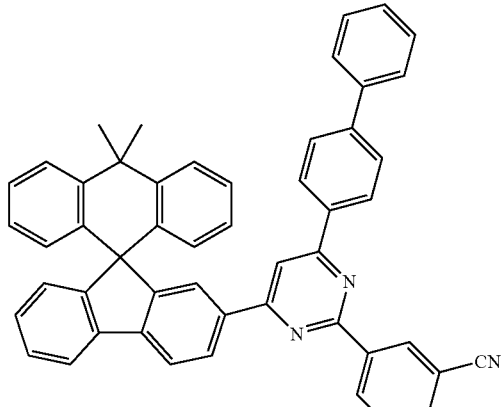
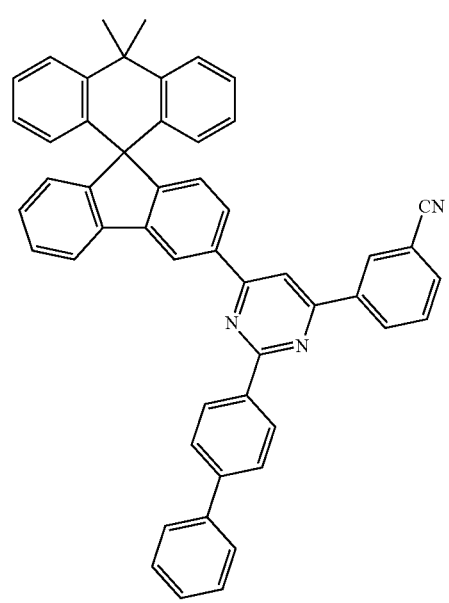
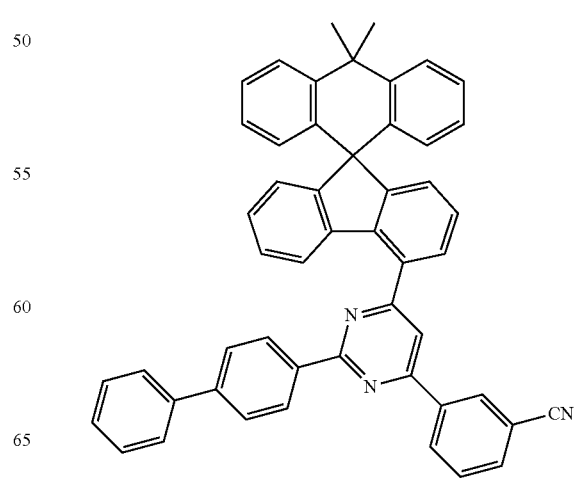

235
-continued
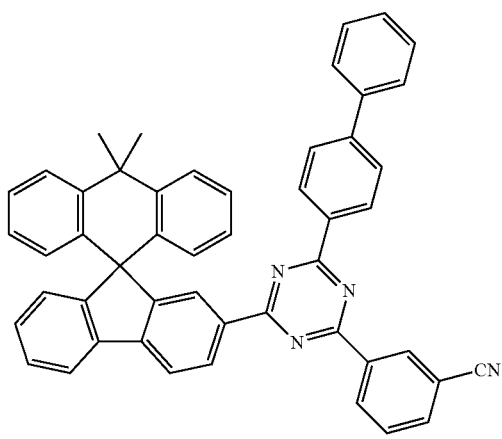
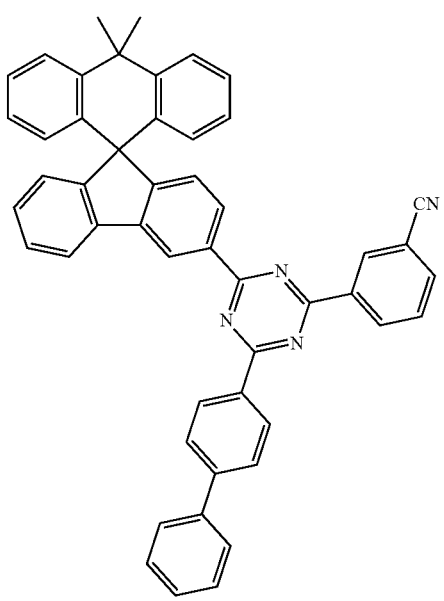
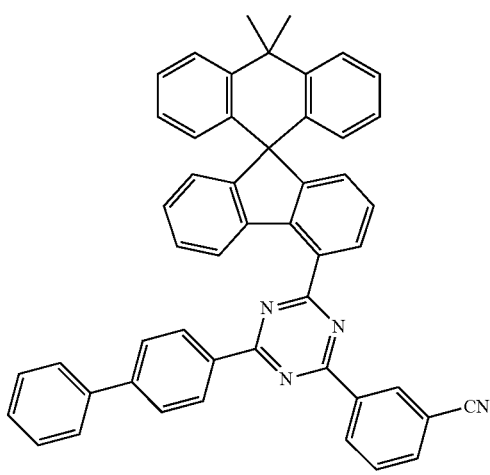
236
-continued
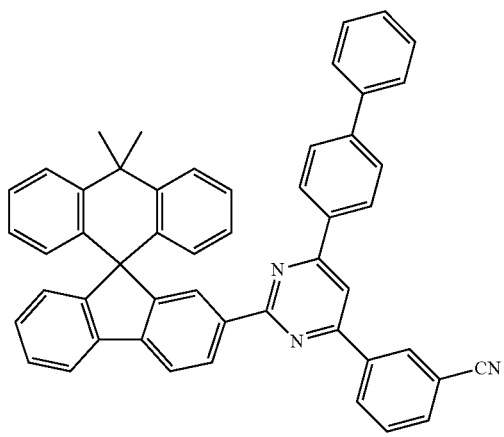
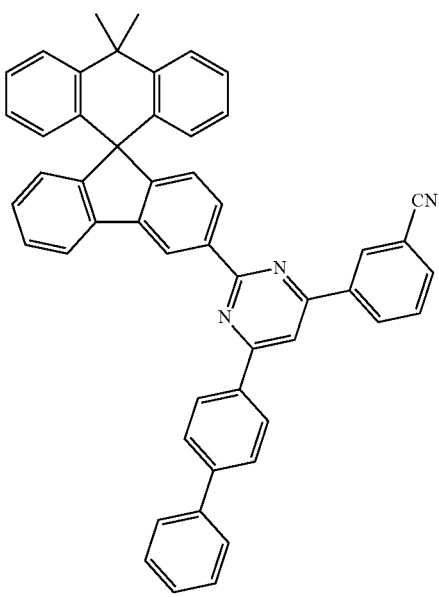
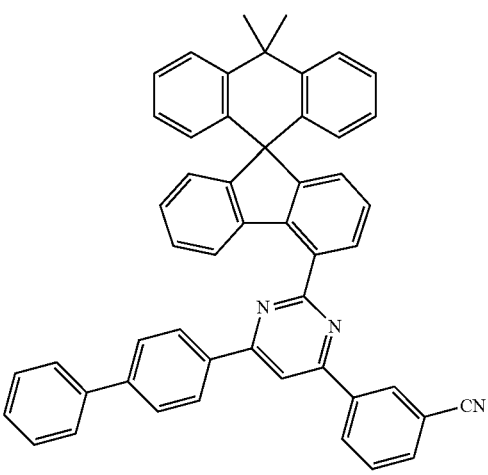

237
-continued
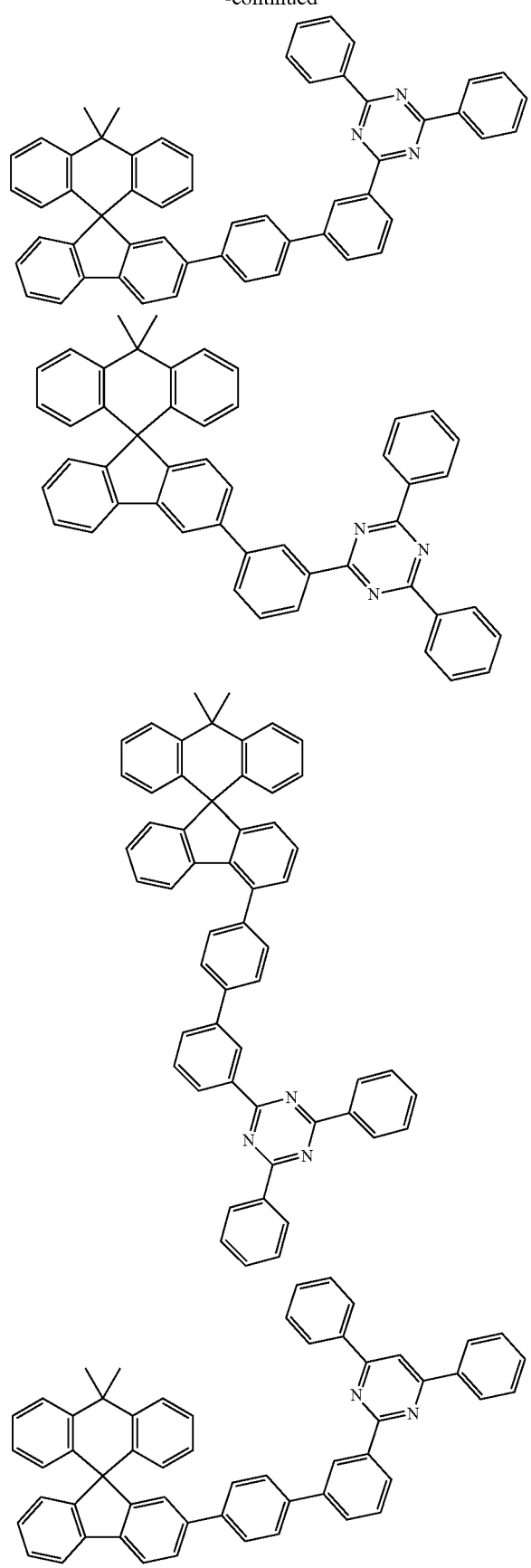
238
-continued
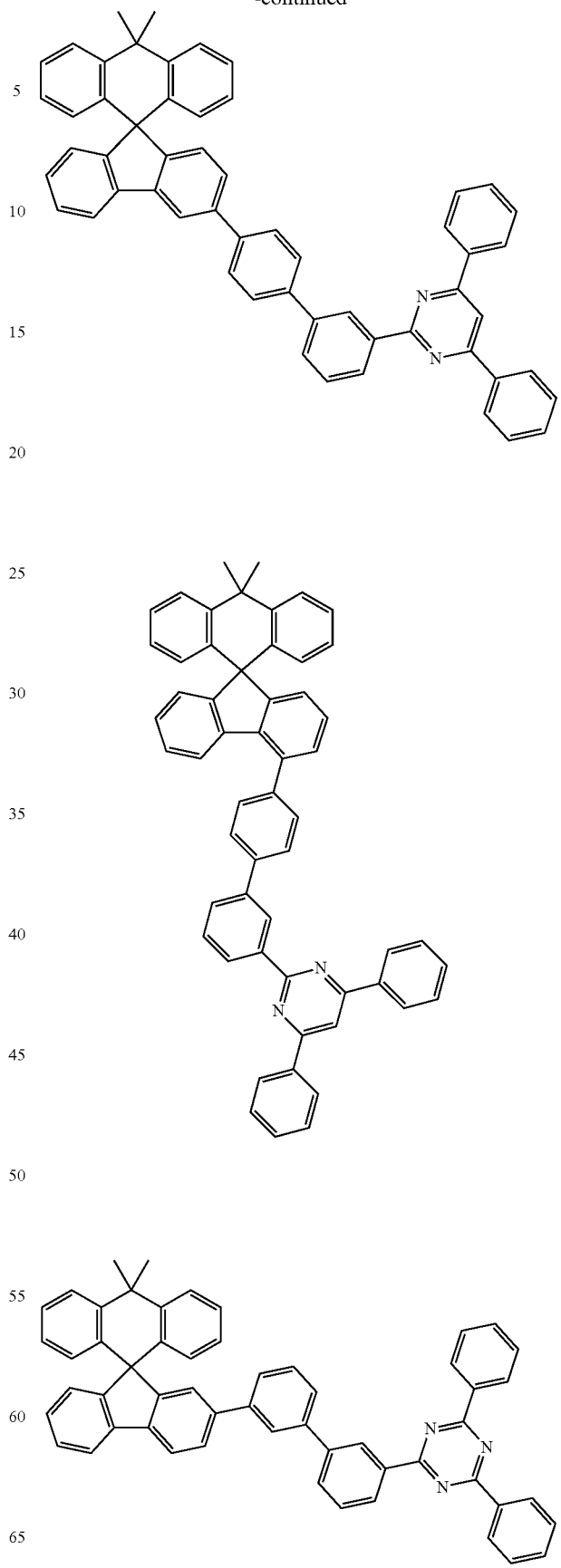

239
-continued
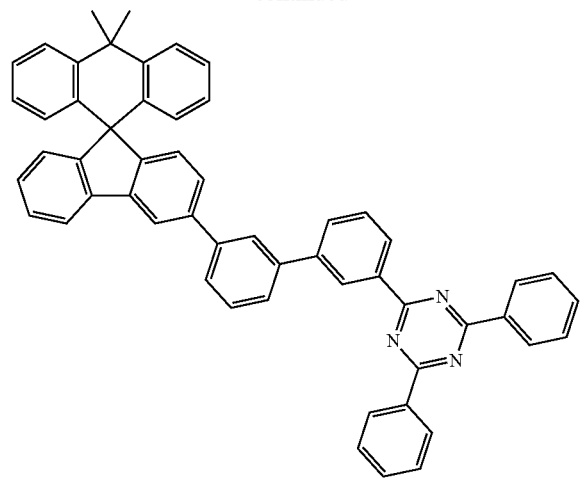
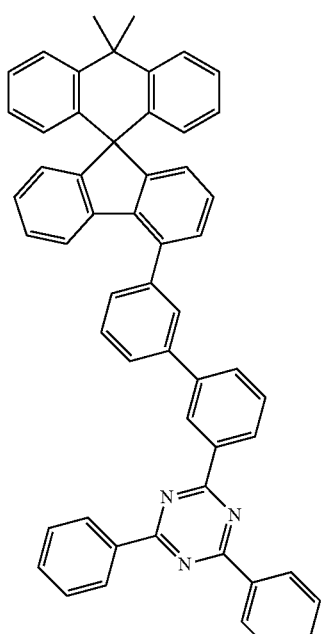
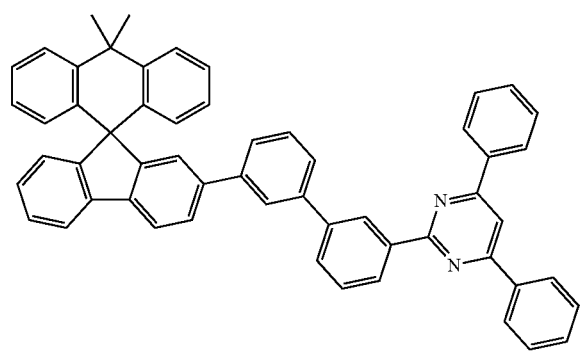
240
-continued
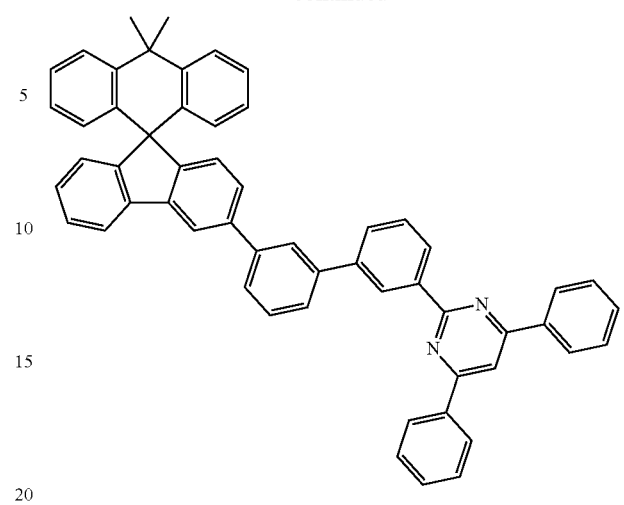
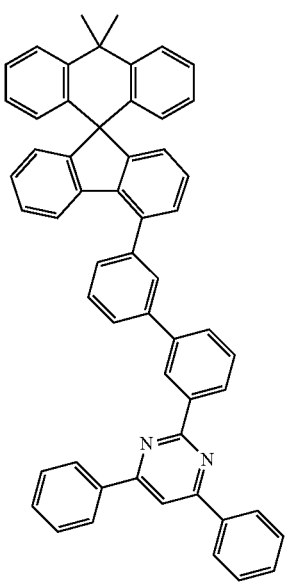
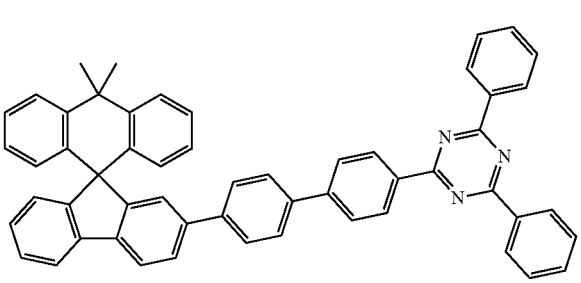

241
-continued
242
-continued
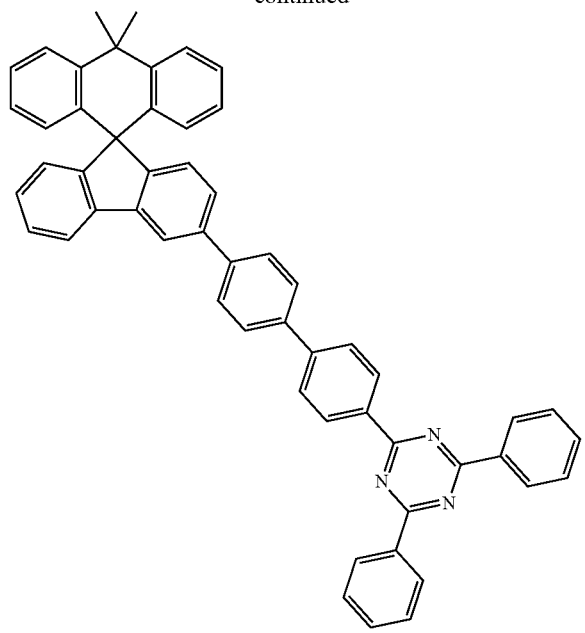
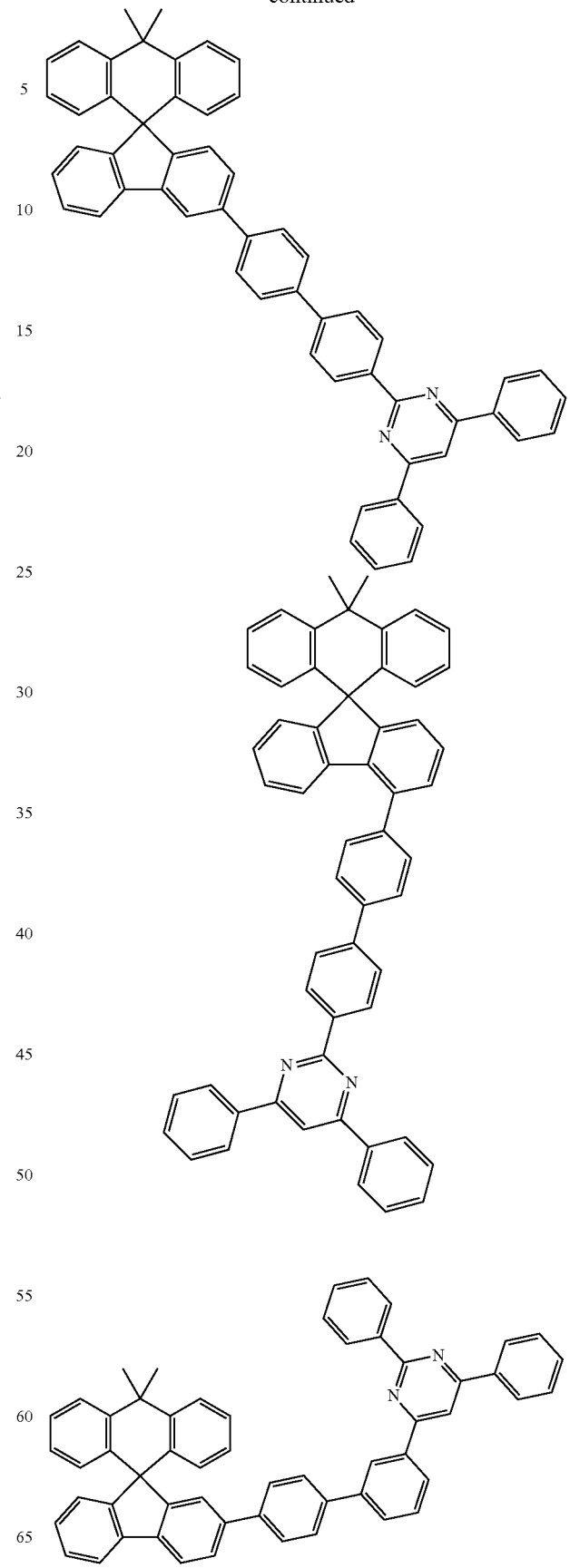

243
-continued
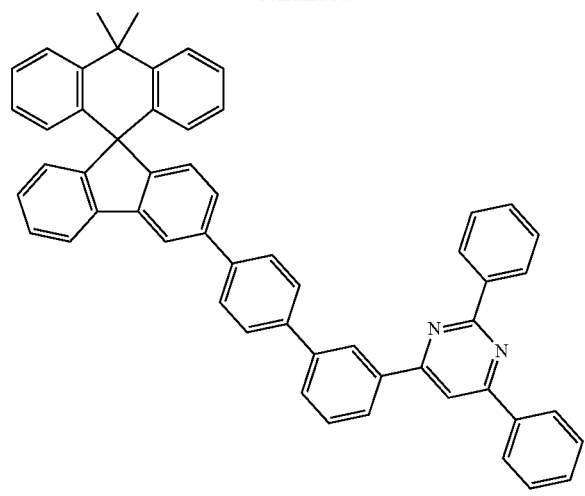
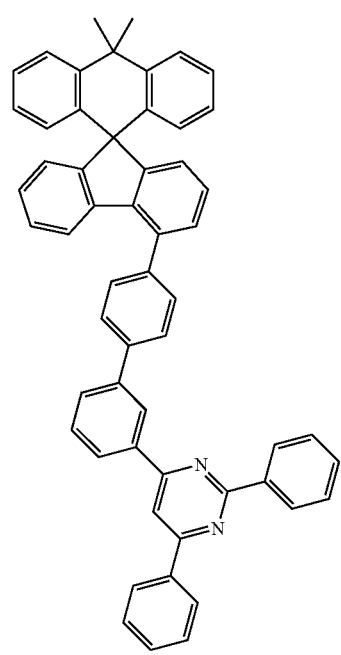
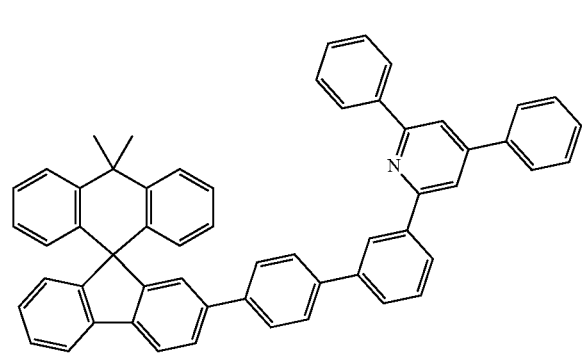
244
-continued
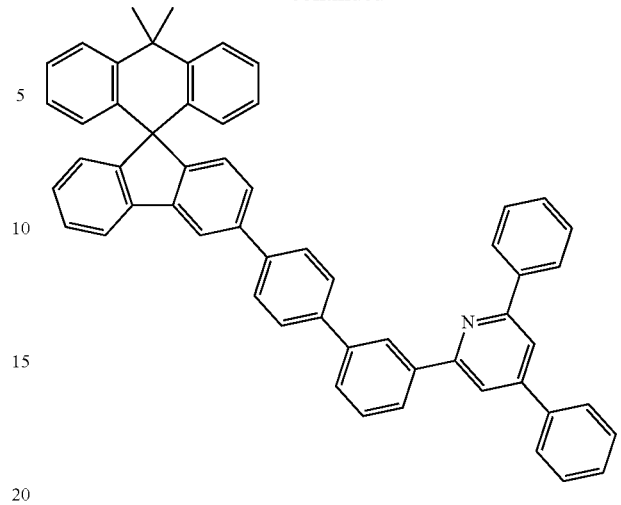
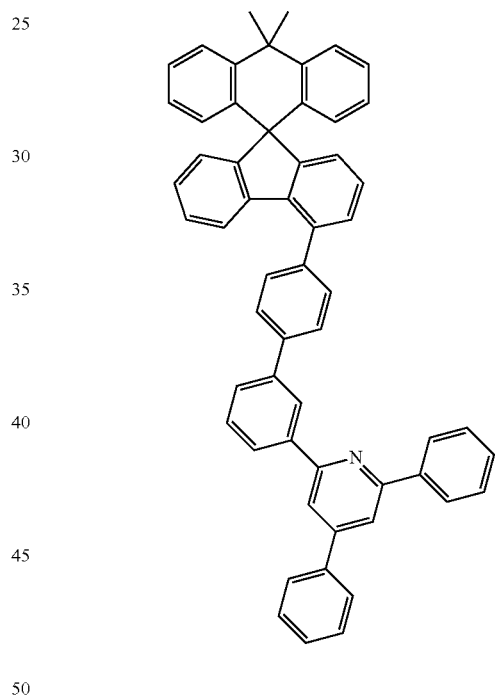
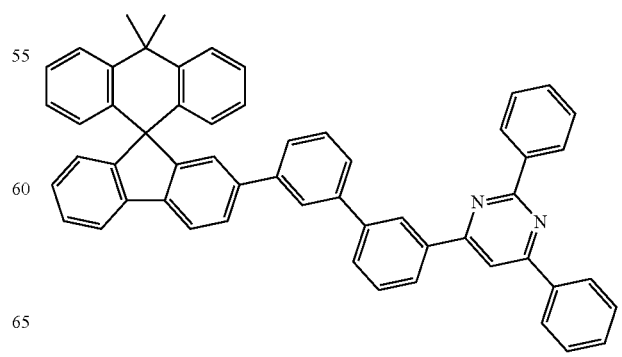

245
-continued
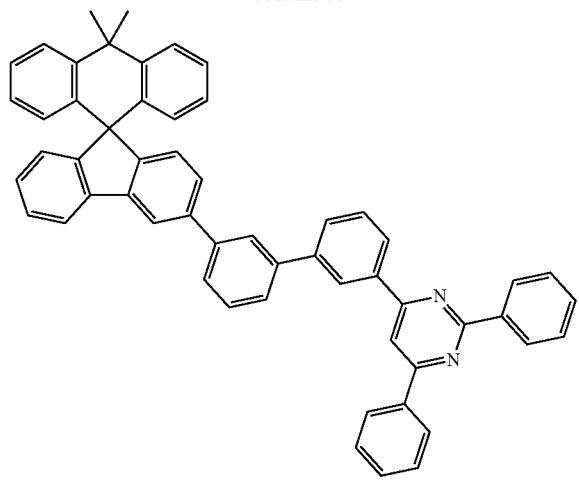
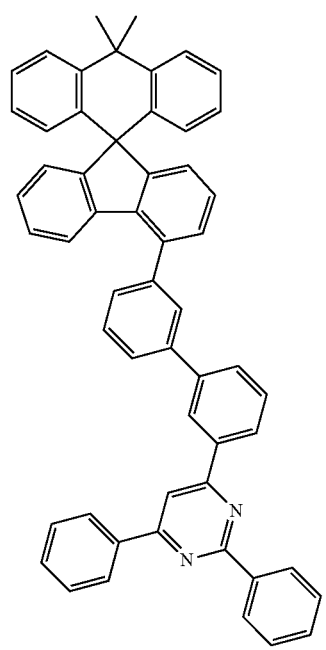
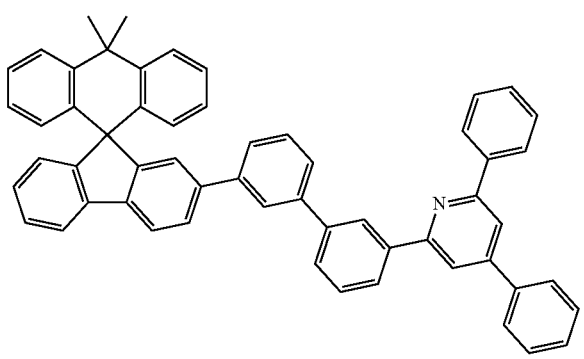
246
-continued
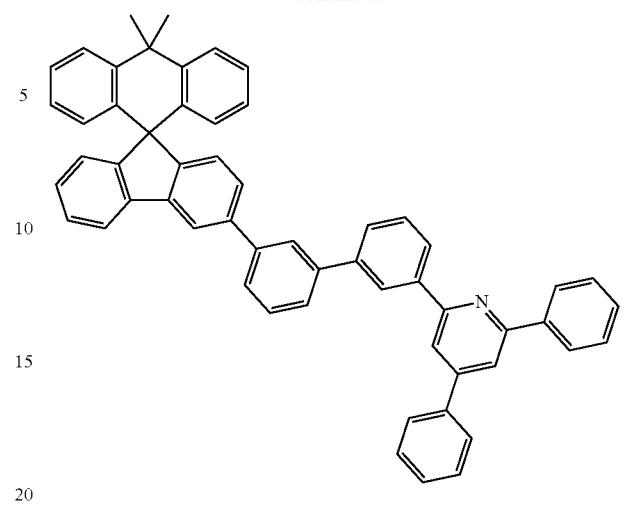
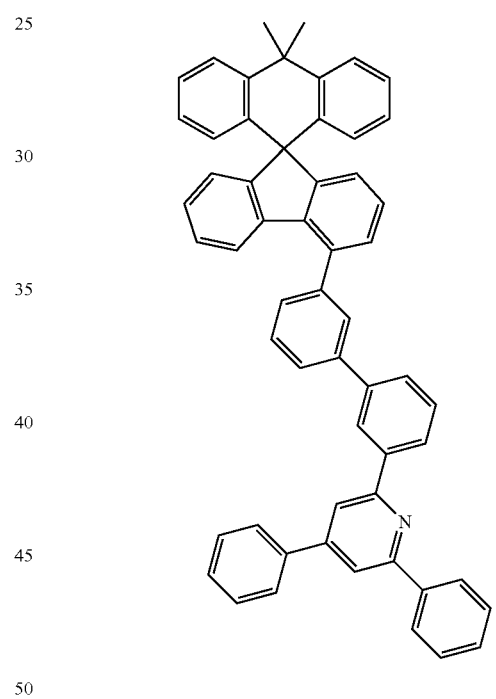
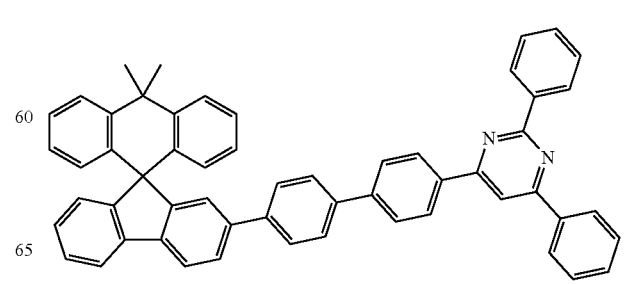

247
-continued
248
-continued
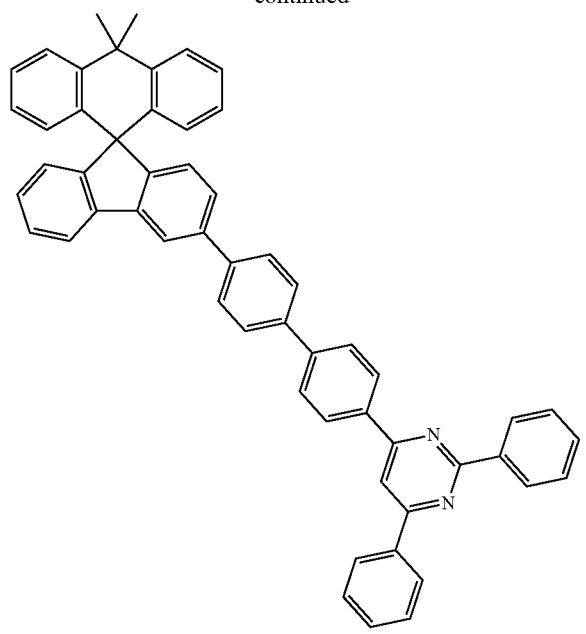
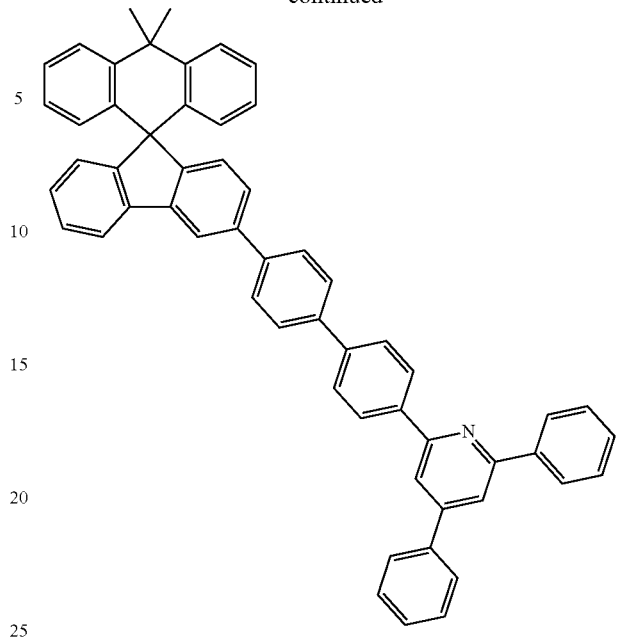
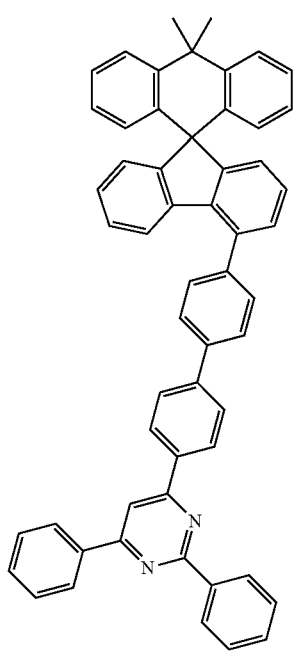
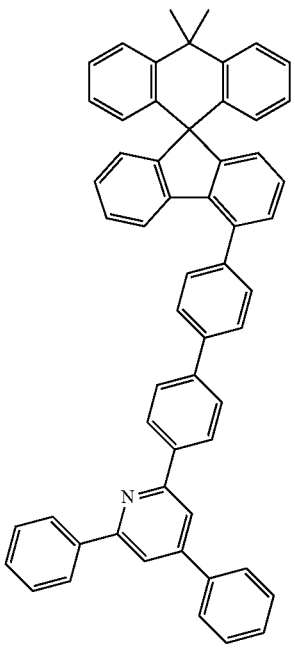
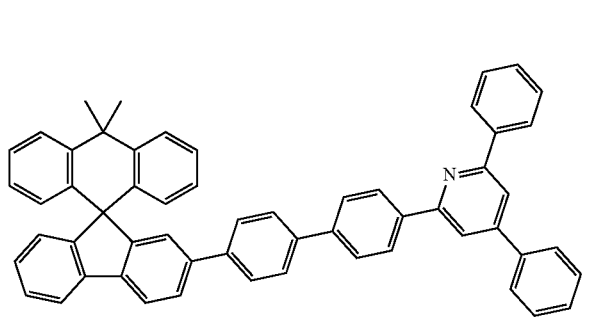
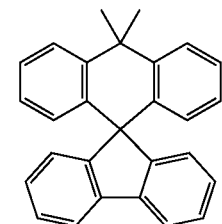

249
-continued
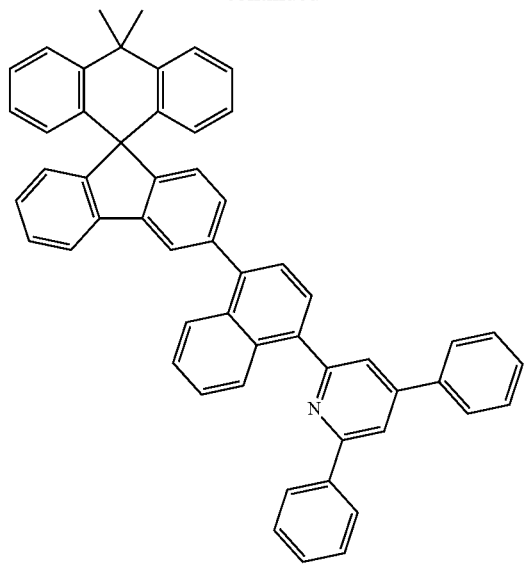
250
-continued
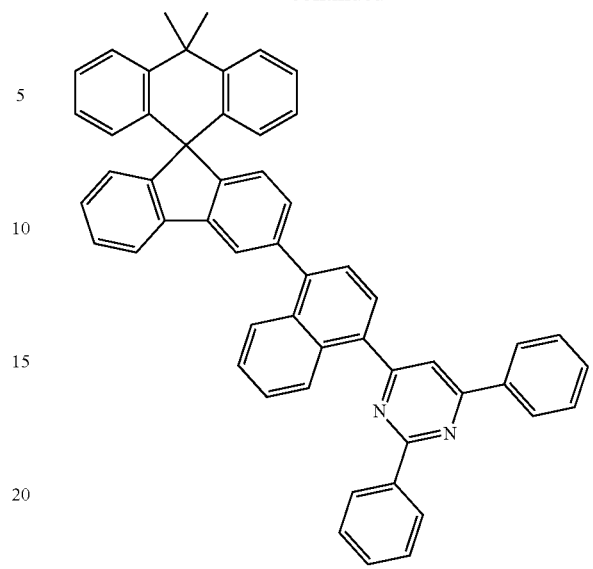
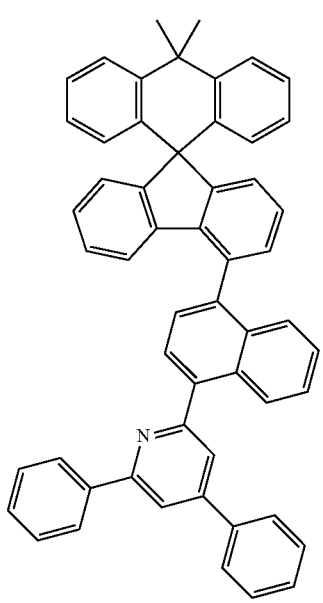
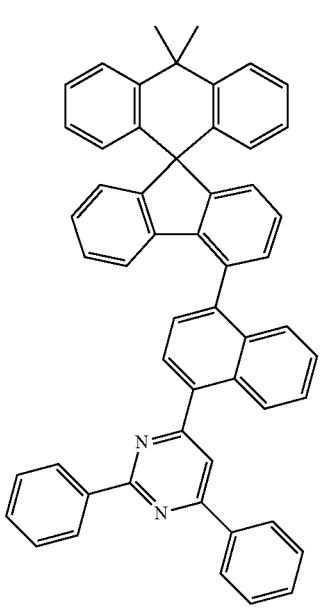
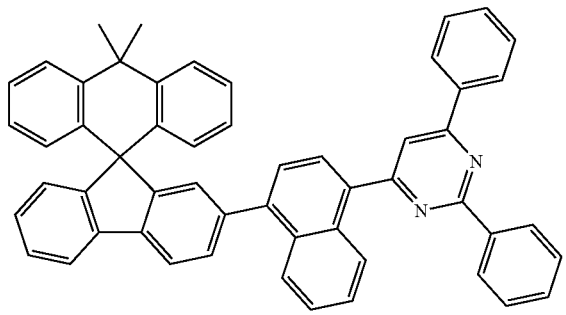
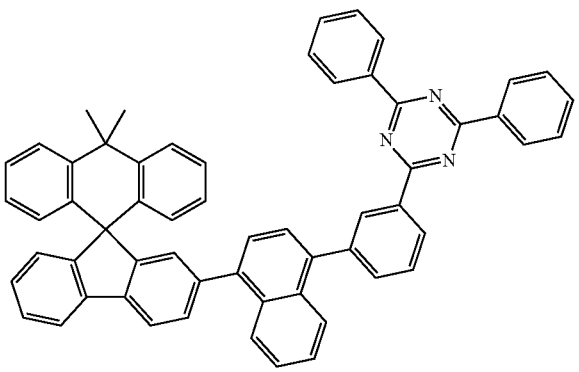

251
-continued
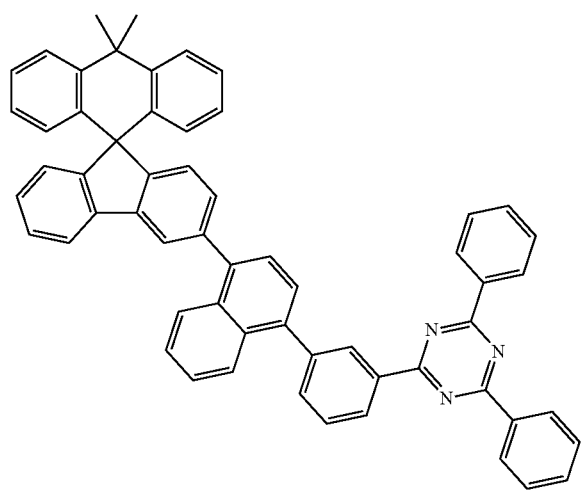
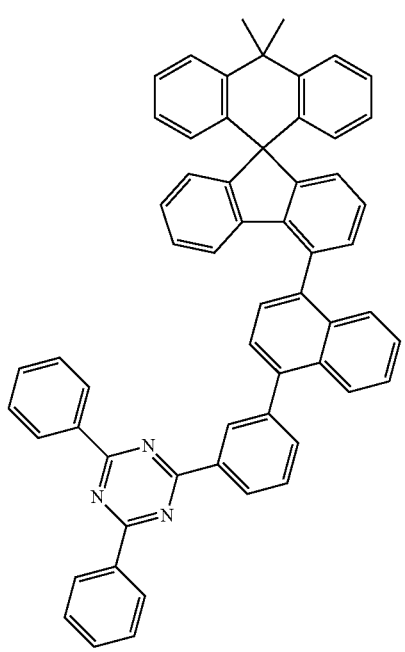
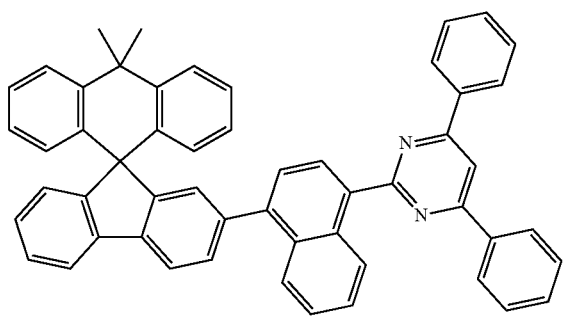
252
-continued
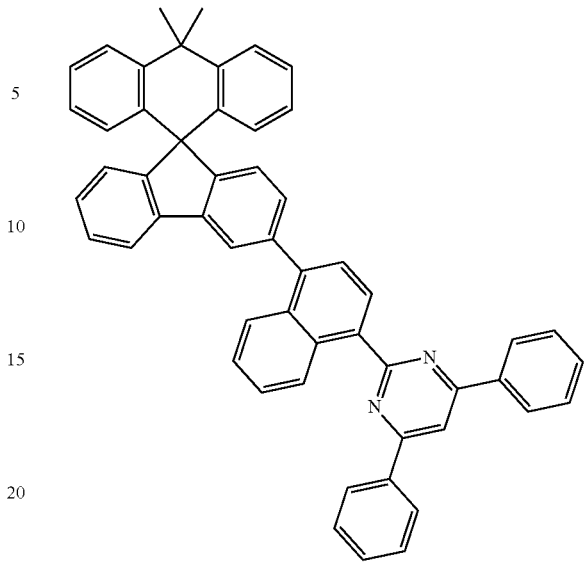
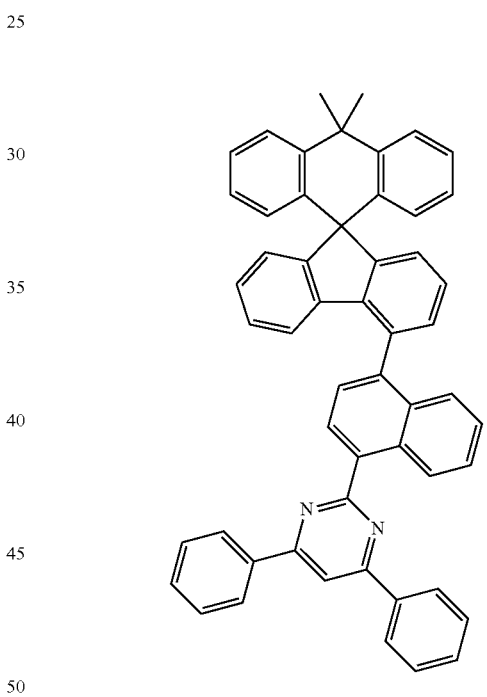
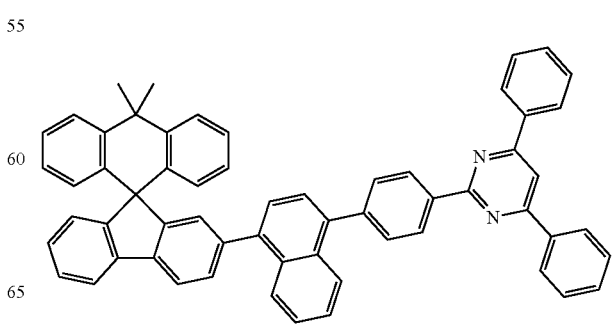

253
-continued
254
-continued
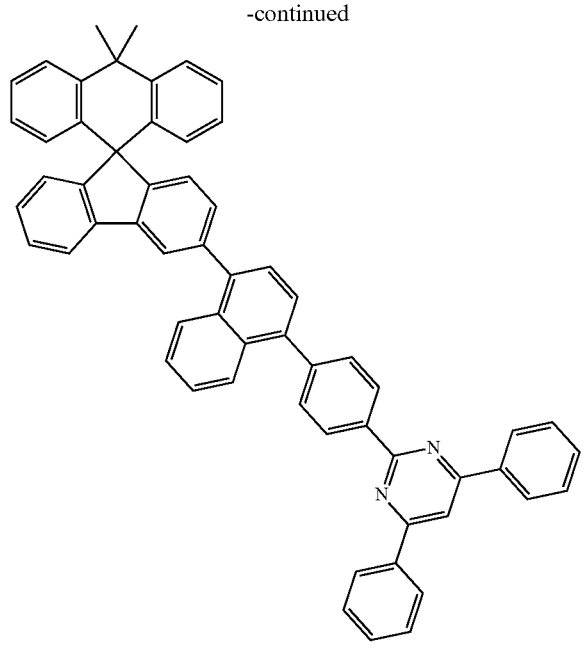
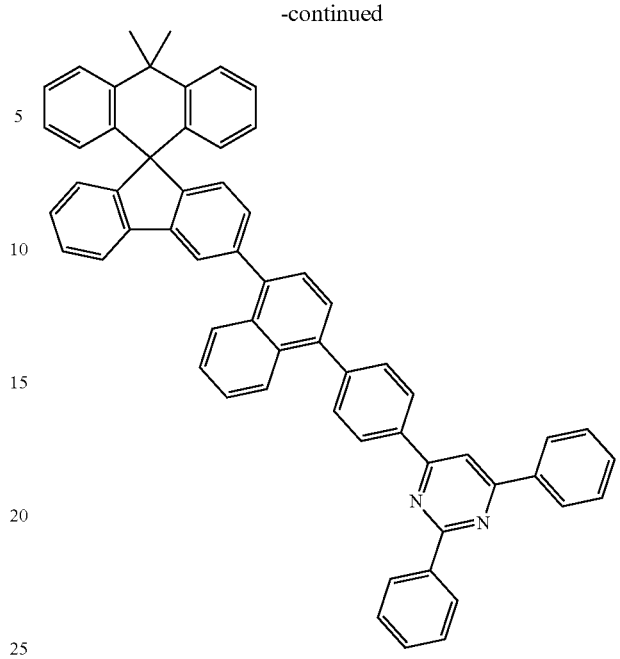
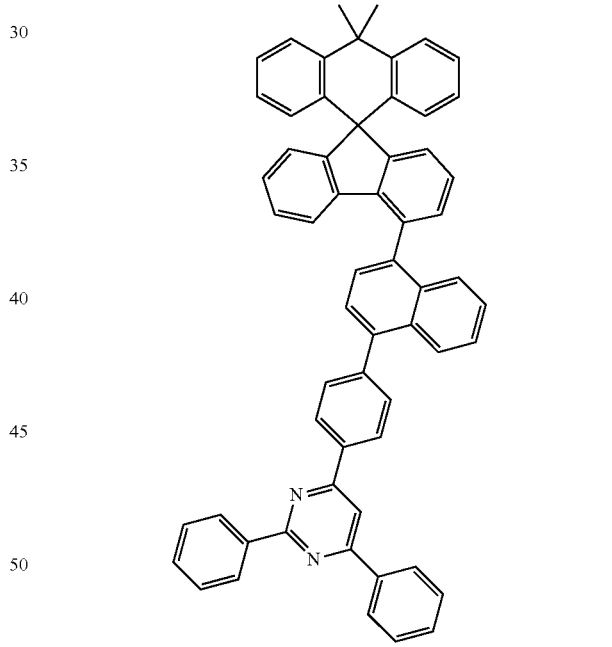
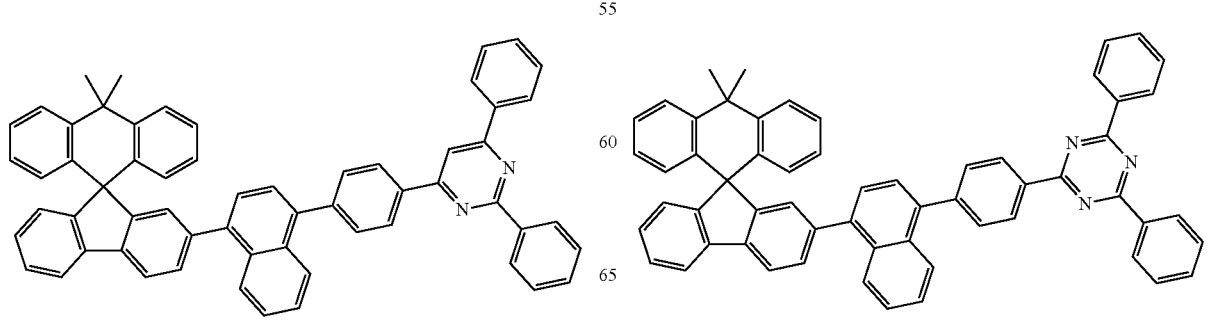

255
-continued
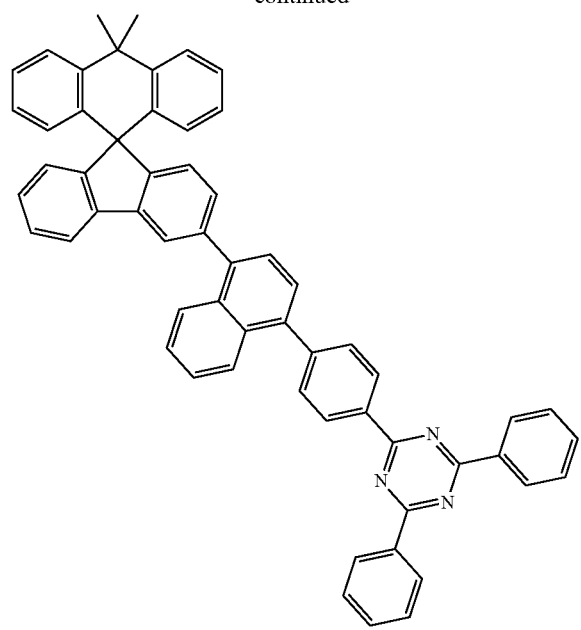
256
-continued
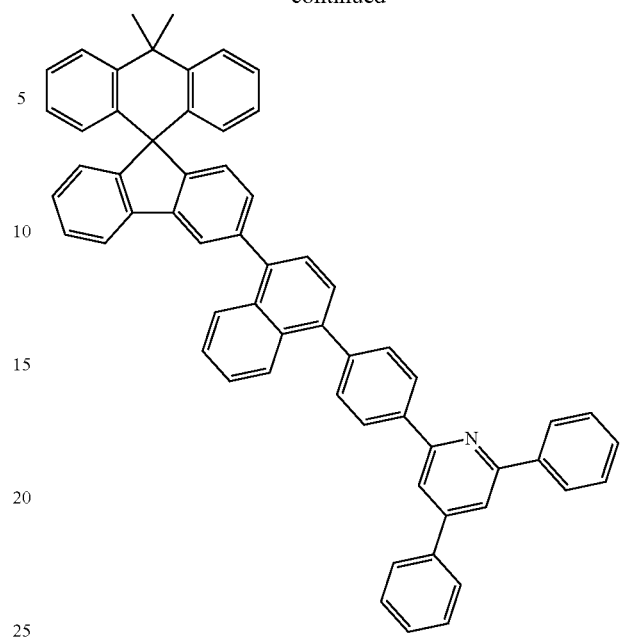
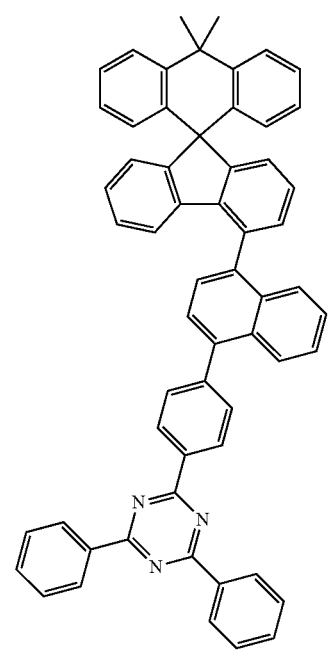
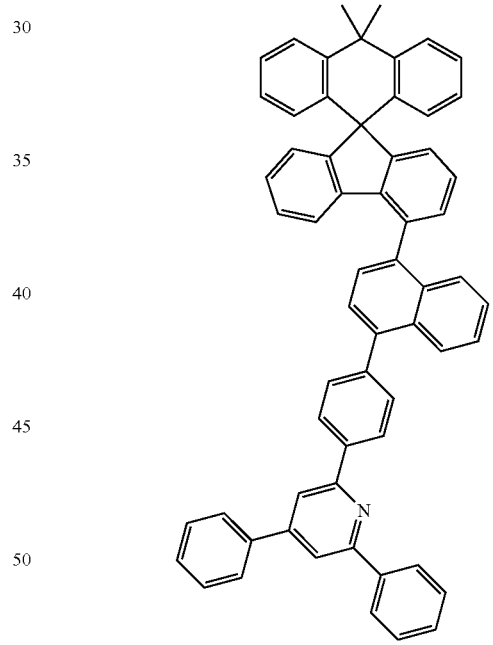
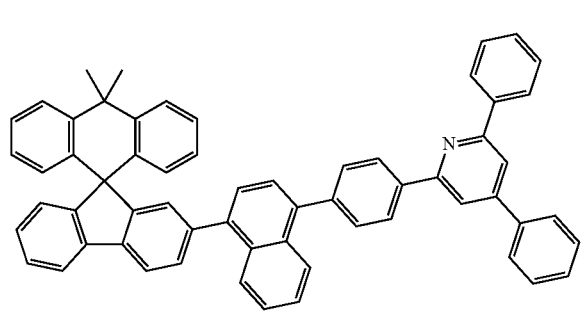
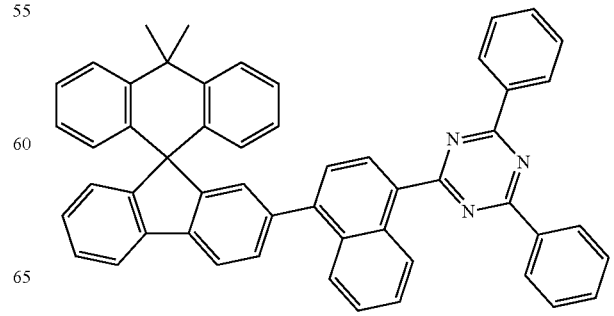

257
-continued
258
-continued
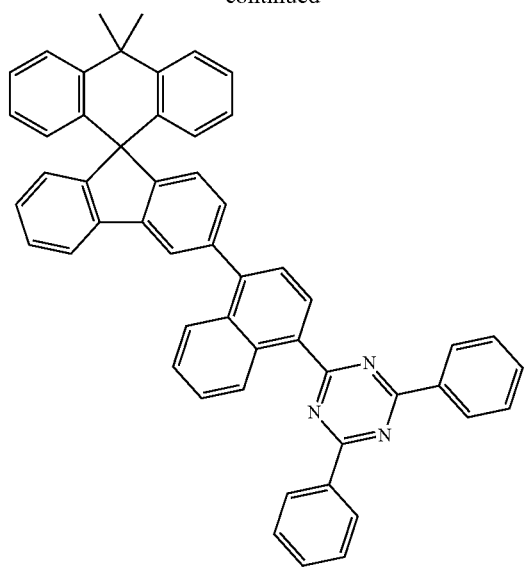
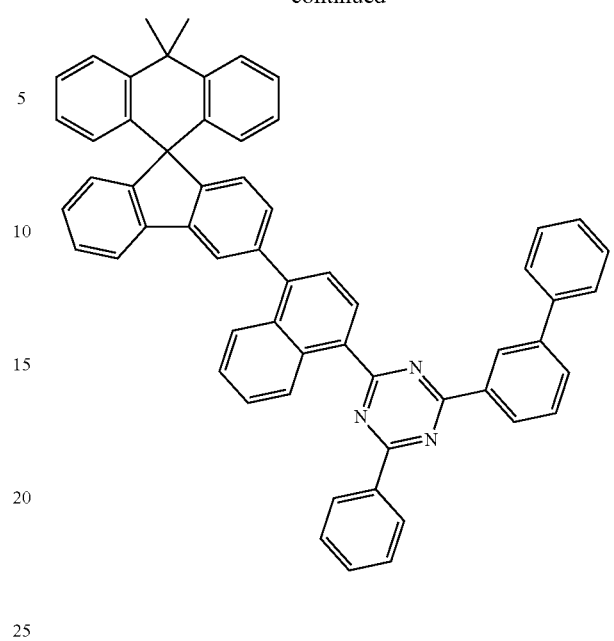
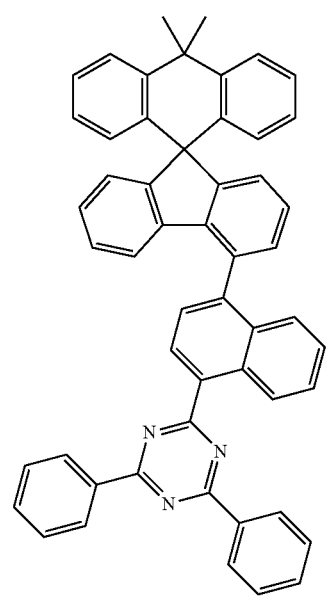
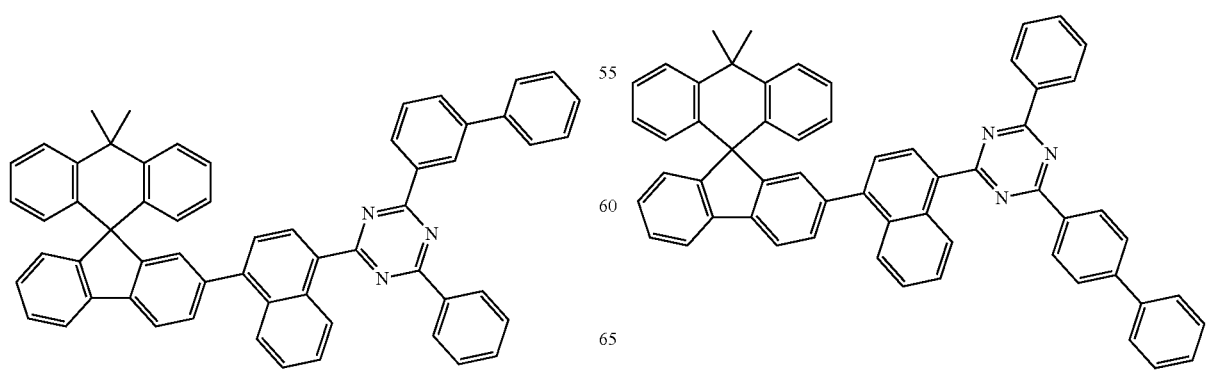

259
-continued
260
-continued
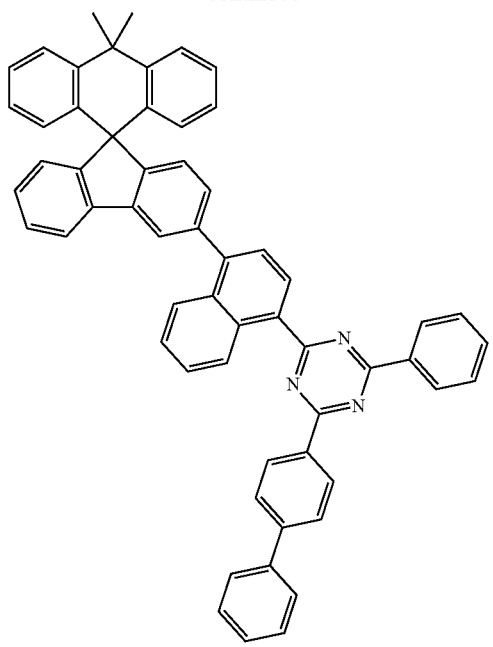
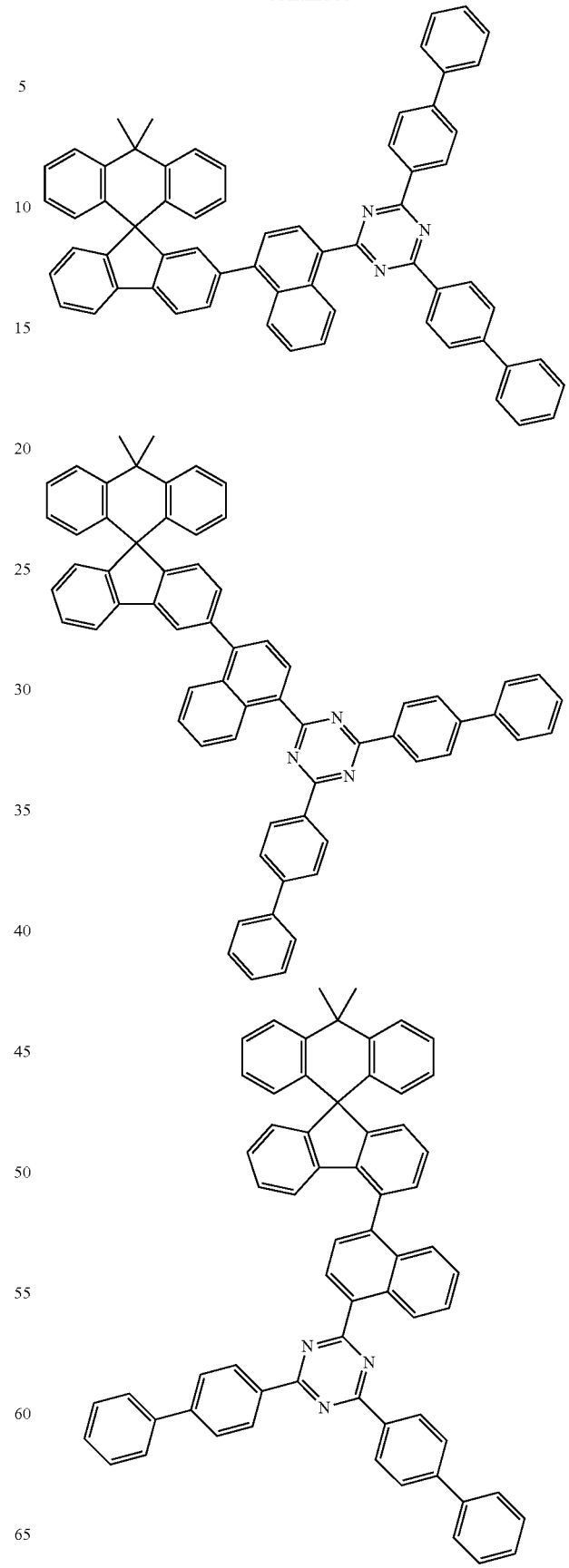
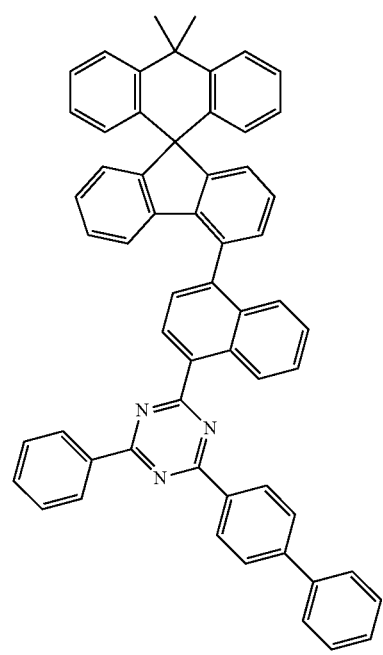

261
-continued
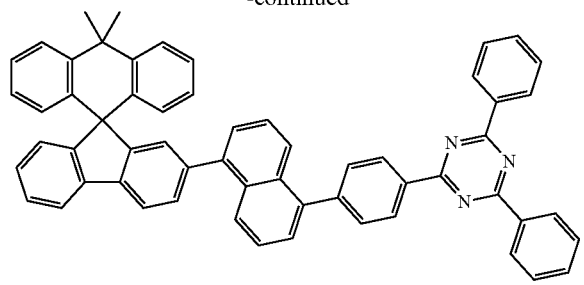
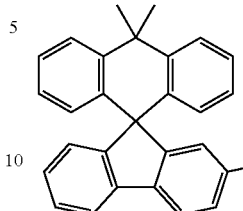
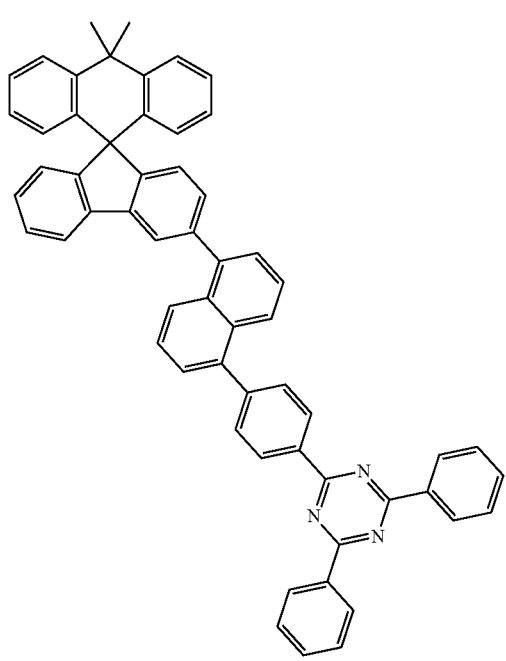
262
-continued
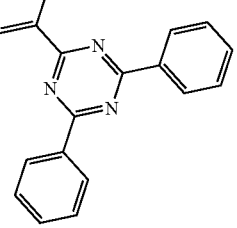
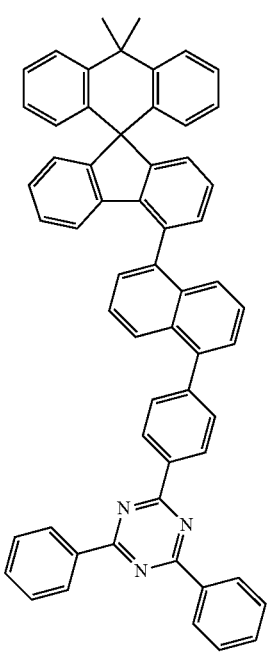
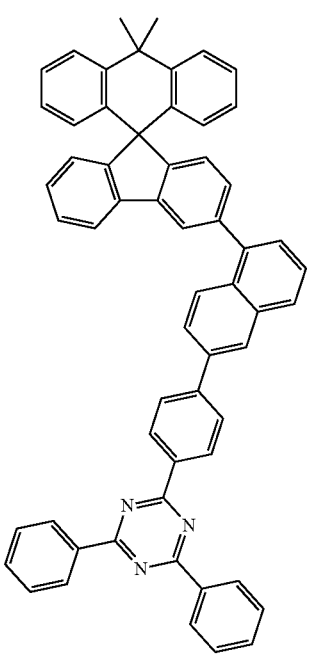

263
-continued
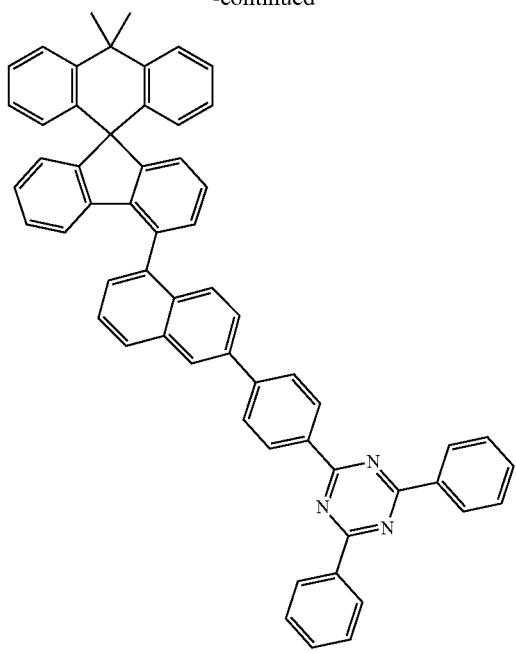
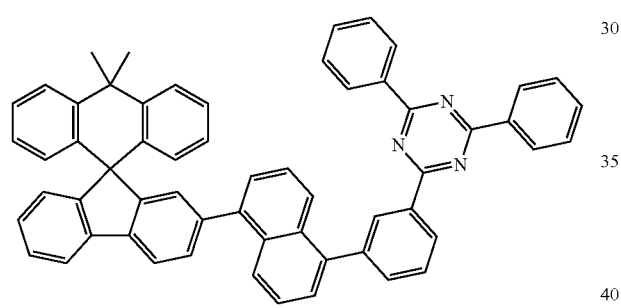
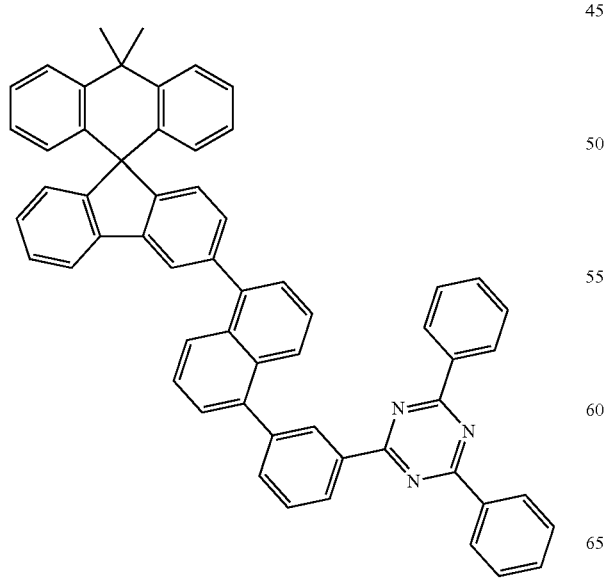
264
-continued
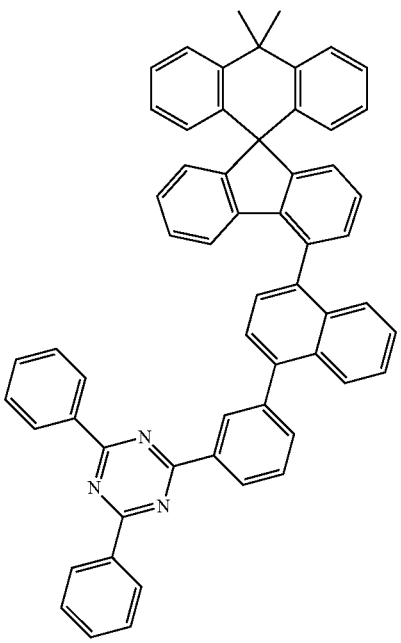
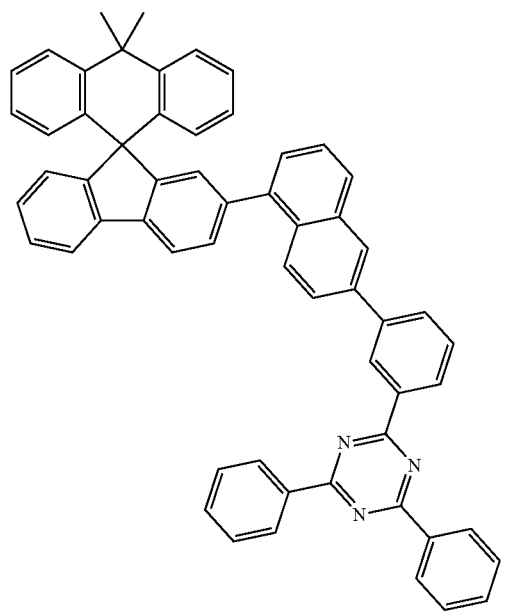

265
-continued
266
-continued
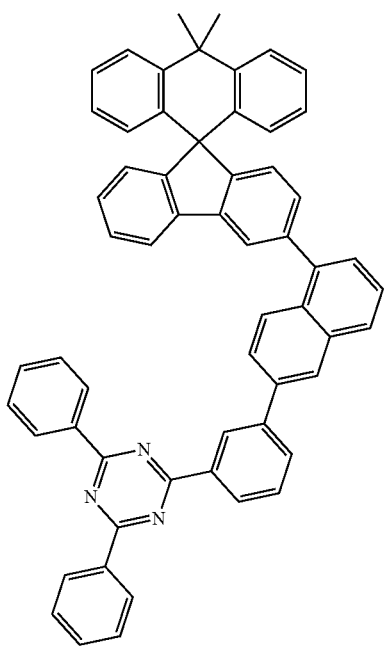
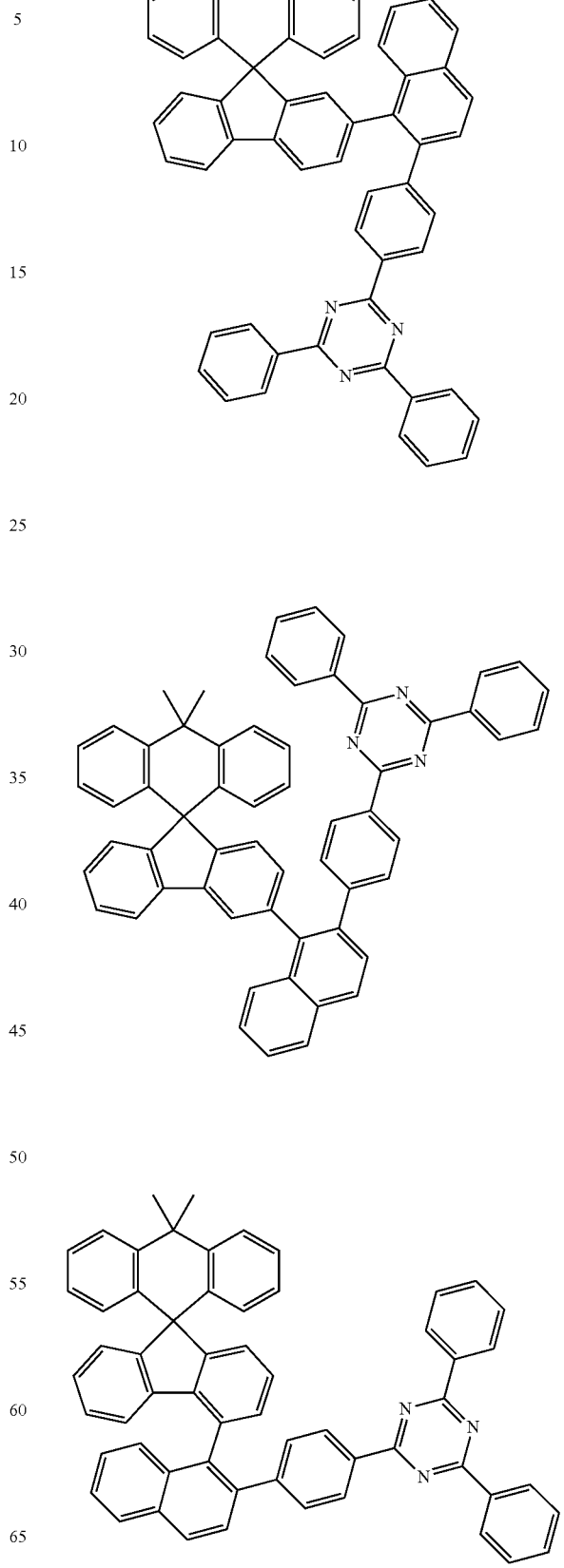

267
-continued
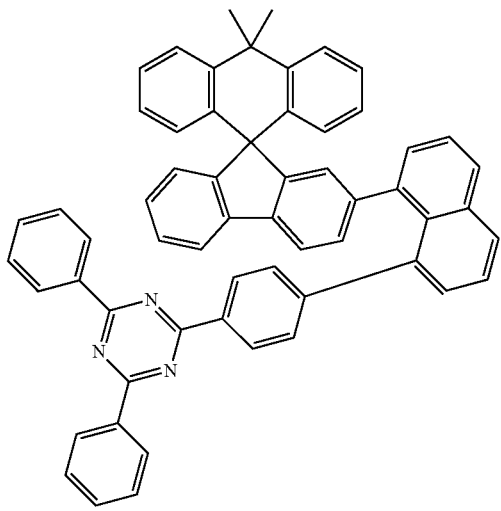
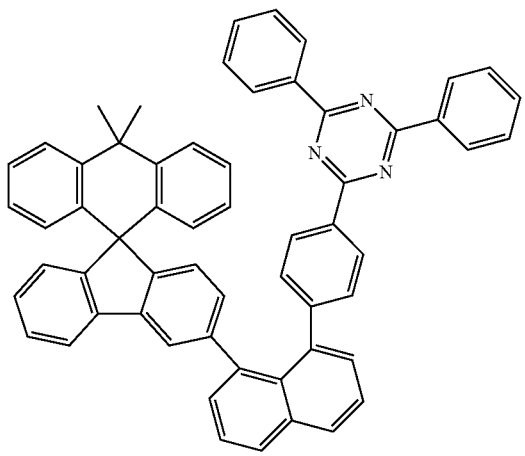
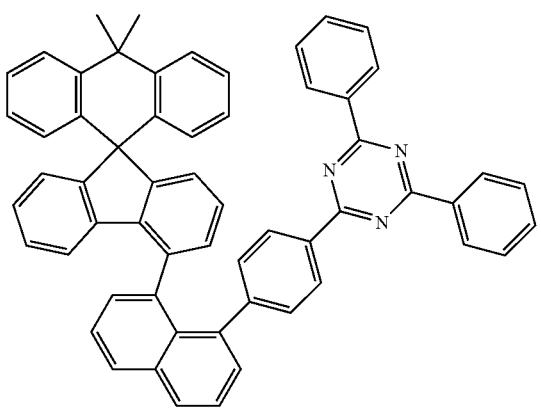
268
-continued
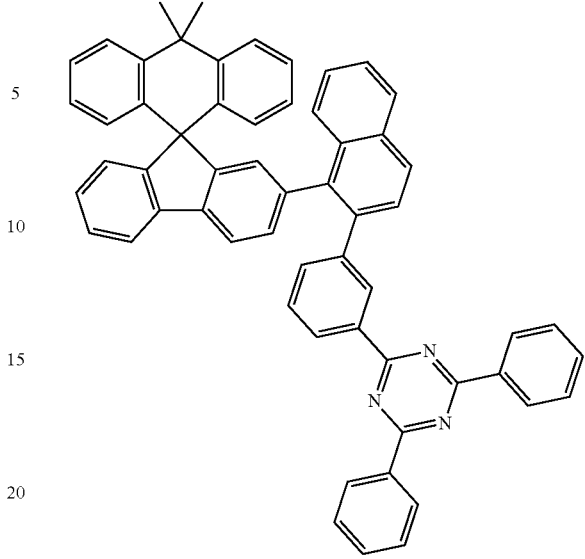
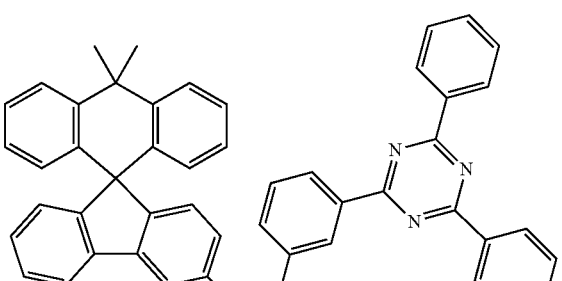
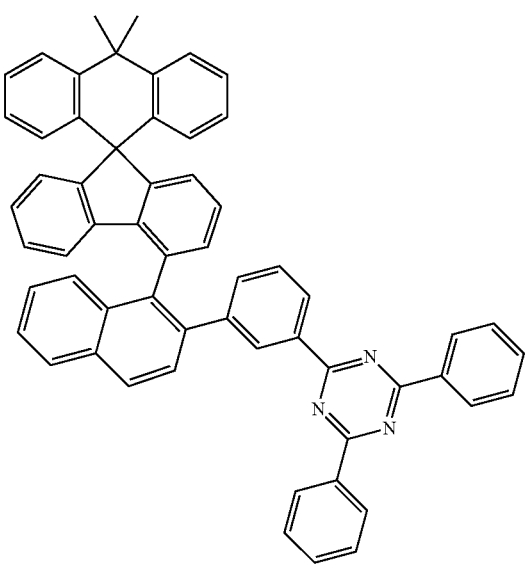

269
-continued
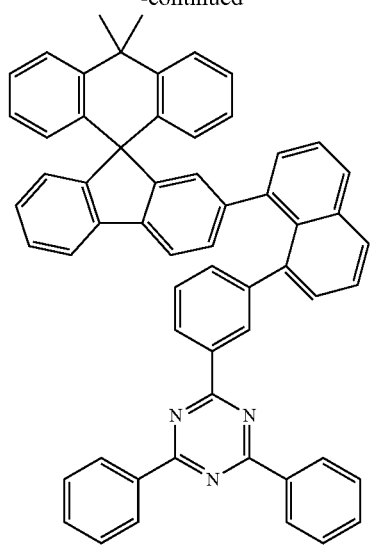
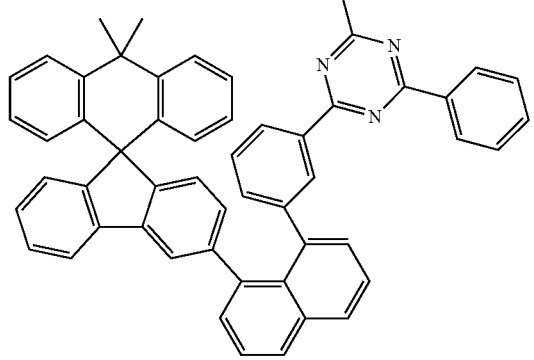
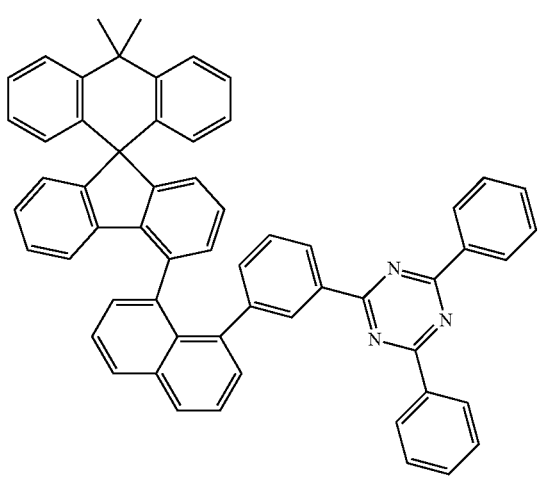
270
-continued
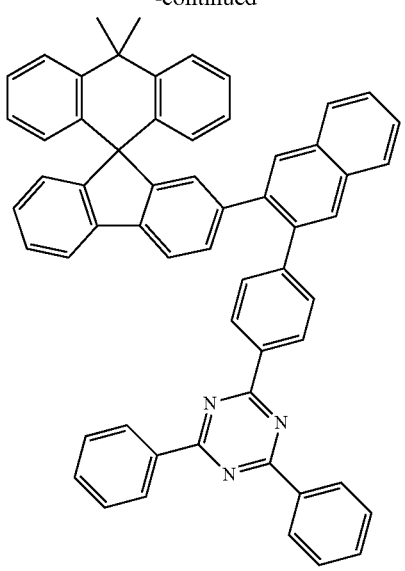
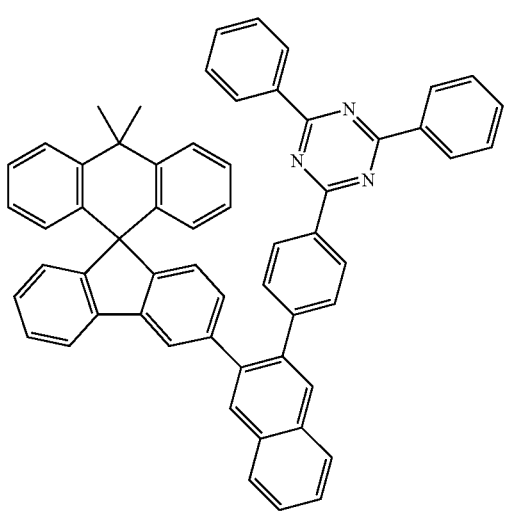
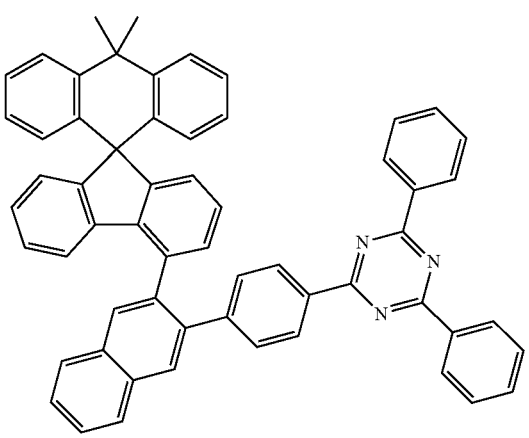

271
-continued
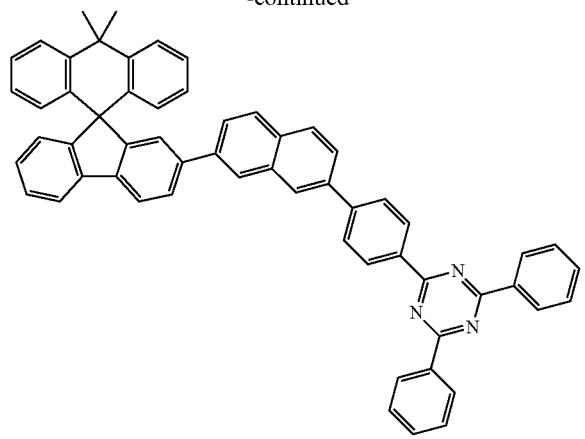
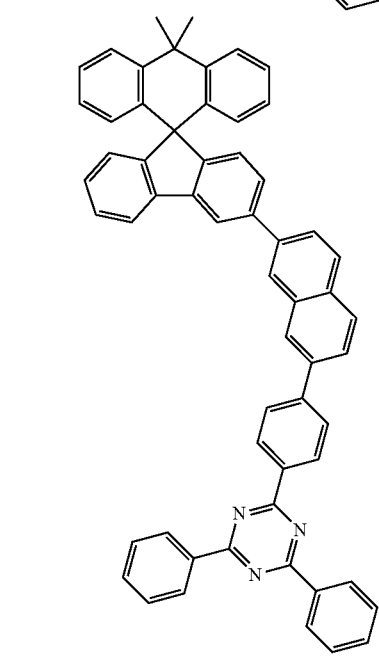
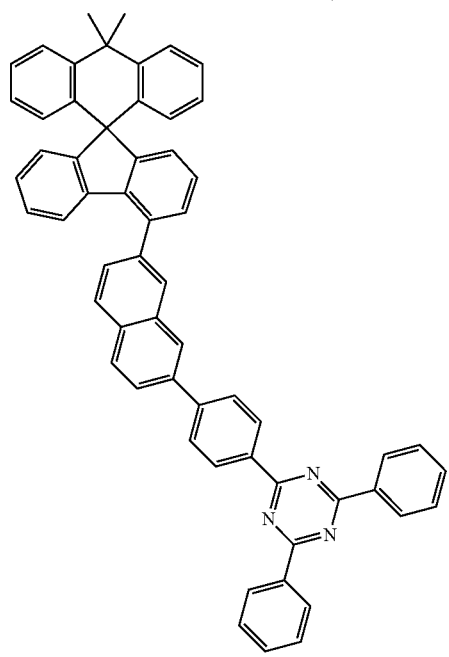
272
-continued
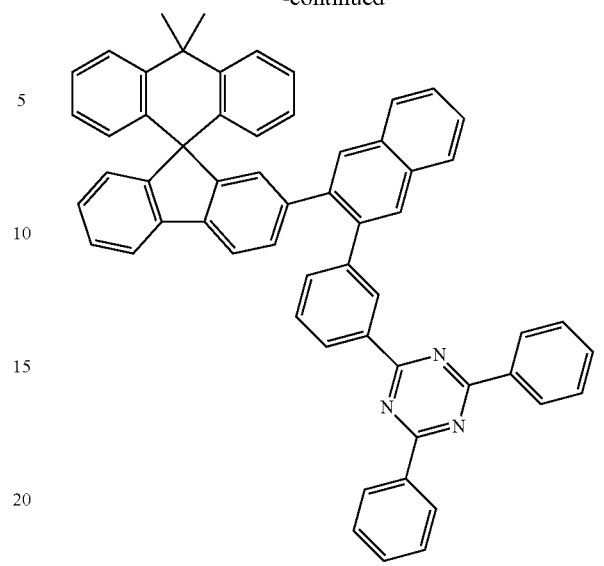
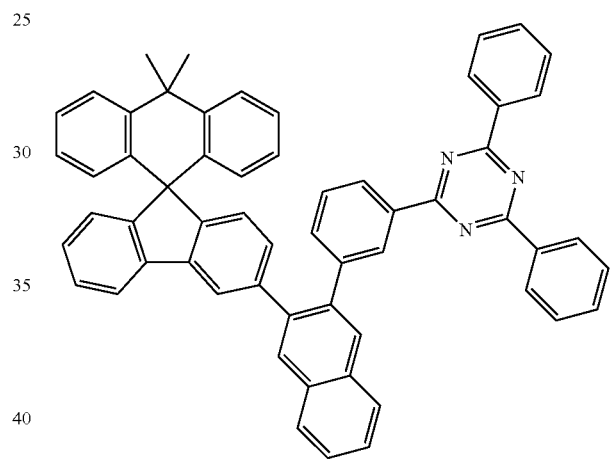
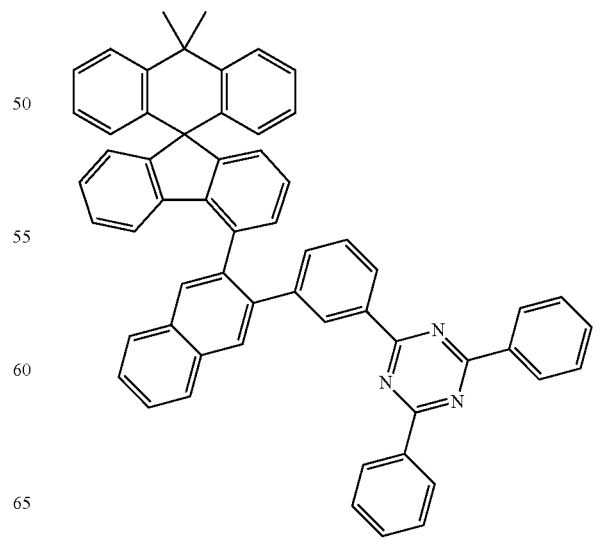

273
-continued
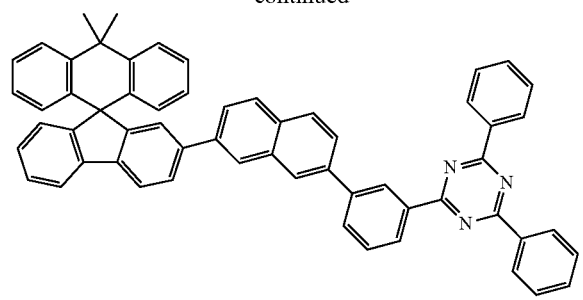
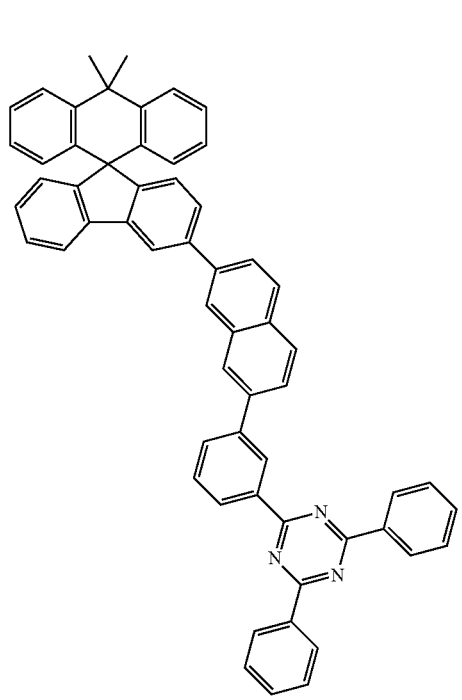
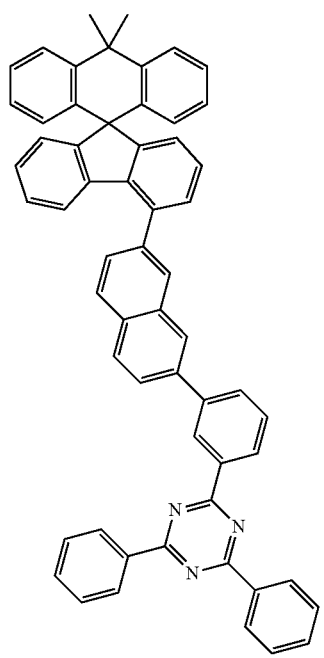
274
-continued
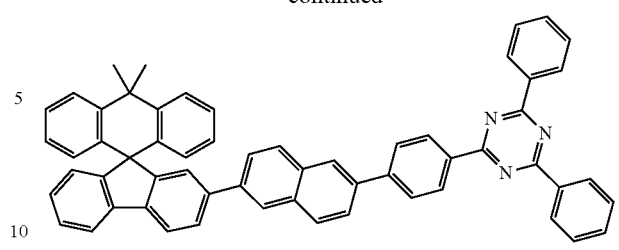
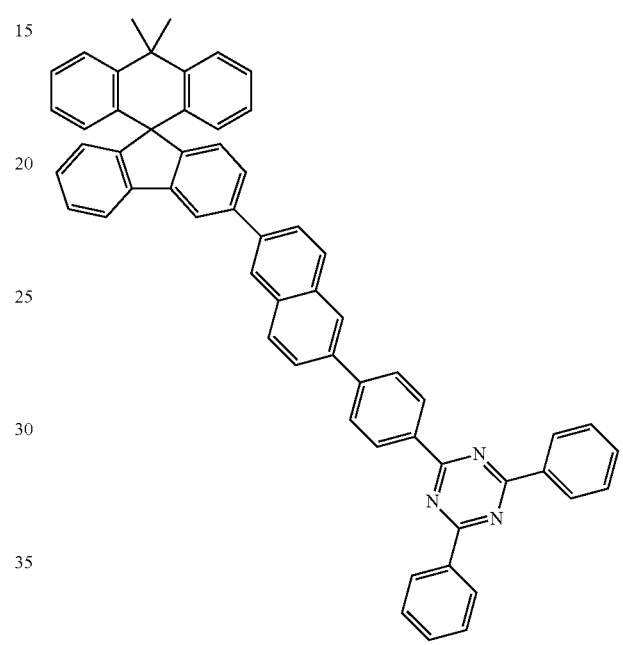

275
-continued
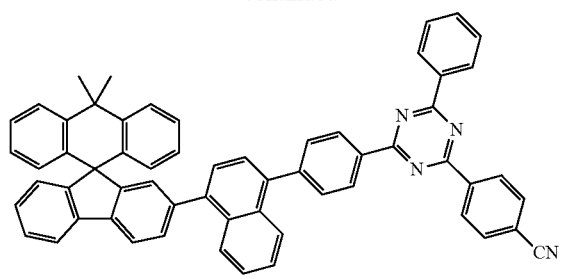
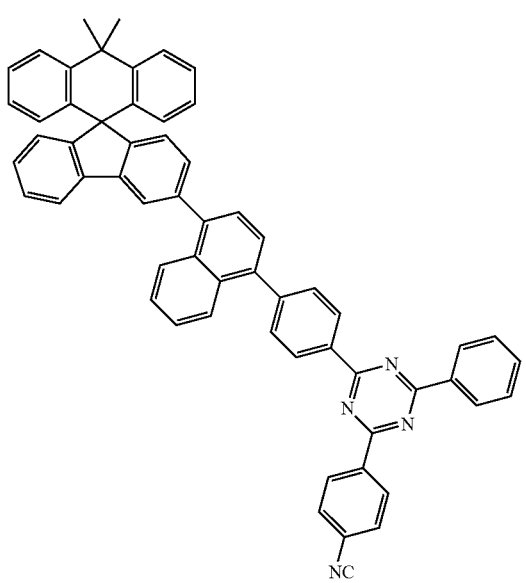
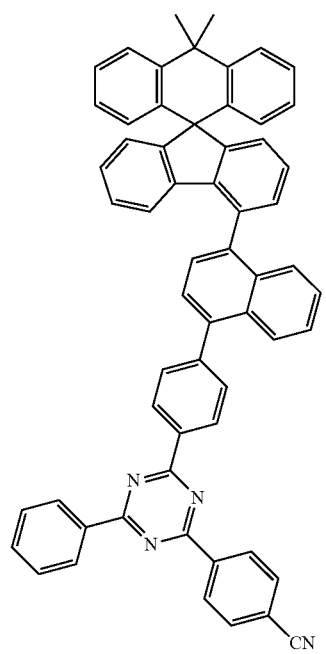
276
-continued
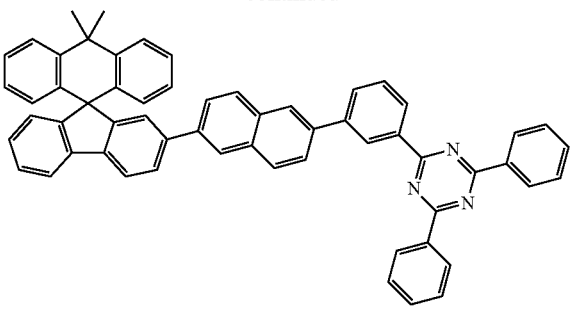
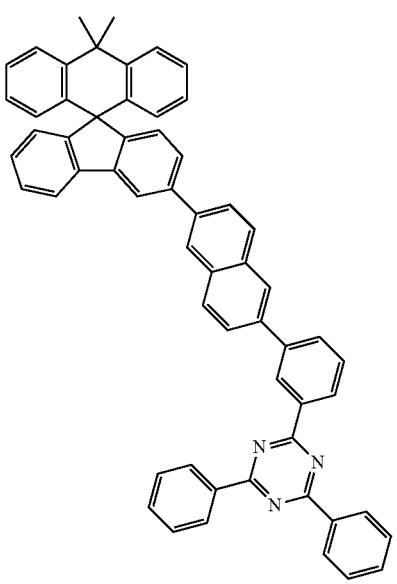
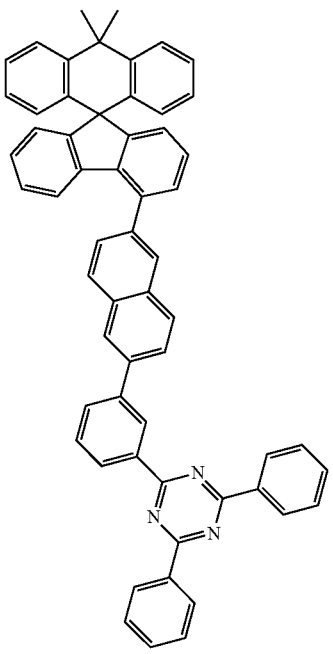

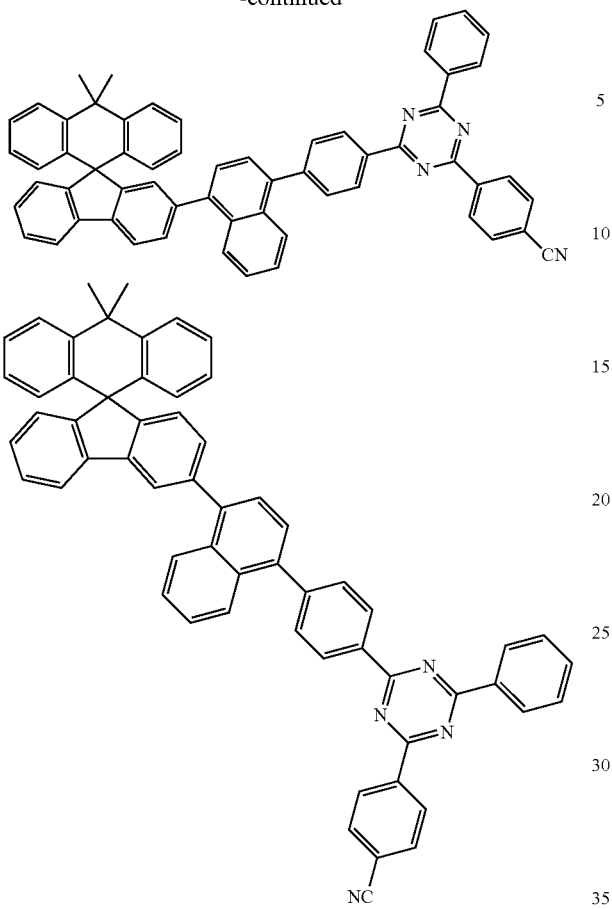
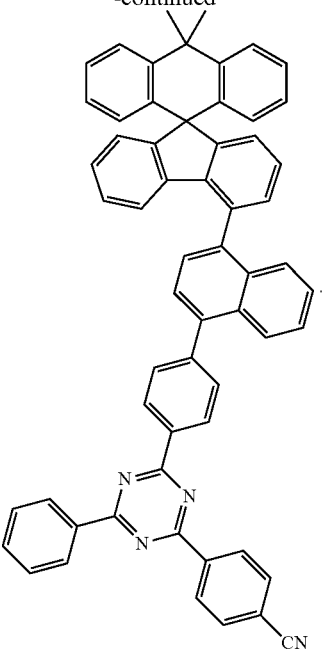
8. An organic light emitting device comprising:
a first electrode,
a second electrode provided to face the first electrode, and
at least one layer of organic material layers provided between the first electrode and the second electrode,
wherein the at least one layer of the organic material layers includes the compound according to claim 1.
* * * * *